United States Patent
Parker et al.

(10) Patent No.: US 10,010,618 B2
(45) Date of Patent: Jul. 3, 2018

(54) METHODS FOR TREATING CANCER USING COMBINATION THERAPIES

(71) Applicant: Endocyte, Inc., West Lafayette, IN (US)

(72) Inventors: Nikki L. Parker, West Lafayette, IN (US); Christopher P. Leamon, West Lafayette, IN (US); Iontcho R. Vlahov, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/950,268

(22) Filed: Nov. 24, 2015

(65) Prior Publication Data

US 2016/0296630 A1 Oct. 13, 2016

Related U.S. Application Data

(63) Continuation of application No. 14/685,181, filed on Apr. 13, 2015, now abandoned, which is a continuation of application No. 13/803,392, filed on Mar. 14, 2013, now abandoned.

(60) Provisional application No. 61/731,561, filed on Nov. 30, 2012.

(51) Int. Cl.
| | |
|---|---|
| *A61K 47/00* | (2006.01) |
| *A61K 31/095* | (2006.01) |
| *A61K 47/48* | (2006.01) |
| *G01N 33/574* | (2006.01) |
| *G01N 33/68* | (2006.01) |
| *A61K 31/454* | (2006.01) |
| *A61K 47/55* | (2017.01) |

(52) U.S. Cl.
CPC ...... *A61K 47/48107* (2013.01); *A61K 31/454* (2013.01); *A61K 47/551* (2017.08); *G01N 33/574* (2013.01); *G01N 33/6893* (2013.01); *G01N 2800/7095* (2013.01)

(58) Field of Classification Search
None
See application file for complete search history.

(56) References Cited

U.S. PATENT DOCUMENTS

| | | | | |
|---|---|---|---|---|
| 7,041,699 B2 * | 5/2006 | Netke | ........ | A23L 33/175 424/630 |
| 2010/0323973 A1 * | 12/2010 | Leamon | ........ | A61K 47/48215 514/20.9 |

OTHER PUBLICATIONS

Sigma catalog entry for N-Maleoyl-β-alanine, downloaded from www.sigmaaldrich.com on Mar. 27, 2017.*
Vlahov et al. "Engineering Folate-Drug Conjugates to Target Cancer: From Chemistry to Clinic" Bioconjugate Chem. 2012, 23, 1357-1369.*

* cited by examiner

*Primary Examiner* — Christina Bradley
(74) *Attorney, Agent, or Firm* — Barnes & Thornburg LLP

(57) ABSTRACT

Described are methods, uses, and kits for utilizing a targeted ligand conjugate in combination with a thiol inhibitor or a system $x_c^-$ inhibitor for the treatment of cancer or inflammation. Also described are in vitro assays utilizing a targeted ligand conjugate in combination with a thiol inhibitor or a system $x_c^-$ inhibitor.

10 Claims, 16 Drawing Sheets

METHODS FOR TREATING CANCER USING COMBINATION THERAPIES

CROSS REFERENCE TO RELATED APPLICATIONS

This application is a continuation of U.S. application Ser. No. 14/685,181 filed Apr. 13, 2015 which is a continuation of U.S. application Ser. No. 13/803,392 filed on Mar. 14, 2013, which claims priority under 35 U.S.C § 119(e) to U.S. Provisional Application Ser. No. 61/731,561, filed on Nov. 30, 2012, the disclosures of which are herein incorporated by reference.

TECHNICAL FIELD

The invention relates to methods, kits, and in vitro assays utilizing targeted ligand conjugates in combination with a thiol inhibitor. The invention also relates to methods, kits, and in vitro assays utilizing targeted ligand conjugates in combination with a system $x_c^-$ inhibitor.

BACKGROUND AND SUMMARY

A number of therapeutic agents comprising targeting ligands linked to a drug contain one or more linkers (e.g. disulfide-based linkers) placed between the targeting ligand and the therapeutically active drug. The targeting ligand allows for specific binding to cells that express a receptor for the ligand (e.g. cancer cells), resulting in delivery of the therapeutically active drug to the cells of interest. The disulfide linker allows for release of the drug inside the cell when the targeting ligand-drug conjugate is internalized and is exposed to the reducing environment inside the cells. For example, specific binding of folate-drug conjugates to the folate receptor (FR) on cancer cells or inflammatory cells allows for targeted delivery and specific therapeutic activity directed to the cancer cells or to sites of inflammation.

Folate is a member of the B family of vitamins and plays an essential role in cell survival by participating in the biosynthesis of nucleic acids and amino acids. This essential vitamin is also a high affinity ligand that enhances the specificity of conjugated anti-cancer drugs by targeting, for example, FR-positive cancer cells or inflammatory cells. The FR, a glycosylphosphatidyl-inositol anchored protein, can actively internalize bound folates and folate conjugated compounds via receptor-mediated endocytosis. It has been found that the FR is up-regulated in more than 90% of non-mucinous ovarian carcinomas, and is also found on inflammatory cells. The FR is also found at high to moderate levels in kidney, brain, lung, and breast carcinomas while it occurs at low levels in most normal tissues. FR density appears to increase as the stage of the cancer becomes more advanced. Folate-targeted drug conjugates have been developed and are being tested in clinical trials as cancer therapeutics, and in pre-clinical testing as therapeutics for inflammatory diseases.

Generally, the disulfide linker of targeted conjugates remains relatively stable in circulation, but rapidly breaks down once the conjugate enters the reductive endocytic process within a targeted cell. However, the possibility exists that a disulfide linker may be broken down outside cells, resulting in release of the drug and non-specific toxicity. The current inventors have hypothesized that instability of the disulfide linker in targeted conjugates may contribute to non-specific toxicity, and that the presence of extracellular thiols may play a role in the instability of the disulfide linker with resulting non-specific toxicity.

Accordingly, two different approaches were undertaken to evaluate the impact of extracellular thiols on non-specific activity of targeted conjugates with disulfide linkers. First, ligand conjugates and thiol inhibitors were tested together to evaluate the effects of co-treatment of cells with ligand conjugates and thiol inhibitors on the nonspecific uptake of the drug into the target cells and on non-ligand specific activity. Second, ligand conjugates and system $x_c^-$ inhibitors were tested together to evaluate the effects of co-treatment of cells with ligand conjugates and system $x_c^-$ inhibitors on the nonspecific uptake of the drug into the target cells and on non-ligand specific activity.

Surprisingly, the inventors have found that extracellular thiols (e.g. cysteine) contribute to non-specific toxicity of targeted conjugates containing one or more disulfide linkers, especially when the extracellular ligand conjugate concentration is exceedingly high. Thus, co-administration of thiol inhibitors or system $x_c^-$ inhibitors to patients along with targeted conjugates with disulfide linkers may decrease non-specific toxicity and increase efficacy of targeted therapeutics.

In one embodiment, a method of treatment of a disease is provided. The method comprises administering a ligand conjugate to a patient, wherein the ligand conjugate comprises a disulfide linkage; and administering a thiol inhibitor to the patient.

In another embodiment, use of a ligand conjugate in combination with a thiol inhibitor for the treatment of a disease is described, wherein the disease is cancer or inflammation, and wherein the ligand conjugate comprises a disulfide linkage.

In another embodiment, use of a ligand conjugate for the manufacture of a medicament for the treatment of a disease is described, wherein the disease is cancer or inflammation, and wherein the treatment comprises treating a patient with the ligand conjugate in combination with a thiol inhibitor, wherein the ligand conjugate comprises a disulfide linkage.

In another embodiment, a kit is provided. The kit comprises a ligand conjugate and one or more thiol inhibitors, wherein the ligand conjugate comprises a disulfide linkage.

In another embodiment, an in vitro assay for identifying a ligand conjugate suitable for co-administration with a thiol inhibitor to a patient is provided. The assay comprises the steps of a) adding the ligand conjugate to the culture medium of a first sample of cultured cells, wherein the ligand conjugate comprises a disulfide linkage; b) adding the thiol inhibitor to the culture medium of the first sample of cultured cells to provide a test sample; c) adding the ligand conjugate to the culture medium of a second sample of cultured cells to provide a control sample; d) measuring the non-ligand-specific activity of the ligand conjugate or the nonspecific uptake of the drug in the test sample; e) measuring the non-ligand-specific activity of the ligand conjugate or the nonspecific uptake of the drug in the control sample; and f) determining that the ligand conjugate is suitable for co-administration to the patient with the thiol inhibitor if the non-ligand-specific activity of the ligand conjugate and/or the nonspecific uptake of the drug are decreased in the test sample relative to the control sample.

In yet another embodiment, a method of treatment of a disease is provided. The method comprises administering a ligand conjugate to a patient, wherein the ligand conjugate comprises a disulfide linkage; and administering a system $x_c^-$ inhibitor to the patient.

In another embodiment, use of a ligand conjugate in combination with a system $x_c^-$ inhibitor for the treatment of a disease is described, wherein the disease is cancer or inflammation, and wherein the ligand conjugate comprises a disulfide linkage.

In another embodiment, use of a ligand conjugate for the manufacture of a medicament for the treatment of a disease wherein the disease is cancer or inflammation is described, and wherein the treatment comprises treating a patient with the ligand conjugate in combination with a system $x_c^-$ inhibitor, wherein the ligand conjugate comprises a disulfide linkage.

In another embodiment, a kit is provided. The kit comprises a ligand conjugate and one or more system $x_c^-$ inhibitors, wherein the ligand conjugate comprises a disulfide linkage.

In another embodiment, an in vitro assay for identifying a ligand conjugate suitable for co-administration to a patient with a system $x_c^-$ inhibitor is provided. The assay comprises the steps of a) adding the ligand conjugate to the culture medium of a first sample of cultured cells, wherein the ligand conjugate comprises a disulfide linkage; b) adding the system $x_c^-$ inhibitor to the culture medium of the first sample of cultured cells to provide a test sample; c) adding the ligand conjugate to the culture medium of a second sample of cultured cells to provide a control sample; d) measuring the non-ligand-specific activity of the ligand conjugate or the nonspecific uptake of the drug in the test sample; e) measuring the non-ligand-specific activity of the ligand conjugate or the nonspecific uptake of the drug in the control sample; and f) determining that the ligand conjugate is suitable for co-administration to the patient with the system $x_c^-$ inhibitor if the non-ligand-specific activity of the ligand conjugate and/or the nonspecific uptake of the drug are decreased in the test sample relative to the control sample. Any of the embodiments described in the following clause list are considered to be part of the invention.

1. A method of treatment of a disease, the method comprising the steps of:
    administering a ligand conjugate to a patient, wherein the ligand conjugate comprises a disulfide linkage; and
    administering a thiol inhibitor to the patient.
2. The method of clause 1, wherein the disease is cancer or inflammation.
3. Use of a ligand conjugate in combination with a thiol inhibitor for the treatment of a disease wherein the disease is cancer or inflammation, and wherein the ligand conjugate comprises a disulfide linkage.
4. Use of a ligand conjugate for the manufacture of a medicament for the treatment of a disease wherein the disease is cancer or inflammation, and wherein the treatment comprises treating a patient with the ligand conjugate in combination with a thiol inhibitor, wherein the ligand conjugate comprises a disulfide linkage.
5. The method or use of any one of clauses 1 to 4, wherein the disease is inflammation.
6. The method or use of any one of clauses 1 to 4, wherein the disease is cancer.
7. The method or use of clause 6, wherein the cancer comprises a primary tumor.
8. The method or use of clause 6, wherein the cancer comprises metastatic tumor cells.
9. The method or use of any one of clauses 1 to 8, wherein the ligand is folate.
10. The method or use of any one of clauses 1 to 8, wherein the ligand is an antibody.
11. The method or use of any one of clauses 1 to 8, wherein the ligand conjugate is of the formula $BLD_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.
12. The method or use of clause 11, wherein B is folate.
13. The method or use of clause 11, wherein B is D-folate.
14. The method or use of clause 11, wherein B is L-folate.
15. The method or use of clause 11, wherein B is a PSMA binding ligand.
16. The method or use of clause 11, wherein B is a radical of the formula

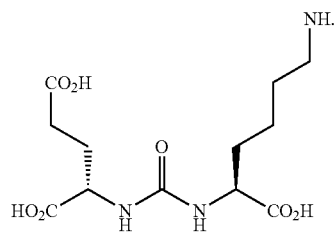

17. The method or use of clause 11, wherein B is a radical of the formula

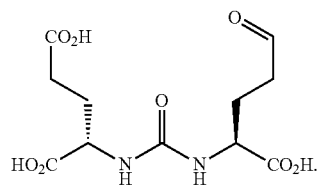

18. The method or use of clause 11, wherein B is a radical of the formula

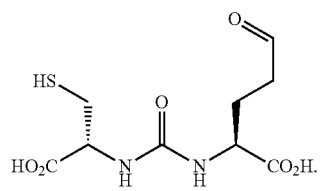

19. The method or use of any one of clauses 11 to 18, wherein the thiol reactive linkage is a disulfide linkage.
20. The method or use of any one of clauses 11 to 19, wherein L comprises a cysteine disulfide diradical.
21. The method or use of any one of clauses 11 to 20, wherein L further comprises one or more divalent hydrophilic radicals.
22. The method or use of any one of clauses 11 to 21, wherein D is a cytotoxic agent.
23. The method or use of any one of clauses 11 to 22, wherein D is a cancer treating agent.
24. The method or use of any one of clauses 11 to 22, wherein D is an anti-inflammatory agent.
25. The method or use of any one of clauses 11 to 24, wherein D is a vinca alkaloid.
26. The method or use of any one of clauses 11 to 24, wherein D is desacetylvinblastine monohydrazide.

27. The method or use of any one of clauses 11 to 24, wherein D is a tubulysin.
28. The method or use of any one of clauses 11 to 24, wherein D is tubulysin A.
29. The method or use of any one of clauses 11 to 24, wherein D is tubulysin B.
30. The method or use of any one of clauses 11 to 24, wherein D is tubulysin A hydrazide.
31. The method or use of any one of clauses 11 to 24, wherein D is tubulysin B hydrazide.
32. The method or use of any one of clauses 11 to 24, wherein D is an antifolate.
33. The method or use of any one of clauses 11 to 24, wherein D is an aminopterin.
34. The method or use of any one of clauses 11 to 24, wherein D is a rapamycin.
35. The method or use of any one of clauses 11 to 24, wherein D is a mitomycin.
36. The method or use of any one of clauses 11 to 24, wherein D is a taxane.
37. The method or use of any one of clauses 11 to 24, wherein D is a doxorubicin.
38. The method or use of any one of clauses 1 to 9 or 11 to 37, wherein the ligand conjugate is a folate conjugate.
39. The method or use of clause 38, wherein the folate conjugate is gallate (EGCG); and 4-acetamido-4'-maleimidylstilbene-2,2'-disulfonic acid (AMS).
42. The method or use of any one of clauses 1 to 41, wherein the thiol inhibitor is DTNB.
43. The method or use of any one of clauses 1 to 41, wherein the thiol inhibitor is a maleimide.
44. The method or use of any one of clauses 1 to 41, wherein the thiol inhibitor is NCEM.
45. The method or use of any one of clauses 1 to 41, wherein the thiol inhibitor is pCMBS.
46. The method or use of any one of clauses 1 to 41, wherein the thiol inhibitor is GSAO.
47. The method or use of any one of clauses 1 to 41, wherein the thiol inhibitor is dimesna.
48. The method or use of any one of clauses 1 to 41, wherein the thiol inhibitor is GSSG.
49. The method or use of any one of clauses 1 to 41, wherein the thiol inhibitor is a vinyl sulfone compound.
50. The method or use of any one of clauses 1 to 41, wherein the thiol inhibitor is methoxy-PEG5000-vinylsulfone.
51. The method or use of any one of clauses 1 to 41, wherein the thiol inhibitor is EGCG.
52. The method or use of any one of clauses 1 to 41, wherein the thiol inhibitor is AMS.
53. The method or use of any one of clauses 1 to 52, wherein the ligand conjugate and the thiol inhibitor are in parenteral dosage forms.

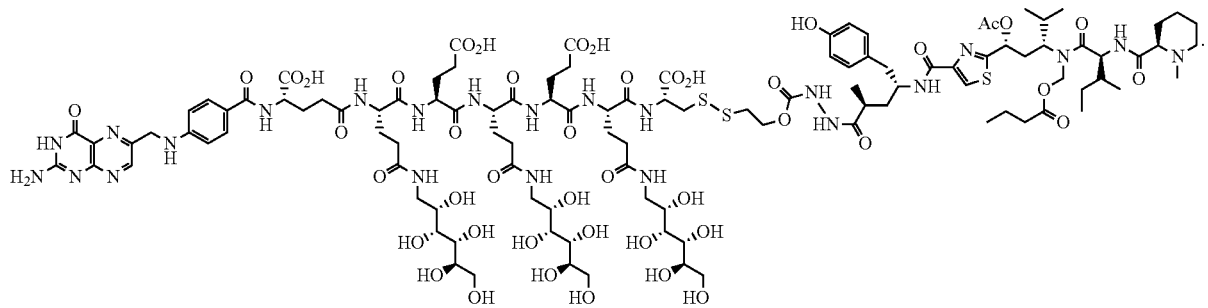 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]

40. The method or use of clause 38, wherein the folate conjugate is

54. The method or use of clause 53, wherein the dosage forms are independently selected from the group con-

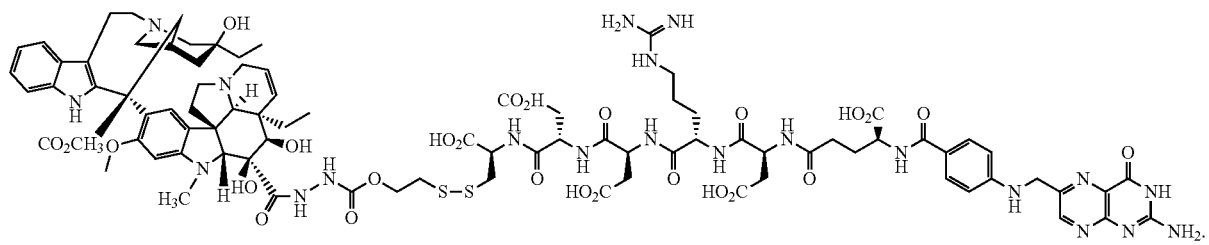

41. The method or use of any one of clauses 1 to 40, wherein the thiol inhibitor is selected from the group consisting of 5,5'-Dithiobis(2-nitrobenzoic acid) (DTNB); maleimides (e.g. N-maleoyl-β-alanine (N-(2-carboxyethyl) maleimide (NCEM)); p-chloromercuribenzene sulfonate (pCMBS); 4-(N—(S-glutathionylacetyl)amino) phenylarsonous acid (GSAO); 2,2'-dithio-bis-ethanesulfonate (dimesna); oxidized glutathione (GSSG); vinyl sulfone compounds (e.g. methoxy-PEG5000-vinylsulfone); epigallocatechin sisting of intradermal, subcutaneous, intramuscular, intraperitoneal, intravenous, and intrathecal.
55. The method or use of any one of clauses 1 to 54, wherein the ligand conjugate is in a composition and the thiol inhibitor is in a composition and wherein the compositions further comprise pharmaceutically acceptable carriers.
56. The method or use of clause 55, wherein the pharmaceutically acceptable carriers are liquid carriers.

57. The method or use of clause 56, wherein the liquid carriers are independently selected from the group consisting of saline, glucose, alcohols, glycols, esters, amides, and a combination thereof.
58. The method or use of any one of clauses 1 to 57, wherein the ligand conjugate and the thiol inhibitor are administered in therapeutically effective amounts.
59. The method or use of clause 58, wherein the effective amounts range from about 1 µg/m² to about 500 mg/m² of body surface area.
60. The method or use of clause 58, wherein the effective amounts range from about 1 µg/m² to about 300 mg/m² of body surface area.
61. The method or use of clause 58, wherein the effective amounts range from about 10 µg/kg to about 100 µg/kg of patient body weight.
62. The method or use of any one of clauses 1 to 61, wherein the ligand conjugate and the thiol inhibitor are in sterile containers or packages.
63. The method or use of any one of clauses 1 to 62, wherein the ligand conjugate and the thiol inhibitor have a purity of at least 90% based on weight percentage.
64. The method or use of any one of clauses 4 to 63, wherein the ligand conjugate is in the form of a reconstitutable lyophilizate.
65. The method or use of any one of clauses 1 to 64, wherein the ligand conjugate and the thiol inhibitor are in sterile, pyrogen-free aqueous solutions.
66. A kit comprising a ligand conjugate and one or more thiol inhibitors, wherein the ligand conjugate comprises a disulfide linkage.
67. The kit of clause 66, wherein the ligand is folate.
68. The kit of clause 66, wherein the ligand is an antibody.
69. The kit of clause 66, wherein the ligand conjugate is of the formula BLD$_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.
70. The kit of clause 69, wherein B is folate.
71. The kit of clause 69, wherein B is D-folate.
72. The kit of clause 69, wherein B is L-folate.
73. The kit of clause 69, wherein B is a PSMA binding ligand.
74. The kit of clause 69, wherein B is a radical of the formula

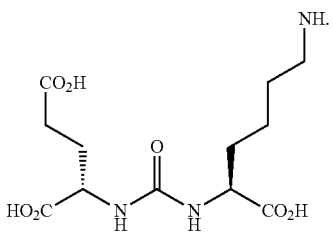

75. The kit of clause 69, wherein B is a radical of the formula

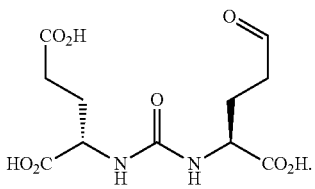

76. The kit of clause 69, wherein B is a radical of the formula

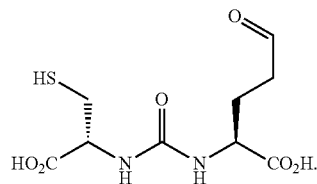

77. The kit of any one of clauses 69 to 76, wherein the thiol reactive linkage is a disulfide linkage.
78. The kit of any one of clauses 69 to 77, wherein L comprises a cysteine disulfide diradical.
79. The kit of any one of clauses 69 to 78, wherein L further comprises one or more divalent hydrophilic radicals.
80. The kit of any one of clauses 69 to 79, wherein D is a cytotoxic agent.
81. The kit of any one of clauses 69 to 80, wherein D is a cancer treating agent.
82. The kit of any one of clauses 69 to 80, wherein D is an anti-inflammatory agent.
83. The kit of any one of clauses 69 to 82, wherein D is a vinca alkaloid.
84. The kit of any one of clauses 69 to 82, wherein D is desacetylvinblastine monohydrazide.
85. The kit of any one of clauses 69 to 82, wherein D is a tubulysin.
86. The kit of any one of clauses 69 to 82, wherein D is tubulysin A.
87. The kit of any one of clauses 69 to 82, wherein D is tubulysin B.
88. The kit of any one of clauses 69 to 82, wherein D is tubulysin A hydrazide.
89. The kit of any one of clauses 69 to 82, wherein D is tubulysin B hydrazide.
90. The kit of any one of clauses 69 to 82, wherein D is an antifolate.
91. The kit of any one of clauses 69 to 82, wherein D is an aminopterin.
92. The kit of any one of clauses 69 to 82, wherein D is a rapamycin.
93. The kit of any one of clauses 69 to 82, wherein D is a mitomycin.
94. The kit of any one of clauses 69 to 82, wherein D is a taxane.
95. The kit of any one of clauses 69 to 82, wherein D is a doxorubicin.
96. The kit of any one of clauses 66 to 67 or 69 to 95, wherein the ligand conjugate is a folate conjugate.

97. The kit of clause 96, wherein the folate conjugate is

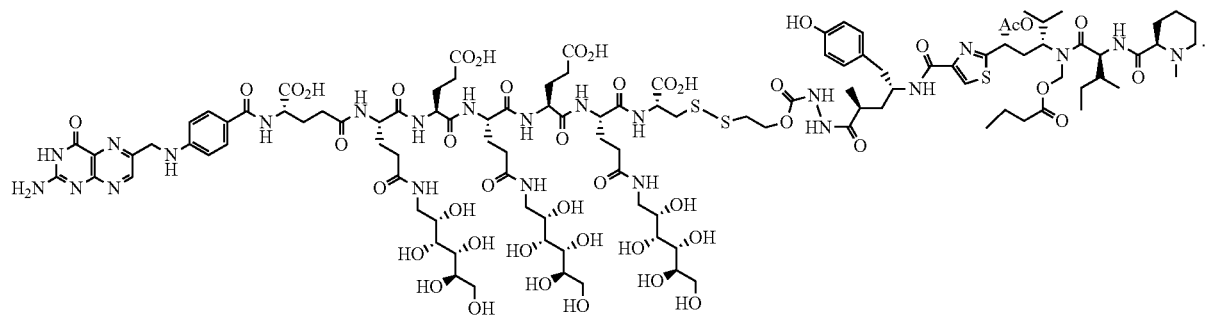 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]

98. The kit of clause 96, wherein the folate conjugate is

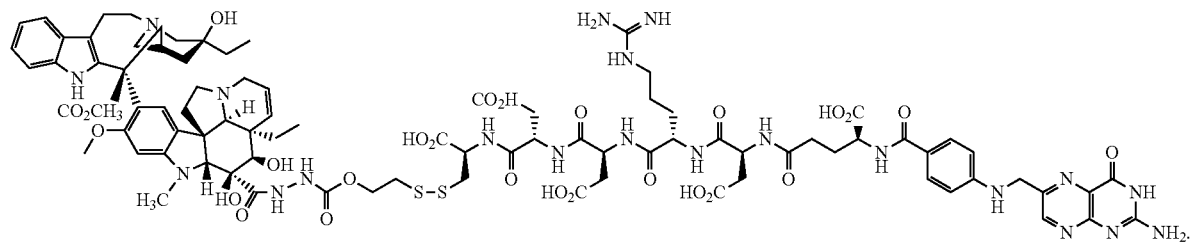

99. The kit of any one of clauses 66 to 98, wherein the thiol inhibitor is selected from the group consisting of 5,5'-Dithiobis(2-nitrobenzoic acid) (DTNB); maleimides (e.g. N-maleoyl-β-alanine (N-(2-carboxyethyl) maleimide (NCEM)); p-chloromercuribenzene sulfonate (pCMBS); 4-(N—(S-glutathionylacetyl)amino) phenylarsonous acid (GSAO); 2,2'-dithio-bis-ethanesulfonate (dimesna); oxidized glutathione (GSSG); vinyl sulfone compounds (e.g. methoxy-PEG5000-vinylsulfone); epigallocatechin gallate (EGCG); and 4-acetamido-4'-maleimidylstilbene-2,2'-disulfonic acid (AMS).
100. The kit of any one of clauses 66 to 99, wherein the thiol inhibitor is DTNB.
101. The kit of any one of clauses 66 to 99, wherein the thiol inhibitor is a maleimide.
102. The kit of any one of clauses 66 to 99, wherein the thiol inhibitor is NCEM.
103. The kit of any one of clauses 66 to 99, wherein the thiol inhibitor is pCMBS.
104. The kit of any one of clauses 66 to 99, wherein the thiol inhibitor is GSAO.
105. The kit of any one of clauses 66 to 99, wherein the thiol inhibitor is dimesna.
106. The kit of any one of clauses 66 to 99, wherein the thiol inhibitor is GSSG.
107. The kit of any one of clauses 66 to 99, wherein the thiol inhibitor is a vinyl sulfone compound.
108. The kit of any one of clauses 66 to 99, wherein the thiol inhibitor is methoxy-PEG5000-vinylsulfone.
109. The kit of any one of clauses 66 to 99, wherein the thiol inhibitor is EGCG.
110. The kit of any one of clauses 66 to 99, wherein the thiol inhibitor is AMS.
111. The kit of any one of clauses 66 to 110, wherein the ligand conjugate and the thiol inhibitor are in parenteral dosage forms.
112. The kit of clause 111, wherein the dosage forms are independently selected from the group consisting of intradermal, subcutaneous, intramuscular, intraperitoneal, intravenous, and intrathecal.
113. The kit of any one of clauses 66 to 112, wherein the ligand conjugate is in a composition and the thiol inhibitor is in a composition and wherein the compositions further comprise pharmaceutically acceptable carriers.
114. The kit of clause 113, wherein the pharmaceutically acceptable carriers are liquid carriers.
115. The kit of clause 114, wherein the liquid carriers are independently selected from the group consisting of saline, glucose, alcohols, glycols, esters, amides, and a combination thereof.
116. The kit of any one of clauses 66 to 115, wherein the ligand conjugate and the thiol inhibitor are in therapeutically effective amounts.
117. The kit of any one of clauses 66 to 116, wherein the ligand conjugate and the thiol inhibitor are in sterile containers or packages.
118. The kit of any one of clauses 66 to 117, wherein the ligand conjugate and the thiol inhibitor have a purity of at least 90% based on weight percentage.
119. The kit of any one of clauses 66 to 117, wherein the ligand conjugate and the thiol inhibitor have a purity of at least 95% based on weight percentage.
120. The kit of any one of clauses 66 to 119, wherein the ligand conjugate is in the form of a lyophilizate.
121. The kit of any one of clauses 66 to 120, wherein the ligand conjugate is in the form of a reconstitutable lyophilizate.
122. The kit of any one of clauses 66 to 121, wherein the ligand conjugate and the thiol inhibitor are in sterile, pyrogen-free aqueous solutions.

123. An in vitro assay for identifying a ligand conjugate suitable for co-administration to a patient with a thiol inhibitor, the assay comprising:
a) adding the ligand conjugate to the culture medium of a first sample of cultured cells, wherein the ligand conjugate comprises a disulfide linkage;
b) adding the thiol inhibitor to the culture medium of the first sample of cultured cells to provide a test sample;
c) adding the ligand conjugate to the culture medium of a second sample of cultured cells to provide a control sample;
d) measuring the non-ligand-specific activity of the ligand conjugate or the nonspecific uptake of the drug in the test sample;
e) measuring the non-ligand-specific activity of the ligand conjugate or the nonspecific uptake of the drug in the control sample; and
f) determining that the ligand conjugate is suitable for co-administration to the patient with the thiol inhibitor if the non-ligand-specific activity of the ligand conjugate and/or the nonspecific uptake of the drug are decreased in the test sample relative to the control sample.

124. The in vitro assay of clause 123 further comprising step g) administering the ligand conjugate and the thiol inhibitor to the patient.

125. The in vitro assay of clause 123 or clause 124 wherein the ligand is folate.

126. The in vitro assay of clause 123 or clause 124 wherein the ligand is an antibody.

127. The in vitro assay of clause 123 or clause 124, wherein the ligand conjugate is of the formula $BLD_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.

128. The in vitro assay of clause 127, wherein B is folate.

129. The in vitro assay of clause 127, wherein B is D-folate.

130. The in vitro assay of clause 127, wherein B is L-folate.

131. The in vitro assay of clause 127, wherein B is a PSMA binding ligand.

132. The in vitro assay of clause 127, wherein B is a radical of the formula

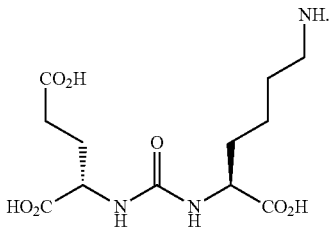

133. The in vitro assay of clause 127, wherein B is a radical of the formula

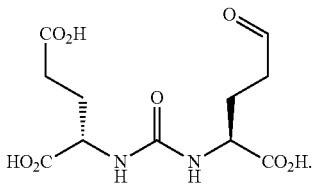

134. The in vitro assay of clause 127, wherein B is a radical of the formula

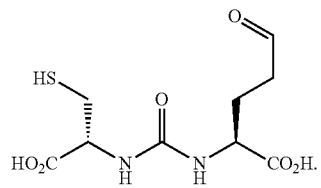

135. The in vitro assay of any one of clauses 127 to 134, wherein the thiol reactive linkage is a disulfide linkage.

136. The in vitro assay of any one of clauses 127 to 135, wherein L comprises a cysteine disulfide diradical.

137. The in vitro assay of any one of clauses 127 to 136, wherein L further comprises one or more divalent hydrophilic radicals.

138. The in vitro assay of any one of clauses 127 to 137, wherein D is a cytotoxic agent.

139. The in vitro assay of any one of clauses 127 to 138, wherein D is a cancer treating agent.

140. The in vitro assay of any one of clauses 127 to 138, wherein D is an anti-inflammatory agent.

141. The in vitro assay of any one of clauses 127 to 140, wherein D is a vinca alkaloid.

142. The in vitro assay of any one of clauses 127 to 140, wherein D is desacetylvinblastine monohydrazide.

143. The in vitro assay of any one of clauses 127 to 140, wherein D is a tubulysin.

144. The in vitro assay of any one of clauses 127 to 140, wherein D is tubulysin A.

145. The in vitro assay of any one of clauses 127 to 140, wherein D is tubulysin B.

146. The in vitro assay of any one of clauses 127 to 140, wherein D is tubulysin A hydrazide.

147. The in vitro assay of any one of clauses 127 to 140, wherein D is tubulysin B hydrazide.

148. The in vitro assay of any one of clauses 127 to 140, wherein D is an antifolate.

149. The in vitro assay of any one of clauses 127 to 140, wherein D is an aminopterin.

150. The in vitro assay of any one of clauses 127 to 140, wherein D is a rapamycin.

151. The in vitro assay of any one of clauses 127 to 140, wherein D is a mitomycin.

152. The in vitro assay of any one of clauses 127 to 140, wherein D is a taxane.

153. The in vitro assay of any one of clauses 127 to 140, wherein D is a doxorubicin.

154. The in vitro assay of any one of clauses 123 to 140, wherein the ligand conjugate is a folate conjugate.

155. The in vitro assay of clause 154, wherein the folate conjugate is

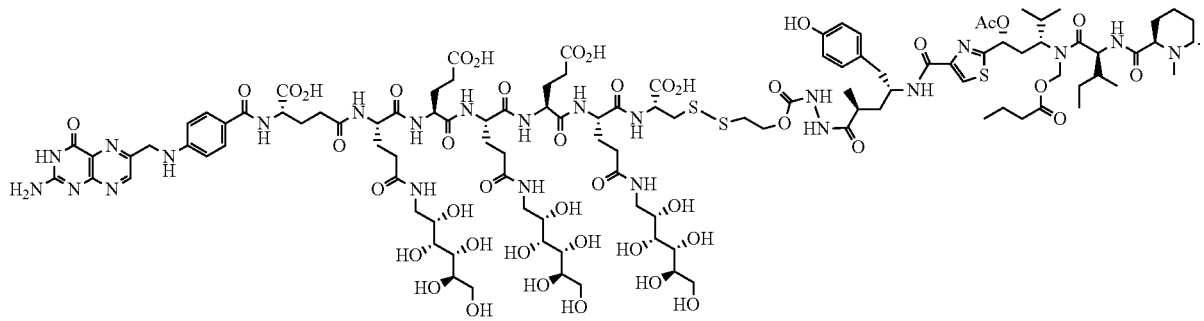 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]

156. The in vitro assay of clause 154, wherein the folate conjugate is

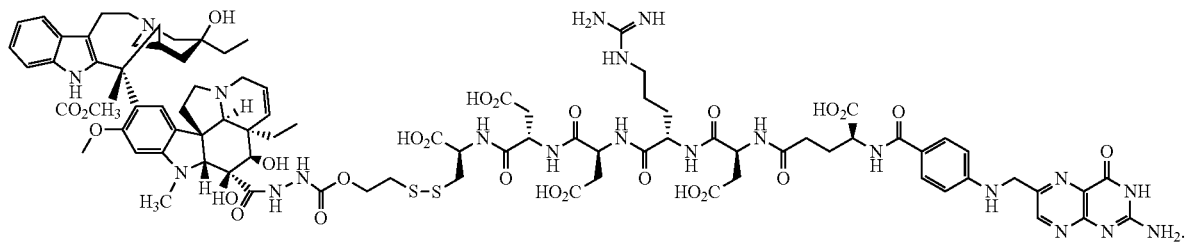

157. The in vitro assay of any one of clauses 123 to 156, wherein the thiol inhibitor is selected from the group consisting of 5,5'-Dithiobis(2-nitrobenzoic acid) (DTNB); maleimides (e.g. N-maleoyl-β-alanine (N-(2-carboxyethyl) maleimide (NCEM)); p-chloromercuribenzene sulfonate (pCMBS); 4-(N—(S-glutathionylacetyl)amino) phenylarsonous acid (GSAO); 2,2'-dithio-bis-ethanesulfonate (dimesna); oxidized glutathione (GSSG); vinyl sulfone compounds (e.g. methoxy-PEG5000-vinylsulfone); epigallocatechin gallate (EGCG); and 4-acetamido-4'-maleimidylstilbene-2,2'-disulfonic acid (AMS).

158. The in vitro assay of any one of clauses 123 to 157, wherein the thiol inhibitor is DTNB.

159. The in vitro assay of any one of clauses 123 to 157, wherein the thiol inhibitor is a maleimide.

160. The in vitro assay of any one of clauses 123 to 157, wherein the thiol inhibitor is NCEM.

161. The in vitro assay of any one of clauses 123 to 157, wherein the thiol inhibitor is pCMBS.

162. The in vitro assay of any one of clauses 123 to 157, wherein the thiol inhibitor is GSAO.

163. The in vitro assay of any one of clauses 123 to 157, wherein the thiol inhibitor is dimesna.

164. The in vitro assay of any one of clauses 123 to 157, wherein the thiol inhibitor is GSSG.

165. The in vitro assay of any one of clauses 123 to 157, wherein the thiol inhibitor is a vinyl sulfone compound.

166. The in vitro assay of any one of clauses 123 to 157, wherein the thiol inhibitor is methoxy-PEG5000-vinylsulfone.

167. The in vitro assay of any one of clauses 123 to 157, wherein the thiol inhibitor is EGCG.

168. The in vitro assay of any one of clauses 123 to 157, wherein the thiol inhibitor is AMS.

169. The in vitro assay of any one of clauses 123 to 168, wherein the cultured cells are KB cells.

170. The in vitro assay of any one of clauses 123 to 168, wherein the cultured cells are A549 cells.

171. The in vitro assay of any one of clauses 123 to 170, wherein the non-ligand-specific activity of the ligand conjugate is decreased by the thiol inhibitor.

172. The in vitro assay of clause 171, wherein the non-ligand-specific activity is cytotoxicity.

173. The in vitro assay of any one of clauses 123 to 170, wherein the nonspecific uptake of the drug is decreased by the thiol inhibitor.

174. The in vitro assay of clause 173, wherein the nonspecific uptake of the drug is measured using competition assays in the presence and absence of an excess of non-radiolabeled ligand.

175. A method of treatment of a disease, the method comprising the steps of:
administering a ligand conjugate to a patient, wherein the ligand conjugate comprises a disulfide linkage; and administering a system $x_c^-$ inhibitor to the patient.
176. The method of clause 175, wherein the disease is cancer or inflammation.
177. Use of a ligand conjugate in combination with a system $x_c^-$ inhibitor for the treatment of a disease wherein the disease is cancer or inflammation, and wherein the ligand conjugate comprises a disulfide linkage.
178. Use of a ligand conjugate for the manufacture of a medicament for the treatment of a disease wherein the disease is cancer or inflammation, and wherein the treatment comprises treating a patient with the ligand conjugate in combination with a system $x_c^-$ inhibitor, wherein the ligand conjugate comprises a disulfide linkage.
179. The method or use of any one of clauses 175 to 178, wherein the disease is inflammation.
180. The method or use of any one of clauses 175 to 178, wherein the disease is cancer.
181. The method or use of clause 180, wherein the cancer comprises a primary tumor.
182. The method or use of clause 180, wherein the cancer comprises metastatic tumor cells.
183. The method or use of any one of clauses 175 to 182, wherein the ligand is folate.
184. The method or use of any one of clauses 175 to 182, wherein the ligand is an antibody.
185. The method or use of any one of clauses 175 to 182, wherein the ligand conjugate is of the formula $BLD_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.
186. The method or use of clause 185, wherein B is folate.
187. The method or use of clause 185, wherein B is D-folate.
188. The method or use of clause 185, wherein B is L-folate.
189. The method or use of clause 185, wherein B is a PSMA binding ligand.
190. The method or use of clause 185, wherein B is a radical of the formula

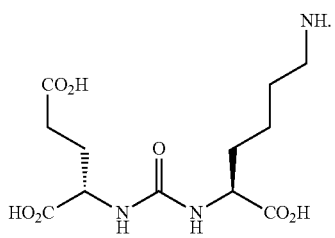

191. The method or use of clause 185, wherein B is a radical of the formula

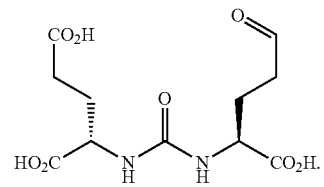

192. The method or use of clause 185, wherein B is a radical of the formula

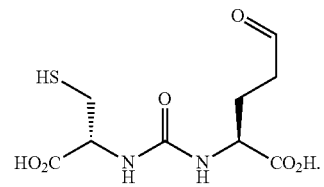

193. The method or use of any one of clauses 185 to 192, wherein the thiol reactive linkage is a disulfide linkage.
194. The method or use of any one of clauses 185 to 193, wherein L comprises a cysteine disulfide diradical.
195. The method or use of any one of clauses 185 to 194, wherein L further comprises one or more divalent hydrophilic radicals.
196. The method or use of any one of clauses 185 to 195, wherein D is a cytotoxic agent.
197. The method or use of any one of clauses 185 to 196, wherein D is a cancer treating agent.
198. The method or use of any one of clauses 185 to 196, wherein D is an anti-inflammatory agent.
199. The method or use of any one of clauses 185 to 198, wherein D is a vinca alkaloid.
200. The method or use of any one of clauses 185 to 198, wherein D is desacetylvinblastine monohydrazide.
201. The method or use of any one of clauses 185 to 198, wherein D is a tubulysin.
202. The method or use of any one of clauses 185 to 198, wherein D is tubulysin A.
203. The method or use of any one of clauses 185 to 198, wherein D is tubulysin B.
204. The method or use of any one of clauses 185 to 198, wherein D is tubulysin A hydrazide.
205. The method or use of any one of clauses 185 to 198, wherein D is tubulysin B hydrazide.
206. The method or use of any one of clauses 185 to 198, wherein D is an antifolate.
207. The method or use of any one of clauses 185 to 198, wherein D is an aminopterin.
208. The method or use of any one of clauses 185 to 198, wherein D is a rapamycin.
209. The method or use of any one of clauses 185 to 198, wherein D is a mitomycin.
210. The method or use of any one of clauses 185 to 198, wherein D is a taxane.
211. The method or use of any one of clauses 185 to 198, wherein D is a doxorubicin.
212. The method or use of any one of clauses 175 to 183 or 185 to 211, wherein the ligand conjugate is a folate conjugate.

213. The method or use of clause 212, wherein the folate conjugate is

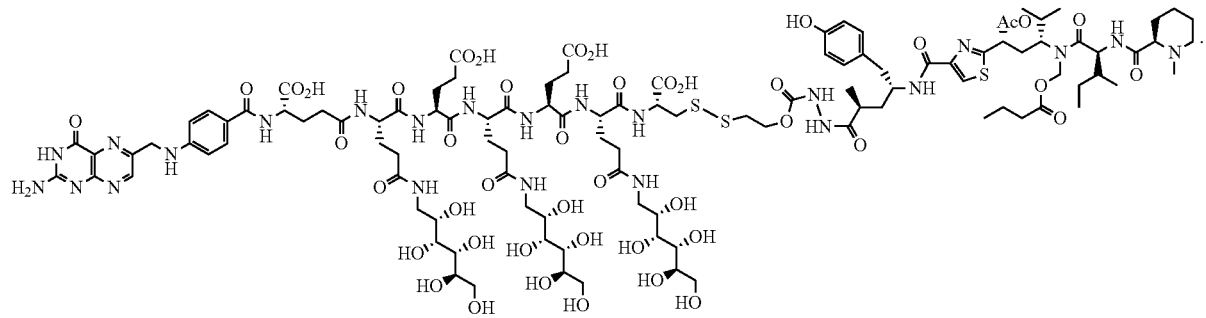 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]

214. The method or use of clause 212, wherein the folate conjugate is

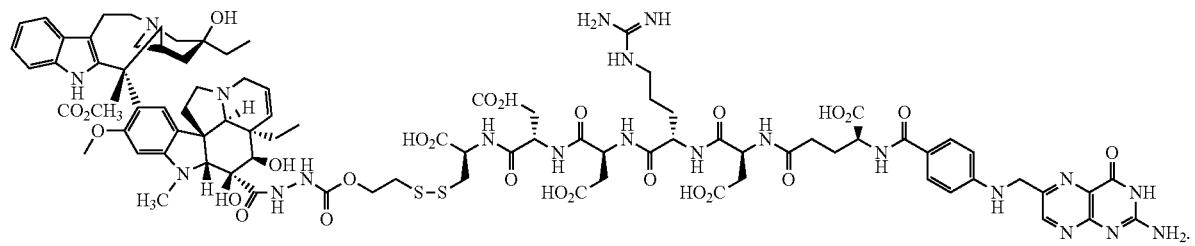

215. The method or use of any one of clauses 175 to 214, wherein the system $x_c^-$ inhibitor is selected from the group consisting of sulfasalazine, glutamate; L-quisqualate; (S)-4-carboxyphenylglycine (4-S—CPG); L-α-aminoadipic acid; and L-homocysteic acid.

216. The method or use of any one of clauses 175 to 215, wherein the system $x_c^-$ inhibitor is sulfasalazine.

217. The method or use of any one of clauses 175 to 215, wherein the system $x_c^-$ inhibitor is glutamate.

218. The method or use of any one of clauses 175 to 215, wherein the system $x_c^-$ inhibitor is L-quisqualate.

219. The method or use of any one of clauses 175 to 215, wherein the system $x_c^-$ inhibitor is 4-S—CPG.

220. The method or use of any one of clauses 175 to 215, wherein the system $x_c^-$ inhibitor is L-α-aminoadipic acid.

221. The method or use of any one of clauses 175 to 215, wherein the system $x_c^-$ inhibitor is L-homocysteic acid.

222. The method or use of any one of clauses 175 to 221, wherein the ligand conjugate and the system $x_c^-$ inhibitor are in parenteral dosage forms.

223. The method or use of clause 222, wherein the dosage forms are independently selected from the group consisting of intradermal, subcutaneous, intramuscular, intraperitoneal, intravenous, and intrathecal.

224. The method or use of any one of clauses 175 to 223, wherein the ligand conjugate is in a composition and the system $x_c^-$ inhibitor is in a composition and wherein the compositions further comprise pharmaceutically acceptable carriers.

225. The method or use of clause 224, wherein the pharmaceutically acceptable carriers are liquid carriers.

226. The method or use of clause 225, wherein the liquid carriers are independently selected from the group consisting of saline, glucose, alcohols, glycols, esters, amides, and a combination thereof.

227. The method or use of any one of clauses 175 to 226, wherein the ligand conjugate and the system $x_c^-$ inhibitor are administered in therapeutically effective amounts.

228. The method or use of clause 227, wherein the effective amounts range from about 1 μg/m² to about 500 mg/m² of body surface area.

229. The method or use of clause 227, wherein the effective amounts range from about 1 μg/m² to about 300 mg/m² of body surface area.

230. The method or use of clause 227, wherein the effective amounts range from about 10 μg/kg to about 100 μg/kg of patient body weight.

231. The method or use of any one of clauses 175 to 230, wherein the ligand conjugate and the system $x_c^-$ inhibitor are in sterile containers or packages.

232. The method or use of any one of clauses 175 to 231, wherein the ligand conjugate and the system $x_c^-$ inhibitor have a purity of at least 90% based on weight percentage.

233. The method or use of any one of clauses 178 to 232, wherein the ligand conjugate is in the form of a reconstitutable lyophilizate.
234. The method or use of any one of clauses 175 to 233, wherein the ligand conjugate and the system $x_c^-$ inhibitor are in sterile, pyrogen-free aqueous solutions.
235. A kit comprising a ligand conjugate and one or more system $x_c^-$ inhibitors, wherein the ligand conjugate comprises a disulfide linkage.
236. The kit of clause 235, wherein the ligand is folate.
237. The kit of clause 235, wherein the ligand is an antibody.
238. The kit of clause 235, wherein the ligand conjugate is of the formula $BLD_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.
239. The kit of clause 238, wherein B is folate.
240. The kit of clause 238, wherein B is D-folate.
241. The kit of clause 238, wherein B is L-folate.
242. The kit of clause 238, wherein B is a PSMA binding ligand.
243. The kit of clause 238, wherein B is a radical of the formula

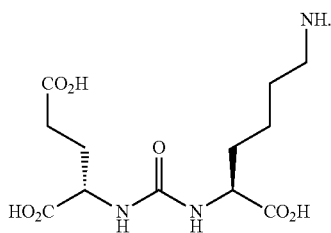

244. The kit of clause 238, wherein B is a radical of the formula

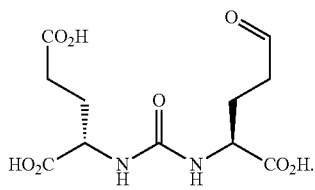

245. The kit of clause 238, wherein B is a radical of the formula

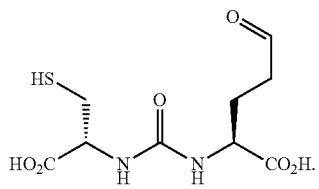

246. The kit of any one of clauses 238 to 245, wherein the thiol reactive linkage is a disulfide linkage.
247. The kit of any one of clauses 238 to 246, wherein L comprises a cysteine disulfide diradical.
248. The kit of any one of clauses 238 to 247, wherein L further comprises one or more divalent hydrophilic radicals.
249. The kit of any one of clauses 238 to 248, wherein D is a cytotoxic agent.
250. The kit of any one of clauses 238 to 249, wherein D is a cancer treating agent.
251. The kit of any one of clauses 238 to 249, wherein D is an anti-inflammatory agent.
252. The kit of any one of clauses 238 to 251, wherein D is a vinca alkaloid.
253. The kit of any one of clauses 238 to 251, wherein D is desacetylvinblastine monohydrazide.
254. The kit of any one of clauses 238 to 251, wherein D is a tubulysin.
255. The kit of any one of clauses 238 to 251, wherein D is tubulysin A.
256. The kit of any one of clauses 238 to 251, wherein D is tubulysin B.
257. The kit of any one of clauses 238 to 251, wherein D is tubulysin A hydrazide.
258. The kit of any one of clauses 238 to 251, wherein D is tubulysin B hydrazide.
259. The kit of any one of clauses 238 to 251, wherein D is an antifolate.
260. The kit of any one of clauses 238 to 251, wherein D is an aminopterin.
261. The kit of any one of clauses 238 to 251, wherein D is a rapamycin.
262. The kit of any one of clauses 238 to 251, wherein D is a mitomycin.
263. The kit of any one of clauses 238 to 251, wherein D is a taxane.
264. The kit of any one of clauses 238 to 251, wherein D is a doxorubicin.
265. The kit of any one of clauses 235 to 236 or 238 to 264, wherein the ligand conjugate is a folate conjugate.
266. The kit of clause 265, wherein the folate conjugate is

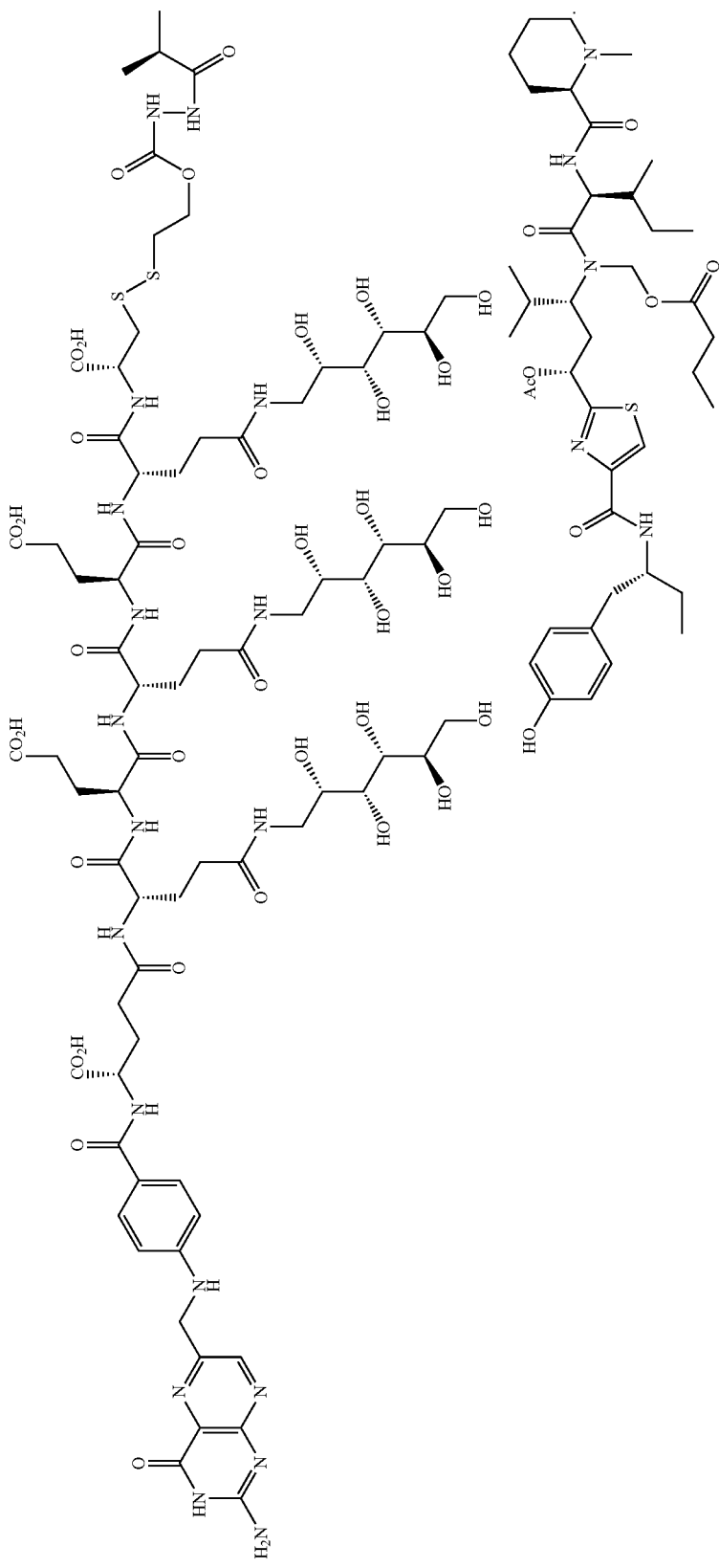

267. The kit of clause 265, wherein the folate conjugate is

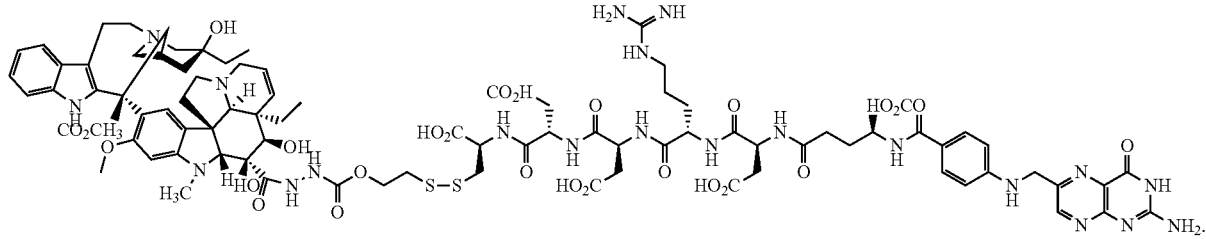

268. The kit of any one of clauses 235 to 267, wherein the system $x_c^-$ inhibitor is selected from the group consisting of sulfasalazine, glutamate; L-quisqualate; (S)-4-carboxyphenylglycine (4-S—CPG); L-α-aminoadipic acid; and L-homocysteic acid.
269. The kit of any one of clauses 235 to 268, wherein the system $x_c^-$ inhibitor is sulfasalazine.
270. The kit of any one of clauses 235 to 268, wherein the system $x_c^-$ inhibitor is glutamate.
271. The kit of any one of clauses 235 to 268, wherein the system $x_c^-$ inhibitor is L-quisqualate.
272. The kit of any one of clauses 235 to 268, wherein the system $x_c^-$ inhibitor is 4-S—CPG.
273. The kit of any one of clauses 235 to 268, wherein the system $x_c^-$ inhibitor is L-α-aminoadipic acid.
274. The kit of any one of clauses 235 to 268, wherein the system $x_c^-$ inhibitor is L-homocysteic acid.
275. The kit of any one of clauses 235 to 274, wherein the ligand conjugate and the system $x_c^-$ inhibitor are in parenteral dosage forms.
276. The kit of clause 275, wherein the dosage forms are independently selected from the group consisting of intradermal, subcutaneous, intramuscular, intraperitoneal, intravenous, and intrathecal.
277. The kit of any one of clauses 235 to 276, wherein the ligand conjugate is in a composition and the system $x_c^-$ inhibitor is in a composition and wherein the compositions further comprise pharmaceutically acceptable carriers.
278. The kit of clause 277, wherein the pharmaceutically acceptable carriers are liquid carriers.
279. The kit of clause 278, wherein the liquid carriers are independently selected from the group consisting of saline, glucose, alcohols, glycols, esters, amides, and a combination thereof.
280. The kit of any one of clauses 235 to 279, wherein the ligand conjugate and the system $x_c^-$ inhibitor are in therapeutically effective amounts.
281. The kit of any one of clauses 235 to 280, wherein the ligand conjugate and the system $x_c^-$ inhibitor are in sterile containers or packages.
282. The kit of any one of clauses 235 to 281, wherein the ligand conjugate and the system $x_c^-$ inhibitor have a purity of at least 90% based on weight percentage.
283. The kit of any one of clauses 235 to 281, wherein the ligand conjugate and the system $x_c^-$ inhibitor have a purity of at least 95% based on weight percentage.
284. The kit of any one of clauses 235 to 283, wherein the ligand conjugate is in the form of a lyophilizate.
285. The kit of any one of clauses 235 to 284, wherein the ligand conjugate is in the form of a reconstitutable lyophilizate.
286. The kit of any one of clauses 235 to 285, wherein the ligand conjugate and the system $x_c^-$ inhibitor are in sterile, pyrogen-free aqueous solutions.
287. An in vitro assay for identifying a ligand conjugate suitable for co-administration to a patient with a system $x_c^-$ inhibitor, the assay comprising:
a) adding the ligand conjugate to the culture medium of a first sample of cultured cells, wherein the ligand conjugate comprises a disulfide linkage;
b) adding the system $x_c^-$ inhibitor to the culture medium of the first sample of cultured cells to provide a test sample;
c) adding the ligand conjugate to the culture medium of a second sample of cultured cells to provide a control sample;
d) measuring the non-ligand-specific activity of the ligand conjugate or the nonspecific uptake of the drug in the test sample;
e) measuring the non-ligand-specific activity of the ligand conjugate or the nonspecific uptake of the drug in the control sample; and
f) determining that the ligand conjugate is suitable for co-administration to the patient with the system $x_c^-$ inhibitor if the non-ligand-specific activity of the ligand conjugate and/or the nonspecific uptake of the drug are decreased in the test sample relative to the control sample.
288. The in vitro assay of clause 287 further comprising step g) administering the ligand conjugate and the system $x_c^-$ inhibitor to the patient.
289. The in vitro assay of clause 287 or clause 288 wherein the ligand is folate.
290. The in vitro assay of clause 287 or clause 288 wherein the ligand is an antibody.
291. The in vitro assay of clause 287 or clause 288, wherein the ligand conjugate is of the formula $BLD_x$, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.
292. The in vitro assay of clause 291, wherein B is folate.
293. The in vitro assay of clause 291, wherein B is D-folate.
294. The in vitro assay of clause 291, wherein B is L-folate.
295. The in vitro assay of clause 291, wherein B is a PSMA binding ligand.
296. The in vitro assay of clause 291, wherein B is a radical of the formula

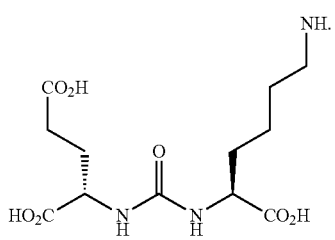

297. The in vitro assay of clause 291, wherein B is a radical of the formula

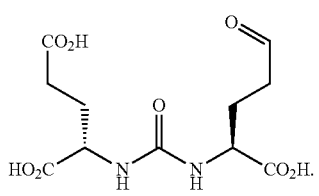

298. The in vitro assay of clause 291, wherein B is a radical of the formula

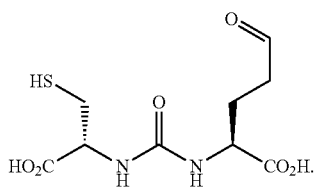

299. The in vitro assay of any one of clauses 291 to 298, wherein the thiol reactive linkage is a disulfide linkage.
300. The in vitro assay of any one of clauses 291 to 299, wherein L comprises a cysteine disulfide diradical.
301. The in vitro assay of any one of clauses 291 to 300, wherein L further comprises one or more divalent hydrophilic radicals.
302. The in vitro assay of any one of clauses 291 to 301, wherein D is a cytotoxic agent.
303. The in vitro assay of any one of clauses 291 to 302, wherein D is a cancer treating agent.
304. The in vitro assay of any one of clauses 291 to 302, wherein D is an anti-inflammatory agent.
305. The in vitro assay of any one of clauses 291 to 304, wherein D is a vinca alkaloid.
306. The in vitro assay of any one of clauses 291 to 304, wherein D is desacetylvinblastine monohydrazide.
307. The in vitro assay of any one of clauses 291 to 304, wherein D is a tubulysin.
308. The in vitro assay of any one of clauses 291 to 304, wherein D is tubulysin A.
309. The in vitro assay of any one of clauses 291 to 304, wherein D is tubulysin B.
310. The in vitro assay of any one of clauses 291 to 304, wherein D is tubulysin A hydrazide.
311. The in vitro assay of any one of clauses 291 to 304, wherein D is tubulysin B hydrazide.
312. The in vitro assay of any one of clauses 291 to 304, wherein D is an antifolate.
313. The in vitro assay of any one of clauses 291 to 304, wherein D is an aminopterin.
314. The in vitro assay of any one of clauses 291 to 304, wherein D is a rapamycin.
315. The in vitro assay of any one of clauses 291 to 304, wherein D is a mitomycin.
316. The in vitro assay of any one of clauses 291 to 304, wherein D is a taxane.
317. The in vitro assay of any one of clauses 291 to 304, wherein D is a doxorubicin.
318. The in vitro assay of any one of clauses 287 to 290, wherein the ligand conjugate is a folate conjugate.
319. The in vitro assay of clause 318, wherein the folate conjugate is

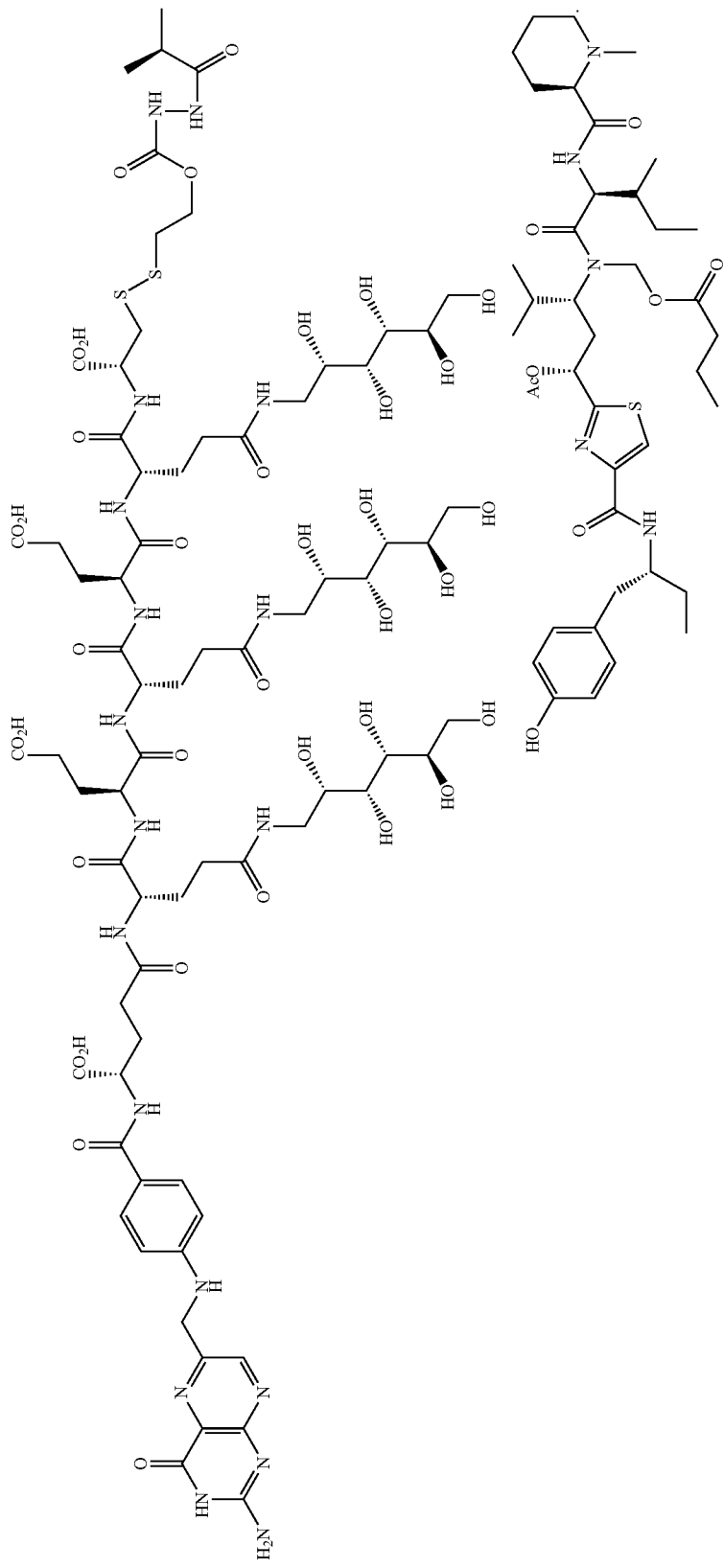

320. The in vitro assay of clause 318, wherein the folate conjugate is

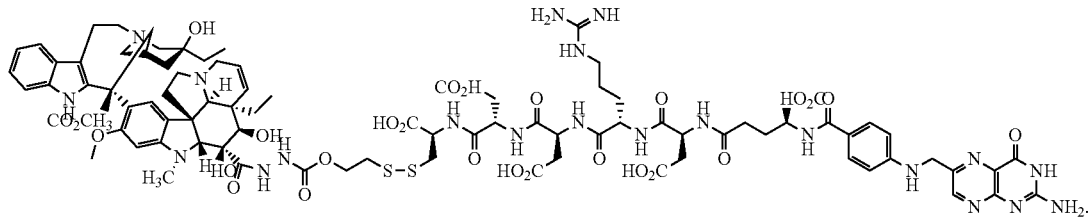

321. The in vitro assay of any one of clauses 287 to 320, wherein the system $x_c^-$ inhibitor is selected from the group consisting of sulfasalazine, glutamate; L-quisqualate; (S)-4-carboxyphenylglycine (4-S—CPG); L-α-aminoadipic acid; and L-homocysteic acid.
322. The in vitro assay of any one of clauses 287 to 321, wherein the system $x_c^-$ inhibitor is sulfasalazine.
323. The in vitro assay of any one of clauses 287 to 321, wherein the system $x_c^-$ inhibitor is glutamate.
324. The in vitro assay of any one of clauses 287 to 321, wherein the system $x_c^-$ inhibitor is L-quisqualate.
325. The in vitro assay of any one of clauses 287 to 321, wherein the system $x_c^-$ inhibitor is 4-S—CPG.
326. The in vitro assay of any one of clauses 287 to 321, wherein the system $x_c^-$ inhibitor is L-α-aminoadipic acid.
327. The in vitro assay of any one of clauses 287 to 321, wherein the system $x_c^-$ inhibitor is L-homocysteic acid.
328. The in vitro assay of any one of clauses 287 to 327, wherein the cultured cells are KB cells.
329. The in vitro assay of any one of clauses 287 to 327, wherein the cultured cells are A549 cells.
330. The in vitro assay of any one of clauses 287 to 329, wherein the non-ligand-specific activity of the ligand conjugate is decreased by the system $x_c^-$ inhibitor.
331. The in vitro assay of clause 330, wherein the non-ligand-specific activity is cytotoxicity.
332. The in vitro assay of any one of clauses 287 to 330, wherein the nonspecific uptake of the drug is decreased by the system $x_c^-$ inhibitor.
333. The in vitro assay of clause 332, wherein the nonspecific uptake of the drug is measured using competition assays in the presence and absence of an excess of non-radiolabeled ligand.

BRIEF DESCRIPTION OF THE DRAWINGS

FIG. 7(a) shows the uptake of $^3$H-EC0531 compared to the uptake of $^3$H-folic acid in KB cells. FIG. 7(b) shows the uptake of $^3$H-EC0531 compared to the uptake of $^3$H-folic acid in A549 cells. Data obtained with $^3$H-EC0531 (closed squares), $^3$H-EC0531 plus excess folic acid (open squares), $^3$H-folic acid (closed triangles) and $^3$H-folic acid plus excess folic acid (open triangles) are shown.

μM DTNB and $^3$H-folate and excess folic acid. The last bar in each set of three data points shows data obtained with co-administration of 100 μM DTNB and $^3$H-folate and excess folic acid.

Figure 9:
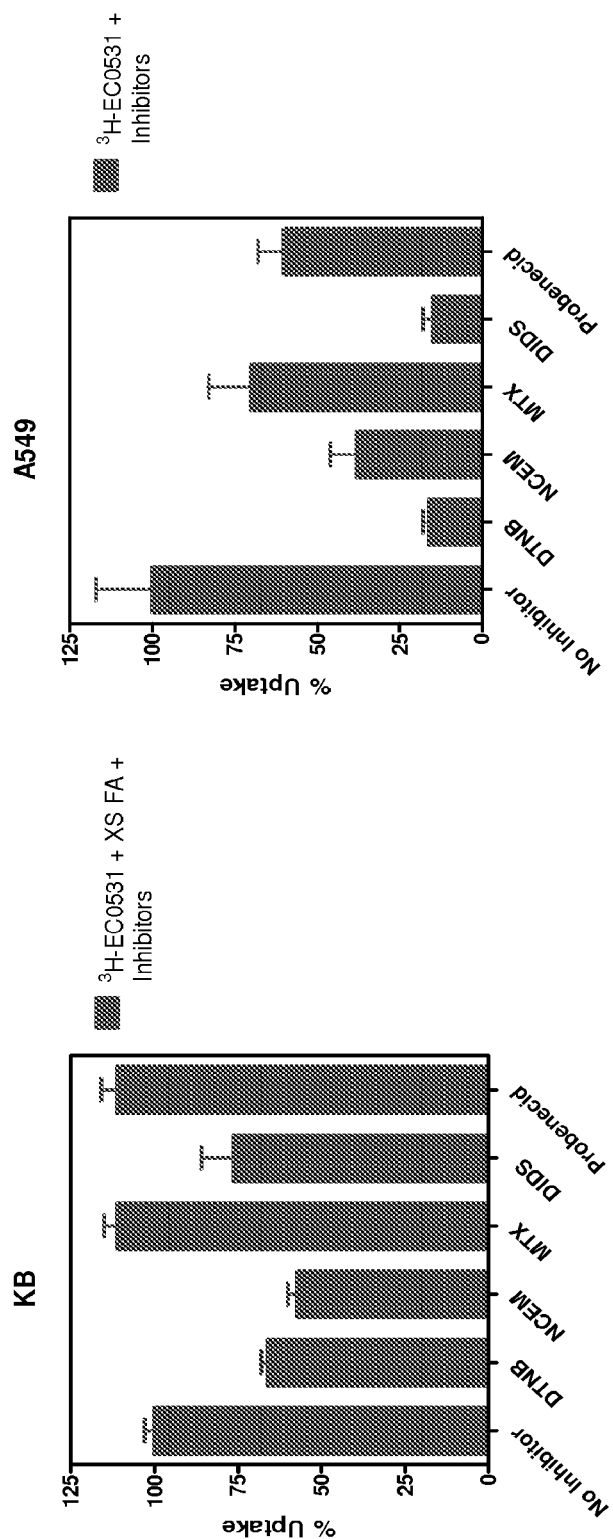

FIG. 9 shows the percent uptake of $^3$H-EC0531 following co-administration of thiol inhibitors and the folate conjugate EC0531 in KB cells (with excess folic acid for the left-hand graph) and A549 cells. In addition, the graphs show the percent uptake of $^3$H-EC0531 following co-administration of methotrexate and EC0531 in both KB cells and A549 cells under the above-described conditions.

Figure 10:
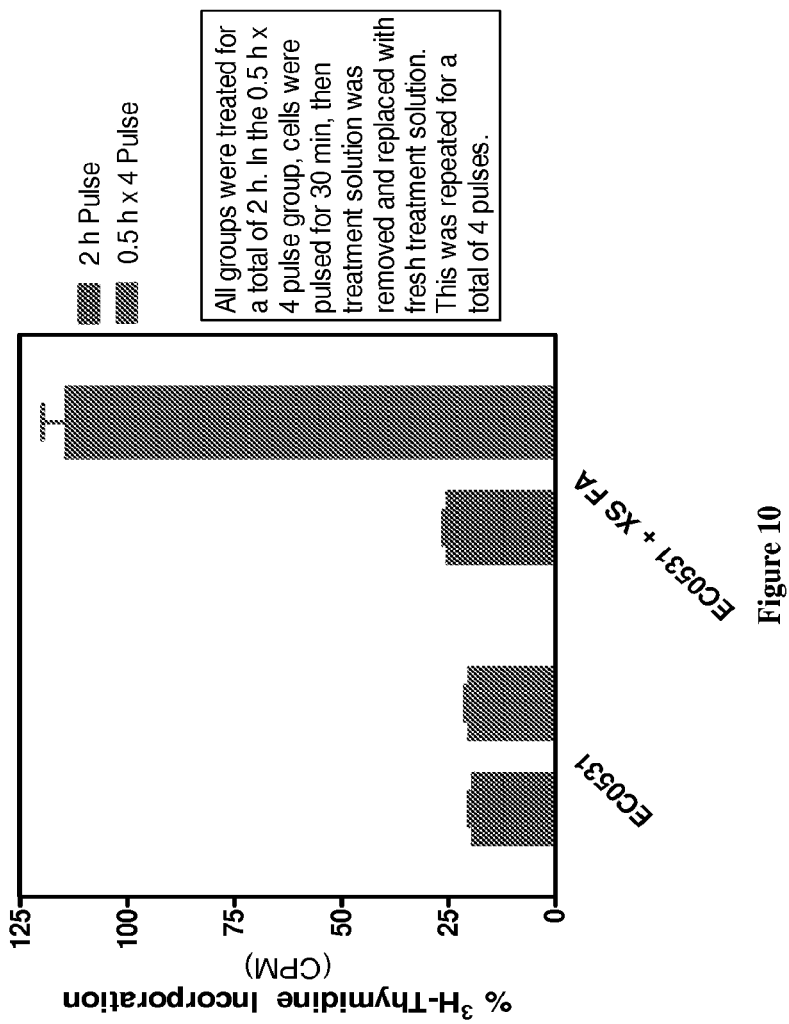

FIG. 10 shows the non-FR-specific activity of EC0531 (% $^3$H-Thymidine incorporation measured in counts per minute (CPM)) in KB cells following replacement of cell culture medium in the cell culture under the above-described conditions. The non-specific activity of EC0531 administered to KB cells is shown in the left pair of bars. The specific activity of EC0531 administered to KB cells in the presence of excess folic acid is shown in the right pair of bars. Data obtained using a two hour pulse (i.e. no replacement of cell culture medium) are shown in the left-most bars in each pair. Data obtained using four separate 30 minute pulses (i.e. four replacements of cell culture medium) are shown in the right-most bars in each pair.

Figure 11:
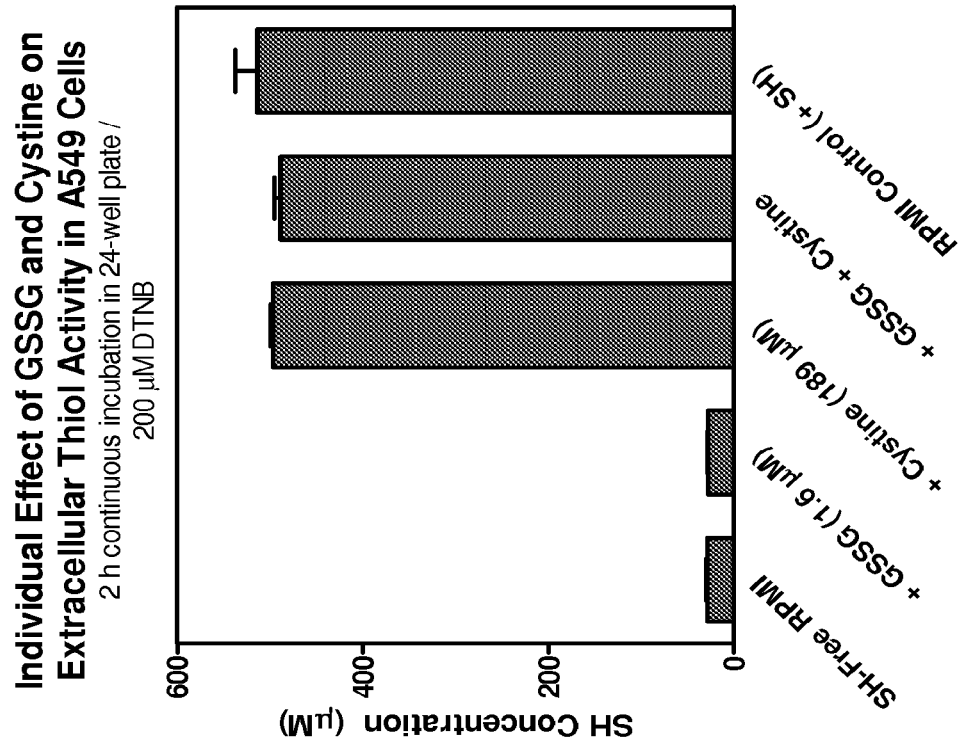

FIG. 11 shows the amount of extracellular thiol (i.e. SH concentration (μM)) for A549 cells following addition of GSSG and/or cysteine. The first bar shows data obtained with thiol-free RPMI cell culture media (SH-free RPMI) with no addition of thiol. The second bar shows data obtained with SH-free RPMI cell culture media with addition of GSSG (1.6 μM). The third bar shows data obtained with SH-free RPMI cell culture media with addition of cysteine (189 μM). The fourth bar shows data obtained with SH-free RPMI cell culture media with addition of GSSG (1.6 μM) and cysteine (189 μM). The fifth bar shows data obtained with RPMI cell culture media containing thiols (SH-containing RPMI).

Figure 12:
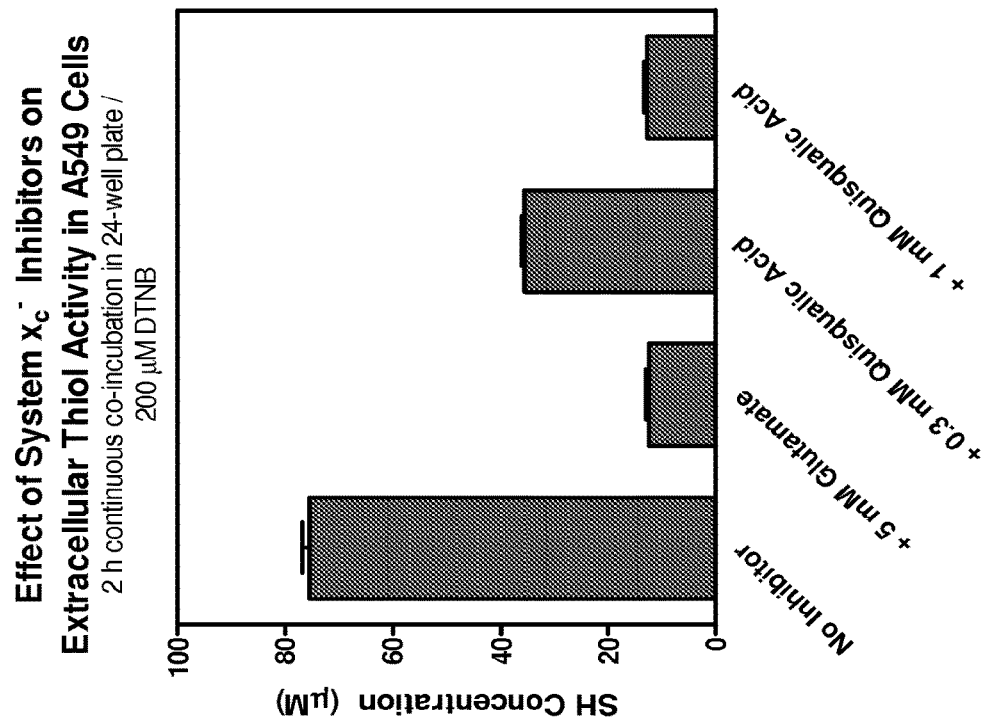

FIG. 12 shows the amount of extracellular thiol (i.e. SH concentration (μM)) in A549 cells following addition of system $x_c^-$ inhibitors. The first bar shows data obtained with no addition of system $x_c^-$ inhibitor. The second bar shows data obtained with addition of glutamate (5 mM). The third bar shows data obtained with addition of quisqualic acid (0.3 mM). The fourth bar shows data obtained with addition of quisqualic acid (1 mM).

Figure 13:
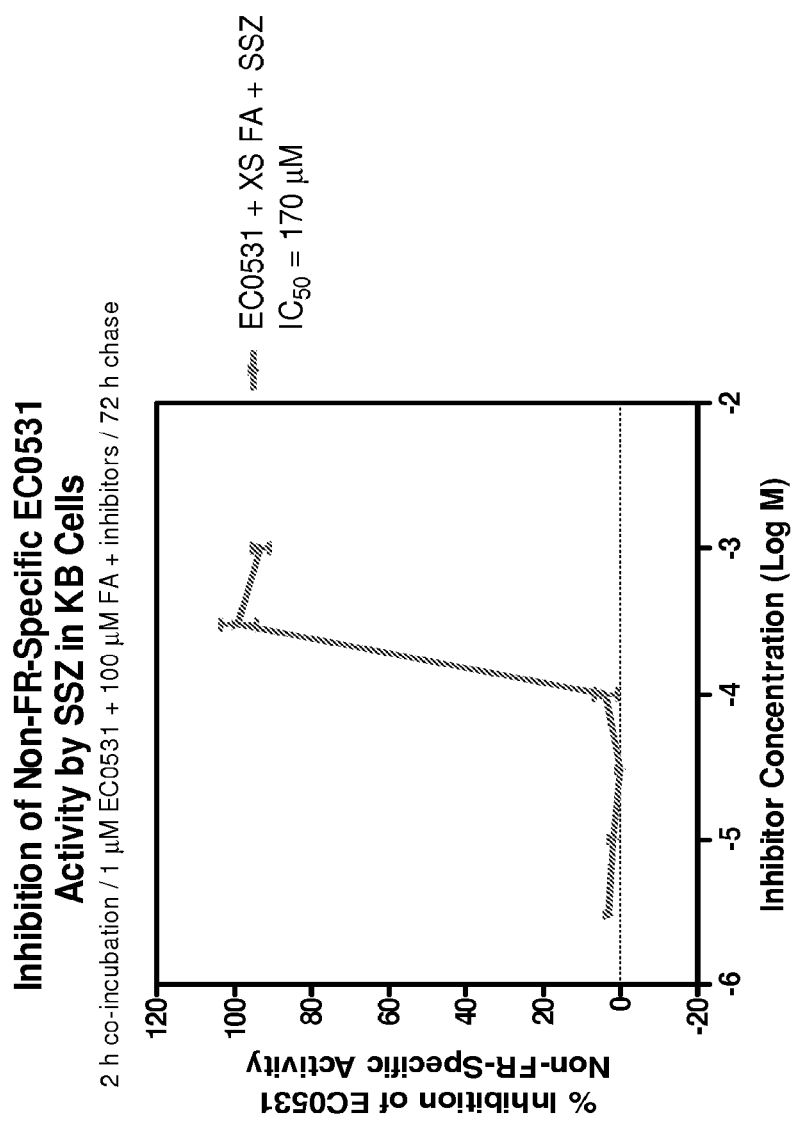

FIG. 13 shows the percent inhibition of non-specific activity of EC0531 (% $^3$H-Thymidine incorporation measured in counts per minute (CPM)) following co-administration of varying concentrations of the system $x_c^-$ inhibitor sulfasalazine and one concentration of the folate conjugate EC0531 along with excess folic acid to the culture medium of KB cells.

Figure 14:
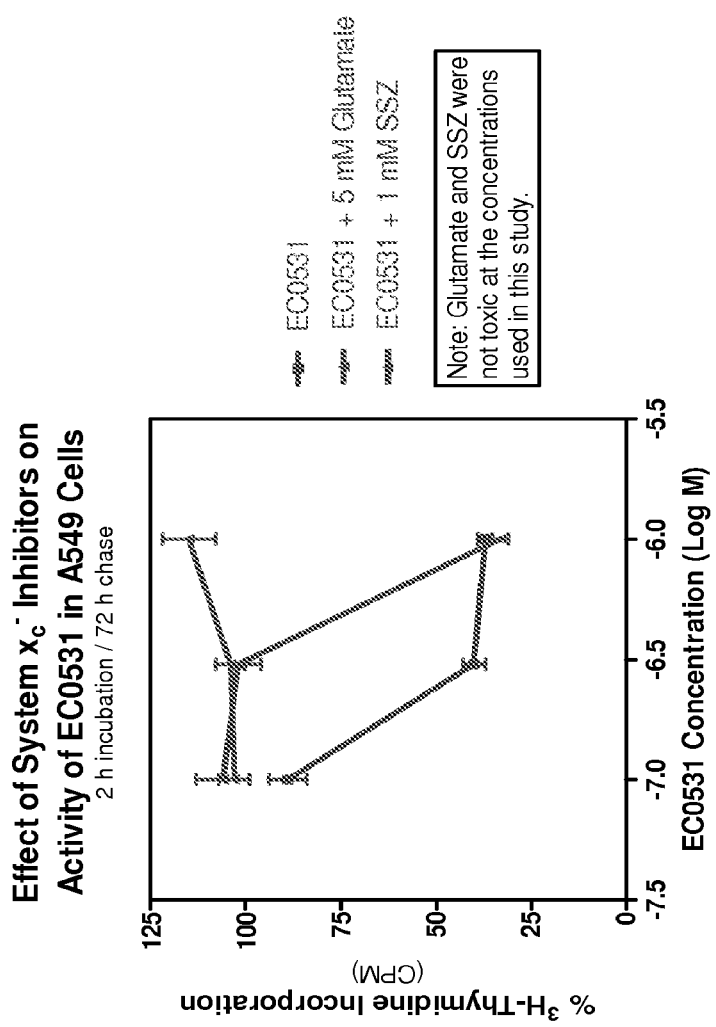

FIG. 14 shows the percent inhibition of non-specific activity of EC0531 (% $^3$H-Thymidine incorporation measured in counts per minute (CPM)) following co-administration of system $x_c^-$ inhibitors and varying concentrations of the folate conjugate EC0531 to the culture medium of A549 cells. The specific activity of EC0531 is shown (closed squares). Data obtained using the system $x_c^-$ inhibitors glutamate (closed triangles, uppermost line with an inhibitor) and sulfasalazine (closed triangles, lowermost line with an inhibitor) are also shown.

Figure 15:
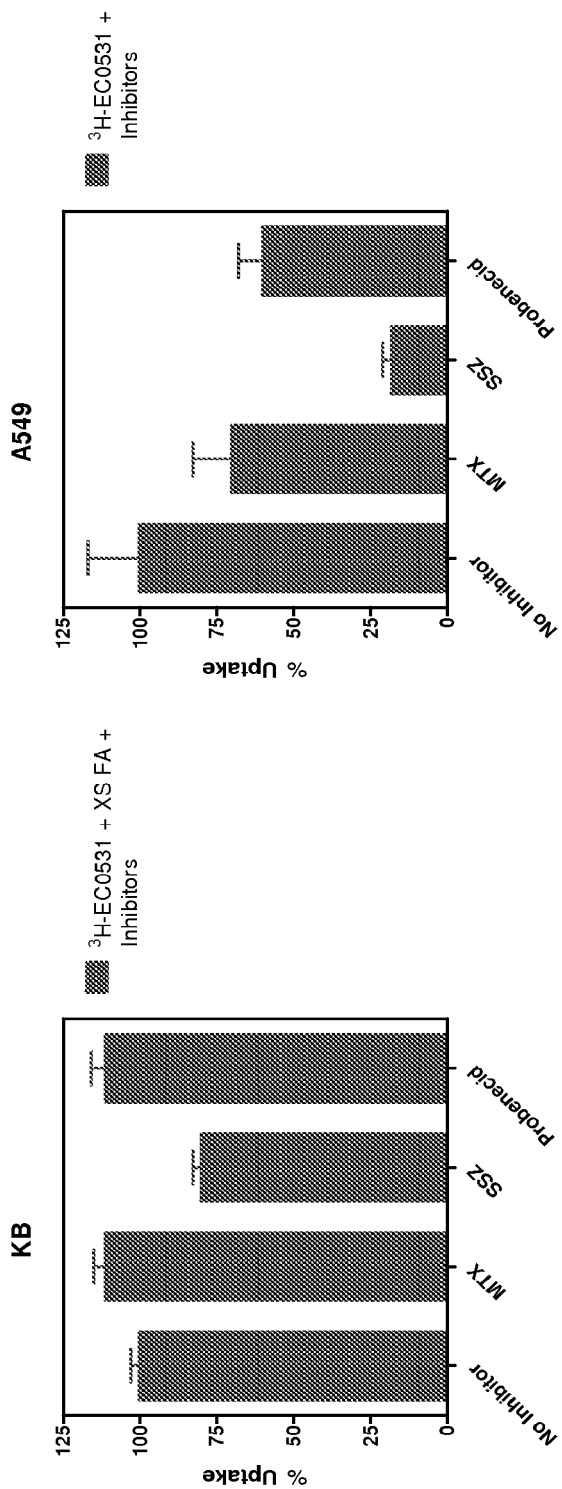

FIG. 15 shows the percent uptake of $^3$H-EC0531 following co-administration of the system $x_c^-$ inhibitor sulfasalazine and the folate conjugate EC0531 in the presence of excess folic acid for KB cells and without excess folic acid for A549 cells. In addition, the figure shows the percent uptake of $^3$H-EC0531 following co-administration of methotrexate (MTX) and EC0531 for both types of cells, as well as the percent uptake of $^3$H-EC0531 following co-administration of probenecid and EC0531 for both types of cells.

Figure 16:
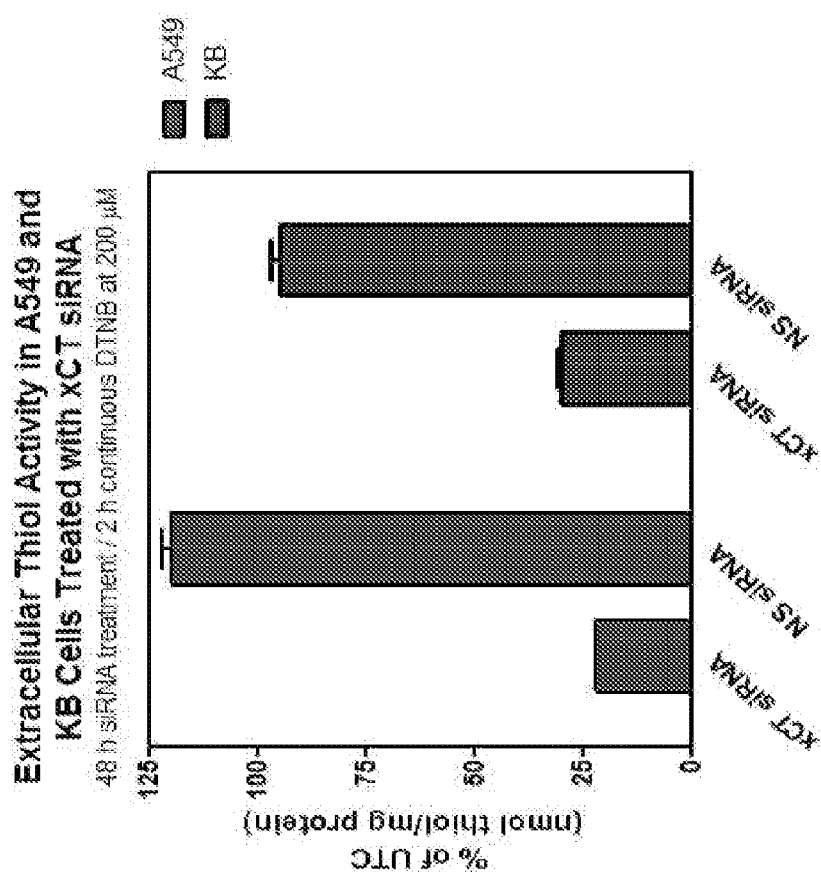

FIG. 16 shows the amount of extracellular thiol activity (percentage of UTC (nmol of thiol/mg protein)) in KB cells and in A549 cells following addition of xCT siRNA to the cell culture medium. The extracellular thiol activity in A549 cells is shown in the left pair of bars. The extracellular thiol activity for KB cells is shown in the right pair of bars. The first bar in each pair shows data for cells administered xCT siRNA. The second bar in each pair shows data for cells administered a non-specific (NS) siRNA.

DETAILED DESCRIPTION OF THE ILLUSTRATIVE EMBODIMENTS

As used herein, the term "thiol inhibitor" means an agent that inhibits disulfide reduction, for example by blocking free thiols.

As used herein, the term "system $x_c^-$ inhibitor" means an agent that inhibits the cystine/glutamate antiporter of cells.

For all of the embodiments described herein, any applicable combination of embodiments is contemplated. Any applicable combination of the embodiments described below is considered to be in accordance with the invention. Any combination of the embodiments described below with the embodiments described in the Summary of Invention section, including the clause list, is considered to be part of the invention.

In one embodiment described herein, a method of treatment of a disease is provided. The method comprises administering a ligand conjugate to a patient, wherein the ligand conjugate comprises a disulfide linkage; and administering a thiol inhibitor to the patient. In illustrative embodiments, the disease can be cancer or inflammation.

In another embodiment, use of a ligand conjugate in combination with a thiol inhibitor for the treatment of a disease is described, wherein the disease is cancer or inflammation, and wherein the ligand conjugate comprises a disulfide linkage.

In yet another embodiment, use of a ligand conjugate for the manufacture of a medicament for the treatment of a disease is described, wherein the disease is cancer or inflammation, and wherein the treatment comprises treating a patient with the ligand conjugate in combination with a thiol inhibitor, wherein the ligand conjugate comprises a disulfide linkage.

In another embodiment, a kit is provided. The kit comprises a ligand conjugate and one or more thiol inhibitors, wherein the ligand conjugate comprises a disulfide linkage.

In various embodiments of the methods and uses described herein, the disease is inflammation. In other embodiments, the disease is cancer. In some embodiments, the cancer comprises a primary tumor. In yet other embodiments, the cancer comprises metastatic tumor cells. The methods and uses described herein can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancers can also be oral, thyroid, endocrine, skin, gastric, esophageal, laryngeal, pancreatic, colon, bladder, bone, ovarian, cervical, uterine, breast, testicular, prostate, rectal, kidney, liver, or lung cancers.

Illustratively, the conjugates described herein can be prepared using synthetic procedures described in WO2007/

022493, WO2007/022494, WO2008/101231, WO2008/112873, WO2011/069116, WO2010/033733, WO2012/047525, WO2003/097647, WO2009/002993, WO2004/069159, WO2009/026177, and WO2011/106639, the contents of each which are incorporated by reference herein in its entirety.

Acceptable ligands include folate, folic acid, analogs of folic acid and other folate receptor-binding molecules, other vitamins, peptide ligands identified from library screens, tumor-specific peptides, tumor-specific aptamers, tumor-specific carbohydrates, antibodies, tumor-specific monoclonal or polyclonal antibodies, Fab or scFv (i.e. a single chain variable region) fragments of antibodies such as, for example, an Fab fragment of an antibody, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of tumor cells or inflammatory cells, or fragments of any of these molecules.

Another acceptable ligand is a prostate-specific membrane antigen (PSMA). PMSA is a biomarker that is over-expressed on prostate cancer. PSMA is also expressed on the neovasculature within many non-prostate solid tumors. PSMA is over-expressed in malignant prostate tissues when compared to other organs in the human body such as kidney, proximal small intestine, and salivary glands.

In any embodiment described herein, a ligand conjugate of the formula $BLD_x$ can be used, wherein B is a cell surface receptor targeting ligand, D is an independently selected drug, x is an integer selected from 1, 2, 3, 4 and 5; and L is a releasable polyvalent linker comprising a thiol reactive linkage; or a pharmaceutically acceptable salt thereof.

Also described is an embodiment where in the preceding embodiment, the thiol reactive linkage is a disulfide linkage.

Also described is an embodiment where in any of the preceding embodiments, B is a folate receptor binding moiety.

Also described is an embodiment where in any of the preceding embodiments, B is a folate.

Also described is an embodiment where in any of the preceding embodiments, B is a folate comprising D-glutamyl.

Also described is an embodiment where in any of the preceding embodiments, B is folate.

Also described is an embodiment where in any of the preceding embodiments, B is an unnatural folate radical of the formula

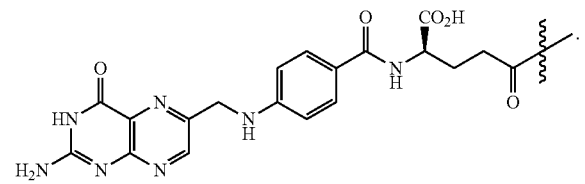

Also described is an embodiment where in any of the preceding embodiments, B is a folate radical of the formula

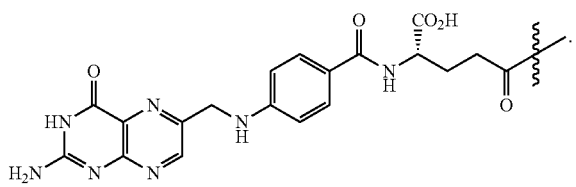

Also described is an embodiment where in any of the preceding embodiments, B is a PSMA ligand.

Also described is an embodiment where in any of the preceding embodiments, the PSMA ligand is a thiourea or a urea of two amino acids.

Also described is an embodiment where in any of the preceding embodiments, the PSMA ligand is a urea of two amino acids.

Also described is an embodiment where in any of the preceding embodiments, B is a PSMA ligand that is a thiourea or urea of lysine and glutamate.

Also described is an embodiment where in any of the preceding embodiments, B is a PSMA ligand that is a urea of lysine and glutamate.

Also described is an embodiment where in any of the preceding embodiments, B is a PSMA ligand that is a thiourea or urea of glutamate and glutamate.

Also described is an embodiment where in any of the preceding embodiments, B is a PSMA ligand that is a urea of glutamate and glutamate.

Also described is an embodiment where in any of the preceding embodiments, B is a PSMA ligand that is a thiourea or urea of cysteine and glutamate.

Also described is an embodiment where in any of the preceding embodiments, B is a PSMA ligand that is a urea of cysteine and glutamate.

Also described is an embodiment where in any of the preceding embodiments, B is a PSMA binding moiety.

Also described is an embodiment where in any of the preceding embodiments, B is a radical of the formula

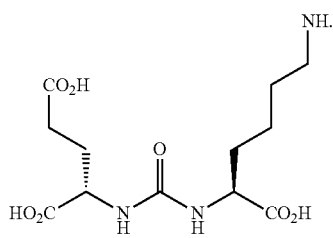

Also described is an embodiment where in any of the preceding embodiments, B is a radical of the formula

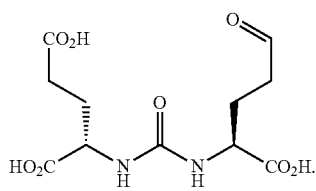

Also described is an embodiment where in any of the preceding embodiments, B is a radical of the formula

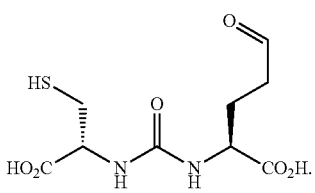

Also described is an embodiment where in any of the preceding embodiments, L comprises one or more aspartic acid diradicals.

Also described is an embodiment where in any of the preceding embodiments, L comprises one or more aspartic acid diradicals.

Also described is an embodiment where in any of the preceding embodiments, the aspartic acid diradicals are L-aspartic acid diradicals.

Also described is an embodiment where in any of the preceding embodiments, L comprises a cysteine diradical.

Also described is an embodiment where in any of the preceding embodiments, L comprises a L-cysteine diradical.

Also described is an embodiment where in any of the preceding embodiments, L comprises L-Asp-L-Asp-L-Cys.

Also described is an embodiment where in any of the preceding embodiments, L is a releasable linker.

Also described is an embodiment where in any of the preceding embodiments, L comprises a disulfide.

Also described is an embodiment where in any of the preceding embodiments, L comprises a cysteine disulfide diradical.

Also described is an embodiment where in any of the preceding embodiments, L comprises a L-cysteine disulfide diradical.

Also described is an embodiment where in any of the preceding embodiments, L comprises L-Asp-L-Asp-L-Cys (S—S).

Also described is an embodiment where in any of the preceding embodiments, L comprises a diradical of the formula O—C(O)—N.

Also described is an embodiment where in any of the preceding embodiments, L comprises a diradical of the formula O—C(O)—NH.

Also described is an embodiment where in any of the preceding embodiments, L and at least one D taken together comprise a diradical of the formula O—C(O)—N.

Also described is an embodiment where in any of the preceding embodiments, L and at least one D taken together comprise a diradical of the formula O—C(O)—NH.

Also described is an embodiment where in any of the preceding embodiments, L comprises a diradical of the formula S—$(CH_2)_m$—O, where m is 2, 3, or 4.

Also described is an embodiment where in any of the preceding embodiments, L comprises a diradical of the formula S—$(CH_2)_m$—O—C(O)—N, where m is 2, 3, or 4.

Also described is an embodiment where in any of the preceding embodiments, L comprises a diradical of the formula S—$(CH_2)_m$—O—C(O)—NH, where m is 2, 3, or 4.

Also described is an embodiment where in any of the preceding embodiments, L and at least one D taken together comprise a diradical of the formula S—$(CH_2)_m$—O—C(O)—N, where m is 2, 3, or 4.

Also described is an embodiment where in any of the preceding embodiments, L and at least one D taken together comprise a diradical of the formula S—$(CH_2)_m$—O—C(O)—NH, where m is 2, 3, or 4.

Also described is an embodiment where in any of the preceding embodiments, m is 2.

Also described is an embodiment where in any of the preceding embodiments, L comprises a chain of at least about 7 atoms, at least about 8 atoms, at least about 9 atoms, at least about 10, atoms, at least about 11, atoms, at least about 12 atoms, at least about 13 atoms, at least about 14 atoms, or at least about 15 atoms.

Also described is an embodiment where in any of the preceding embodiments, L comprises a chain of at least about 16 atoms, at least about 17 atoms, at least about 18 atoms, at least about 19, atoms, at least about 20, atoms, at least about 21 atoms, at least about 22 atoms, at least about 23 atoms, at least about 24 atoms, at least about 25 atoms, or at least about 26 atoms.

Also described is an embodiment where in any of the preceding embodiments, L comprises a chain of between about 7 and about 35 atoms, between about 7 and about 30 atoms, or between about 7 and about 26 atoms.

Also described is an embodiment where in any of the preceding embodiments, L comprises a diradical of the formula

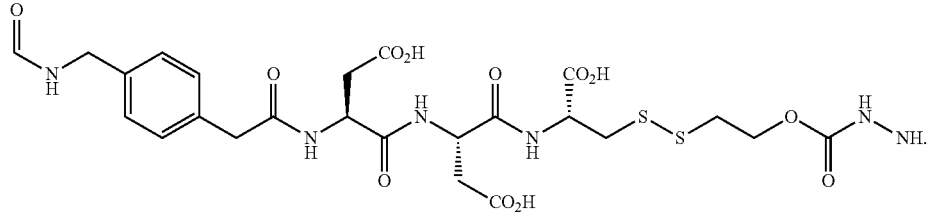

Also described is an embodiment where in any of the preceding embodiments, L comprises a diradical of the formula

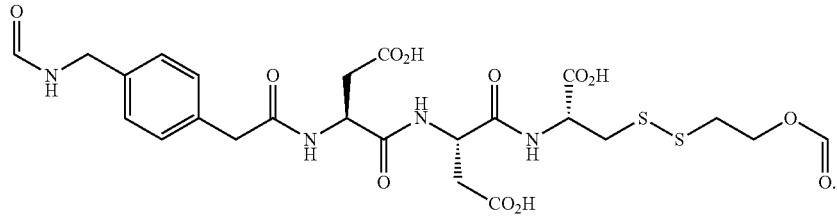

Also described is an embodiment where in any of the preceding embodiments, L comprises a diradical of the formula

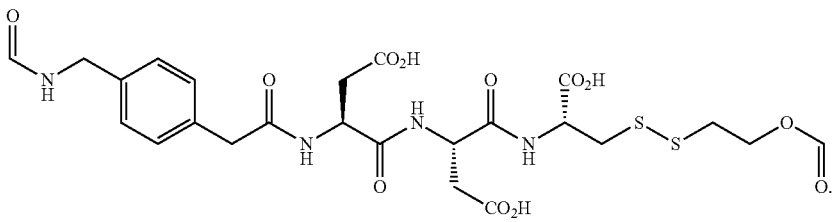

Also described is an embodiment where in any of the preceding embodiments, L comprises a diradical of the formula

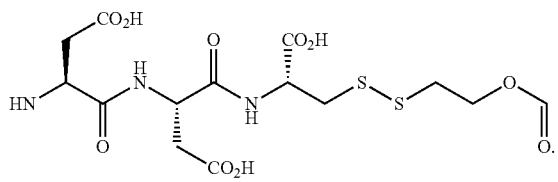

Also described is an embodiment where in any of the preceding embodiments, L comprises at least one unnatural amino acid which is selected from D-alanine, D-aspartic acid, D-asparagine, D-cysteine, D-glutamic acid, D-phenylalanine, D-histidine, D-isoleucine, D-lysine, D-leucine, D-methionine, D-proline, D-glutamine, D-arginine, D-serine, D-threonine, D-valine, D-tryptophan, D-tyrosine, and D-ornithine, or a derivative thereof.

Also described is an embodiment where in any of the preceding embodiments, L comprises two or more unnatural amino acids.

Also described is an embodiment where in any of the preceding embodiments, L comprises three or more unnatural amino acids.

Also described is an embodiment where in any of the preceding embodiments, L comprises four or more unnatural amino acids.

Also described is an embodiment where in any of the preceding embodiments, L further comprises one or more disulfides.

Also described is an embodiment where in any of the preceding embodiments, at least one disulfide comprises D-cysteinyl.

Also described is an embodiment where in any of the preceding embodiments, L further comprises one or more divalent hydrophilic radicals.

Also described is an embodiment where in any of the preceding embodiments, L further comprises two or more divalent hydrophilic radicals.

Also described is an embodiment where in any of the preceding embodiments, L further comprises three or more divalent hydrophilic radicals.

Also described is an embodiment where in any of the preceding embodiments, L further comprises four or more divalent hydrophilic radicals.

Also described is an embodiment where in any of the preceding embodiments, L further comprises one or more divalent polyoxy radicals.

Also described is an embodiment where in any of the preceding embodiments, L further comprises two or more divalent polyoxy radicals.

Also described is an embodiment where in any of the preceding embodiments, L further comprises three or more divalent polyoxy radicals.

Also described is an embodiment where in any of the preceding embodiments, L further comprises four or more divalent polyoxy radicals.

Also described is an embodiment where in any of the preceding embodiments, L further comprises one or more divalent polyhydroxy radicals.

Also described is an embodiment where in any of the preceding embodiments, L further comprises two or more divalent polyhydroxy radicals.

Also described is an embodiment where in any of the preceding embodiments, L further comprises three or more divalent polyhydroxy radicals.

Also described is an embodiment where in any of the preceding embodiments, L further comprises four or more divalent polyhydroxy radicals.

Also described is an embodiment where in any of the preceding embodiments, at least one unnatural amino acid comprises a polyhydroxy radical.

Also described is an embodiment where in any of the preceding embodiments, at least two unnatural amino acids comprise a polyhydroxy radical.

Also described is an embodiment where in any of the preceding embodiments, at least three unnatural amino acids comprise a polyhydroxy radical.

Also described is an embodiment where in any of the preceding embodiments, at least four unnatural amino acids comprise a polyhydroxy radical.

Also described is an embodiment where in any of the preceding embodiments, at least one of the polyhydroxy radicals is of the formula

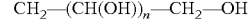

where n is selected from 1, 2, 3, 4, 5, and 6.

Also described is an embodiment where in any of the preceding embodiments, n is selected from 1, 2, 3, and 4.

Also described is an embodiment where in any of the preceding embodiments, n is selected from 3 and 4.

Also described is an embodiment where in any of the preceding embodiments, L comprises a divalent polyglutamic acid radical, where at least one glutamic acid forms an amide with an aminopolyhydroxy radical.

Also described is an embodiment where in any of the preceding embodiments, L comprises a divalent polyglutamic acid radical, where at least two glutamic acids form an amide with an aminopolyhydroxy radical.

Also described is an embodiment where in any of the preceding embodiments, L comprises a divalent polyglutamic acid radical, where at least three glutamic acids form an amide with an aminopolyhydroxy radical.

Also described is an embodiment where in any of the preceding embodiments, L comprises a divalent polyglutamic acid radical, where at least four glutamic acids form an amide with an aminopolyhydroxy radical.

Also described is an embodiment where in any of the preceding embodiments, L comprises a divalent poly(D-glutamic acid) radical, where at least one glutamic acid forms an amide with an aminopolyhydroxy radical.

Also described is an embodiment where in any of the preceding embodiments, L comprises a divalent poly(D-glutamic acid) radical, where at least two glutamic acids form an amide with an aminopolyhydroxy radical.

Also described is an embodiment where in any of the preceding embodiments, L comprises a divalent poly(D-glutamic acid) radical, where at least three glutamic acids form an amide with an aminopolyhydroxy radical.

Also described is an embodiment where in any of the preceding embodiments, L comprises a divalent poly(D-glutamic acid) radical, where at least four glutamic acids form an amide with an aminopolyhydroxy radical.

Also described is an embodiment where in any of the preceding embodiments, at least one of the aminopolyhydroxy radicals is of the formula

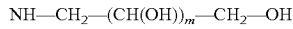

$NH-CH_2-(CH(OH))_m-CH_2-OH$ where m is selected from 1, 2, 3, 4, 5, and 6.

Also described is an embodiment where in any of the preceding embodiments, L comprises a diradical of the formula

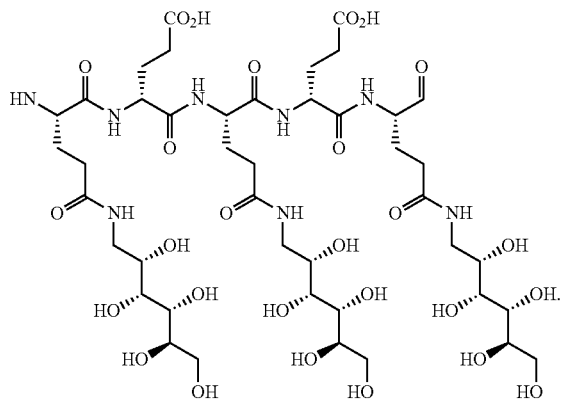

Also described is an embodiment where in any of the preceding embodiments, L comprises at least one unnatural amino acid having the D-configuration.

Also described is an embodiment where in any of the preceding embodiments, x is 3.

Also described is an embodiment where in any of the preceding embodiments, x is 2.

Also described is an embodiment where in any of the preceding embodiments, x is 1.

Also described is an embodiment where in any of the preceding embodiments, at least one D is a cytotoxic agent.

Also described is an embodiment where in any of the preceding embodiments, at least one D is a cancer treating agent.

Also described is an embodiment where in any of the preceding embodiments, at least one D is an anti-inflammatory agent.

Also described is an embodiment where in any of the preceding embodiments, at least one D is a vinca alkaloid.

Also described is an embodiment where in any of the preceding embodiments, at least one D is desacetylvinblastine monohydrazide.

Also described is an embodiment where in any of the preceding embodiments, at least one D is a tubulysin.

Also described is an embodiment where in any of the preceding embodiments, at least one D is tubulysin A.

Also described is an embodiment where in any of the preceding embodiments, at least one D is tubulysin B.

Also described is an embodiment where in any of the preceding embodiments, at least one D is tubulysin A hydrazide.

Also described is an embodiment where in any of the preceding embodiments, at least one D is tubulysin B hydrazide.

Also described is an embodiment where in any of the preceding embodiments, at least one D is an antifolate.

Also described is an embodiment where in any of the preceding embodiments, at least one D is an aminopterin.

Also described is an embodiment where in any of the preceding embodiments, at least one D is a rapamycin.

Also described is an embodiment where in any of the preceding embodiments, at least one D is a mitomycin.

Also described is an embodiment where in any of the preceding embodiments, at least one D is a taxane.

Also described is an embodiment where in any of the preceding embodiments, at least one D is a doxorubicin.

It is to be understood that every combination of the various embodiments of each of B, L, D, and x described herein form illustrative embodiments of the conjugates of the invention, whether those various embodiments of each of B, L, D are species, subgenera, or genera. It is to be further understood that each of those additional illustrative embodiments of compounds may be used in any of the kits, methods and/or uses described herein.

In some embodiments, the ligand is a vitamin analog or a vitamin derivative. Illustrative embodiments of vitamin analogs and/or derivatives include folate and analogs and derivatives of folate such as folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate, folinic acid, pteropolyglutamic acid, and folate receptor-binding pteridines such as tetrahydropterins, dihydrofolates, and tetrahydrofolates. The dideaza analogs include, for example, 1,5-dideaza, 5,10-dideaza, 8,10-dideaza, and 5,8-dideaza analogs of folate, folinic acid, pteropolyglutamic acid, and folate receptor-binding pteridines such as tetrahydropterins, dihydrofolates, and tetrahydrofolates. Other folates useful as complex forming ligands for this invention are the folate receptor-binding analogs aminopterin, amethopterin (also known as methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed "folates," reflecting their ability to bind with folate-receptors, and such ligands when conjugated with exogenous molecules are effective to enhance transmembrane transport, such as via folate-mediated endocytosis as described herein.

In another embodiment, the ligand is capable of binding or targeting PSMA. In another embodiment, the ligand capable of binding or targeting PSMA is a phosphoric, phosphonic, or phosphinic acid or derivative thereof. In one aspect, the phosphoric, phosphonic, or phosphinic acid or derivative thereof includes one or more carboxylic acid groups. In another aspect, the phosphoric, phosphonic, or phosphinic acid or derivative thereof includes one or more thiol groups or derivatives thereof. In another aspect, the phosphoric, phosphonic, or phosphinic acid or derivative thereof includes one or more carboxylic acid bioisosteres, such as an optionally substituted tetrazole, and the like.

In another embodiment, the PSMA ligand is a derivative of pentanedioic acid. Illustratively, the pentanedioic acid derivative is a compound of the formula:

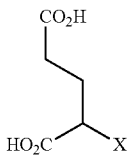

wherein X is RP(O)(OH)CH$_2$— (see, e.g. U.S. Pat. No. 5,968,915 incorporated herein by reference); RP(O)(OH)N (R$^1$)— (see, e.g. U.S. Pat. No. 5,863,536 incorporated herein by reference); RP(O)(OH)O— (see, e.g. U.S. Pat. No. 5,795,877 incorporated herein by reference); RN(OH)C— (O)Y— or RC(O)NH(OH)Y, wherein Y is —CR$_1$R$_2$—, —NR$_3$— or —O— (see, e.g. U.S. Pat. No. 5,962,521 incorporated herein by reference); RS(O)Y, RSO$_2$Y, or RS(O)(NH)Y, wherein Y is —CR$_1$R$_2$—, —NR$_3$— or —O— (see, e.g. U.S. Pat. No. 5,902,817 incorporated herein by reference); and RS-alkyl, wherein R is for example hydrogen, alkyl, aryl, or arylalkyl, each of which may be optionally substituted (see, e.g. J. Med. Chem. 46:1989-1996 (2003) incorporated herein by reference).

In each of the foregoing formulae, R, R$_1$, R$_2$, and R$_3$ are each independently selected from hydrogen, C$_1$-C$_9$ straight or branched chain alkyl, C$_2$-C$_9$ straight or branched chain alkenyl, C$_3$-C$_8$ cycloalkyl, C$_5$-C$_7$ cycloalkenyl, and aryl. In addition, in each case, each of R, R$_1$, R$_2$, and R$_3$ may be optionally substituted, such as with one or more groups selected from C$_3$-C$_8$ cycloalkyl, C$_5$-C$_7$ cycloalkenyl, halo, hydroxy, nitro, trifluoromethyl, C$_1$-C$_6$ straight or branched chain alkyl, C$_2$-C$_6$ straight or branched chain alkenyl, C$_1$-C$_4$ alkoxy, C$_2$-C$_4$ alkenyloxy, phenoxy, benzyloxy, amino, aryl. In one aspect, aryl is selected from 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl, and phenyl, and in each case aryl may be optionally substituted with one or more, illustratively with one to three, groups selected from halo, hydroxy, nitro, trifluoromethyl, C$_1$-C$_6$ straight or branched chain alkyl, C$_2$-C$_6$ straight or branched chain alkenyl, C$_1$-C$_4$ alkoxy, C$_2$-C$_4$ alkenyloxy, phenoxy, benzyloxy, and amino. In one variation of each of the above formulae, R is not hydrogen.

Illustrative PSMA ligands described in U.S. Pat. No. 5,968,915 include 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid; 2-[[cyclohexylhydroxyphosphinyl]methyl]pentanedioic acid; 2-[[phenylhydroxyphosphinyl]methyl]pentanedioic acid; 2-[[2-(tetrahydrofuranyl)hydroxyphosphinyl]methyl]pentanedioic acid; 2-[[(2-tetrahydropyranyl)hydroxyphosphinyl]methyl]pentanedioic acid; 2-[[((4-pyridyl)methyl)hydroxyphosphinyl]methyl]pentanedioic acid; 2-[[((2-pyridyl)methyl)hydroxyphosphinyl]methyl]pentanedioic acid; 2-[[(phenylmethyl)hydroxyphosphinyl]methyl]pentanedioic acid; 2-[[((2-phenylethyl)methyl)hydroxyphosphinyl]methyl]pentanedioic acid; 2-[[((3-phenylpropyl)methyl)hydroxyphosphinyl]methyl]pentanedioic acid; 2-[[((3-phenylbutyl)methyl)hydroxyphosphinyl]methyl]pentanedioic acid; 2-[[((2-phenylbutyl)methyl)hydroxyphosphinyl]methyl]pentanedioic acid; 2-[[(4-phenylbutyl)hydroxyphosphinyl]methyl]pentanedioic acid; and 2-[[(aminomethyl)hydroxyphosphinyl]methyl]pentanedioic acid.

Illustrative PSMA ligands described in U.S. Pat. No. 5,863,536 include N-[methylhydroxyphosphinyl]glutamic acid; N-[ethylhydroxyphosphinyl]glutamic acid; N-[propylhydroxyphosphinyl]glutamic acid; N-[butylhydroxyphosphinyl]glutamic acid; N-[phenylhydroxyphosphinyl]glutamic acid; N-[(phenylmethyl)hydroxyphosphinyl]glutamic acid; N-[((2-phenylethyl)methyl)hydroxyphosphinyl]glutamic acid; and N-methyl-N-[phenylhydroxyphosphinyl]glutamic acid.

Illustrative PSMA ligands described in U.S. Pat. No. 5,795,877 include 2-[[methylhydroxyphosphinyl]oxy]pentanedioic acid; 2-[[ethylhydroxyphosphinyl]oxy]pentanedioic acid; 2-[[propylhydroxyphosphinyl]oxy]pentanedioic acid; 2-[[butylhydroxyphosphinyl]oxy]pentanedioic acid; 2-[[phenylhydroxyphosphinyl]oxy]pentanedioic acid; 2-[[((4-pyridyl)methyl)hydroxyphosphinyl]oxy]pentanedioic acid; 2-[[((2-pyridyl)methyl)hydroxyphosphinyl]oxy]pentanedioic acid; 2-[[(phenylmethyl)hydroxyphosphinyl]oxy]pentanedioic acid; and 2[[((2-phenylethyl)methyl)hydroxyphosphinyl]oxy]pentanedioic acid.

Illustrative PSMA ligands described in U.S. Pat. No. 5,962,521 include 2-[[(N-hydroxy)carbamoyl]methyl]pentanedioic acid; 2-[[(N-hydroxy-N-methyl)carbamoyl]methyl]pentanedioic acid; 2-[[(N-butyl-N-hydroxy) carbamoyl]methyl]pentanedioic acid; 2-[[(N-benzyl-N-hydroxy)carbamoyl]methyl]pentanedioic acid; 2-[[(N-hydroxy-N-phenyl)carbamoyl]methyl]pentanedioic acid; 2-[[(N-hydroxy-N-2-phenylethyl)carbamoyl]methyl]pentanedioic acid; 2-[[(N-ethyl-N-hydroxy) carbamoyl]methyl]pentanedioic acid; 2-[[(N-hydroxy-N-propyl)carbamoyl]methyl]pentanedioic acid; 2-[[(N-hydroxy-N-3-phenylpropyl)carbamoyl]methyl]pentanedioic acid; 2-[[(N-hydroxy-N-4-pyridyl) carbamoyl]methyl]pentanedioic acid; 2-[[(N-hydroxy)carboxamido]methyl]pentanedioic acid; 2-[[N-hydroxy (methyl) carboxamido]methyl]pentanedioic acid; 2-[[N-hydroxy (benzyl) carboxamido]methyl]pentanedioic acid; 2-[[N-hydroxy(phenyl)carboxamido]methyl]pentanedioic acid; 2-[[N-hydroxy(2-phenylethyl)carboxamido]methyl]pentanedioic acid; 2-[[N-hydroxy(ethyl) carboxamido]methyl]pentanedioic acid; 2-[[N-hydroxy (propyl) carboxamido]methyl]pentanedioic acid; 2-[[N-hydroxy (3-phenylpropyl) carboxamido]methyl]pentanedioic acid; and 2-[[N-hydroxy(4-pyridyl) carboxamido]methyl]pentanedioic acid.

Illustrative PSMA ligands described in U.S. Pat. No. 5,902,817 include 2-[(sulfinyl)methyl]pentanedioic acid; 2-[(methylsulfinyl)methyl]pentanedioic acid; 2-[(ethylsulfinyl)methyl]pentanedioic acid; 2-[(propylsulfinyl)methyl]pentanedioic acid; 2-[(butylsulfinyl)methyl]pentanedioic acid; 2-[(phenylsulfinyl)methyl]pentanedioic acid; 2-[[(2-phenylethyl)sulfinyl]methyl]pentanedioic acid; 2-[[(3-phenylpropyl)sulfinyl]methyl]pentanedioic acid; 2-[[(4-pyridyl)

sulfinyl]methyl]pentanedioic acid; 2-[(benzylsulfinyl)methyl]pentanedioic acid; 2-[(sulfonyl)methyl]pentanedioic acid; 2-[(methylsulfonyl)methyl]pentanedioic acid; 2-[(ethylsulfonyl)methyl]pentanedioic acid; 2-[(propylsulfonyl)methyl]pentanedioic acid; 2-[(butylsulfonyl)methyl]pentanedioic acid; 2-[(phenylsulfonyl)methyl]pentanedioic acid; 2-[[(2-phenylethyl)sulfonyl]methyl]pentanedioic acid; 2-[[(3-phenylpropyl)sulfonyl]methyl]pentanedioic acid; 2-[[(4-pyridyl) sulfonyl]methyl]pentanedioic acid; 2-[(benzylsulfonyl)methyl]pentanedioic acid; 2-[(sulfoximinyl)methyl]pentanedioic acid; 2-[(methylsulfoximinyl)methyl]pentanedioic acid; 2-[(ethylsulfoximinyl)methyl]pentanedioic acid; 2-[(propylsulfoximinyl)methyl]pentanedioic acid; 2-[(butylsulfoximinyl)methyl]pentanedioic acid; 2-[(phenylsulfoximinyl)methyl]pentanedioic acid; 2-[[(2-phenylethyl)sulfoximinyl]methyl]pentanedioic acid; 2-[[(3-phenylpropyl) sulfoximinyl]methyl]pentanedioic acid; 2-[[(4-pyridyl)sulfoximinyl]methyl]pentanedioic acid; and 2-[(benzylsulfoximinyl)methyl]pentanedioic acid.

Pentanedioic acid derivatives described herein have been reported to have high binding affinity at PSMA, including but not limited to the following phosphonic and phosphinic acid derivatives

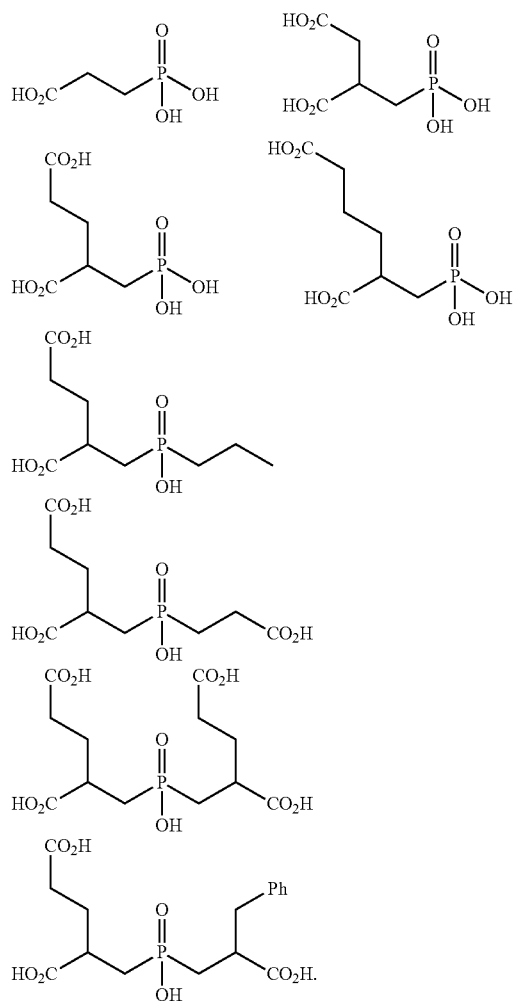

In another illustrative embodiment, the pentanedioic acid derivative includes a thiol group, such as compounds of the following formulae:

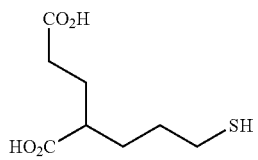

with configuration (R,S), (R), and (S).

In another embodiment, the PSMA ligand is a urea of two amino acids. In one aspect, the amino acids include one or more additional carboxylic acids. In another aspect, the amino acids include one or more additional phosphoric, phosphonic, phosphinic, sulfinic, sulfonic, or boronic acids. In another aspect, the amino acids include one or more thiol groups or derivatives thereof. In another aspect, the amino acids include one or more amino groups or derivatives thereof. In another aspect, the amino acids includes one or more carboxylic acid bioisosteres, such as tetrazoles and the like.

In another embodiment, the PSMA ligand is a aminocarbonyl derivative of pentanedioic acid. Illustratively, the aminocarbonylpentanedioic acid derivative is a compound of the formula:

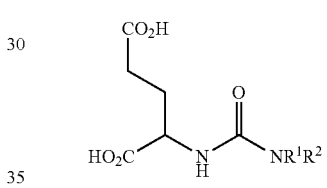

wherein $R^1$ and $R^2$ are each selected from hydrogen, optionally substituted carboxylic acids, such as thiolacetic acids, thiolpropionic acids, and the like; malonic acids, succinic acids, glutamic acids, adipic acids, and the like; and others. Illustrative aminocarbonylpentanedioic acid derivatives are described in J. Med. Chem. 44:298-301 (2001) and J. Med. Chem. 47:1729-38 (2004), the disclosures of which are incorporated herein by reference.

In another embodiment, the PSMA ligand is a compound of the formula:

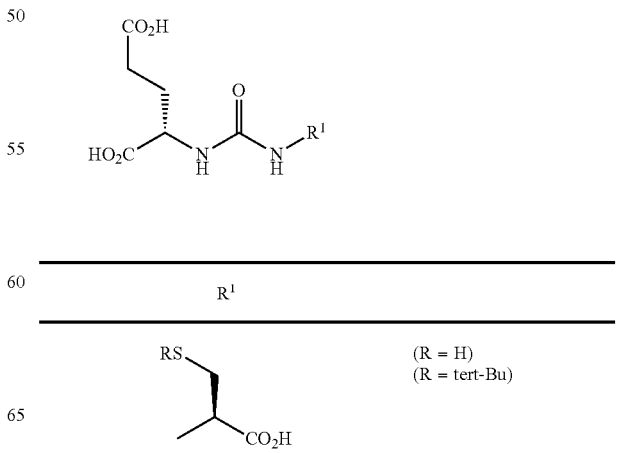

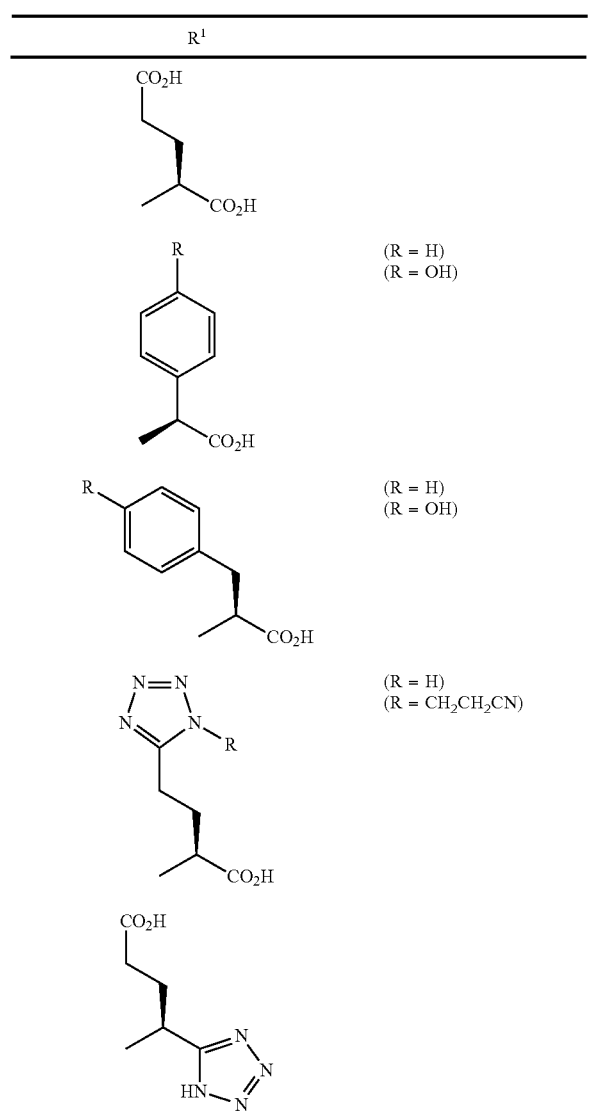

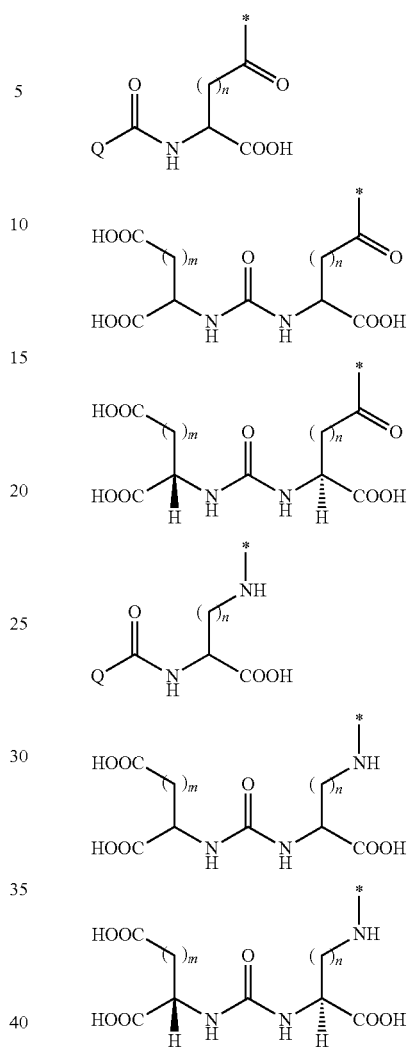

It is appreciated that the urea compounds described herein may also be advantageous in the preparation of the ligands also described herein due to the sub-nanomolar potency, water solubility, and/or long term stability of these compounds. The urea compounds described herein may generally be prepared from commercially available starting materials as described herein.

It is appreciated that in each of the above illustrative pentanedioic acid compounds and urea compounds, there is at least one asymmetric carbon atom. Accordingly, the above illustrative formulae are intended to refer both individually and collectively to all stereoisomers as pure enantiomers, or mixtures of enantiomers and/or diastereomers, including but not limited to racemic mixtures, mixtures that include one epimer at a first asymmetric carbon but allow mixtures at other asymmetric carbons, including racemic mixtures, and the like.

In another illustrative embodiment, the ligand is a urea of an amino dicarboxylic acid, such as aspartic acid, glutamic acid, and the like, and another amino dicarboxylic acid, or an analog thereof, such as a ligand of the formulae wherein Q is a an amino dicarboxylic acid, such as aspartic acid, glutamic acid, or an analog thereof, n and m are each selected from an integer between 1 and about 6, and (*) represents the point of attachment for the linker L.

In another illustrative embodiment, the ligand is a thiourea of an amino dicarboxylic acid, such as aspartic acid, glutamic acid, and the like, and another amino dicarboxylic acid, or an analog thereof, such as a ligand of the formulae

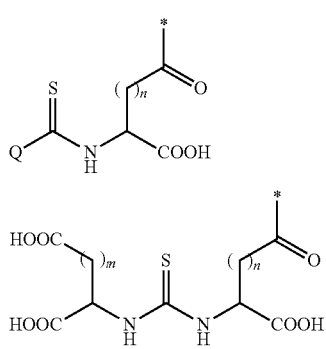

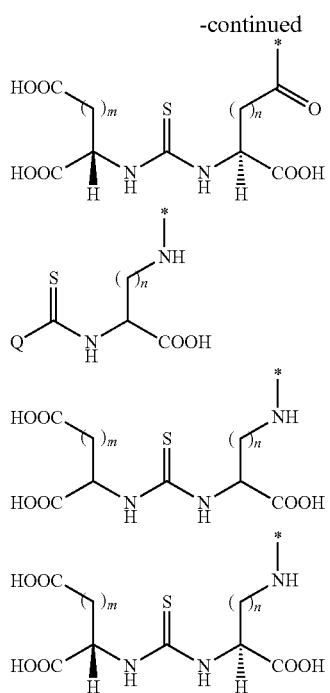

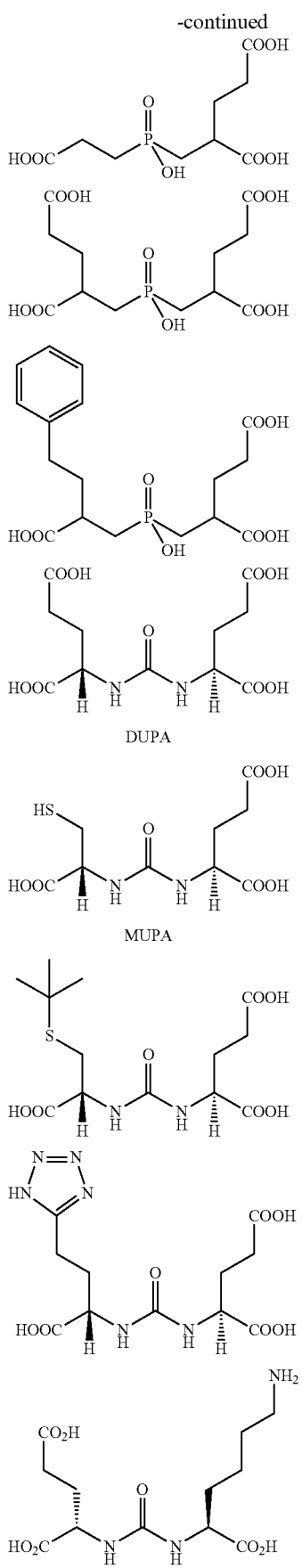

wherein Q is a an amino dicarboxylic acid, such as aspartic acid, glutamic acid, or an analog thereof, n and m are each selected from an integer between 1 and about 6, and (*) represents the point of attachment for the linker L.

In another embodiment, the PSMA ligand includes at least four carboxylic acid groups, or at least three free carboxylic acid groups after the PSMA ligand is conjugated to the ligand or linker. It is understood that as described herein, carboxylic acid groups on the PSMA ligand include bioisosteres of carboxylic acids.

Illustratively, the PSMA ligand is a compound of the formulae:

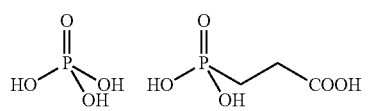

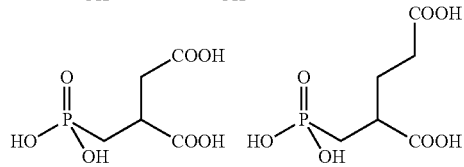

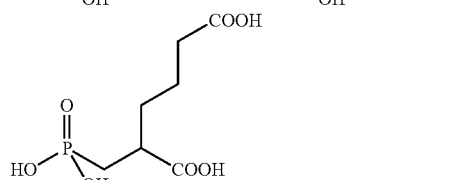

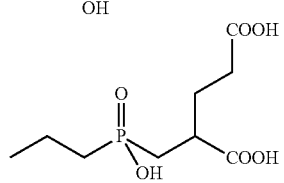

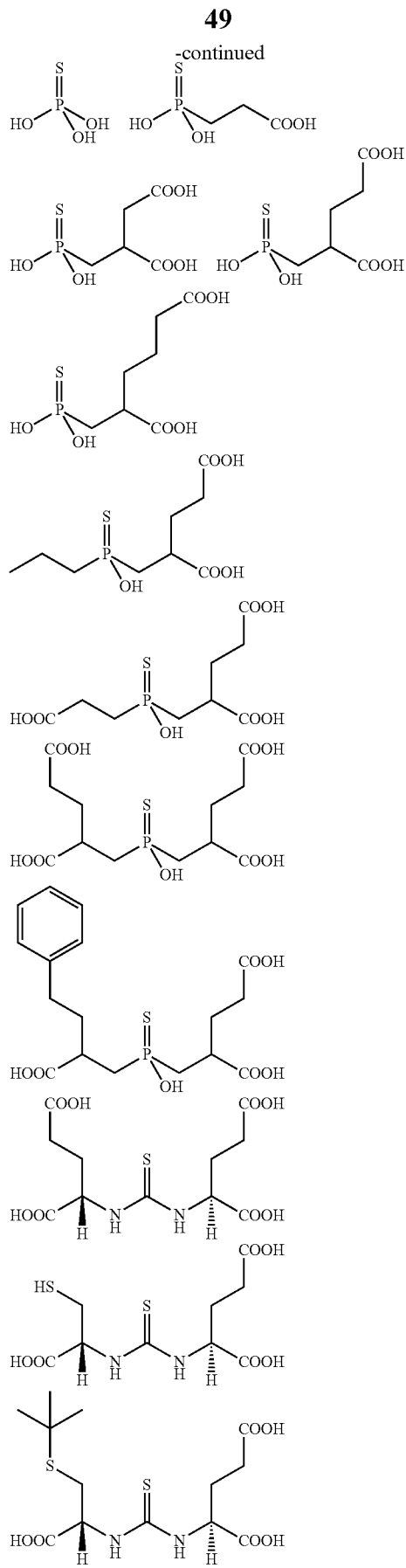

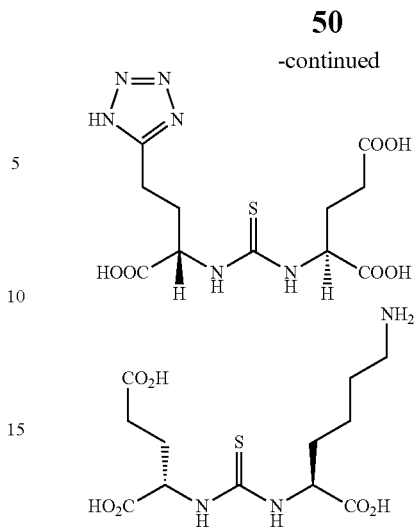

In another embodiment, the PSMA ligand is 2-[3-(1-Carboxy-2-mercapto-ethyl)-ureido]-pentanedioic acid (MUPA) or 2-[3-(1,3-Dicarboxy-propyl)-ureido]-pentanedioic acid (DUPA).

In another embodiment, the PSMA ligand is a urea or thiourea of lysine and glutamate, or one or more carboxylic acid derivatives thereof. In another embodiment, the PSMA ligand is a urea of lysine and glutamate. In another embodiment, the PSMA ligand is a urea or thiourea of L-lysine and L-glutamate, or one or more carboxylic acid derivatives thereof. In another embodiment, the PSMA ligand is a urea of L-lysine and L-glutamate.

Other illustrative examples of PSMA ligands include peptide analogs such as quisqualic acid, aspartate glutamate (Asp-Glu), Glu-Glu, Gly-Glu, γ-Glu-Glu, beta-N-acetyl-L-aspartate-L-glutamate (β-NAAG), and the like.

As used herein, the term "linker" includes is a chain of atoms that connects two or more functional parts of a molecule to form a conjugate. As used herein, the terms "linker," "linkers," and "L" are used interchangeably. Illustratively, the chain of atoms is selected from C, N, O, S, Si, and P, or C, N, O, S, and P, C, N, O, and S. The chain of atoms covalently connects different functional capabilities of the conjugate, such as ligands and drugs. The linker may have a wide variety of lengths, such as in the range from about 2 to about 100 atoms in the contiguous backbone. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, thus forming single, double, or triple bonds, such that for example, alkanes, alkenes, alkynes, imines, and the like may be radicals that are included in the linker. In addition, it is to be understood that the atoms forming the linker may also be cyclized upon each other or be part of cyclic structure to form divalent cyclic structures that form the linker, including cyclo alkanes, cyclic ethers, cyclic amines, and other heterocycles, arylenes, heteroarylenes, and the like in the linker. In this latter arrangement, it is to be understood that the linker length may be defined by any pathway through the one or more cyclic structures. Illustratively, the linker length is defined by the shortest pathway through the each one of the cyclic structures. It is to be understood that the linkers may be optionally substituted at any one or more of the open valences along the chain of atoms, such as optional substituents on any of the carbon, nitrogen, silicon, or phosphorus atoms. It is also to be understood that the linker may connect the two or more functional parts of a molecule to form a conjugate at any open valence, and it is not necessary that any of the two or more functional parts of a molecule forming the conjugate are attached at any apparent end of the linker.

In any of the embodiments described herein heteroatom linkers can be —$NR^1R^2$—, oxygen, sulfur, and the formulae —($NHR^1NHR^2$)—, —SO—, —($SO_2$)—, and —$N(R^3)O$—, wherein $R^1$, $R^2$, and $R^3$ are each independently selected from hydrogen, alkyl, aryl, arylalkyl, substituted aryl, substituted arylalkyl, heteroaryl, substituted heteroaryl, and alkoxyalkyl.

The releasable linkers can be methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In any of the embodiments described herein, the heteroatom linker can be oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the heteroatom linker can be oxygen, and the releasable linker can be methylene, wherein the methylene is substituted with an optionally-substituted aryl, and the releasable linker is bonded to the oxygen to form an acetal or ketal. Further, the heteroatom linker can be oxygen, and the releasable linker can be sulfonylalkyl, and the releasable linker is bonded to the oxygen to form an alkylsulfonate.

In another embodiment of the above releasable linker embodiment, the heteroatom linker can be nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the heteroatom linker can be oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the heteroatom linker can be nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug can include an oxygen atom, the heteroatom linker can be nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom linker nitrogen to form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^2$ and the heteroatom linker can be taken together with the releasable linker to which they are bound to form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In one aspect of the various conjugates described herein, the polyvalent linker comprises a 3-thiosuccinimid-1-ylalkyloxymethyloxy moiety, where the methyl is optionally substituted with alkyl or substituted aryl.

In another aspect, the polyvalent linker comprises a 3-thiosuccinimid-1-ylalkylcarbonyl, where the carbonyl forms an acylaziridine with the drug, or analog or derivative thereof.

In another aspect, the polyvalent linker comprises a 1-alkoxycycloalkylenoxy moiety.

In another aspect, the polyvalent linker comprises an alkyleneaminocarbonyl(dicarboxylarylene)carboxylate.

In another aspect, the polyvalent linker comprises a dithioalkylcarbonylhydrazide, where the hydrazide forms an hydrazone with the drug, or analog or derivative thereof.

In another aspect, the polyvalent linker comprises a 3-thiosuccinimid-1-ylalkylcarbonylhydrazide, where the hydrazide forms a hydrazone with the drug, or analog or derivative thereof.

In another aspect, the polyvalent linker comprises a 3-thioalkylsulfonylalkyl(disubstituted silyl)oxy, where the disubstituted silyl is substituted with alkyl or optionally substituted aryl.

In another aspect, the polyvalent linker comprises a plurality of spacer linkers selected from the group consisting of the naturally occurring amino acids and stereoisomers thereof.

In another aspect, the polyvalent linker comprises a 2-dithioalkyloxycarbonyl, where the carbonyl forms a carbonate with the drug, or analog or derivative thereof.

In another aspect, the polyvalent linker comprises a 2-dithioarylalkyloxycarbonyl, where the carbonyl forms a carbonate with the drug, or analog or derivative thereof, and the aryl is optionally substituted.

In another aspect, the polyvalent linker comprises a 4-dithioarylalkyloxycarbonyl, where the carbonyl forms a carbonate with the drug, or analog or derivative thereof, and the aryl is optionally substituted.

In another aspect, the polyvalent linker comprises a 3-thiosuccinimid-1-ylalkyloxyalkyloxyalkylidene, where the alkylidene forms an hydrazone with the drug, or analog or derivative thereof, each alkyl is independently selected, and the oxyalkyloxy is optionally substituted with alkyl or optionally substituted aryl.

In another aspect, the polyvalent linker comprises a 2-dithioalkyloxycarbonylhydrazide.

In another aspect, the polyvalent linker comprises a 2- or 3-dithioalkylamino, where the amino forms a vinylogous amide with the drug, or analog or derivative thereof.

In another aspect, the polyvalent linker comprises a 2-dithioalkylamino, where the amino forms a vinylogous amide with the drug, or analog or derivative thereof, and the alkyl is ethyl.

In another aspect, the polyvalent linker comprises a 2- or 3-dithioalkylaminocarbonyl, where the carbonyl forms a carbamate with the drug, or analog or derivative thereof.

In another aspect, the polyvalent linker comprises a releasable linker, a spacer linker, and a releasable linker taken together to form 2-dithioalkylaminocarbonyl, where the carbonyl forms a carbamate with the drug, or analog or derivative thereof, and the alkyl is ethyl.

In another aspect, the polyvalent linker comprises a 2-dithioarylalkyloxycarbonyl, where the carbonyl forms a carbamate or a carbamoylaziridine with the drug, or analog or derivative thereof.

In another aspect, the polyvalent linker comprises a 4-dithioarylalkyloxycarbonyl, where the carbonyl forms a carbamate or a carbamoylaziridine with the drug, or analog or derivative thereof.

In one embodiment, the polyvalent linkers described herein comprise divalent linkers of formulae (II)

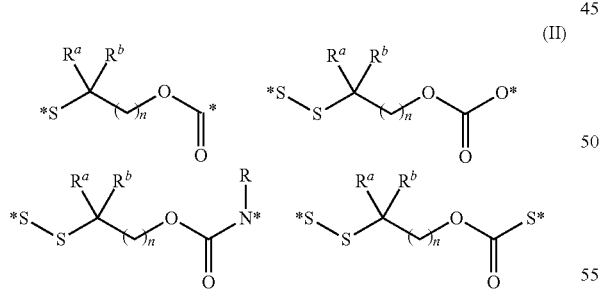

(II)

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the polyvalent linkers described herein comprise divalent linkers of formulae (III)

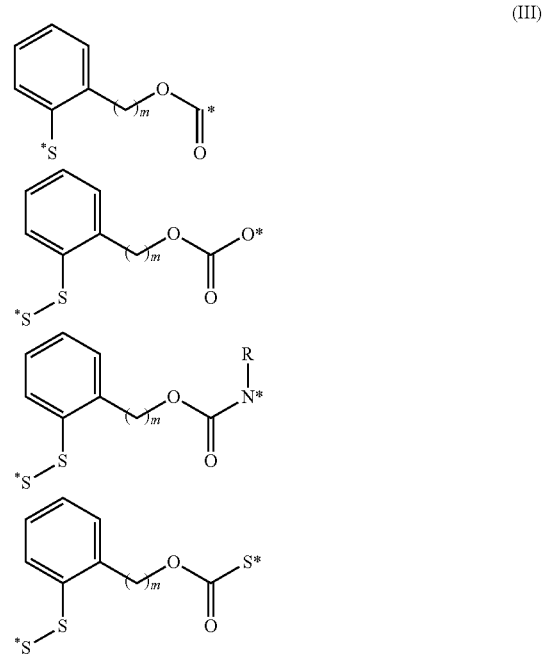

(III)

where m is an integer selected from 1 to about 4; R is an optionally substituted alkyl group, an optionally substituted acyl group, or a suitably selected nitrogen protecting group; and (*) indicates points of attachment for the drug, other bivalent linkers, or other parts of the conjugate.

In another embodiment, the polyvalent linkers described herein comprise divalent linkers of formulae (IV)

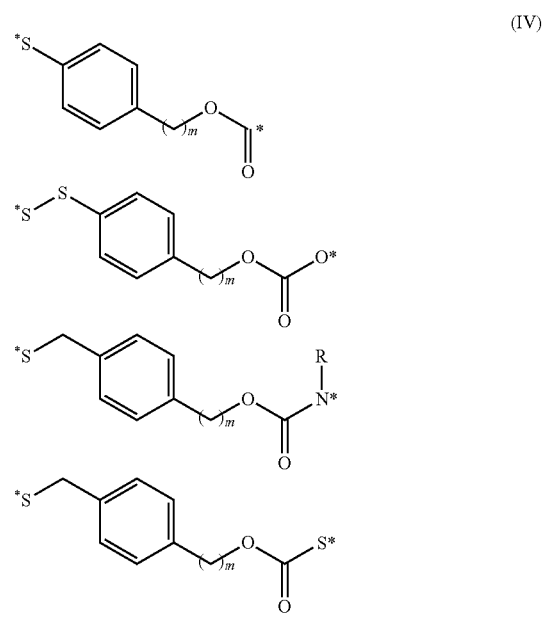

(IV)

where m is an integer selected from 1 to about 4; R is an optionally substituted alkyl group, an optionally substituted acyl group, or a suitably selected nitrogen protecting group;

and (*) indicates points of attachment for the drug, ligand, other divalent linkers, or other parts of the conjugate.

In another embodiment, the polyvalent linkers described herein comprise one or more hydrophilic linkers. It is appreciated that the arrangement and/or orientation of the various hydrophilic linkers may be in a linear or branched fashion, or both. For example, the hydrophilic linkers may form the backbone of the linker forming the conjugate between the binding ligand and the drug. Alternatively, the hydrophilic portion of the linker may be pendant to or attached to the backbone of the chain of atoms connecting the binding ligand B to the agent A. In this latter arrangement, the hydrophilic portion may be proximal or distal to the backbone chain of atoms.

In another embodiment, the linker is more or less linear, and the hydrophilic groups are arranged largely in a series to form a chain-like linker in the conjugate. Said another way, the hydrophilic groups form some or all of the backbone of the linker in this linear embodiment.

In another embodiment, the linker is branched with hydrophilic groups. In this branched embodiment, the hydrophilic groups may be proximal to the backbone or distal to the backbone. In each of these arrangements, the linker is more spherical or cylindrical in shape. In one variation, the linker is shaped like a bottle-brush. In one aspect, the backbone of the linker is formed by a linear series of amides, and the hydrophilic portion of the linker is formed by a parallel arrangement of branching side chains, such as by connecting monosaccharides, sulfonates, and the like, and derivatives and analogs thereof.

It is understood that the linker may be neutral or ionizable under certain conditions, such as physiological conditions encountered in vivo. For ionizable linkers, under the selected conditions, the linker may deprotonate to form a negative ion, or alternatively become protonated to form a positive ion. It is appreciated that more than one deprotonation or protonation event may occur. In addition, it is understood that the same linker may deprotonate and protonate to form inner salts or zwitterionic compounds.

In another embodiment, the hydrophilic spacer linkers are neutral, i.e. under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker is protonated in vivo. In another embodiment, the spacers include both regions that are neutral and regions that may be protonated to carry one or more positive charges. In another embodiment, the spacers include both regions that may be deprotonated to carry one or more negative charges and regions that may be protonated to carry one or more positive charges. It is understood that in this latter embodiment that zwitterions or inner salts may be formed.

In one aspect, the regions of the linkers that may be deprotonated to carry a negative charge include carboxylic acids, such as aspartic acid, glutamic acid, and longer chain carboxylic acid groups, and sulfuric acid esters, such as alkyl esters of sulfuric acid. In another aspect, the regions of the linkers that may be protonated to carry a positive charge include amino groups, such as polyaminoalkylenes including ethylene diamines, propylene diamines, butylene diamines and the like, and/or heterocycles including pyrollidines, piperidines, piperazines, and other amino groups, each of which is optionally substituted. In another embodiment, the regions of the linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In one embodiment, the hydrophilic spacer linkers described herein include are formed primarily from carbon, hydrogen, and oxygen, and have a carbon/oxygen ratio of about 3:1 or less, or of about 2:1 or less. In one aspect, the hydrophilic linkers described herein include a plurality of ether functional groups. In another aspect, the hydrophilic linkers described herein include a plurality of hydroxyl functional groups. Illustrative fragments that may be used to form such linkers include polyhydroxyl compounds such as carbohydrates, polyether compounds such as polyethylene glycol units, and acid groups such as carboxyl and alkyl sulfuric acids. In one variation, oligoamide spacers, and the like may also be included in the linker.

Illustrative carbohydrate spacers include saccharopeptides as described herein that include both a peptide feature and sugar feature; glucuronides, which may be incorporated via [2+3] Huisgen cyclization, also known as click chemistry; β-alkyl glycosides, such as of 2-deoxyhexapyranoses (2-deoxyglucose, 2-deoxyglucuronide, and the like), and β-alkyl mannopyranosides. Illustrative PEG groups include those of a specific length range from about 4 to about 20 PEG groups. Illustrative alkyl sulfuric acid esters may also be introduced with click chemistry directly into the backbone. Illustrative oligoamide spacers include EDTA and DTPA spacers, β-amino acids, and the like.

In another embodiment, the hydrophilic spacer linkers described herein include a polyether, such as the linkers of the following formulae:

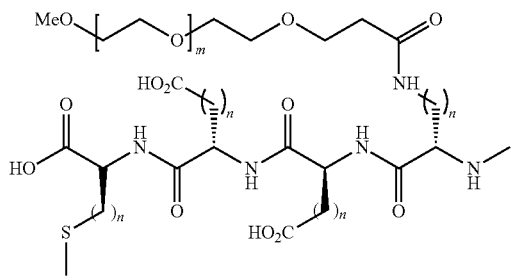

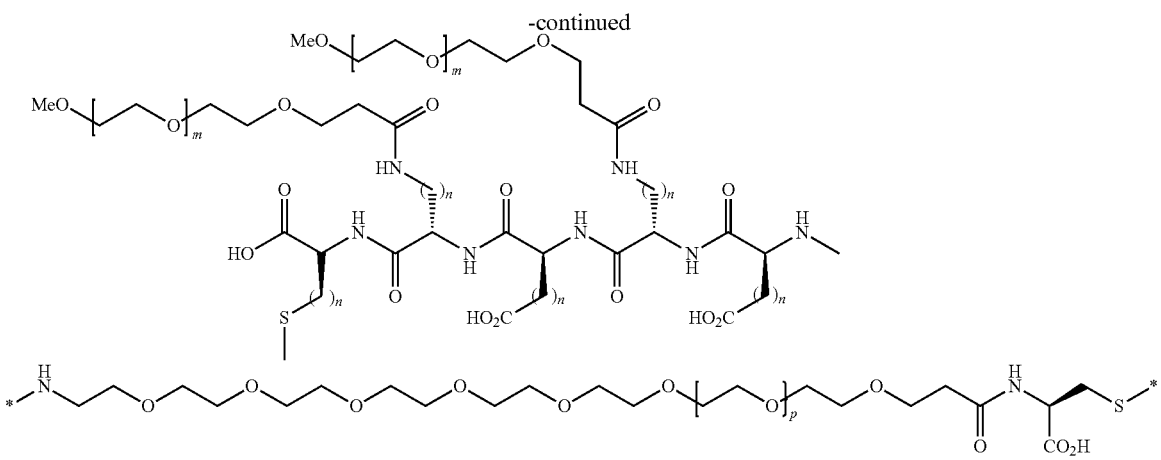

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether compounds, such as those that include tetrahydrofuranyl, 1,3-dioxanes, 1,4-dioxanes, and the like are contemplated herein.

In another illustrative embodiment, the hydrophilic spacer linkers described herein include a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the spacer linkers include one or more of the following fragments:

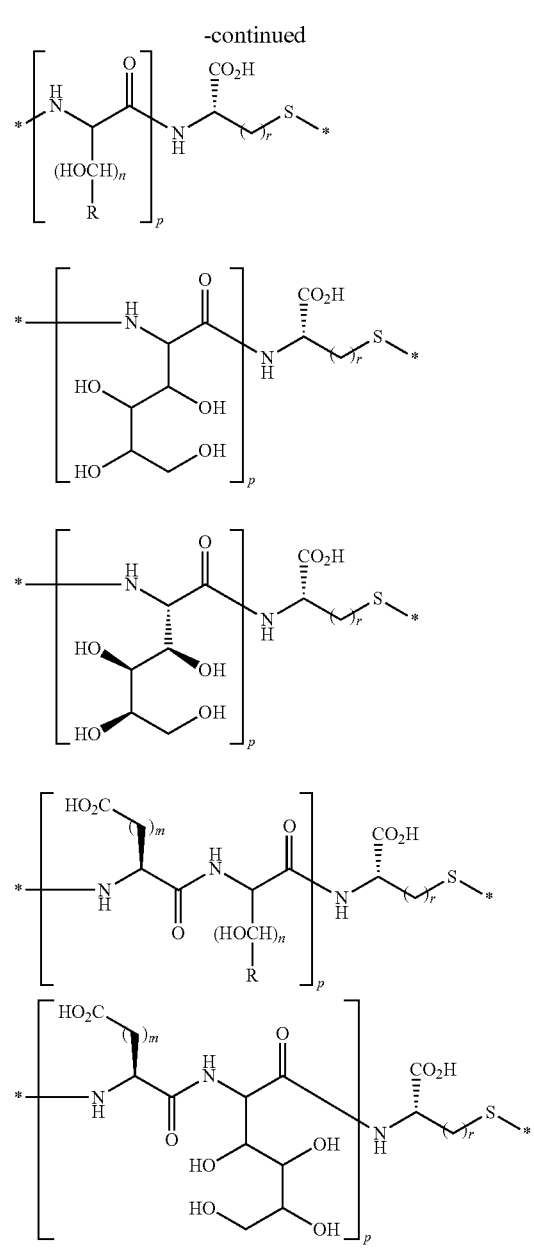

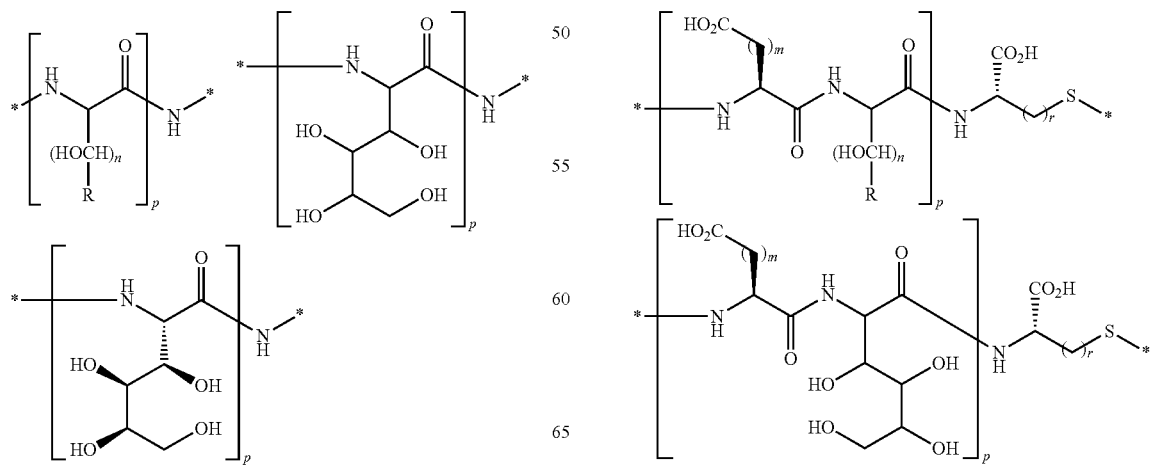

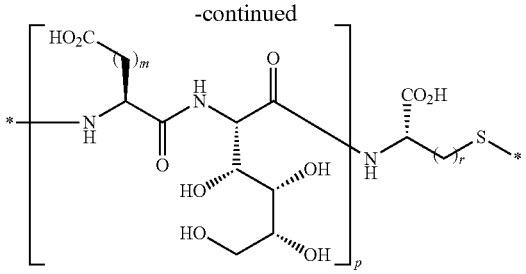
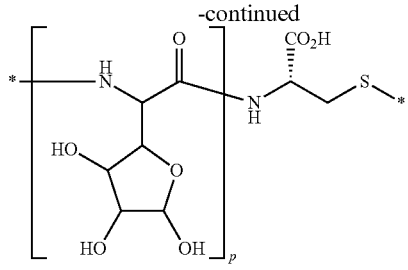
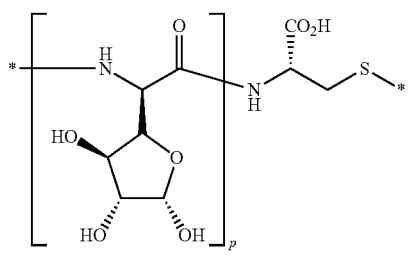

wherein R is H, alkyl, cycloalkyl, or arylalkyl; m is an integer from 1 to about 3; n is an integer from 1 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the spacer linker includes one or more of the following cyclic polyhydroxyl groups:

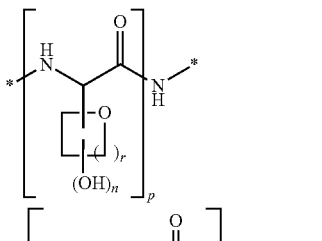
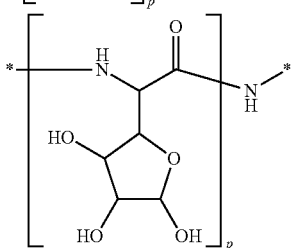
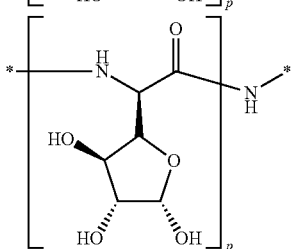
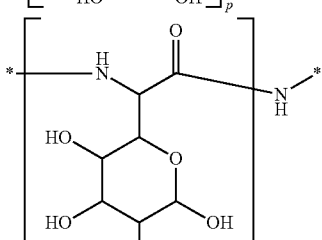
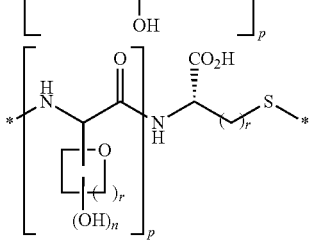
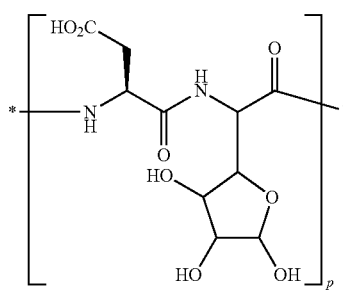
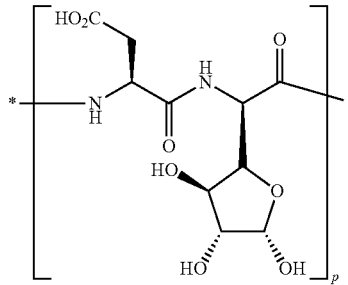
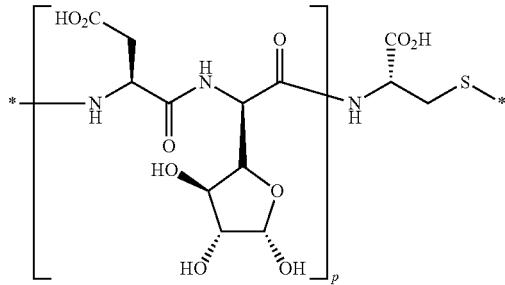

-continued

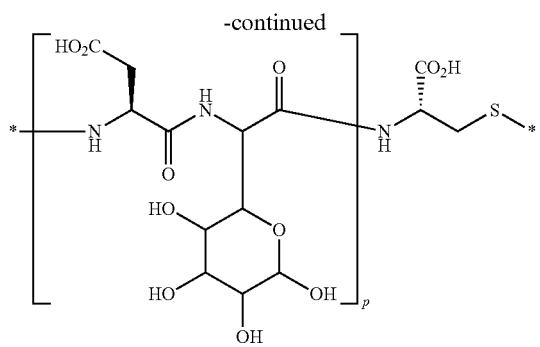

wherein n is an integer from 2 to about 5, p is an integer from 1 to about 5, and r is an integer from 1 to about 4. In one aspect, the integer n is 3 or 4. In another aspect, the integer p is 3 or 4. In another aspect, the integer r is 2 or 3. It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, compounds of the following formulae are contemplated:

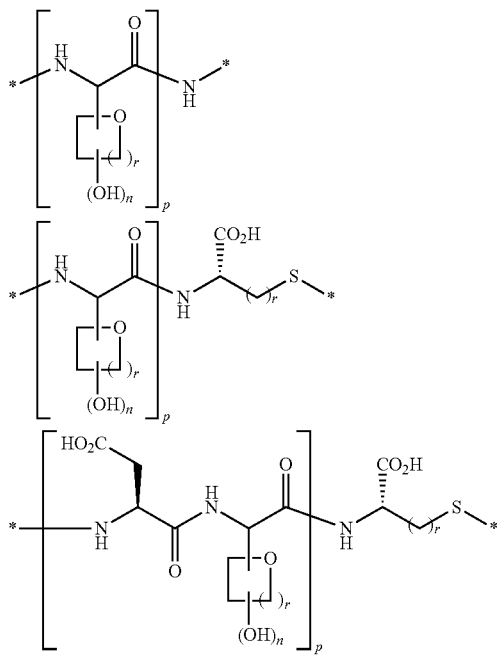

wherein n is equal to or less than r, such as when r is 2 or 3, n is 1 or 2, or 1, 2, or 3, respectively.

In another embodiment, the spacer linker includes a polyhydroxyl compound of the following formula:

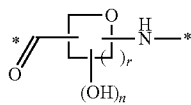

wherein n and r are each an integer selected from 1 to about 3. In one aspect, the spacer linker includes one or more polyhydroxyl compounds of the following formulae:

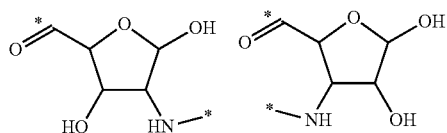

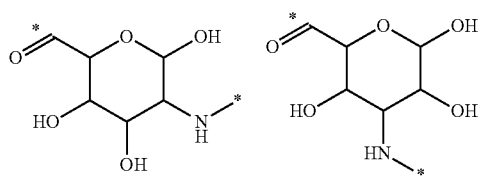

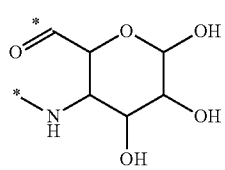

It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules.

In another configuration, the hydrophilic linkers L described herein include polyhydroxyl groups that are spaced away from the backbone of the linker. In one embodiment, such carbohydrate groups or polyhydroxyl groups are connected to the back bone by a triazole group, forming triazole-linked hydrophilic spacer linkers. Illustratively, such linkers include fragments of the following formulae:

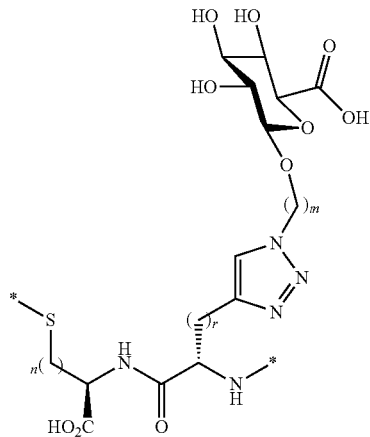

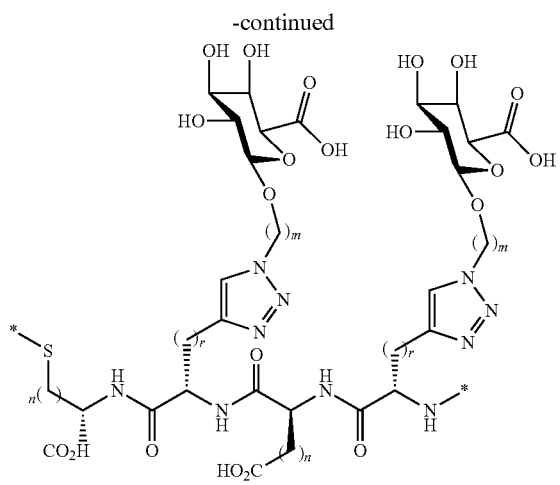

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are contemplated. Other variations of the foregoing illustrative hydrophilic spacer linkers include oxyalkylene groups, such as the following formulae:

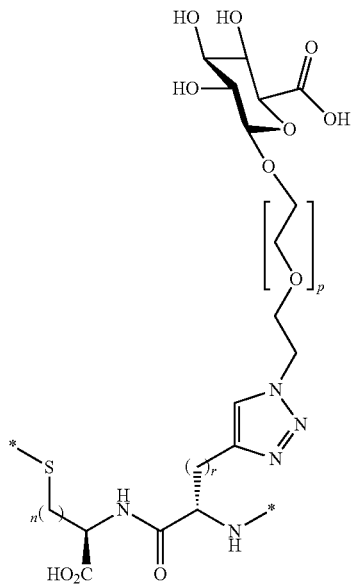

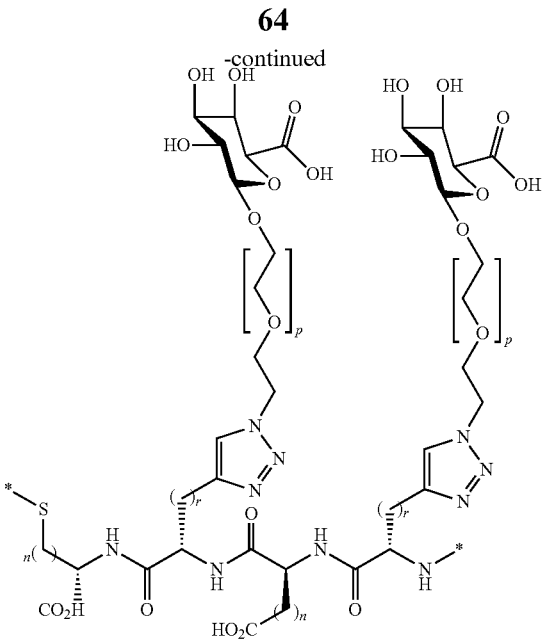

wherein n and r are integers and are each independently selected in each instance from 1 to about 5; and p is an integer selected from 1 to about 4.

In another embodiment, such carbohydrate groups or polyhydroxyl groups are connected to the back bone by an amide group, forming amide-linked hydrophilic spacer linkers. Illustratively, such linkers include fragments of the following formulae:

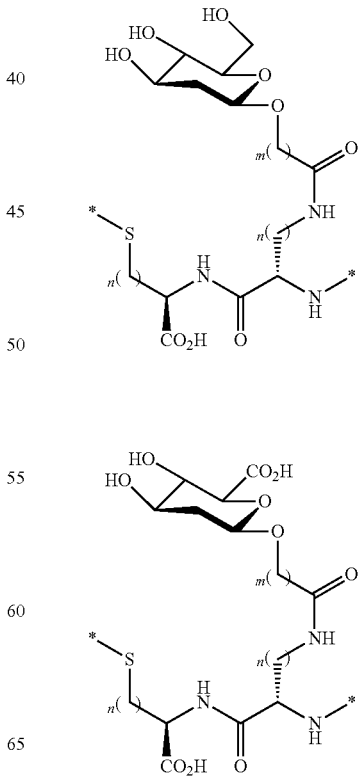

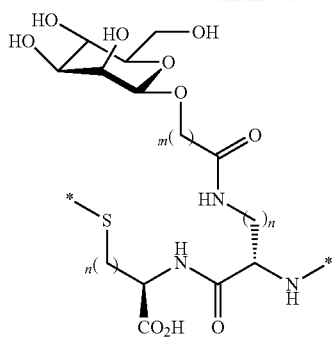

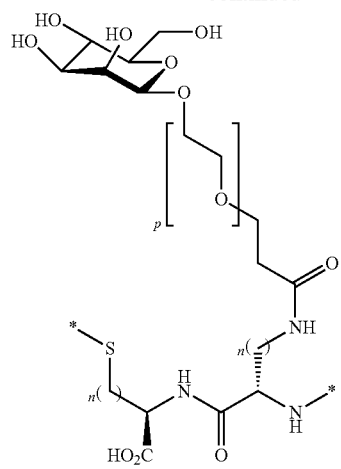

wherein n is an integer selected from 1 to about 3, and m is an integer selected from 1 to about 22. In one illustrative aspect, n is 1 or 2. In another illustrative aspect, m is selected from about 6 to about 10, illustratively 8. In one variation, the group connecting the polyhydroxyl group to the backbone of the linker is a different functional group, including but not limited to, esters, ureas, carbamates, acylhydrazones, and the like. Similarly, cyclic variations are contemplated. Other variations of the foregoing illustrative hydrophilic spacer linkers include oxyalkylene groups, such as the following formulae:

wherein n and r are integers and are each independently selected in each instance from 1 to about 5; and p is an integer selected from 1 to about 4.

In another embodiment, the spacer linkers include one or more of the following fragments:

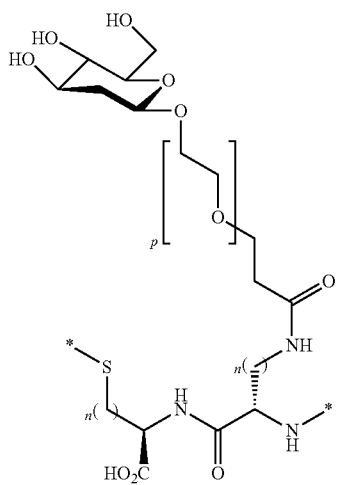

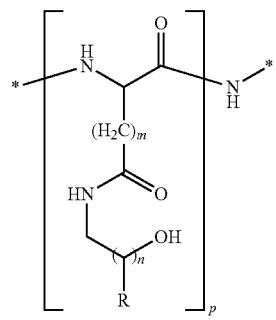

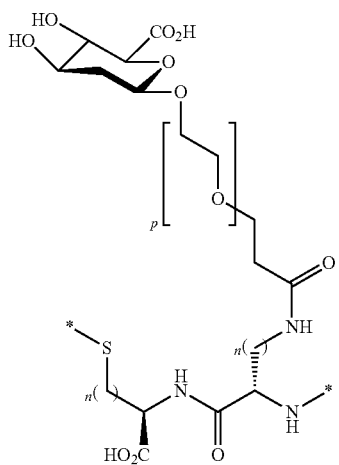

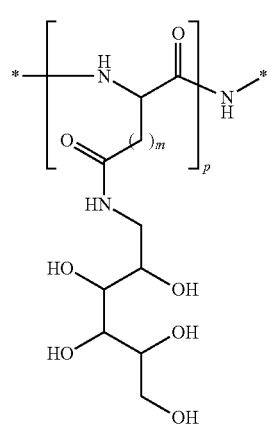

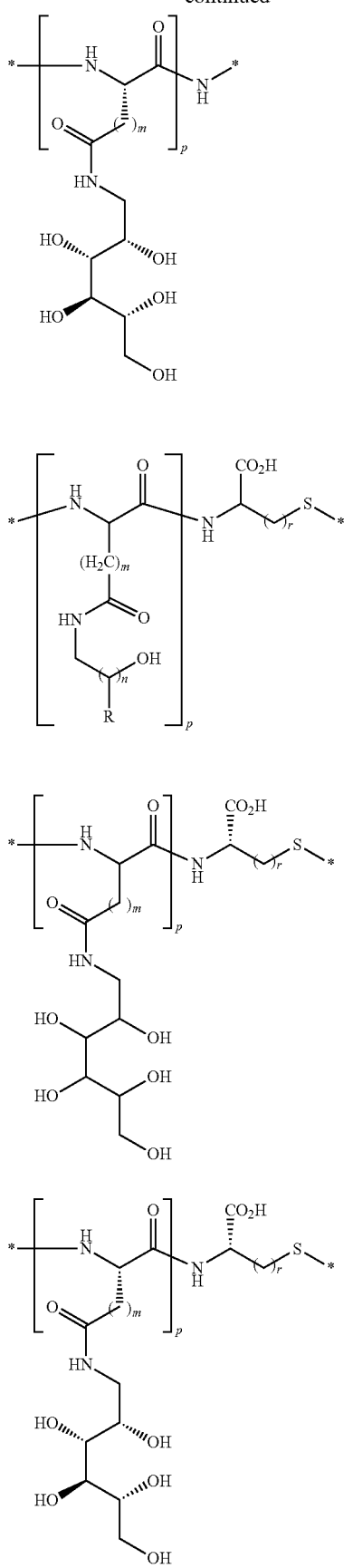
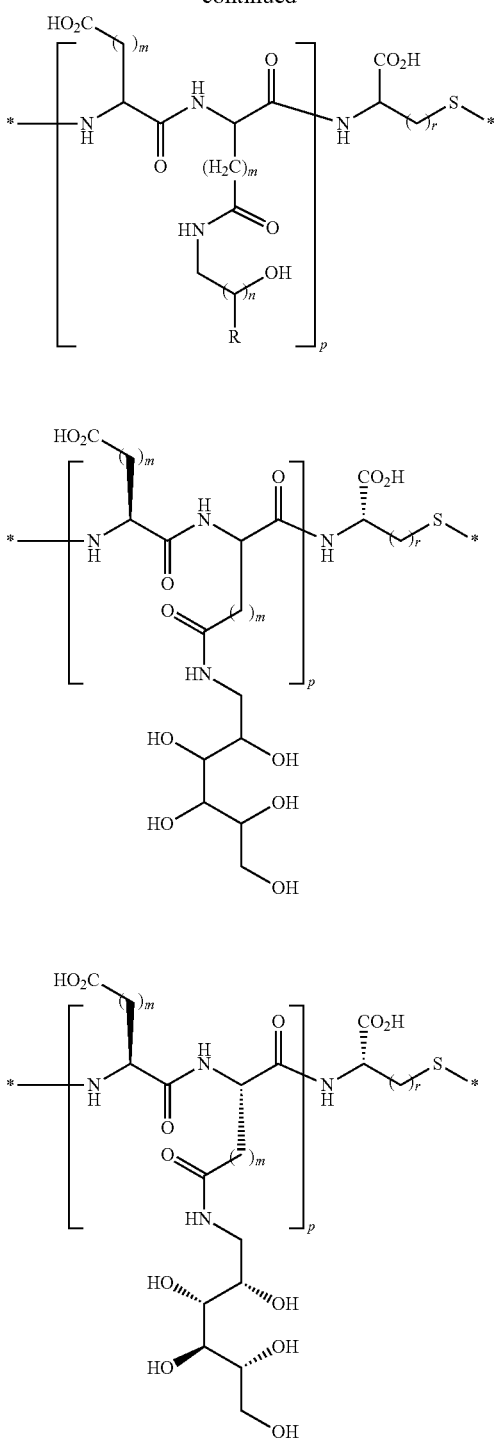

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the spacer linkers include one or more of the following fragments:

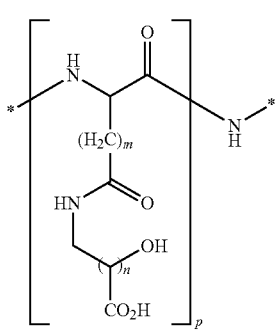
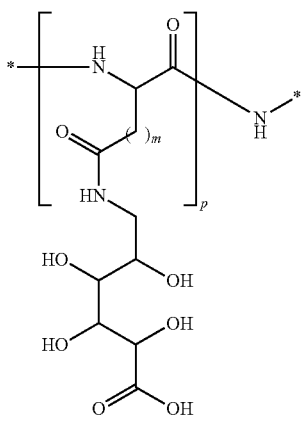
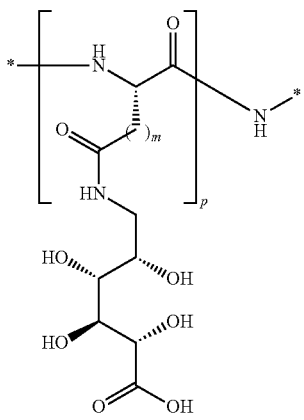
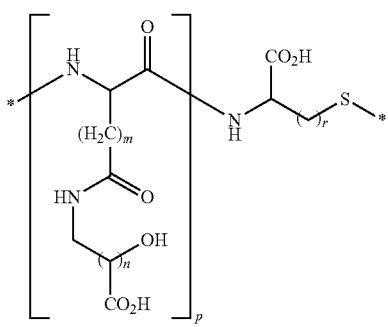
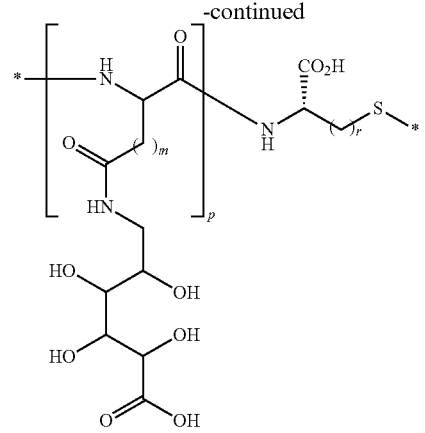
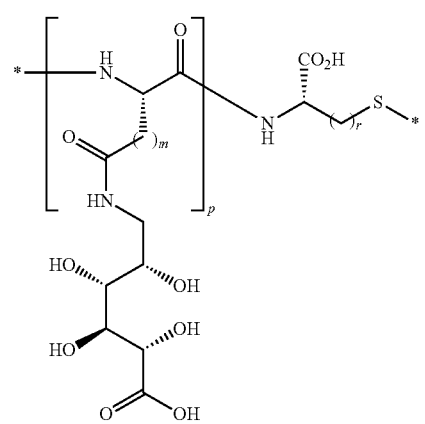
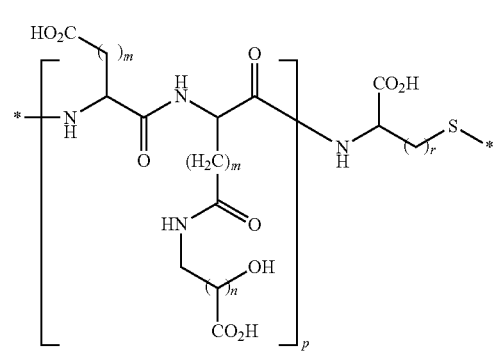
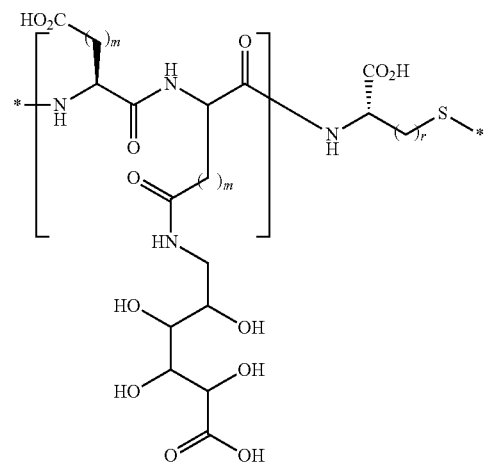

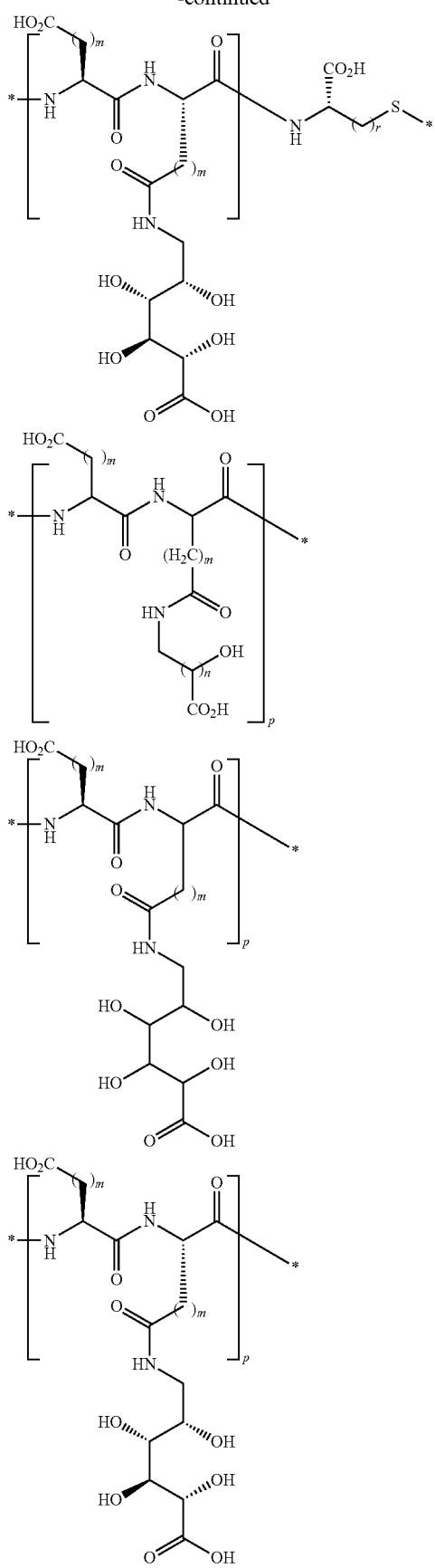
wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.
In another embodiment, the spacer linkers include one or more of the following fragments:
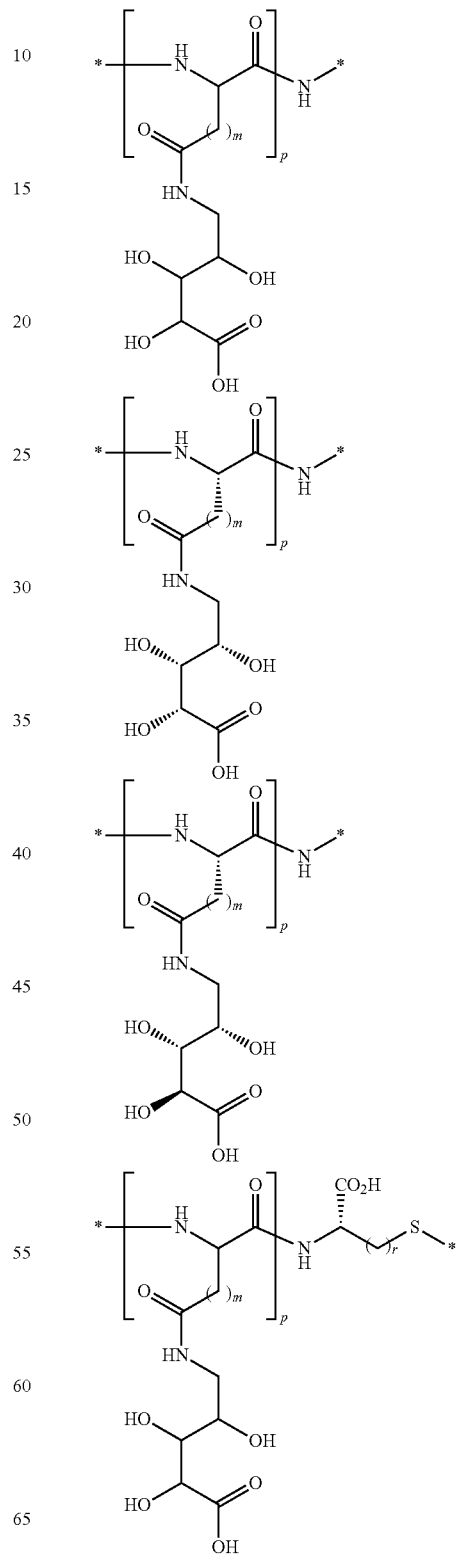

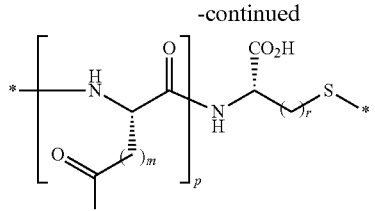

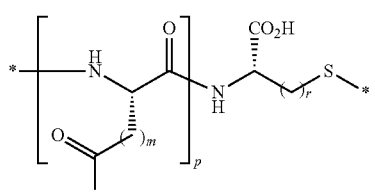

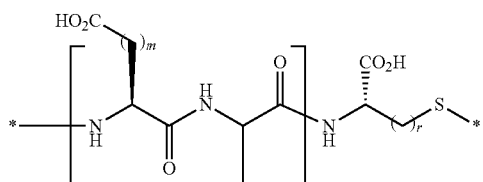

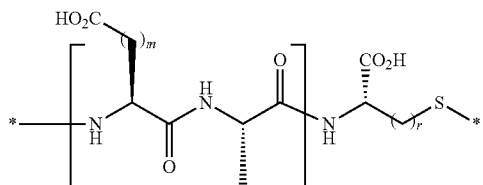

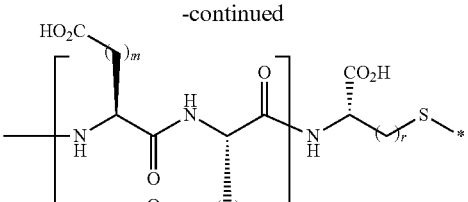

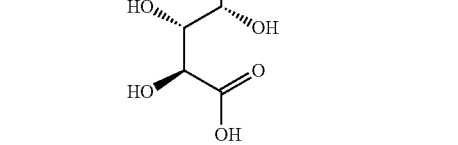

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the hydrophilic spacer linker is a combination of backbone and branching side motifs such as is illustrated by the following formulae

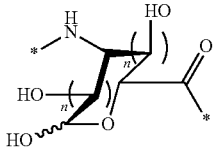

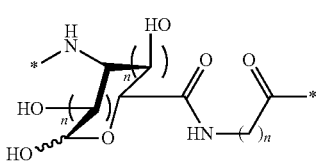

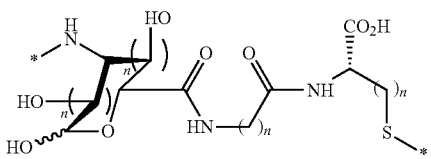

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are contemplated by the above formulae, where one or more of the hydroxyl groups is oxidized to the corresponding carbonyl. In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical fragments, including additional sugars to prepare the corresponding oligosaccharides. Other variations of this embodiment are also contemplated, including inserting the pyranose or other sugar into the backbone at a single carbon, i.e. a spiro arrangement, at a geminal pair of carbons, and like arrangements. For example, one or two ends of the linker, or the ligand may be connected to the sugar to be inserted into the backbone in a 1,1; 1,2; 1,3; 1,4; 2,3, or other arrangement.

In another embodiment, the hydrophilic spacer linkers described herein include are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

In another embodiment, the spacer linkers include one or more amino groups of the following formulae:

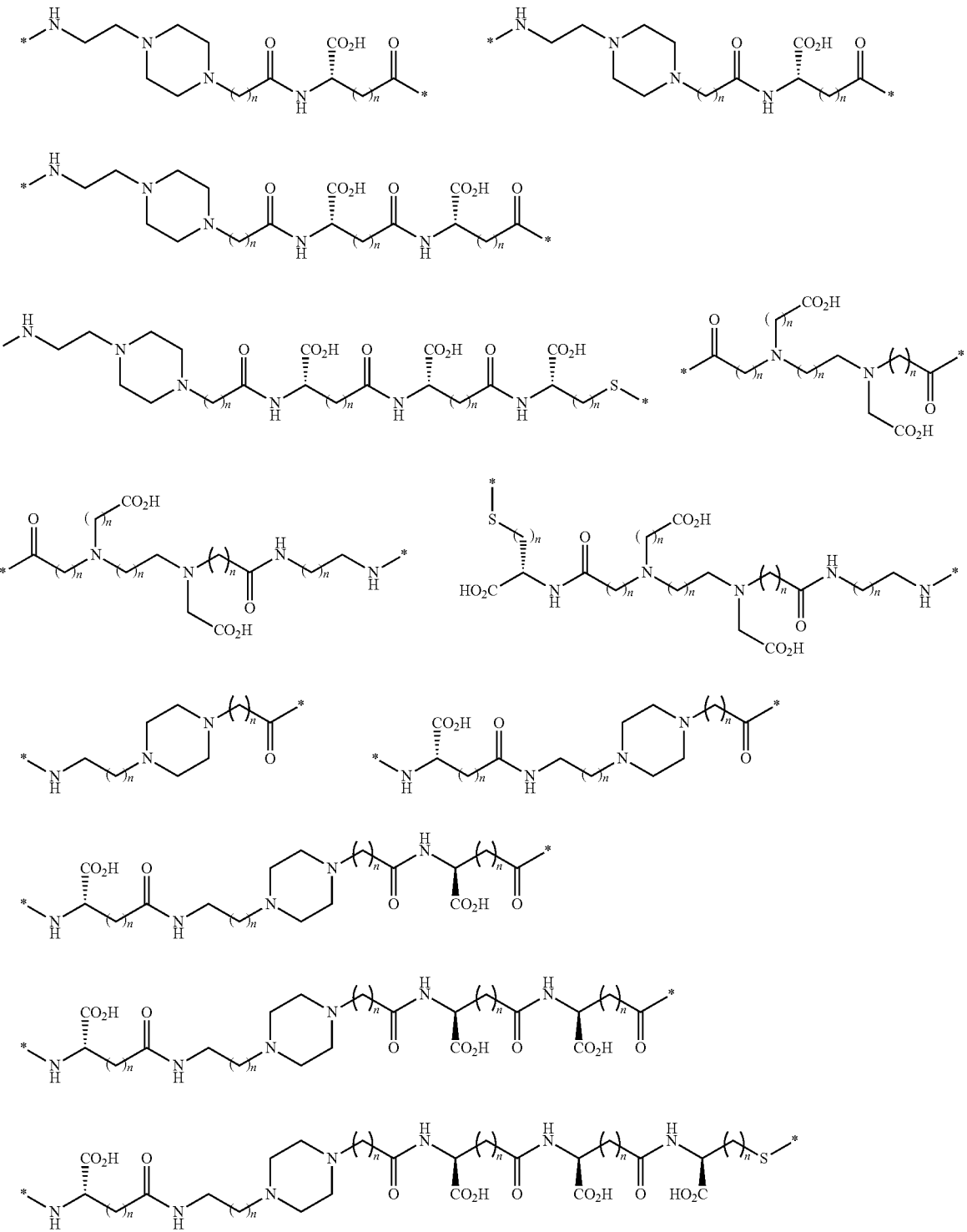

where n is an integer independently selected in each instance from 1 to about 3. In one aspect, the integer n is independently 1 or 2 in each instance. In another aspect, the integer n is 1 in each instance.

In another embodiment, the hydrophilic spacer linker is a sulfuric acid ester, such as an alkyl ester of sulfuric acid. Illustratively, the spacer linker is of the following formula:

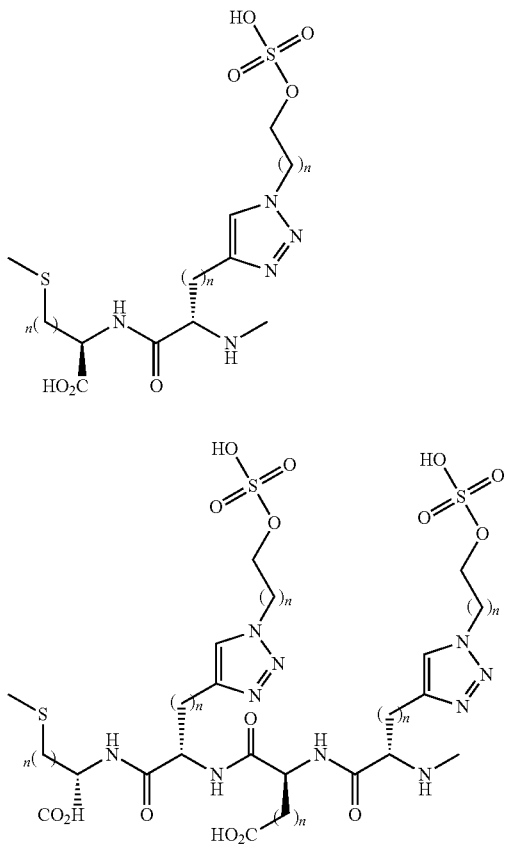

where n is an integer independently selected in each instance from 1 to about 3. Illustratively, n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In each of the foregoing illustrative examples of linkers L, there are also included in some cases additional spacer linkers, and/or additional releasable linkers. Those spacer linker and releasable linkers also may include asymmetric carbon atoms. It is to be further understood that the stereochemical configurations shown herein are merely illustrative, and other stereochemical configurations are contemplated. For example in one variation, the corresponding unnatural amino acid configurations may be included in the conjugated described herein as follows:

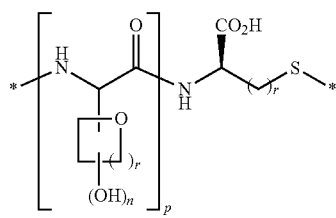

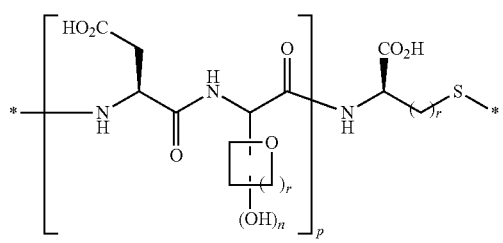

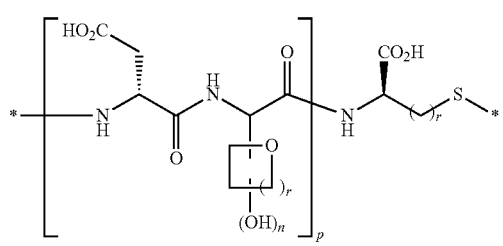

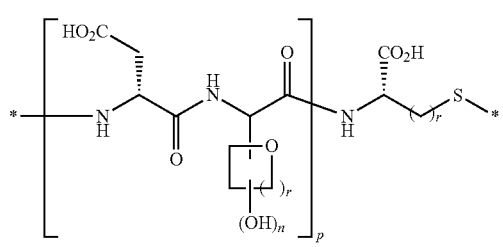

wherein n is an integer from 2 to about 5, p is an integer from 1 to about 5, and r is an integer from 1 to about 4, as described above.

It is to be further understood that in the foregoing embodiments, open positions, such as (*) atoms are locations for attachment of the ligand or the drug. In addition, it is to be understood that such attachment of either or both of B and A may be direct or through an intervening linker. Intervening linkers include other spacer linkers and/or releasable linkers. Illustrative additional spacer linkers and releasable linkers that are included in the conjugated described herein are described in U.S. patent application Ser. No. 10/765,335, the disclosure of which is incorporated herein by reference.

In one embodiment, the hydrophilic spacer linker comprises one or more carbohydrate containing or polyhydroxyl group containing linkers. In another embodiment, the hydrophilic spacer linker comprises at least three carbohydrate containing or polyhydroxyl group containing linkers. In another embodiment, the hydrophilic spacer linker comprises one or more carbohydrate containing or polyhydroxyl group containing linkers, and one or more aspartic acids. In another embodiment, the hydrophilic spacer linker comprises one or more carbohydrate containing or polyhydroxyl group containing linkers, and one or more glutamic acids. In another embodiment, the hydrophilic spacer linker comprises one or more carbohydrate containing or polyhydroxyl group containing linkers, one or more glutamic acids, one or more aspartic acids, and one or more beta amino alanines. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more divalent 1,4-piperazines that are included in the chain of atoms connecting at least one of the ligands with at least one of the drugs. In one variation, the hydrophilic spacer linker includes one or more carbohydrate containing or polyhydroxyl group containing linkers. In another variation, the hydrophilic spacer linker includes one or more carbohydrate containing or polyhydroxyl group containing linkers and one or more aspartic acids. In another variation, the hydrophilic spacer linker includes one or more carbohydrate containing or polyhydroxyl group containing linkers and one or more glutamic acids. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more oligoamide hydrophilic spacers, such as but not limited to aminoethylpiperazinylacetamide.

In another embodiment, the hydrophilic spacer linker comprises one or more triazole linked carbohydrate containing or polyhydroxyl group containing linkers. In another embodiment, the hydrophilic spacer linker comprises one or more amide linked carbohydrate containing or polyhydroxyl group containing linkers. In another embodiment, the hydrophilic spacer linker comprises one or more PEG groups and one or more cysteines. In another embodiment, the hydrophilic spacer linker comprises one or more EDTE derivatives.

In another embodiment, a folate ligand intermediate is described having the following formula

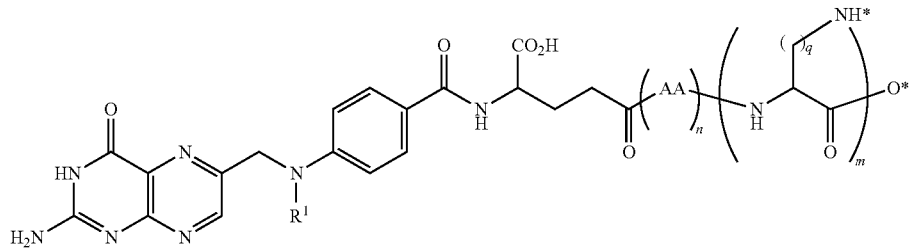

wherein m, n, and q are integers that are independently selected from the range of u to about 8; AA is an amino acid, $R^1$ is hydrogen, alkyl, or a nitrogen protecting group, and drugs are optionally attached at the (*) atoms. In one aspect, AA is a naturally occurring amino acid of either the natural or unnatural configuration. In another aspect, one or more of AA is a hydrophilic amino acid. In another aspect, one or more of AA is Asp and/or Arg. In another aspect, the integer o is 1 or greater. In another aspect, the integer m is 2 or greater. The drugs, or analogs or derivatives thereof, and optionally additional linkers and additional ligands may be connected to the above formula at the free NH side chains of the 2,ω-diaminoalkanoic acid fragments, or at the terminal carboxylate as indicated by the free valences therein.

In another embodiment, a folate ligand intermediate is described having the following formula

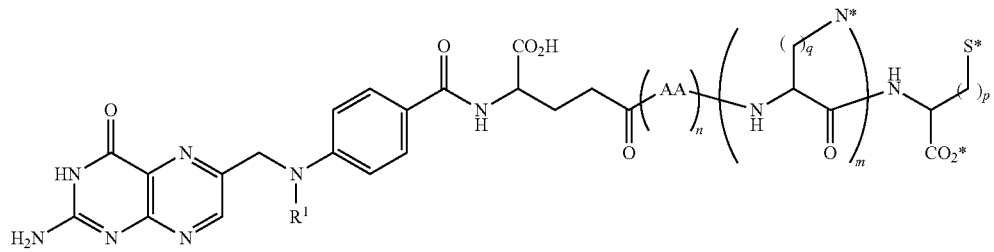

wherein m, n, q, and p are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA is a hydrophilic amino acid. In another aspect, one or more of AA is Asp and/or Arg. In another aspect, the integers o and p are 1 or greater. In another aspect, the integer m is 2 or greater. The drugs, or analogs or derivatives thereof, and optionally additional linkers and additional ligands may be connected to the above formula at the free NH side chains of the 2,ω-diaminoalkanoic acid fragments, at the cysteinyl thiol groups, or at the terminal carboxylate, as indicated by the free valences therein.

In another embodiment, a folate ligand intermediate is described having the following formula

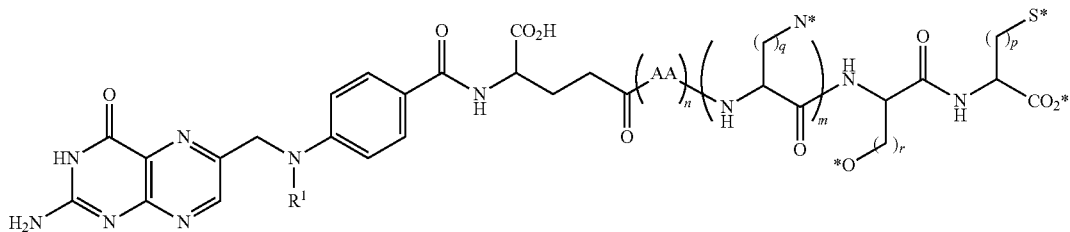

wherein m, n, q, p, and r are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA is a hydrophilic amino acid. In another aspect, one or more of AA is Asp and/or Arg. In another aspect, the integers o, p, and r are 1 or greater. In another aspect, the integer m is 2 or greater. The drugs, or analogs or derivatives thereof, and optionally additional linkers and additional ligands may be connected to the above formula at the free NH side chains of the 2,ω-diaminoalkanoic acid fragments, at the cyteinyl thiol groups, at the serinyl hydroxy groups, or at the terminal carboxylate, as indicated by the free valences therein.

In another embodiment, the compound of any of the embodiment described herein wherein L comprises a divalent linker of the formula

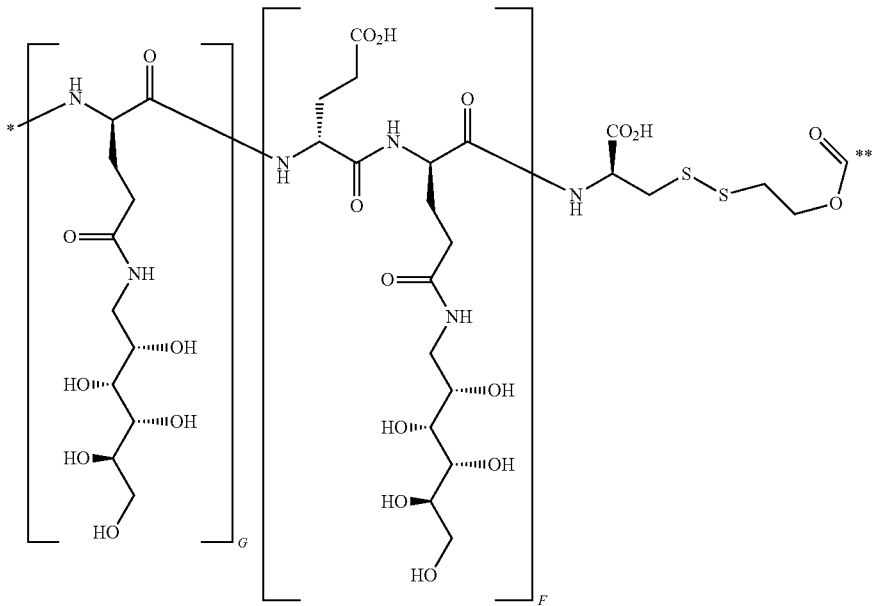

wherein * indicates the point of attachment to a folate and ** indicates the point of attachment to a drug; and F and G are each independently 1, 2, 3 or 4 are described.

In another embodiment, the of any one of the embodiments described herein wherein L is a linker comprises a divalent linker of the formula

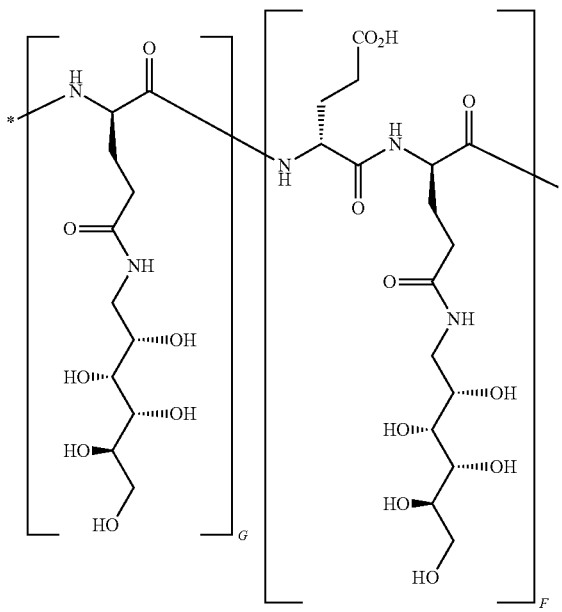
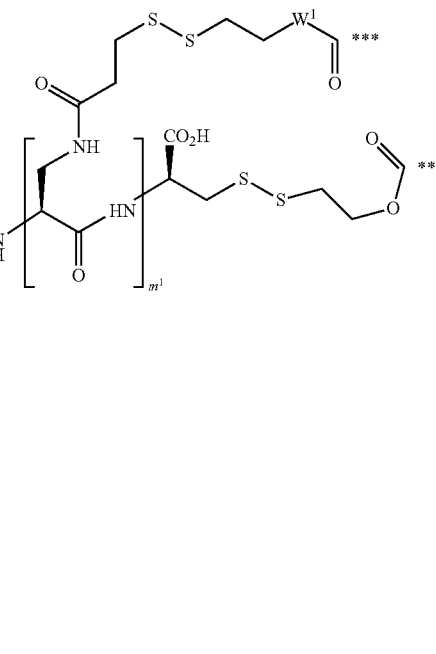

wherein *, , * each indicate points of attachment to the ligand, and the one or more drugs D. It is to be understood that when there are fewer drugs, *, , * are substituted with hydrogen or a heteroatom. F and G are each independently 1, 2, 3 or 4; and $W^1$ is NH or O is described. In another aspect, $m^1$ is 0 or 1.

In another embodiment, amino acid refers to beta, gamma, and longer amino acids, such as amino acids of the formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarhonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes SO$_2$H and salts thereof, and esters and amides thereof.

As used herein, the term "sulfonic acid or a derivative thereof" includes SO$_3$H and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

As used herein, the term "phosphinic acid or a derivative thereof" includes P(R)O$_2$H and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonic acid or a derivative thereof" includes PO$_3$H$_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —(CH$_2$)$_x$Z$^X$, where x is an integer from 0-6 and Z$^X$ is selected from halogen, hydroxy, alkanoyloxy, including C$_1$-C$_6$ alkanoyloxy, optionally substituted aroyloxy, alkyl, including C$_1$-C$_6$ alkyl, alkoxy, including C$_1$-C$_6$ alkoxy, cycloalkyl, including C$_3$-C$_8$ cycloalkyl, cycloalkoxy, including C$_3$-C$_8$ cycloalkoxy, alkenyl, including C$_2$-C$_6$ alkenyl, alkynyl, including C$_2$-C$_6$ alkynyl, haloalkyl, including C$_1$-C$_6$ haloalkyl, haloalkoxy, including C$_1$-C$_6$ haloalkoxy, halocycloalkyl, including C$_3$-C$_8$ halocycloalkyl, halocycloalkoxy, including C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, and nitro; or Z$^X$ is selected from —CO$_2$R$^4$ and —CONR$^5$R$^6$, where R$^4$, R$^5$, and R$^6$ are each independently selected in each occurrence from hydrogen, C$_1$-C$_6$ alkyl, aryl-C$_1$-C$_6$ alkyl, and heteroaryl-C$_1$-C$_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al. Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl and optionally substituted heteroaryl$(C_2-C_{16})$alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; immunosuppressants, stimulants; decongestants; antiemetics; diuretics; antispasmodics; antiasthmatics; anti-Parkinson agents; expectorants; cough suppressants; mucolytics; and mineral and nutritional additives.

Further, the drug can be any drug known in the art which is cytotoxic, enhances tumor permeability, inhibits tumor cell proliferation, promotes apoptosis, decreases anti-apoptotic activity in target cells, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysins, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vinca alkaloids, such as vincristine, vinblastine, vindesine, vinorelbine and analogs and derivative thereof such as deacetylvinblastine monohydrazide (DAVLBH), colchicine, colchicine derivatives, allocolchicine, thiocolchicine, trityl cysteine, halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include rapamycins, such as sirolimus or everolimus, penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

In another embodiment, the drug is selected from a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, everolimus, ispinesib, budesonide, dasatinib, an epothilone, a maytansine, and a tyrosine kinase inhibitor, including analogs and derivatives of the foregoing. In another embodiment, the ligand conjugate includes at least two drugs (D) selected illustratively from a vinca alkaloid, a cryptophycin, bortezomib, thiobortezomib, a tubulysin, aminopterin, a rapamycin, such as everolimus or sirolimus, paclitaxel, docetaxel, doxorubicin, daunorubicin, everolimus, α-amanatin, verucarin, didemnin B, geldanomycin, purvalanol A, ispinesib, budesonide, dasatinib, an epothilone, a maytansine, and a tyrosine kinase inhibitor, including analogs and derivatives of the foregoing. In one variation, the drugs (D) are the same. In another variation, the drugs (D) are different.

As used herein, tubulysins refer generally to tetrapeptide compounds of the formula

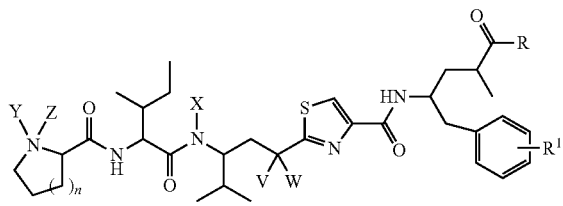

and pharmaceutical salts thereof, where n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl, each of which is optionally substituted;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, and $OR^6$, where $R^6$ is hydrogen or optionally substituted aryl, a phenol protecting group, a prodrug moiety, alkyl, arylalkyl, $C(O)R^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative.

Conjugates of each of the foregoing tubulysins are described herein. In one variation, Z is methyl. In another variation, $R^1$ is H. In another variation, $R^1$ is $OR^6$ at C(4), where $R^6$ is H, alkyl, or COR'. In another variation, V is H, and W is $OC(O)R^3$.

Natural tubulysins are generally linear tetrapeptides consisting of N-methyl pipecolic acid (Mep), isoleucine (Ile), an unnatural aminoacid called tubuvalin (Tuv), and either an unnatural aminoacid called tubutyrosine (Tut, an analog of tyrosine) or an unnatural aminoacid called tubuphenylalanine (Tup, an analog of phenylalanine). In another embodiment, naturally occurring tubulysins, and analogs and derivatives thereof, of the following general formula are described

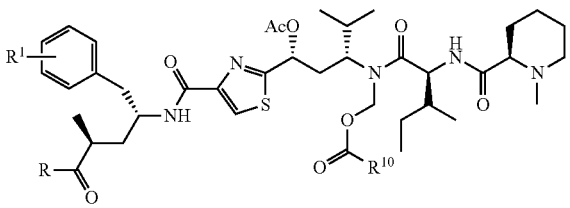

and pharmaceutical salts thereof, where R, $R^1$, and $R^{10}$ are as described in the various embodiments herein. Conjugates of each of the foregoing tubulysins are described herein.

In another embodiment, conjugates of naturally occurring tubulysins of the following general formula are described

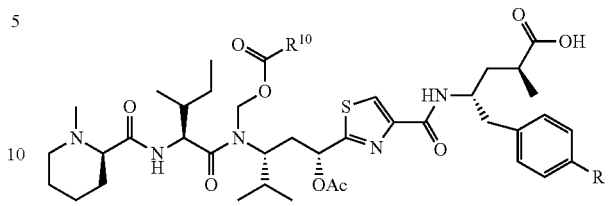

| Factor | $R^{10}$ | $R^1$ |
| --- | --- | --- |
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C=CH$ | OH |
| H | $CH_3$ | H |
| I | $CH_3$ | OH | and pharmaceutical salts thereof.

In another embodiment, the drug has the formula

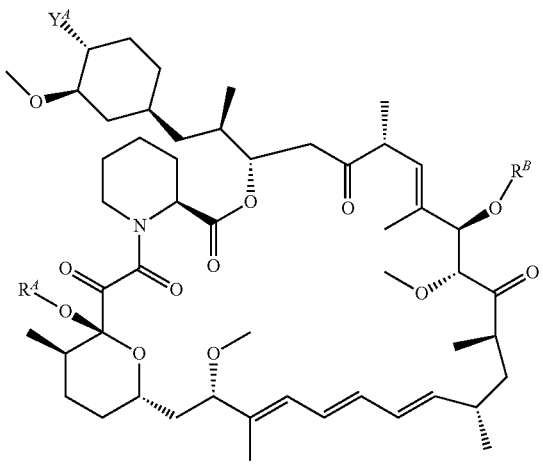

wherein $Y^A$ is $OR^C$ or $OCH_2CH_2OR^C$;

one of $R^A$, $R^B$, or $R^C$ is a bond connected to L; and the other two of $R^A$, $R^B$, and $R^C$ are independently selected in each case from the group consisting of hydrogen, optionally substituted heteroalkyl, prodrug forming group, and $C(O)R^D$, where $R^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

The ligand conjugates described herein can be administered in a combination therapy with any other known drug whether or not the additional drug is targeted. Illustrative additional drugs include, but are not limited to, peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins, antigens and antibodies thereto, haptens and antibodies thereto, hormones, lipids, phospholipids, liposomes, toxins, antibiotics, analgesics, bronchodilators, beta-blockers, antimicrobial agents, antihypertensive agents, cardiovascular agents including antiarrhythmics, cardiac glycosides, antianginals, vasodilators, central nervous system agents including stimulants, psychotropics, antimanics, and depressants, antiviral agents, antihistamines, cancer drugs including chemotherapeutic agents, tranquilizers, anti-depressants, H-2 antagonists, anticonvulsants, antinauseants, prostaglandins and prostaglandin analogs, muscle relaxants, anti-inflammatory substances, stimulants, decongestants, antiemetics, diuretics, antispasmodics, antiasthmatics, anti-Parkinson agents, expectorants, cough suppressants, mucolytics, and mineral and nutritional additives.

Illustrative examples of ligand conjugates are described below:

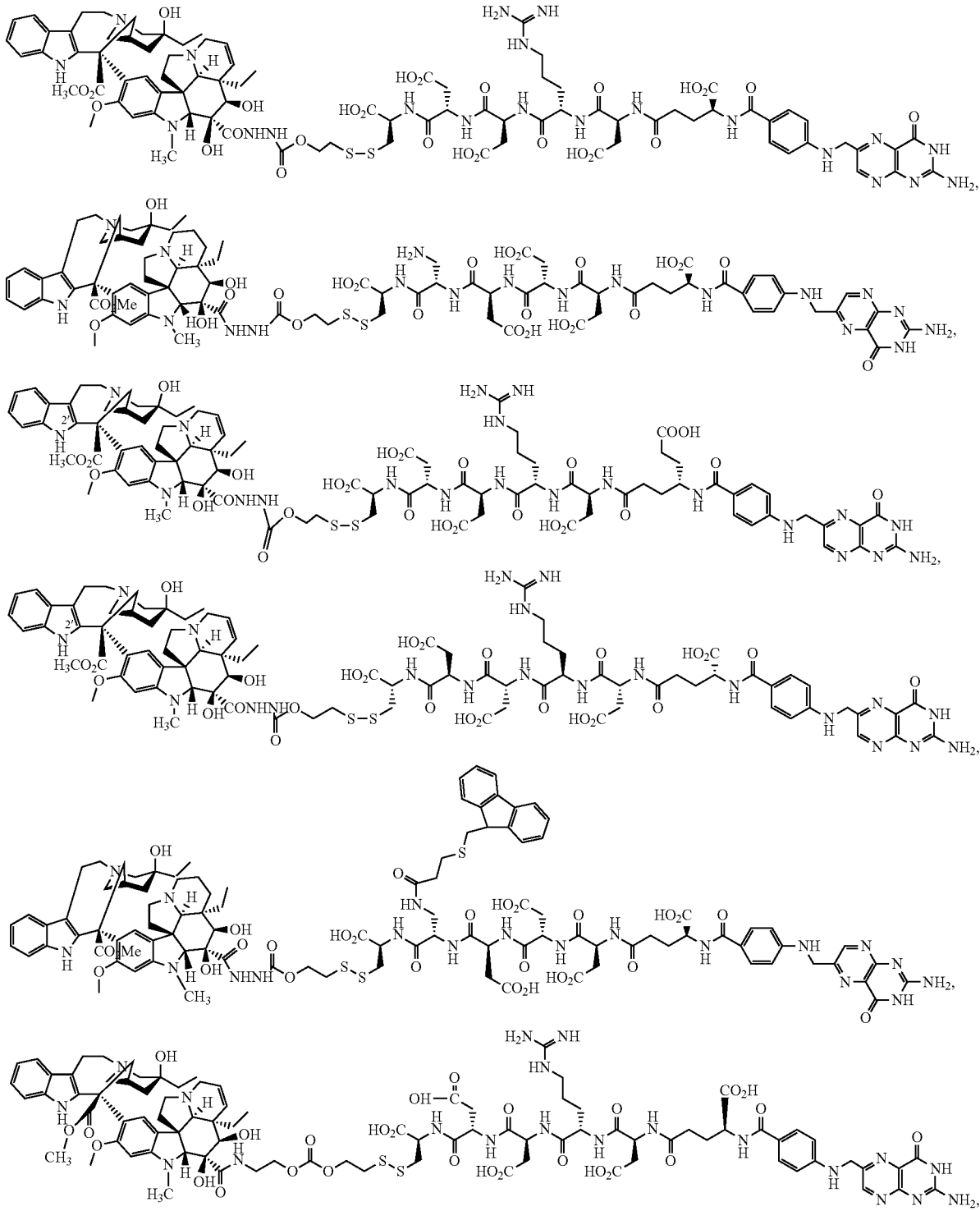

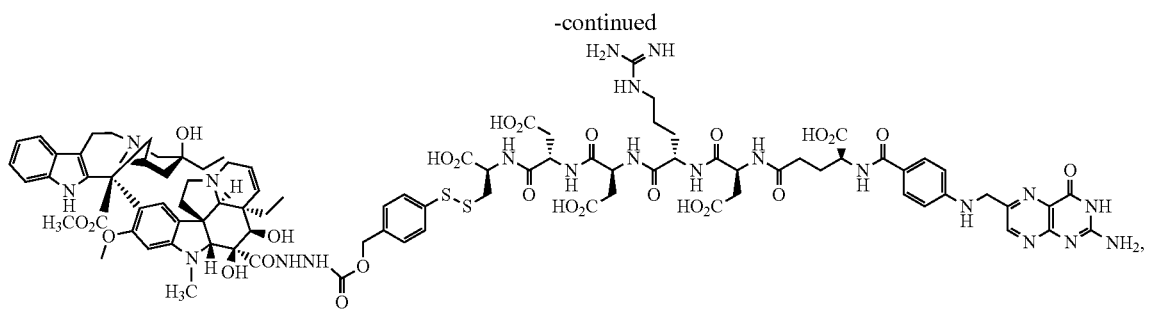
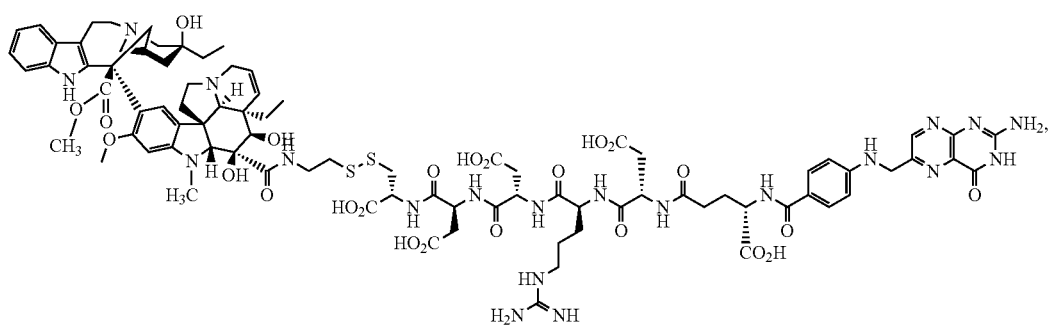
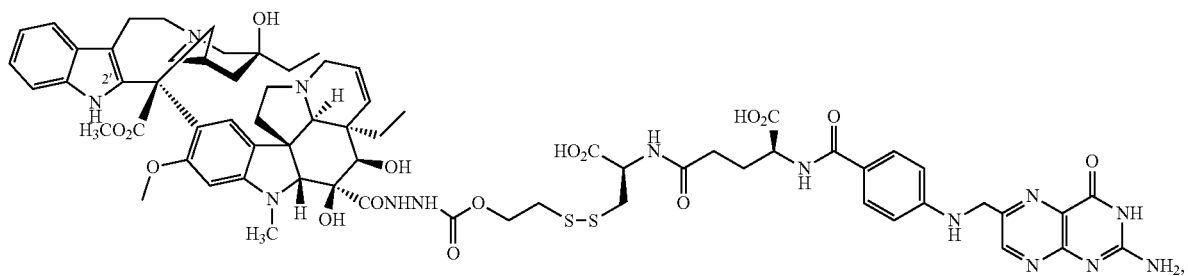
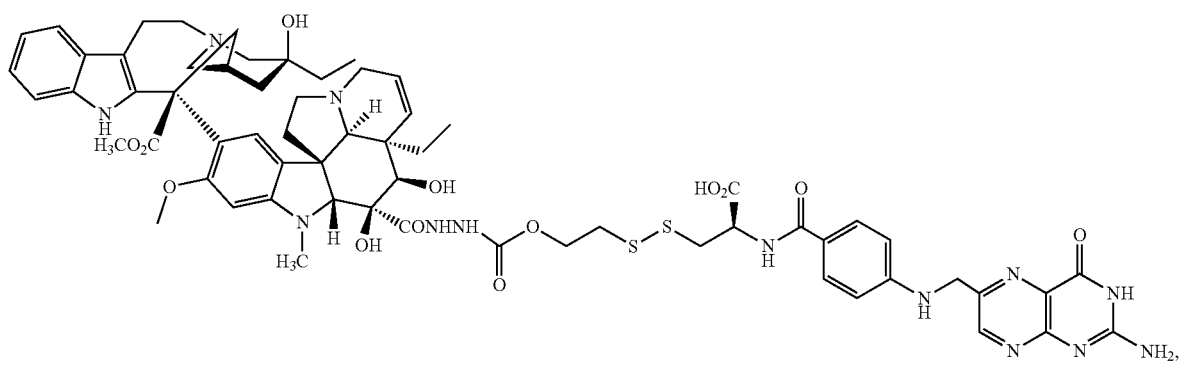

-continued
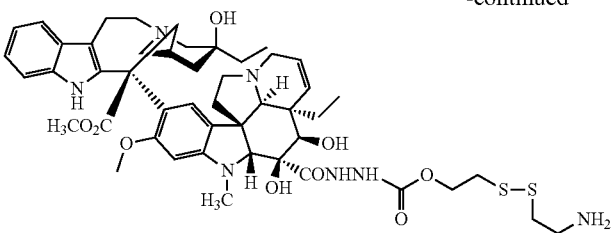
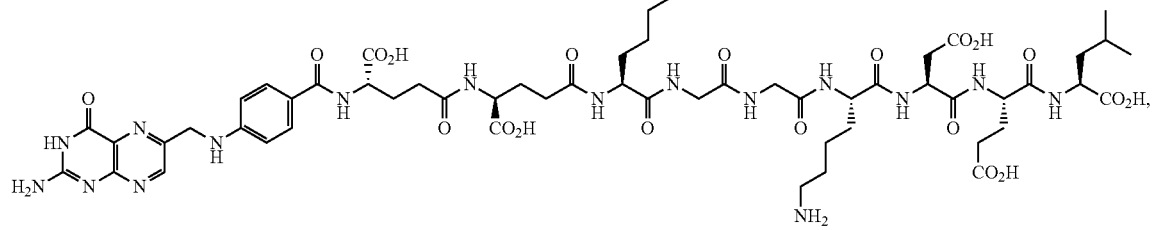
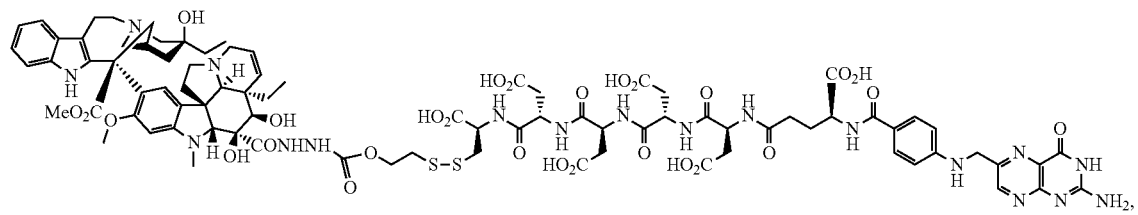
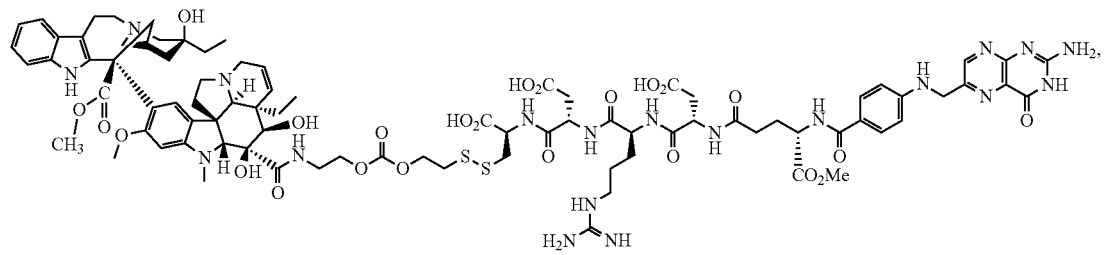
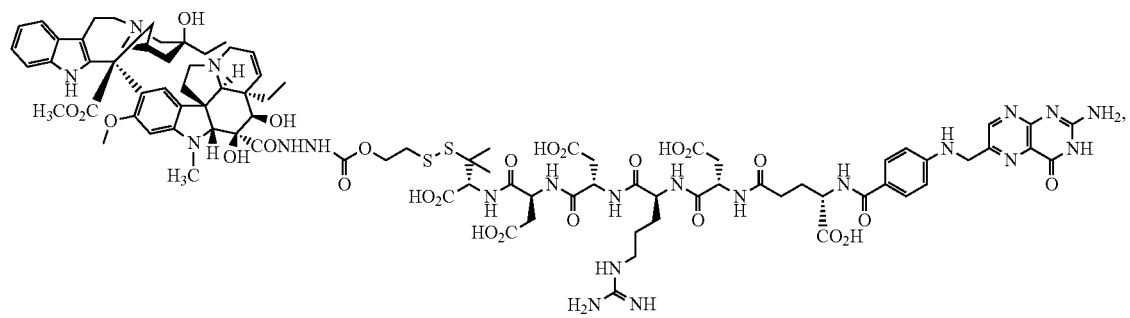
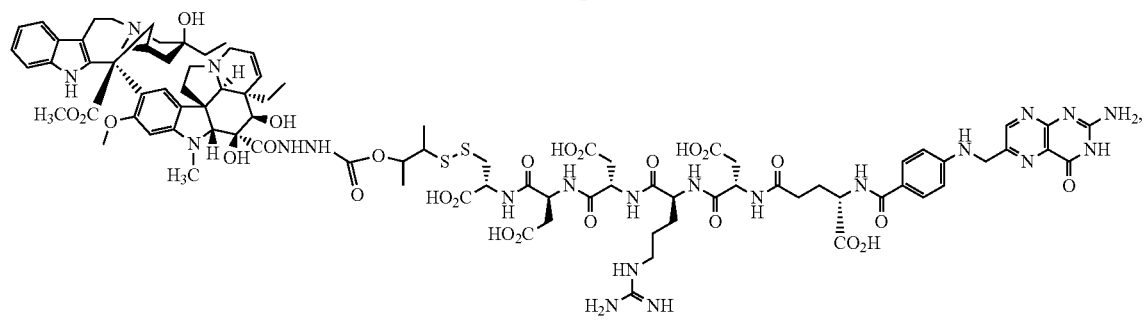

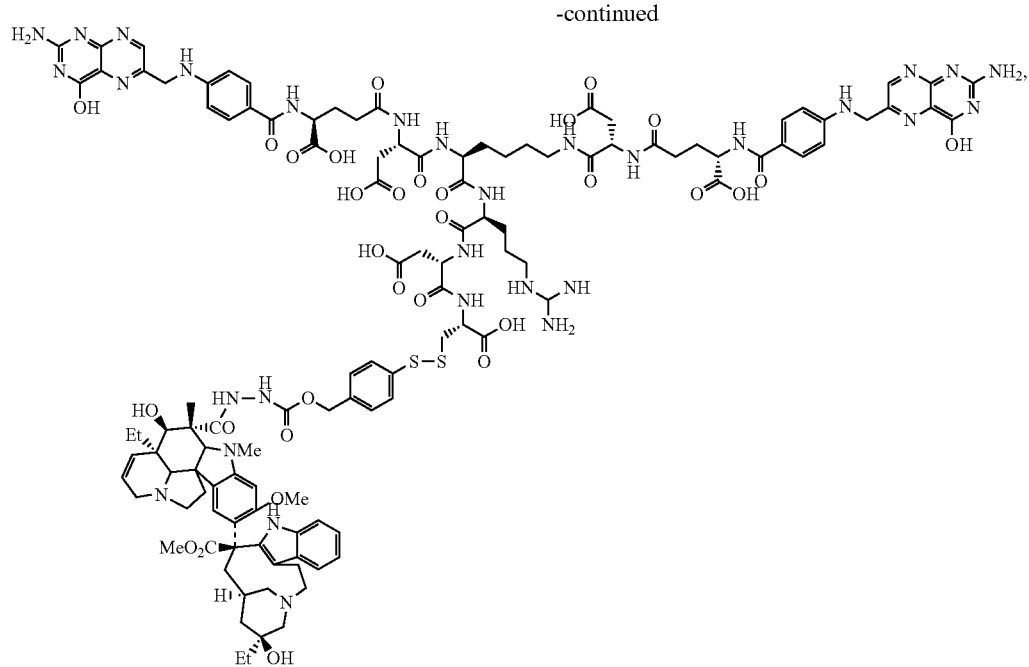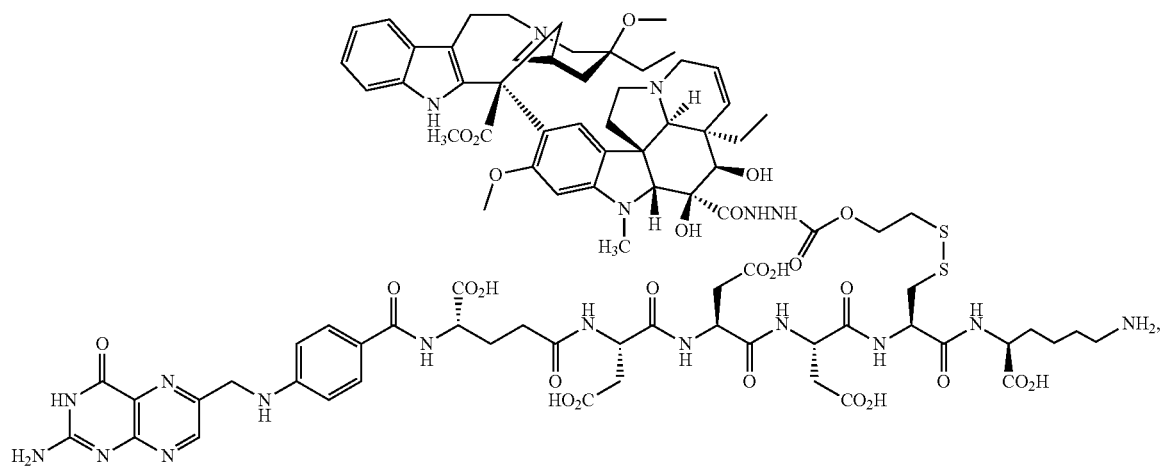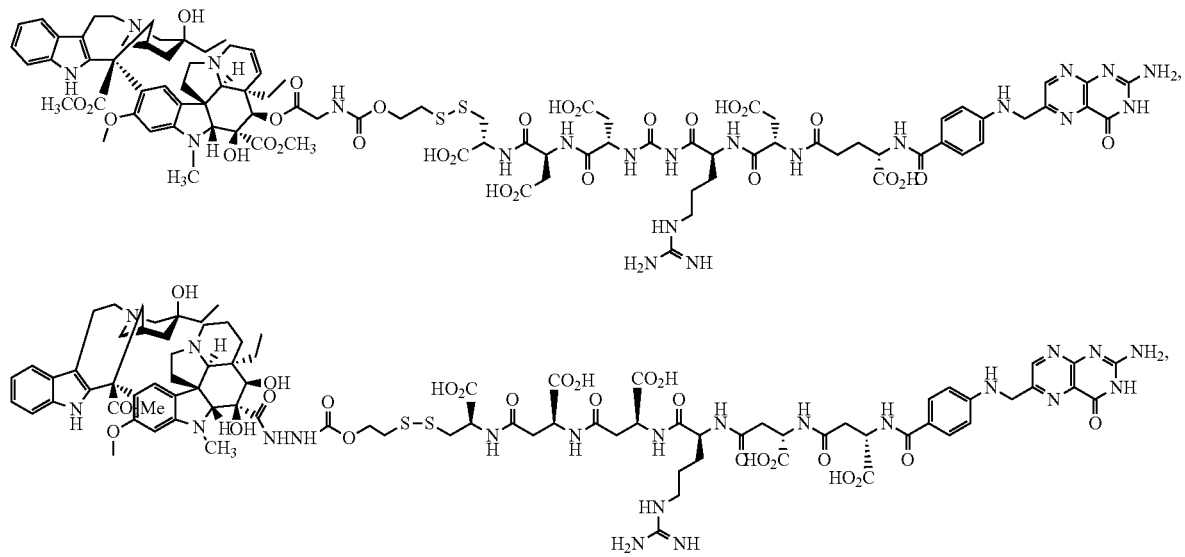

-continued
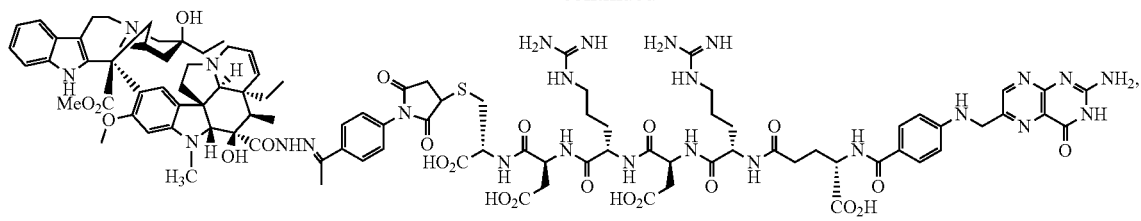
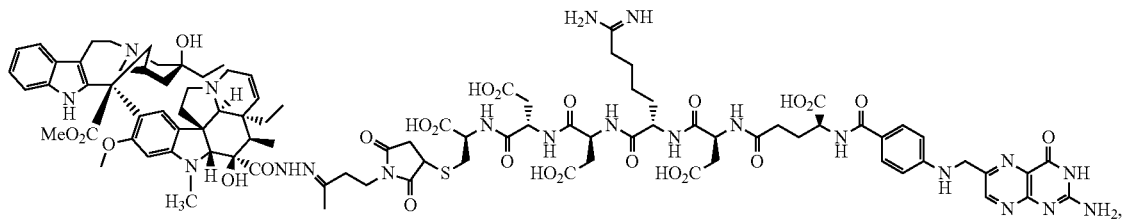
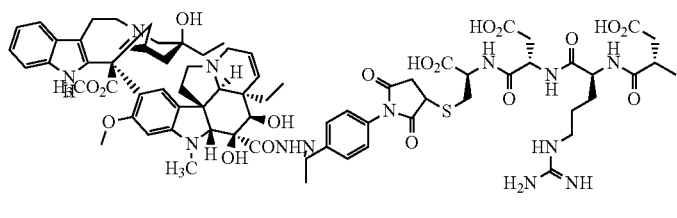
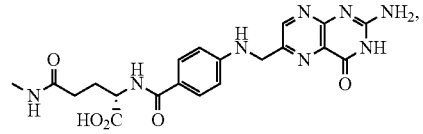
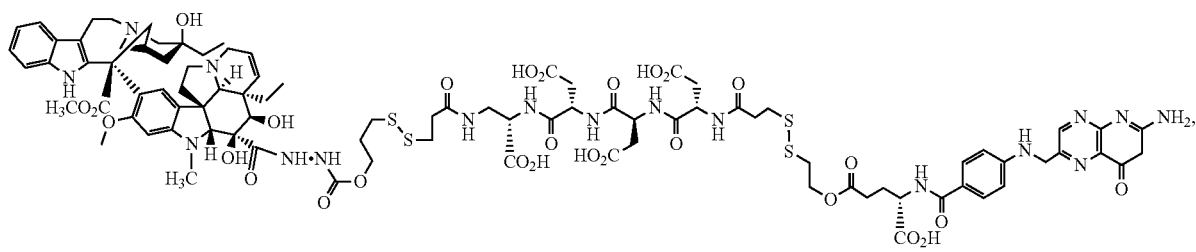
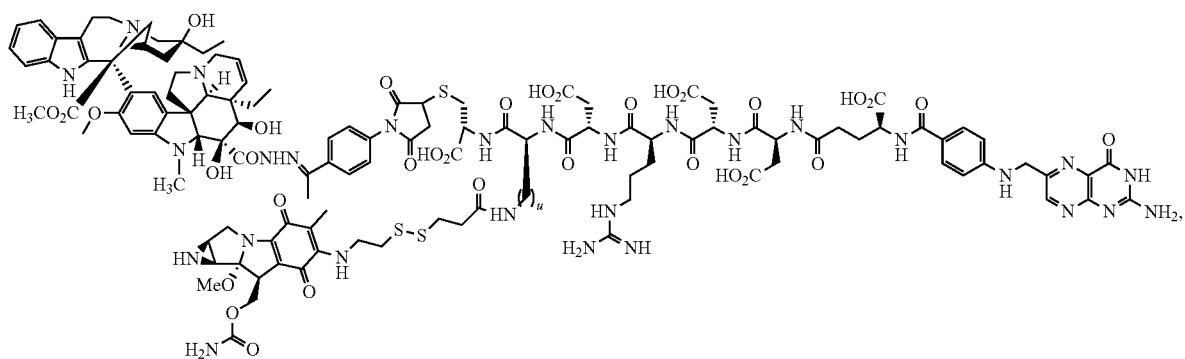

-continued
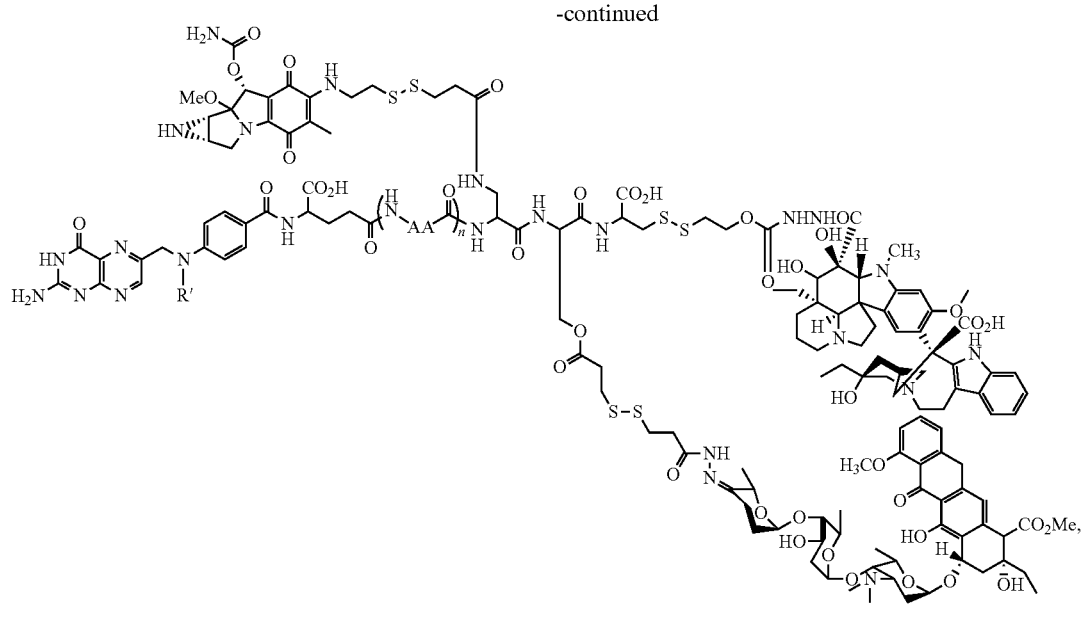
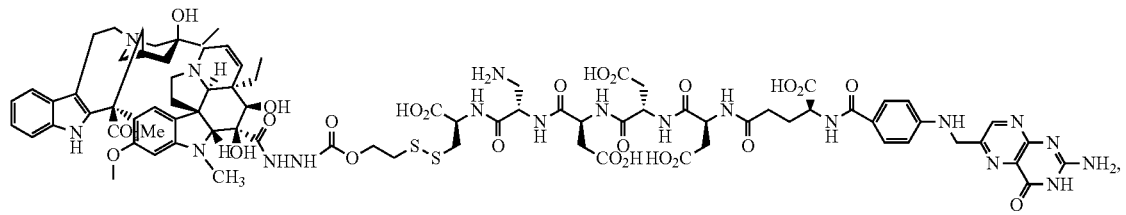
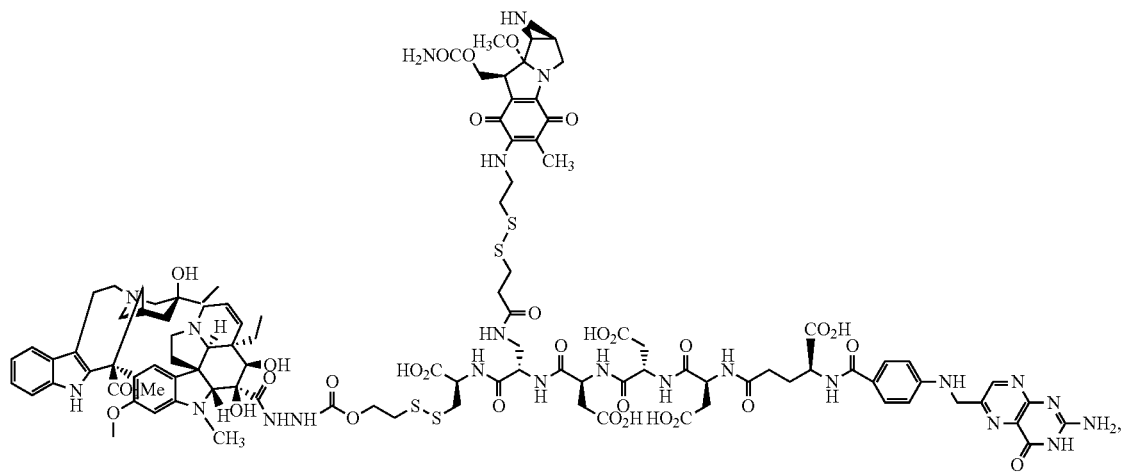
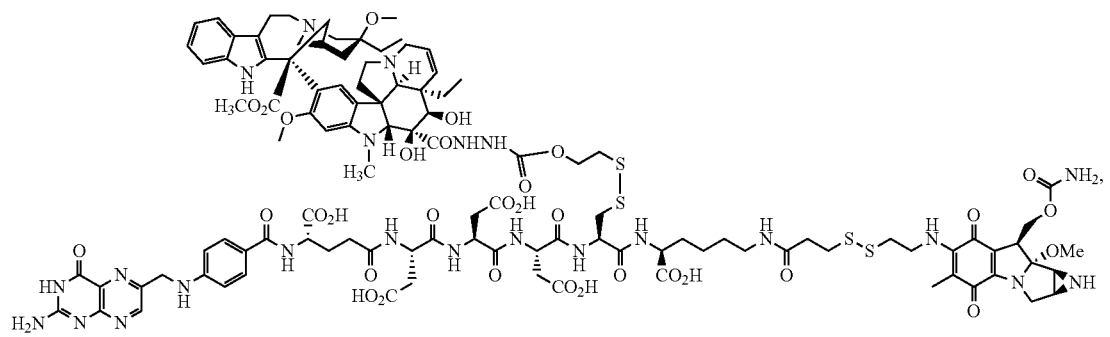

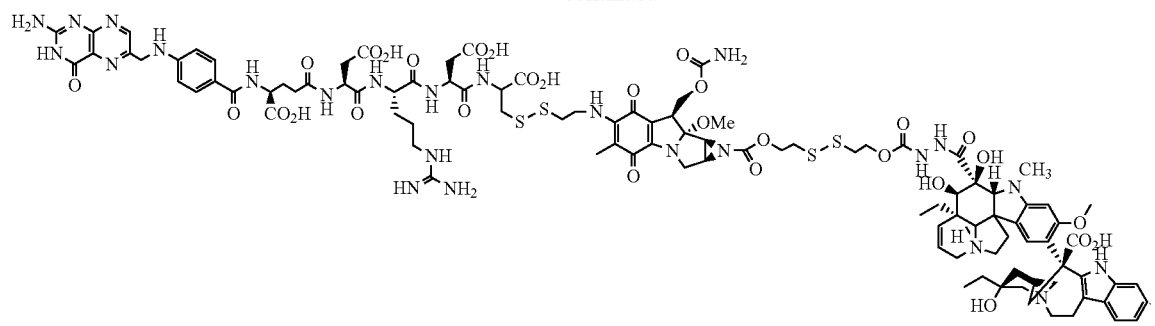
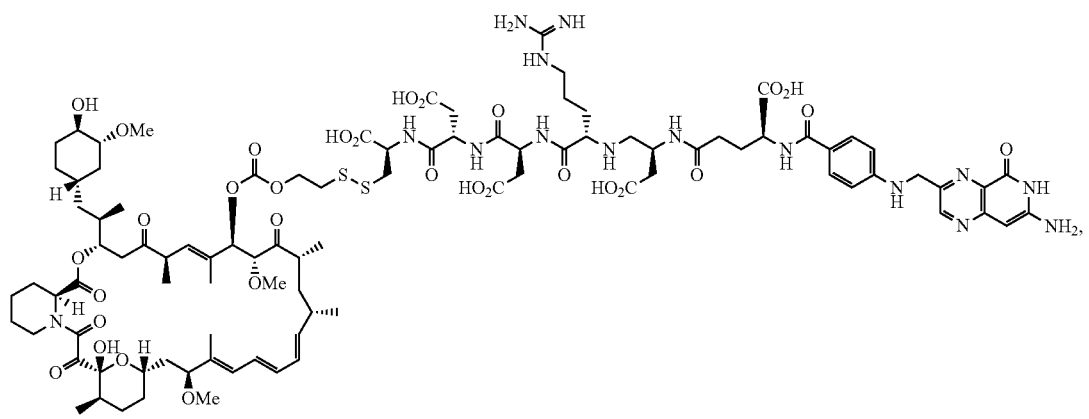
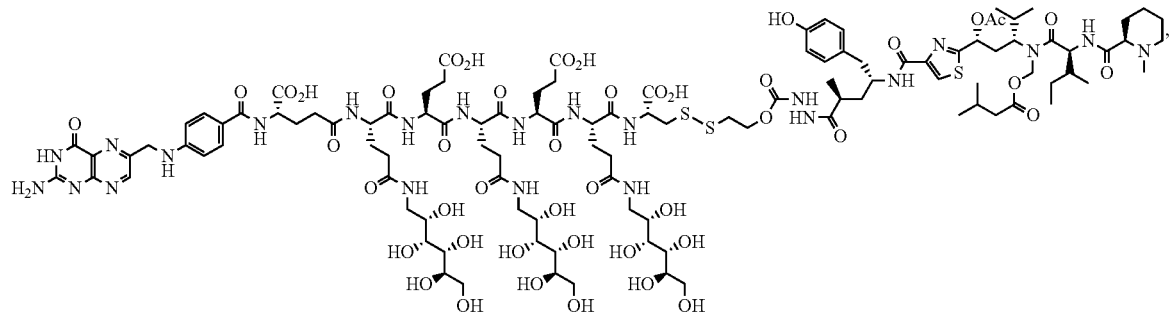 [SMILES: CCC(C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]
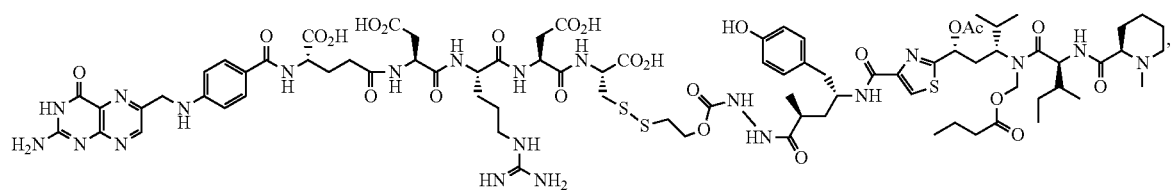
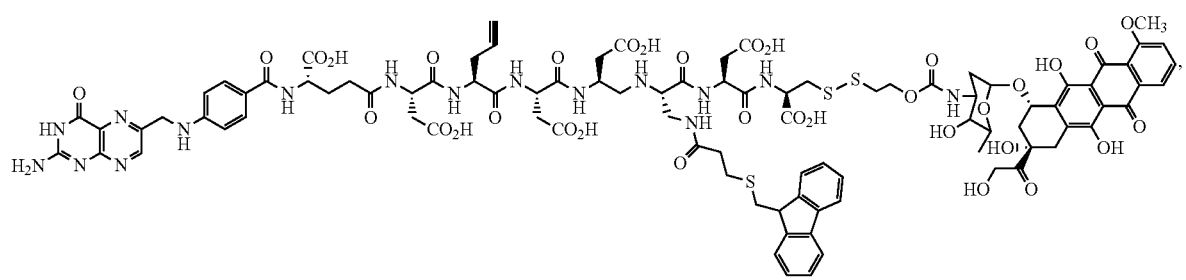

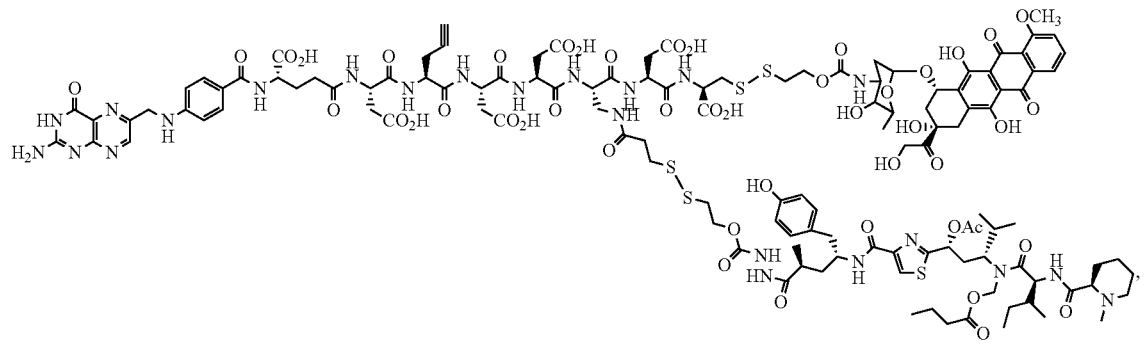
EC0247
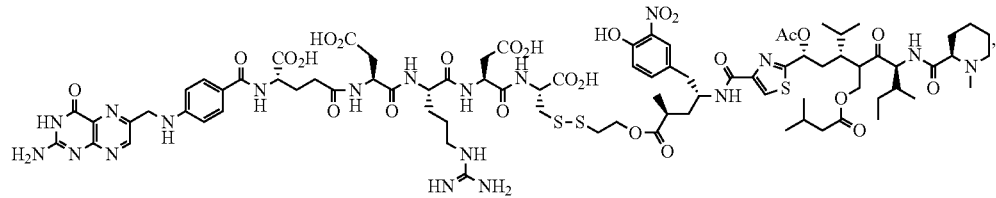
EC0302
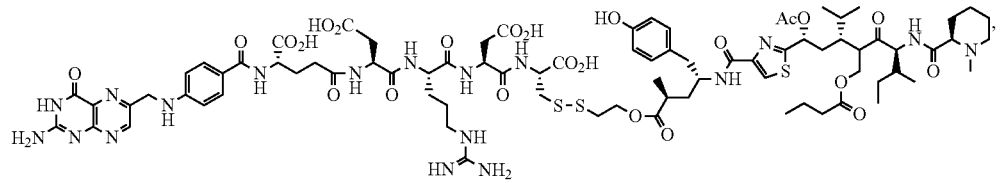
EC0317
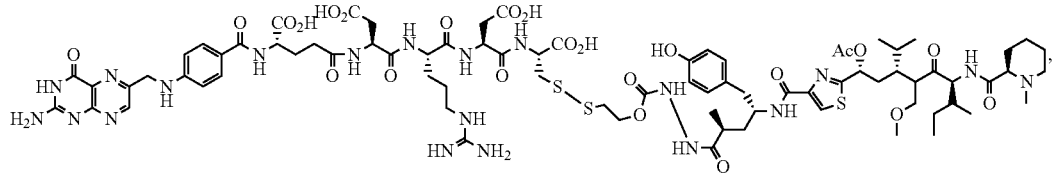
EC0436
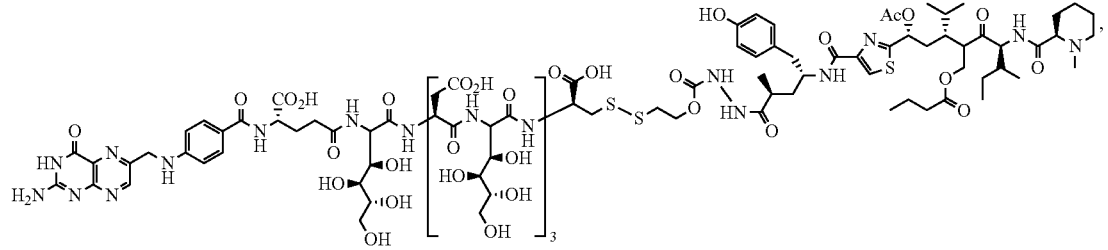
EC0334
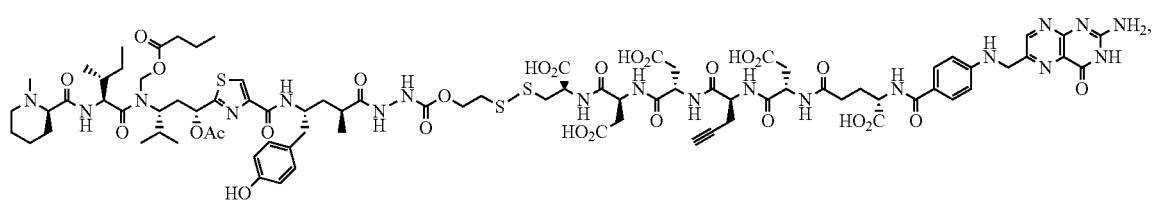
EC0444
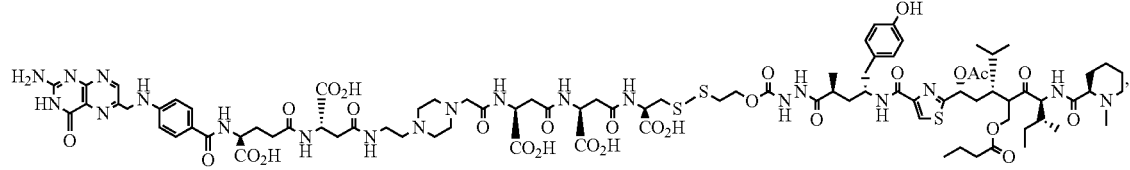

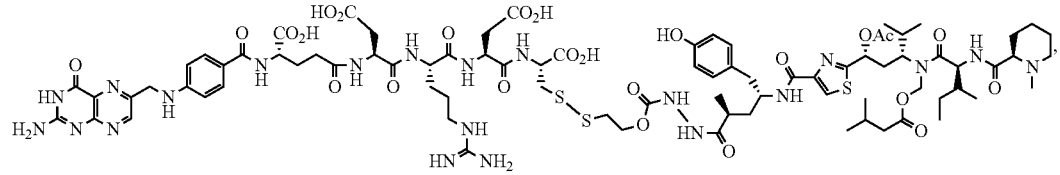
EC0510
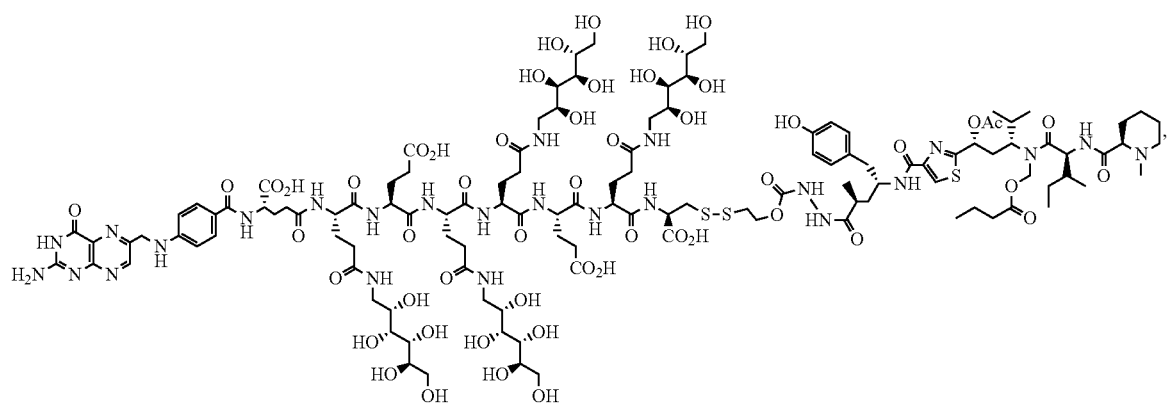
EC0530
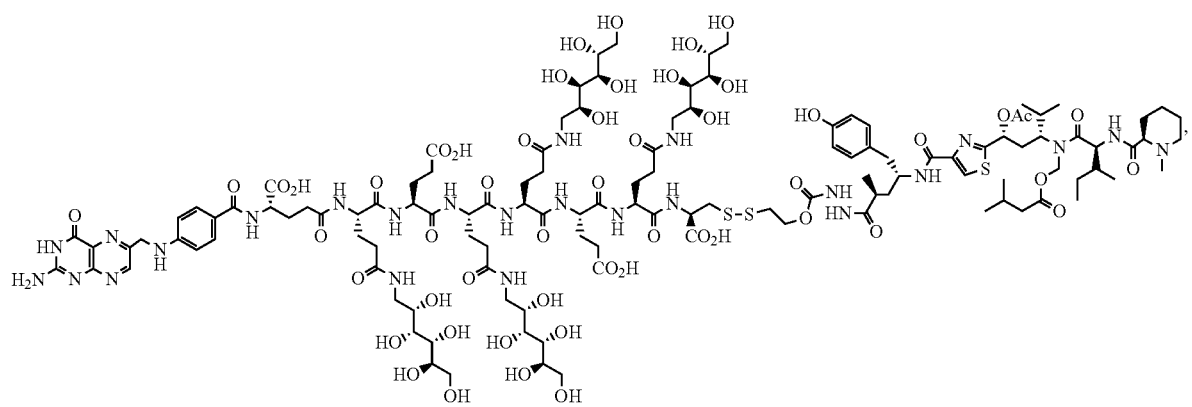
EC0533
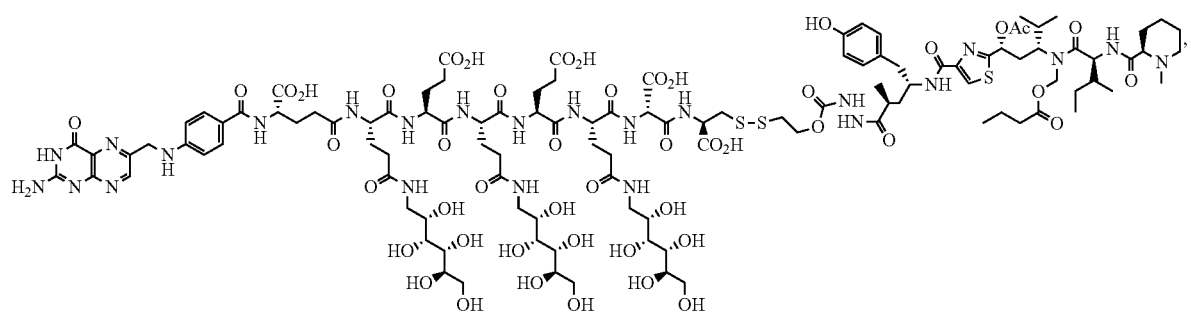
EC0543
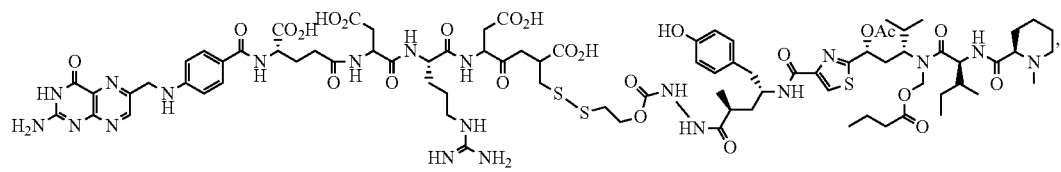
EC0305

-continued
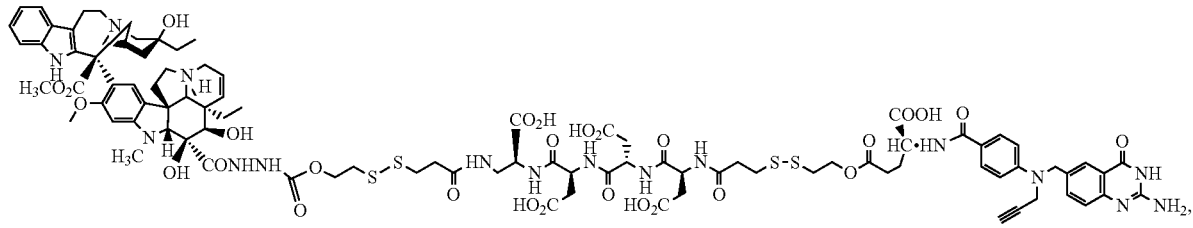
EC0358
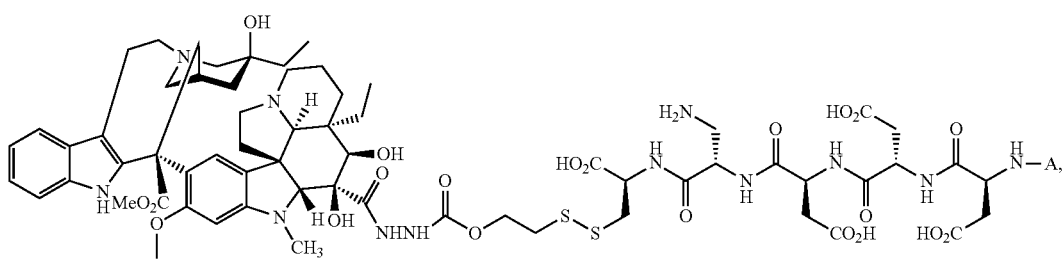
EC0284
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
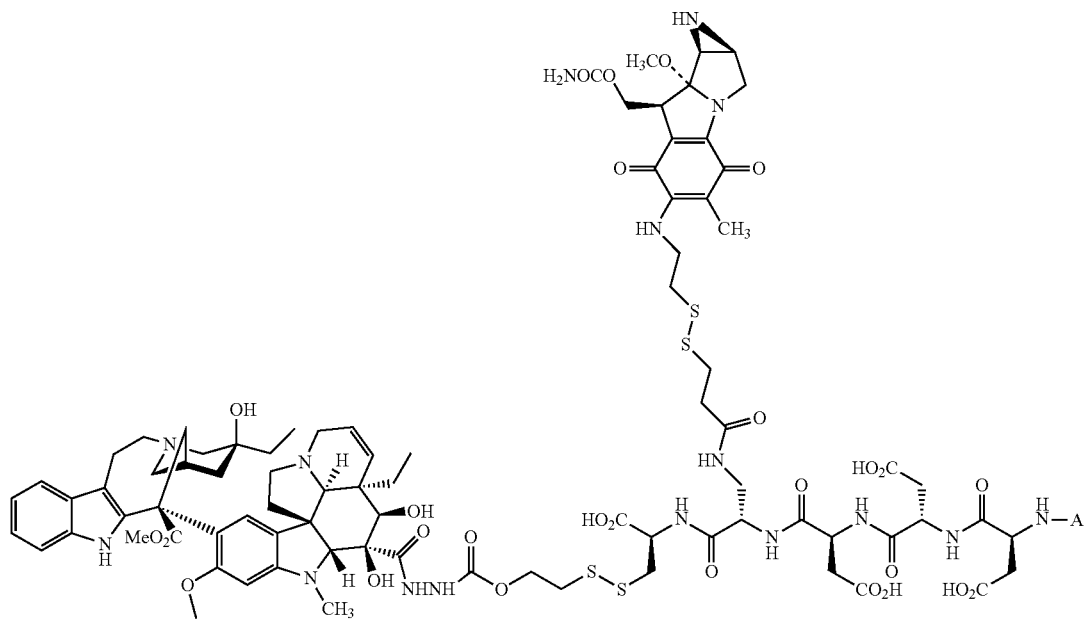
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.

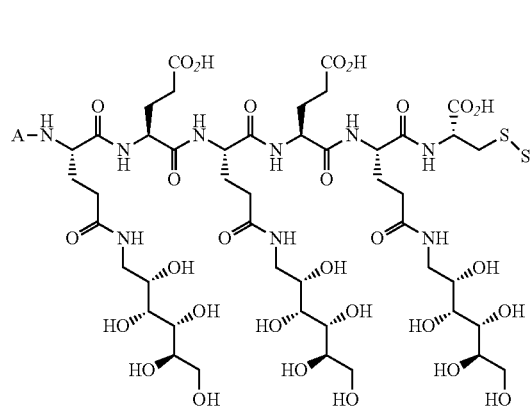
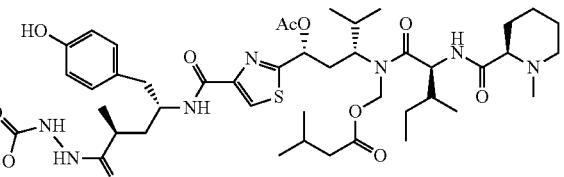
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
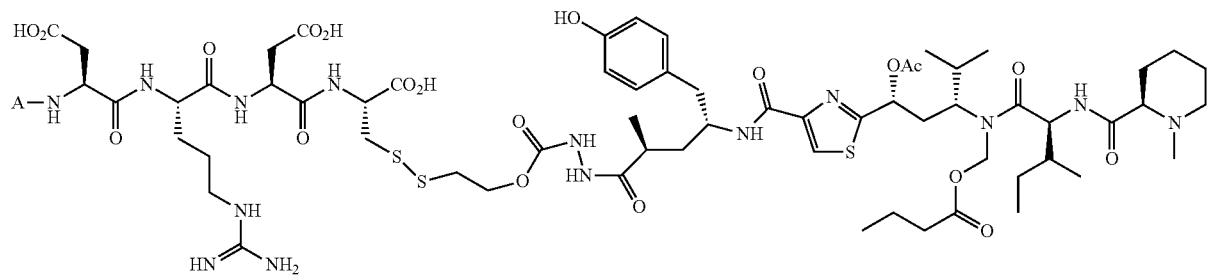
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
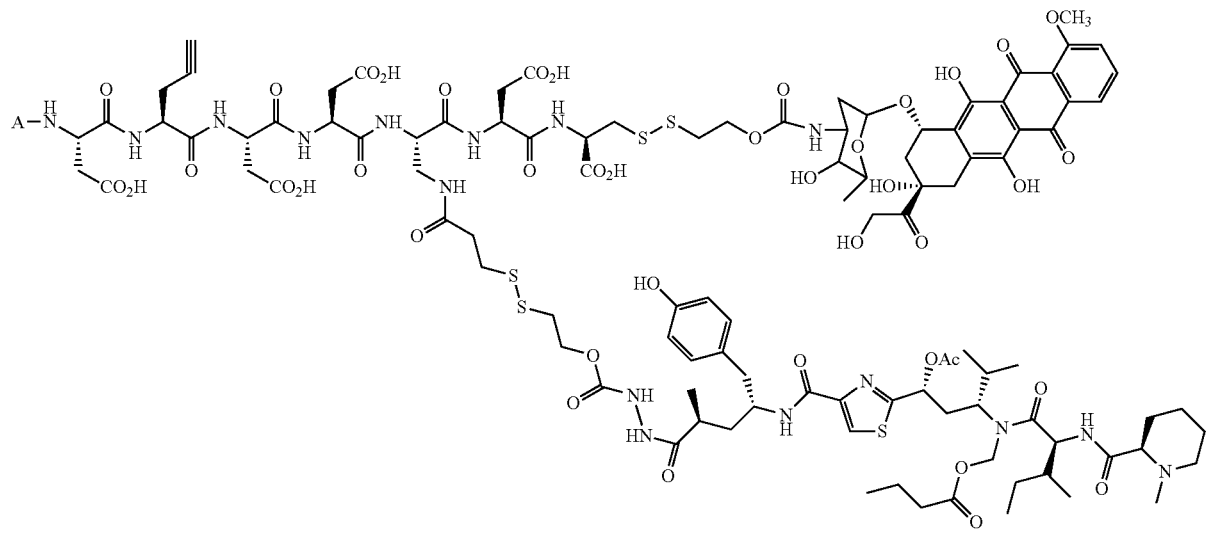
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.

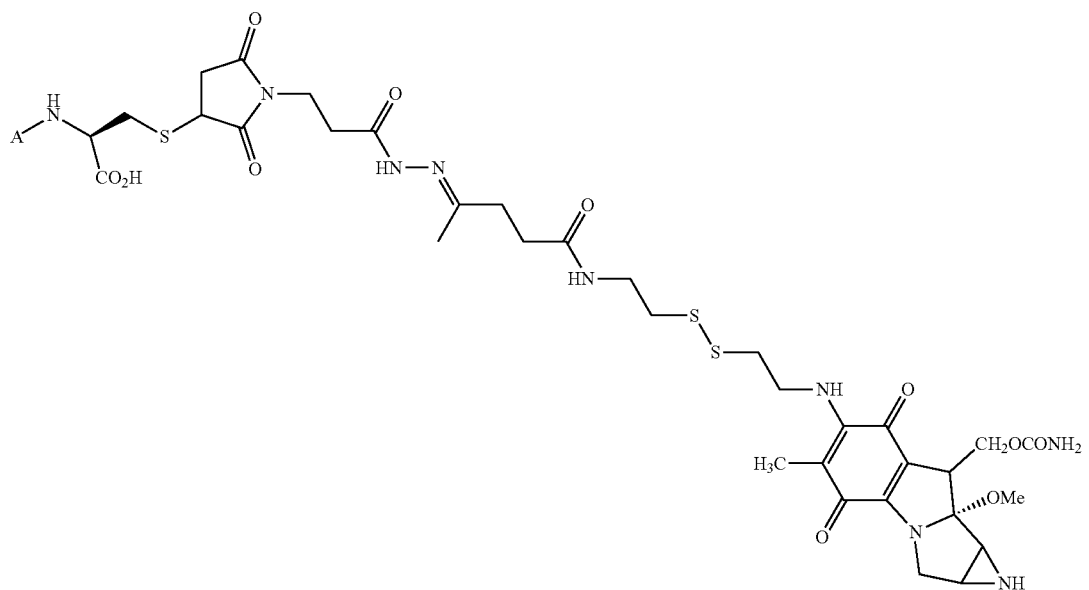
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
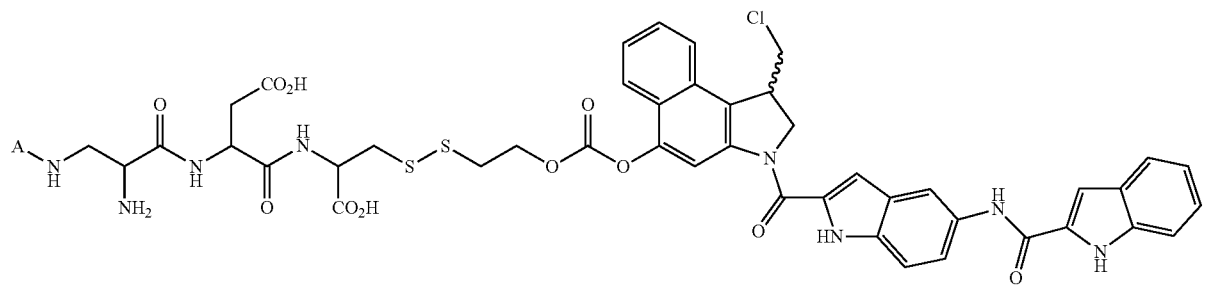
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
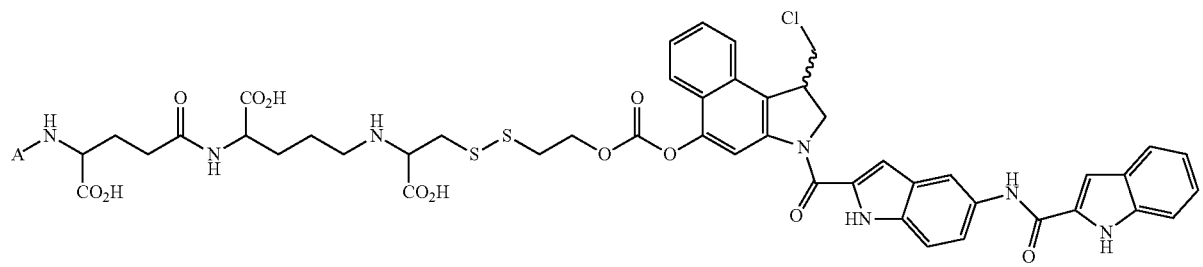
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.

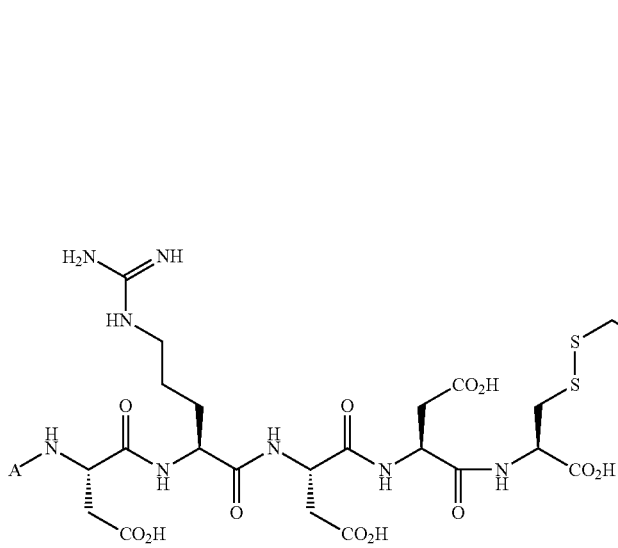
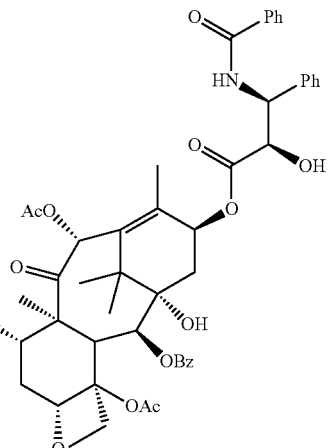
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
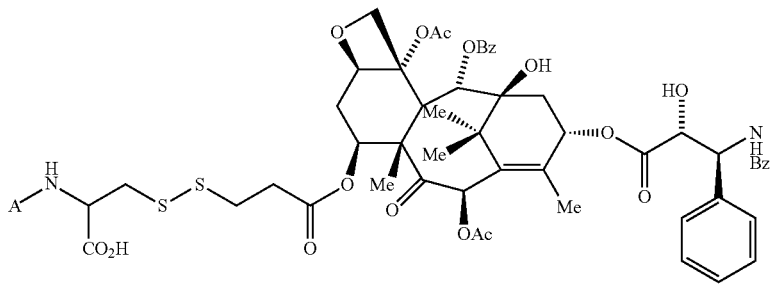
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
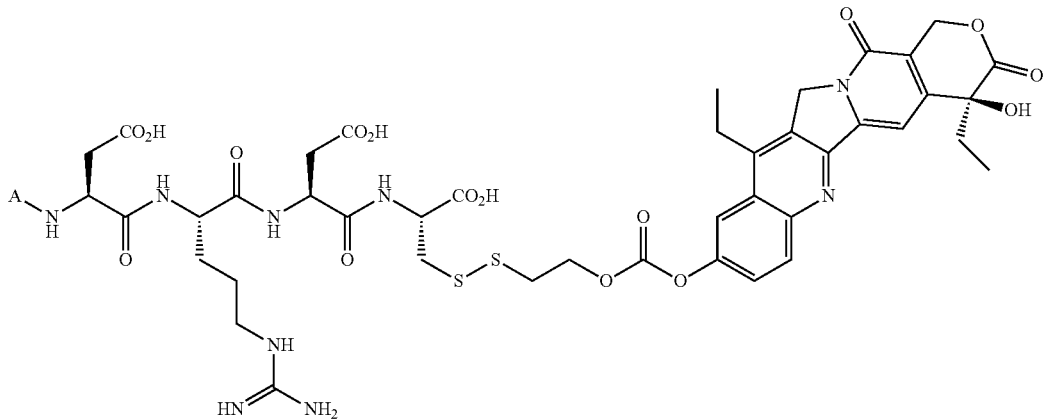
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.

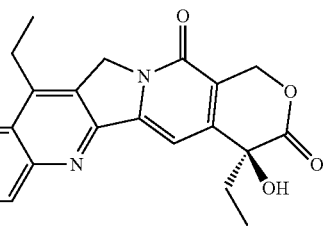
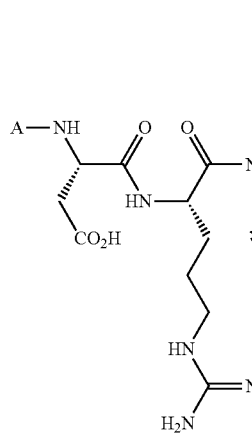
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
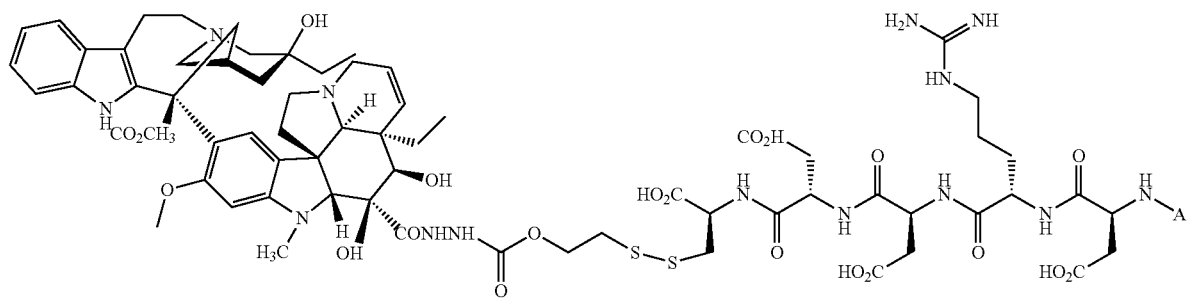
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
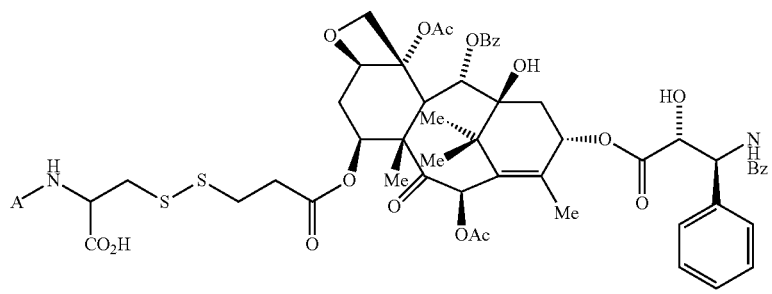
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.

121
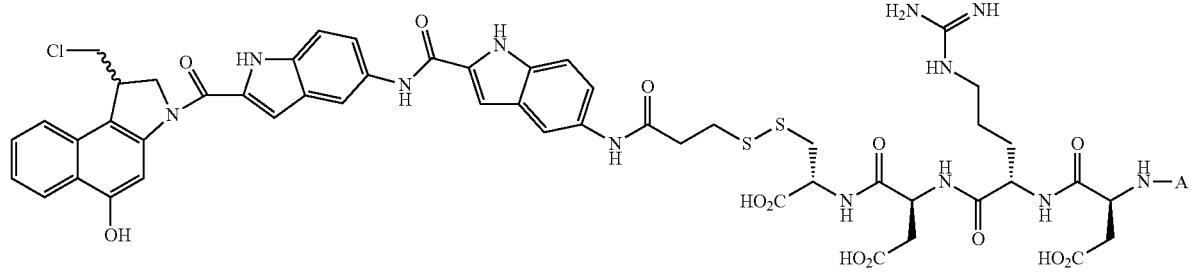
122
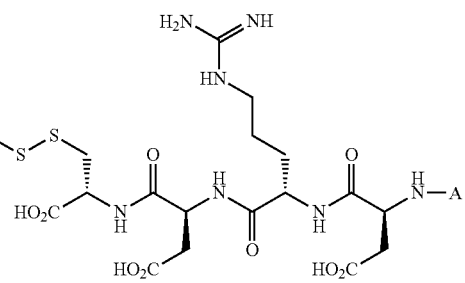
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
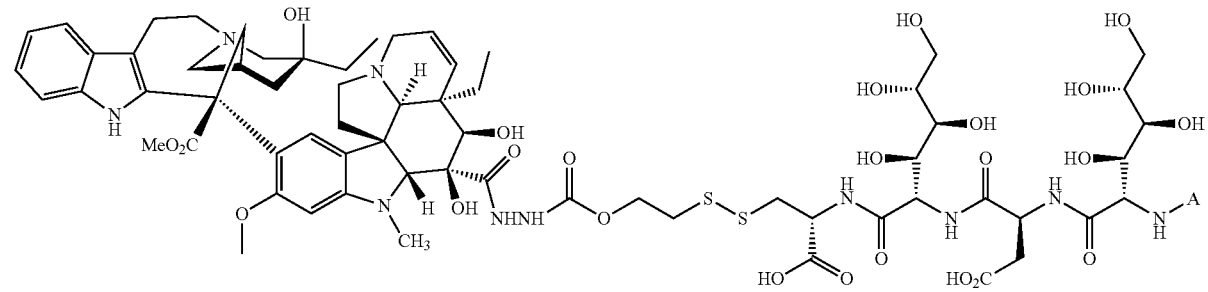
30
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
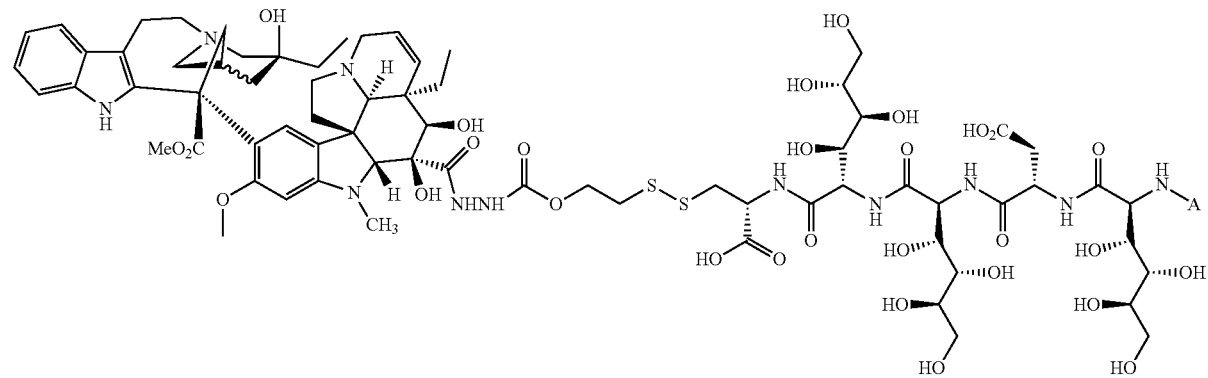

wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
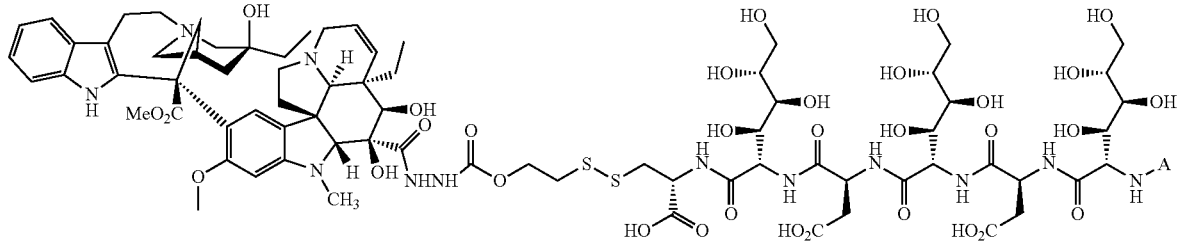
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
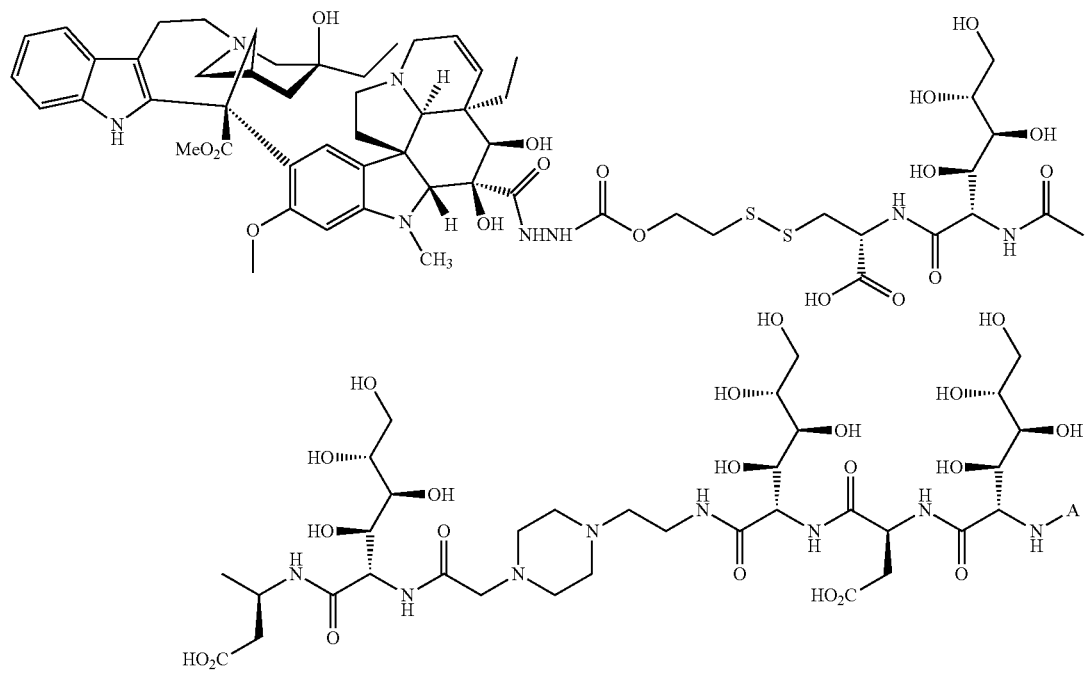
wherein A is N⁹—CH₃-5-d(i)PteGlu, 5-d(i)PteGlu, IAHQ, BW1843U89, 2-NH₂—ZD1694, ZD1694, CB3717, 5-dH₄PteAPBA, 5-dPteHCysA, or DDATHF.
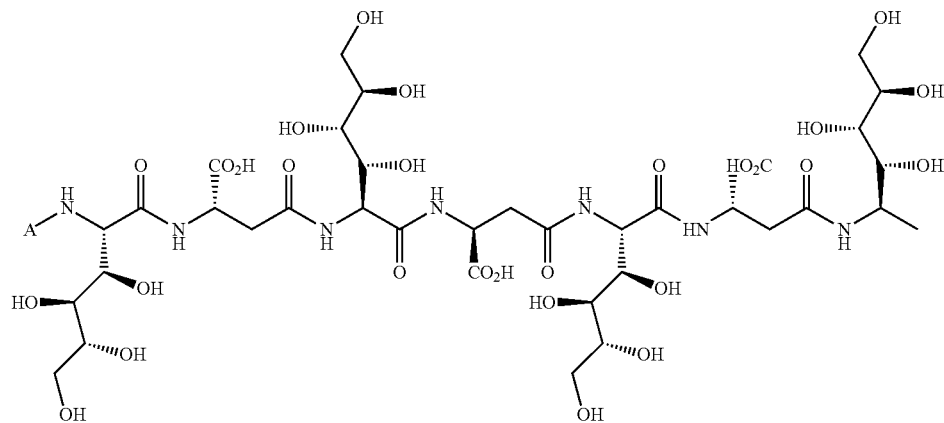

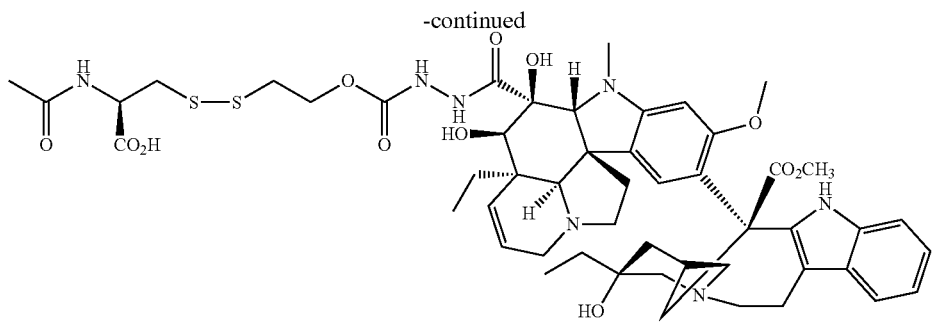
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF.
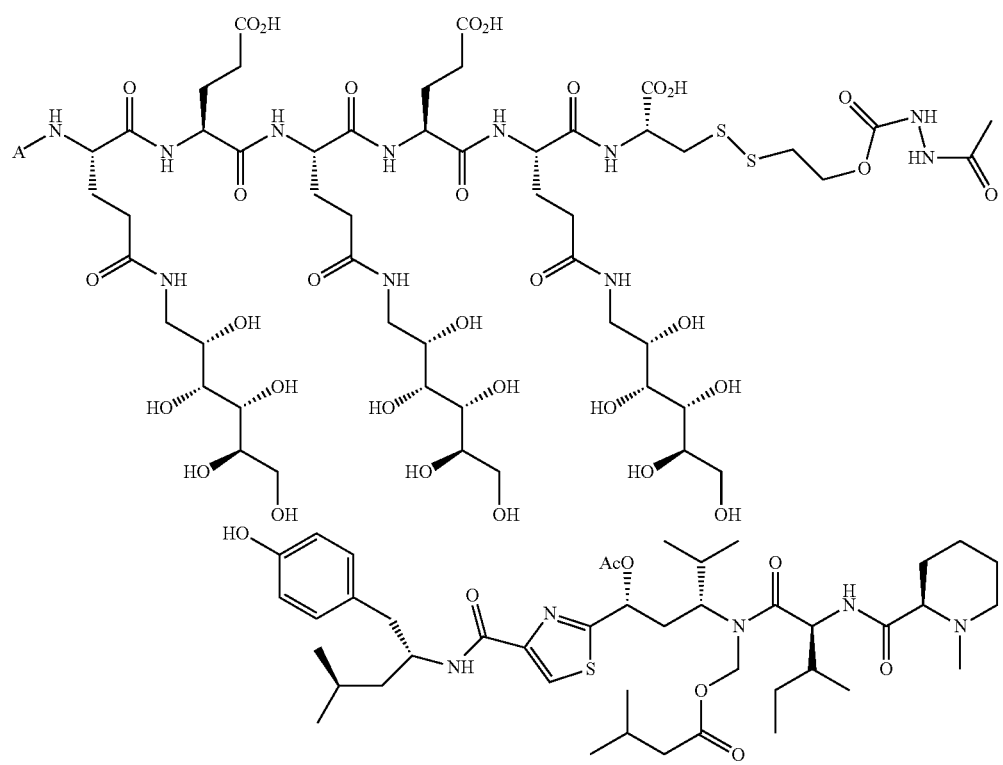
wherein A is $N^9$—$CH_3$-5-d(i)PteGlu, 5-d(i)PteGlu, IAHQ, BW1843U89, 2-$NH_2$—ZD1694, ZD1694, CB3717, 5-$dH_4$PteAPBA, 5-dPteHCysA, or DDATHF,

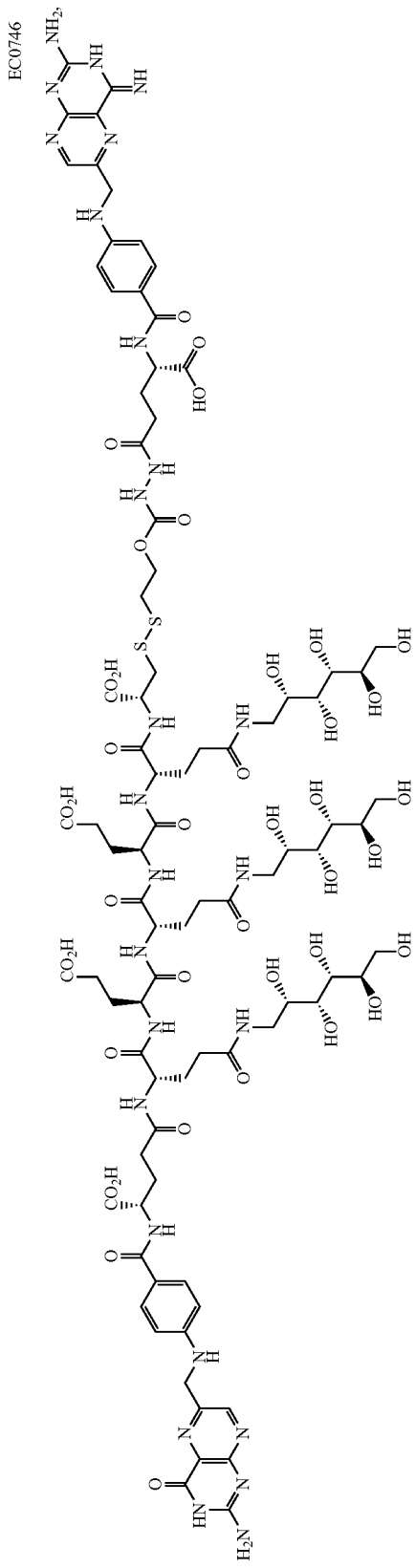
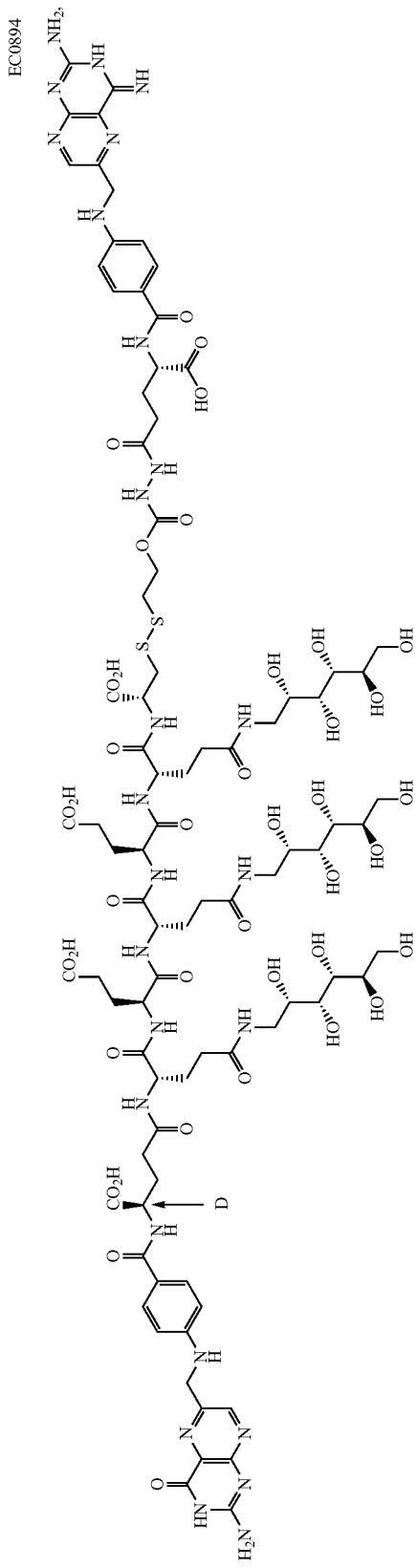

-continued
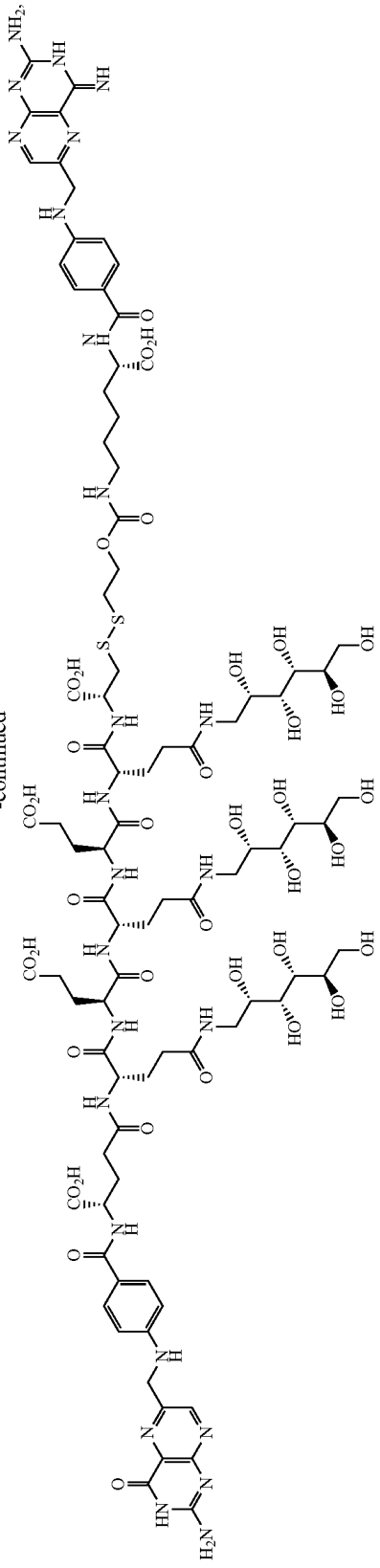
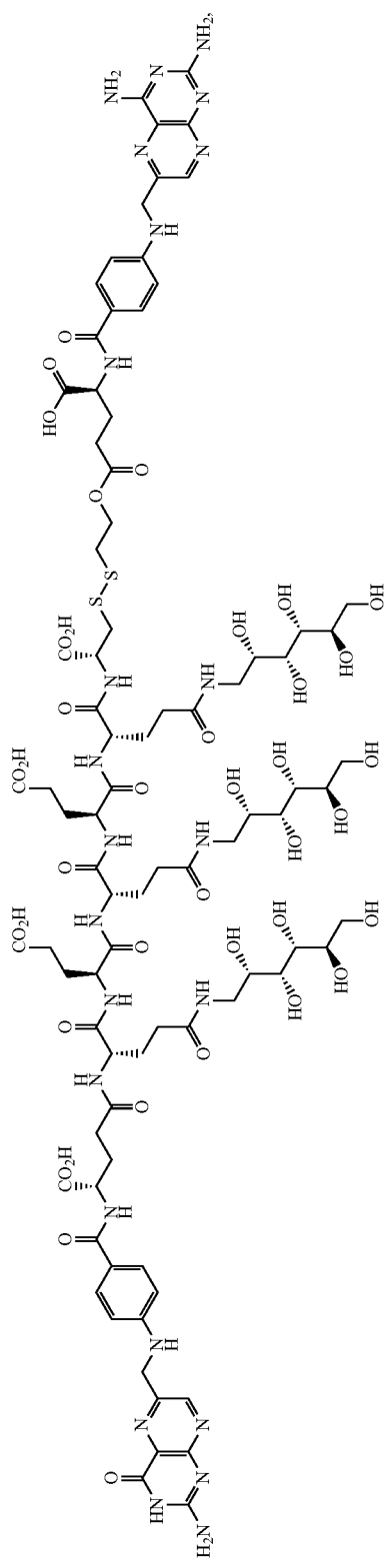

-continued
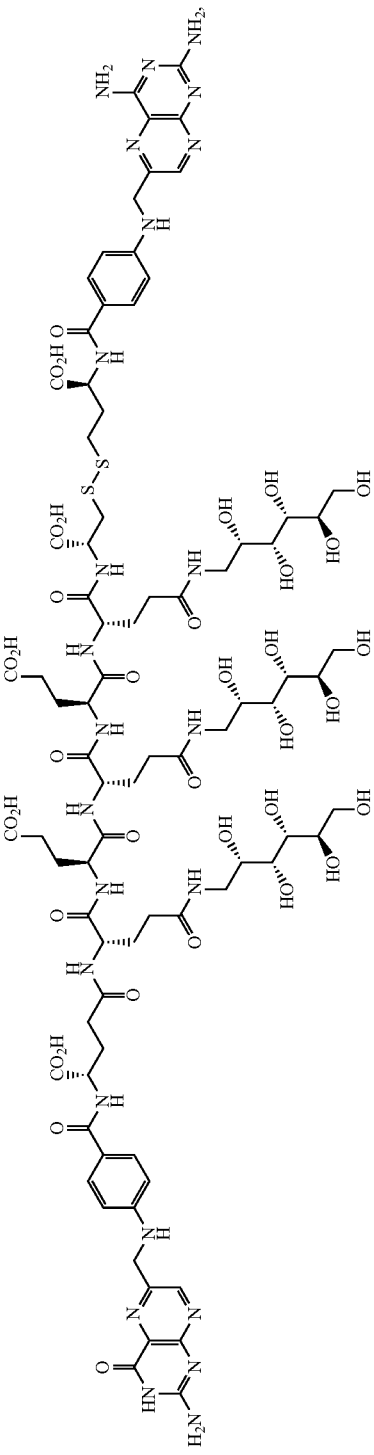
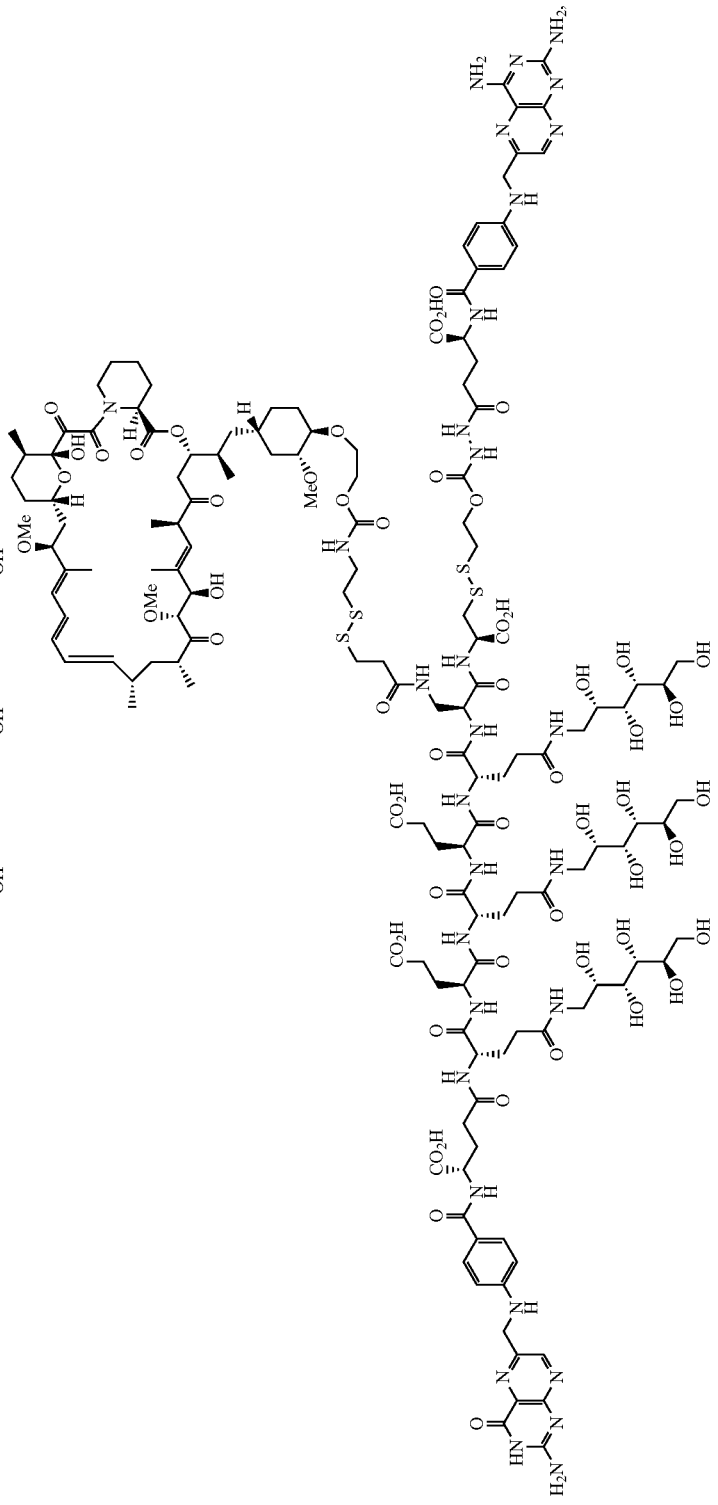

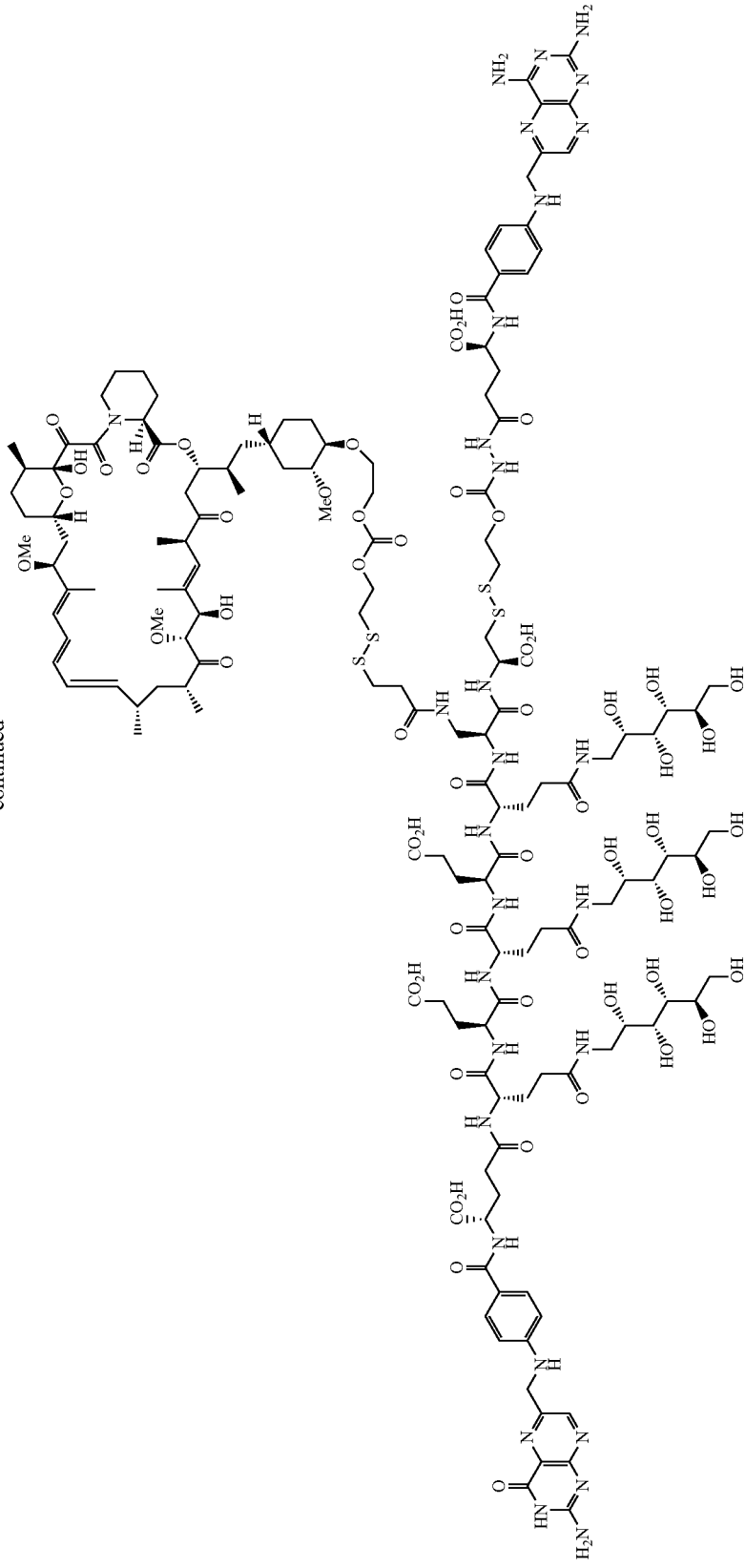

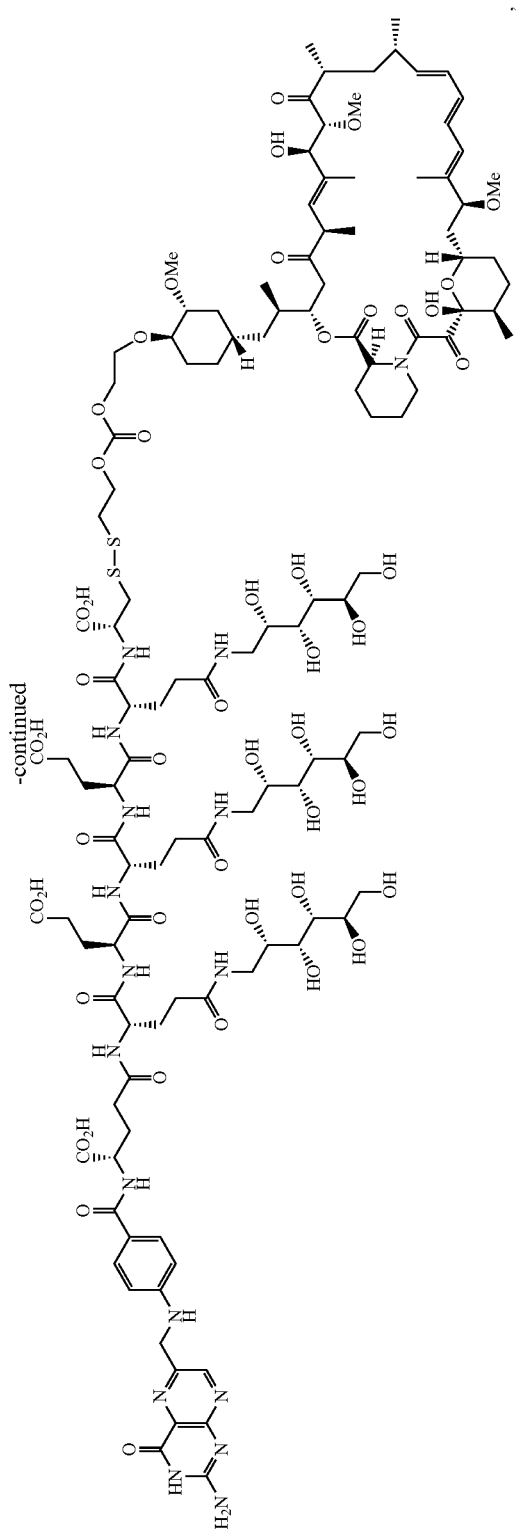
-continued

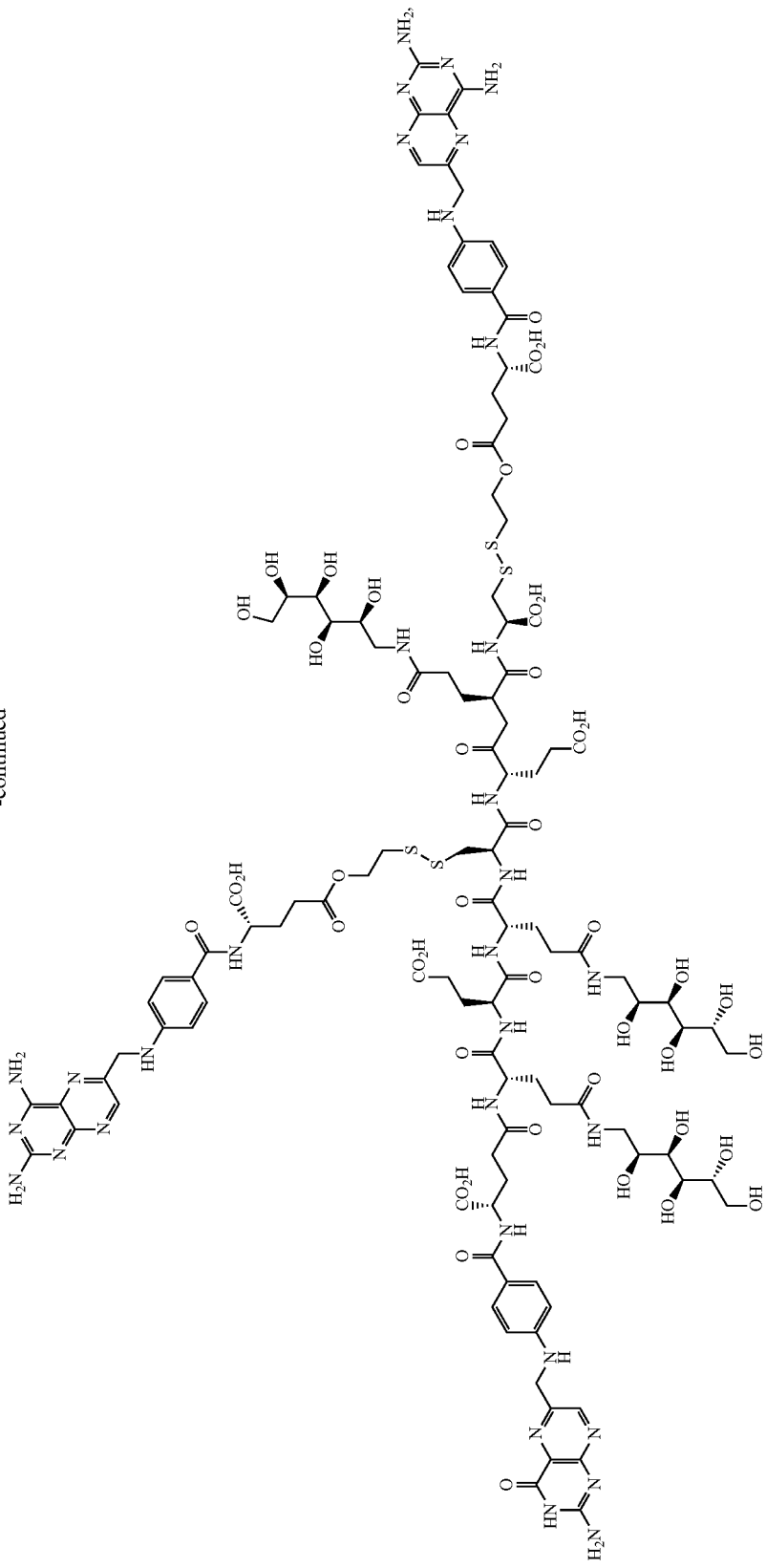

-continued
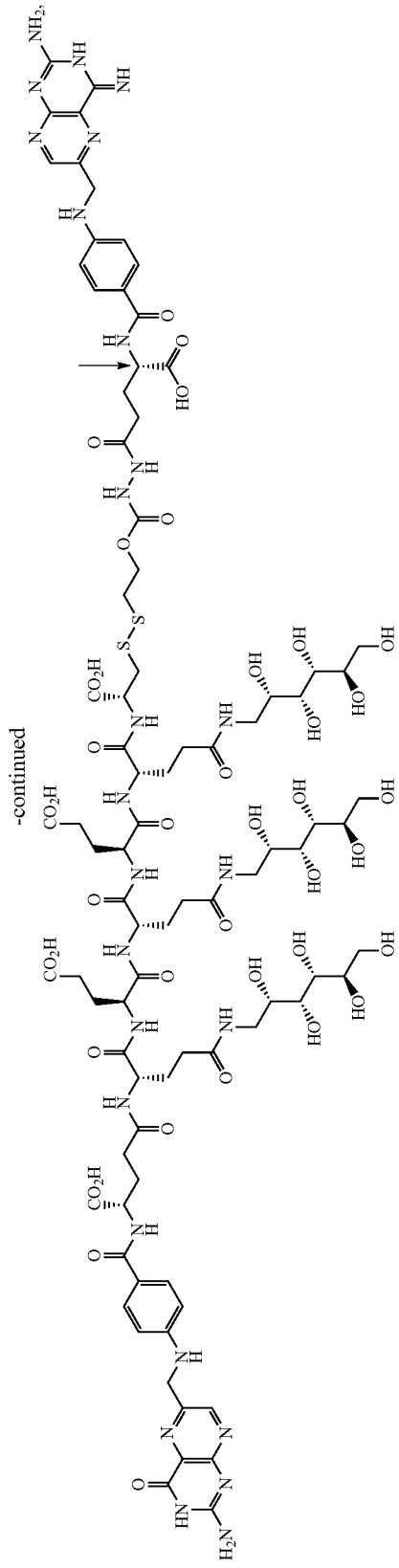
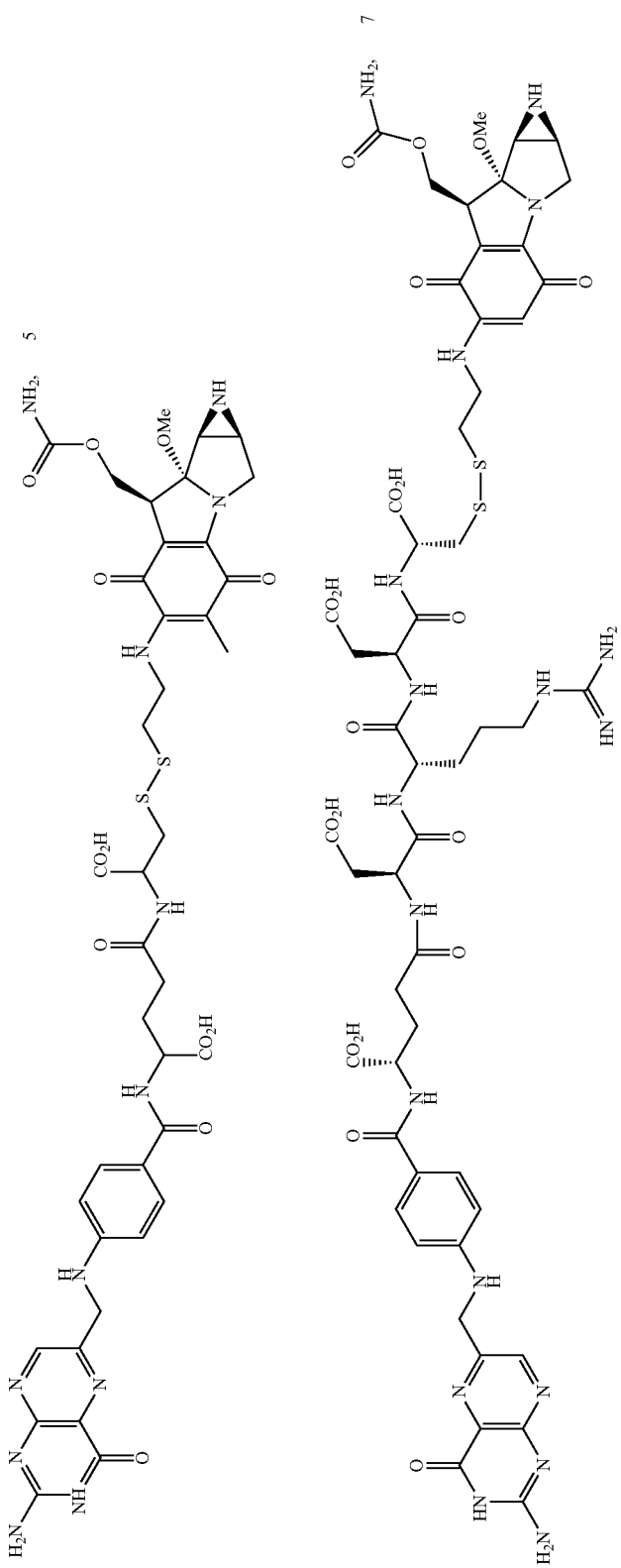

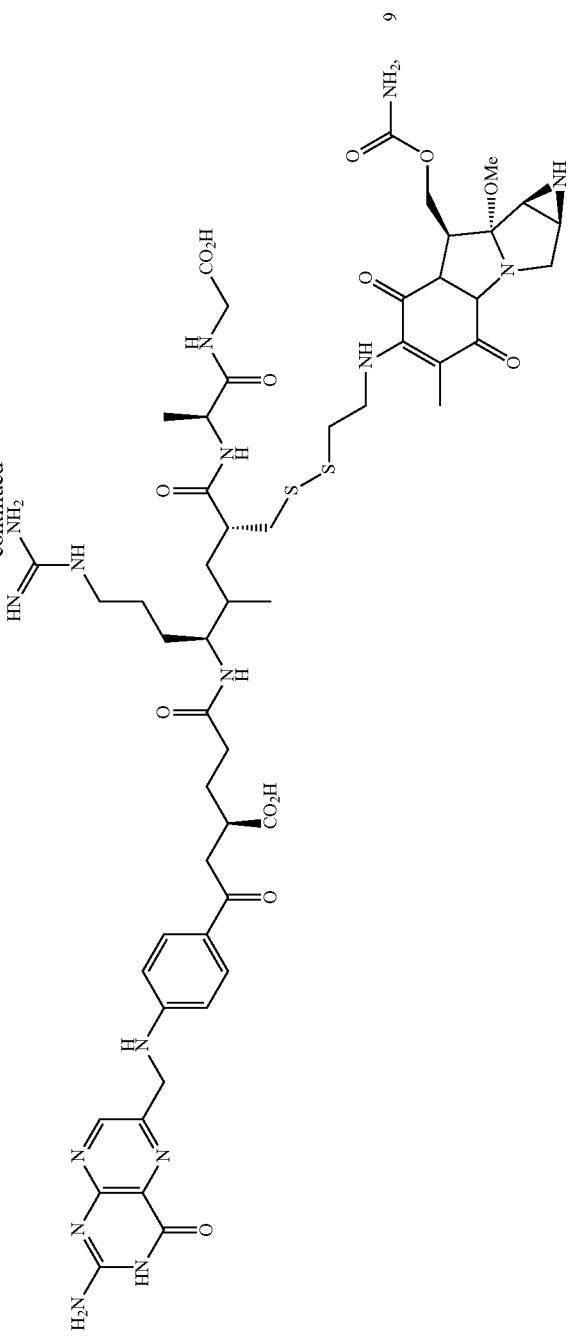

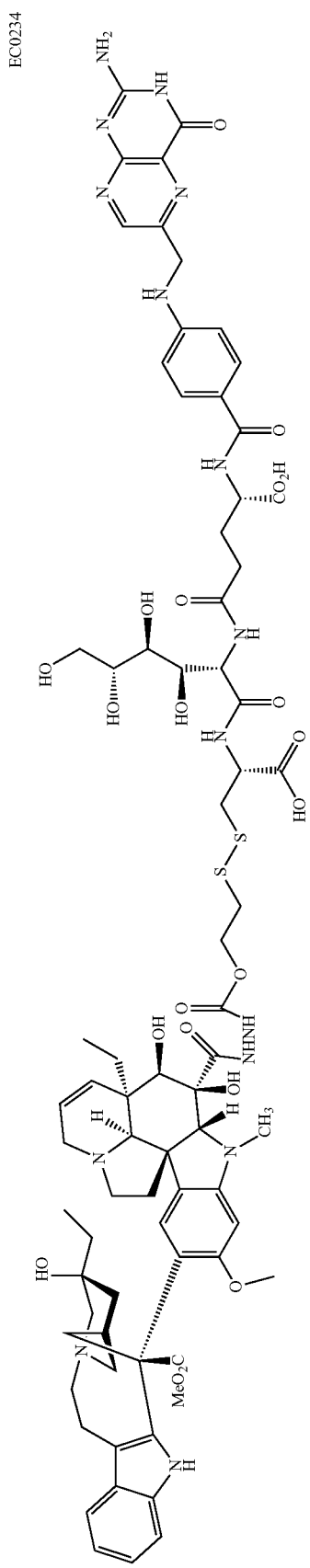
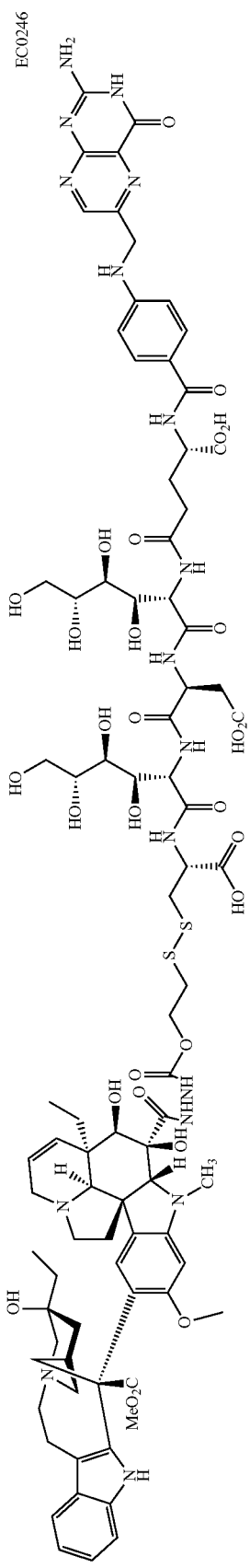

-continued
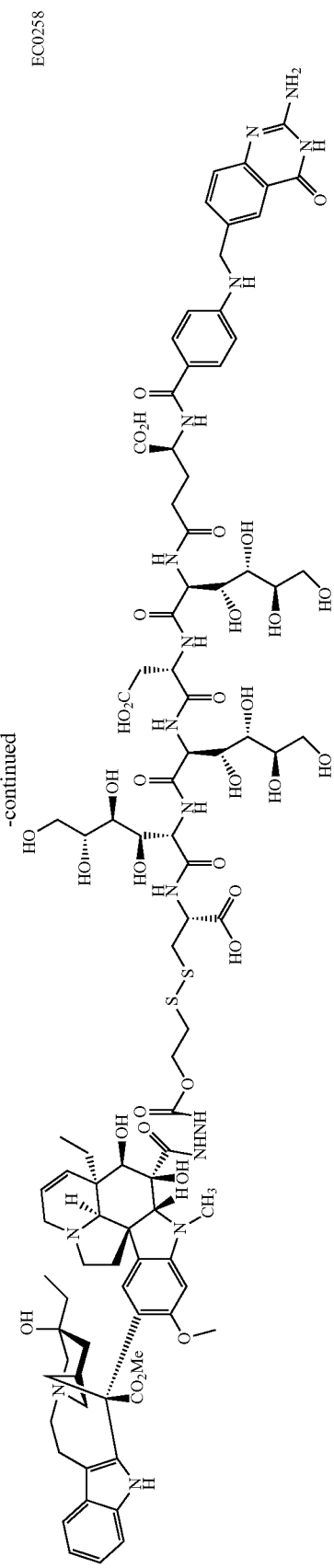
EC0258
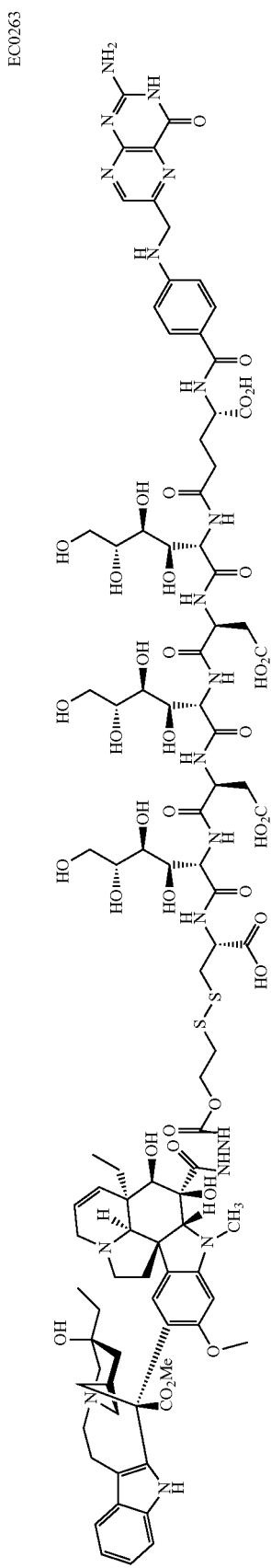
EC0263

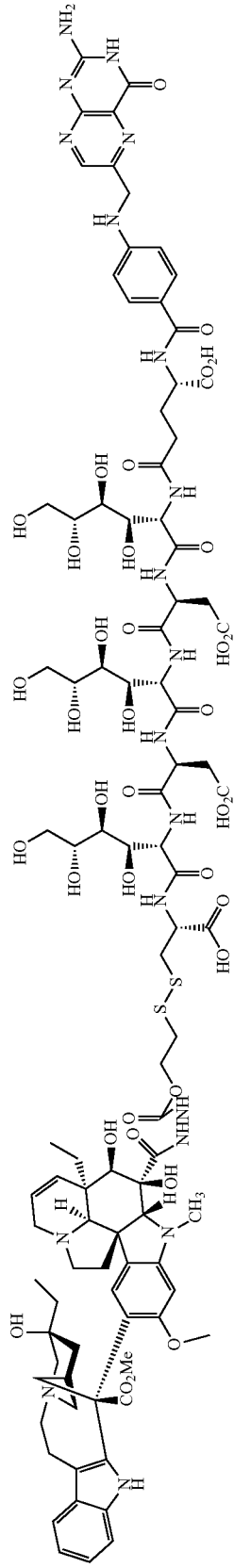
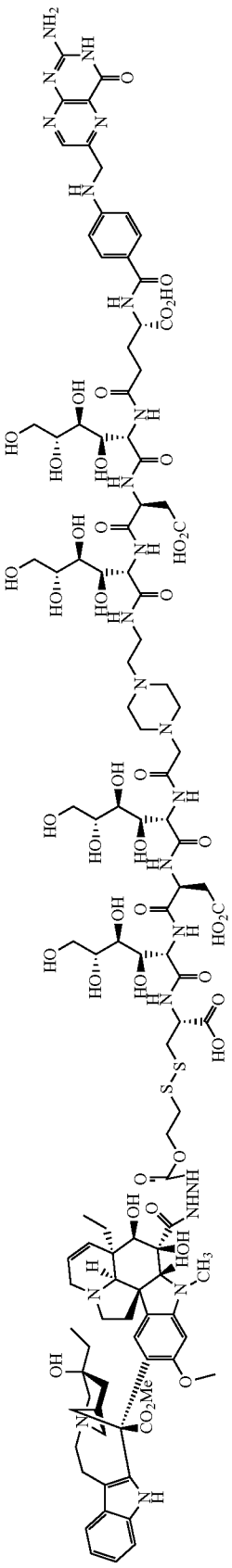

-continued
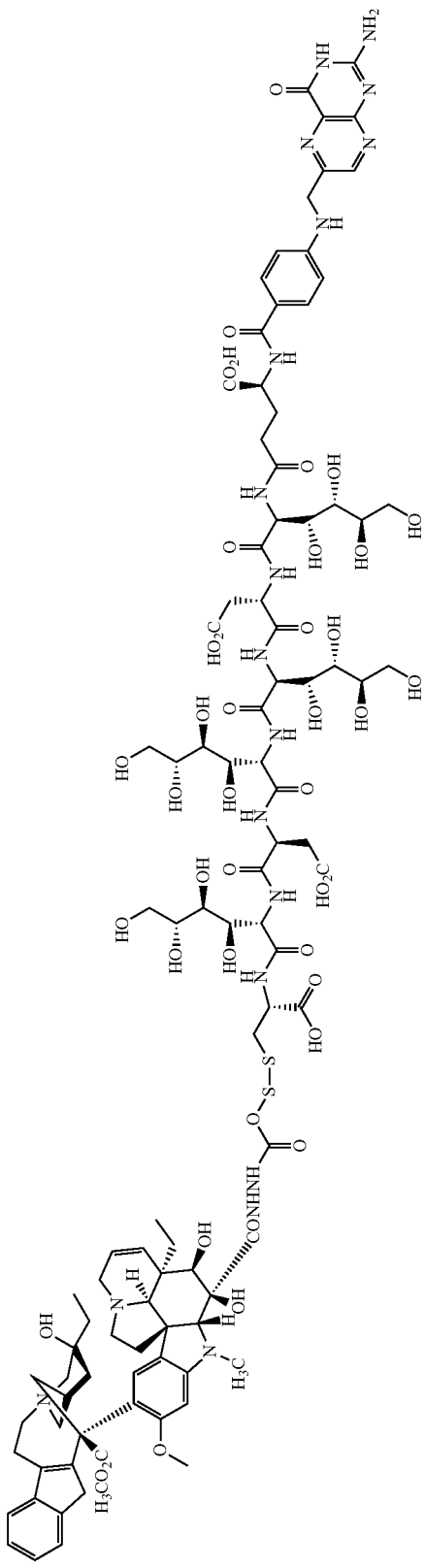
EC0455
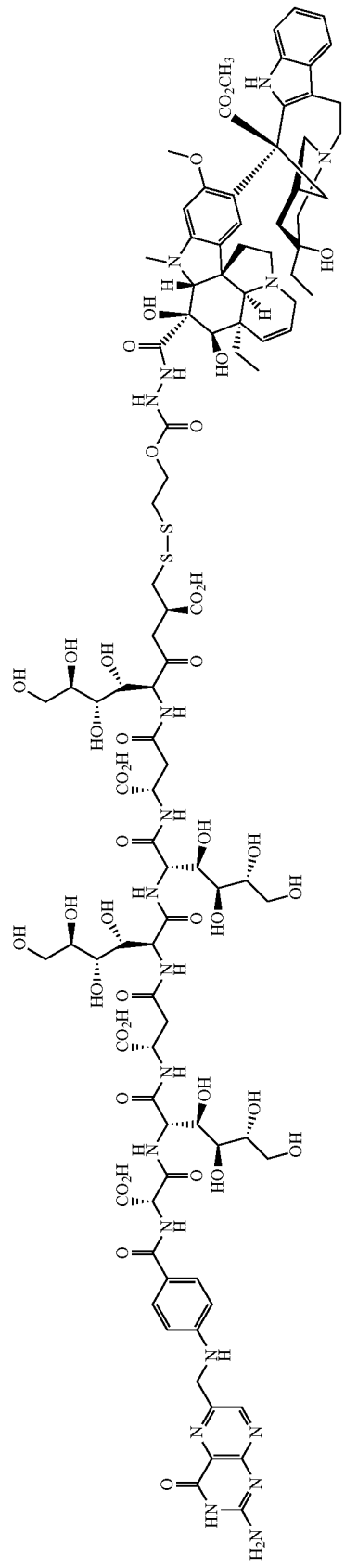
EC0456

-continued
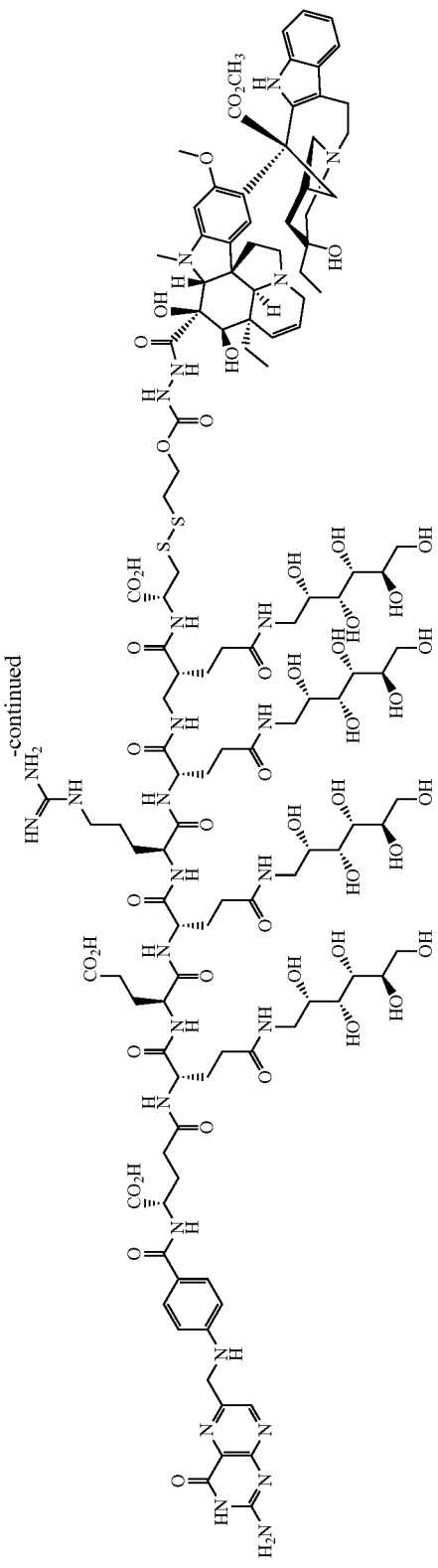
EC0481
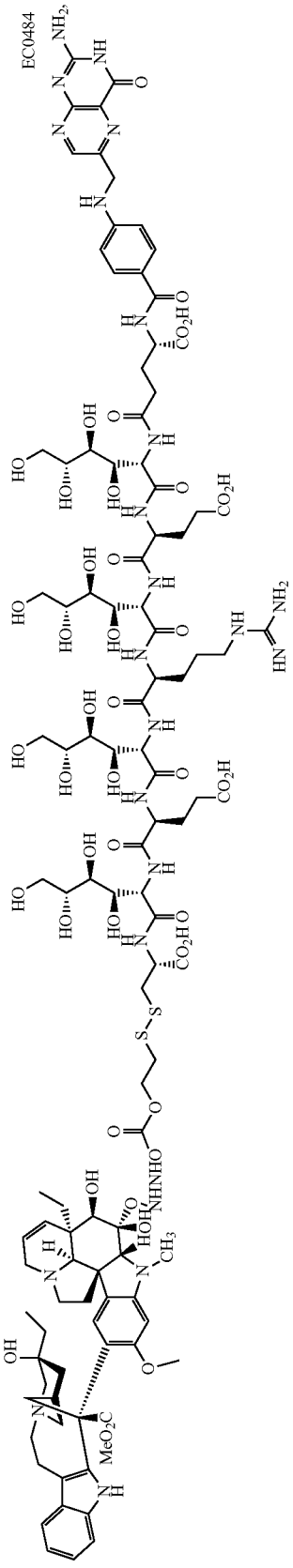
EC0484

-continued
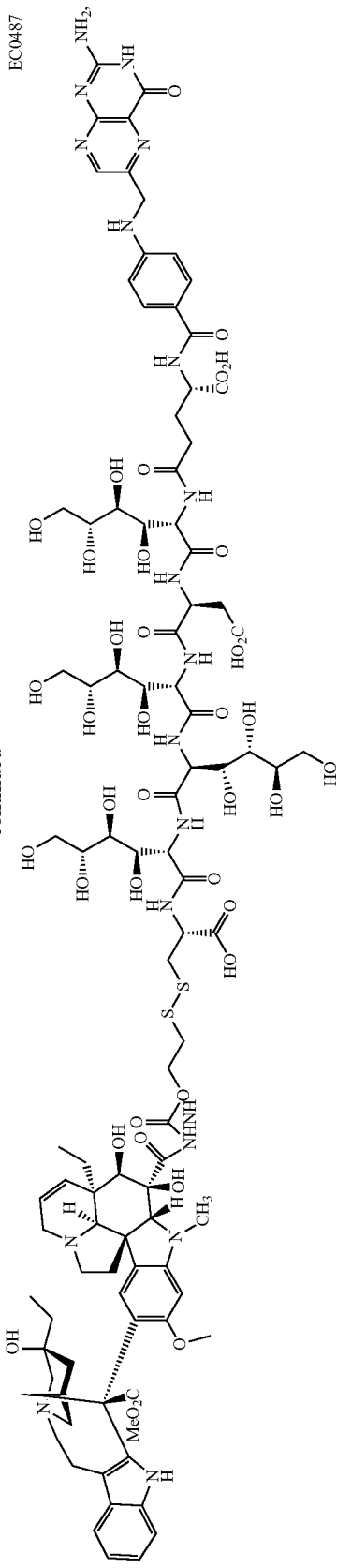
EC0487
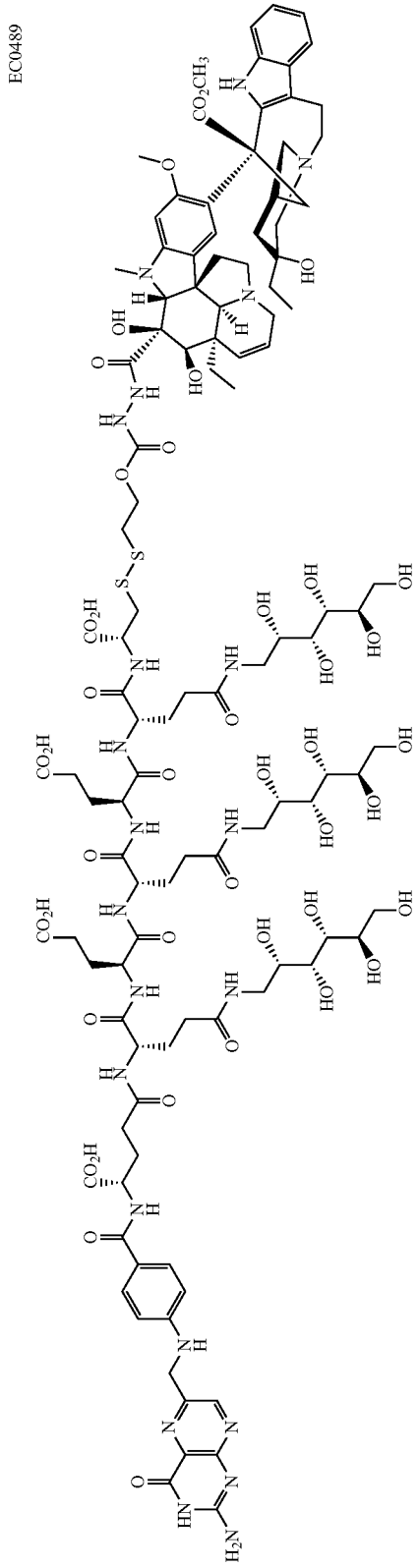
EC0489

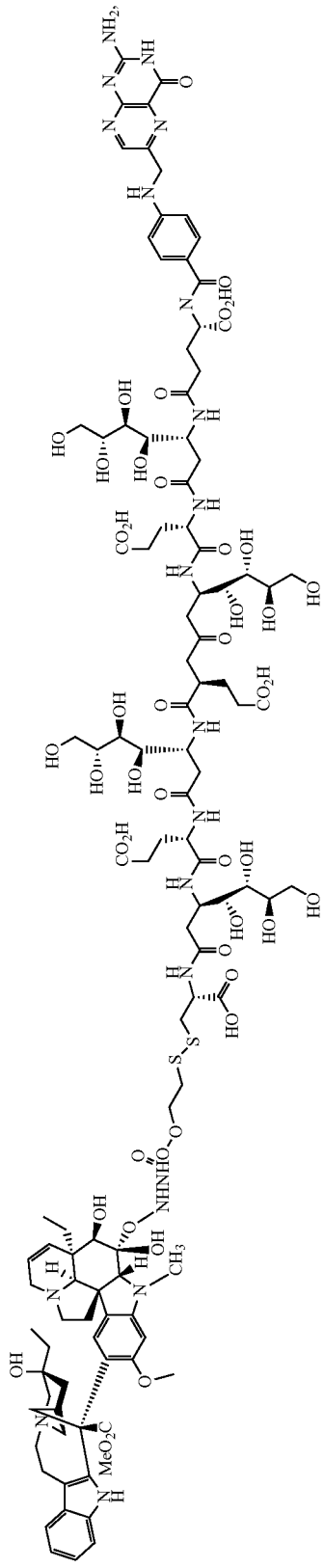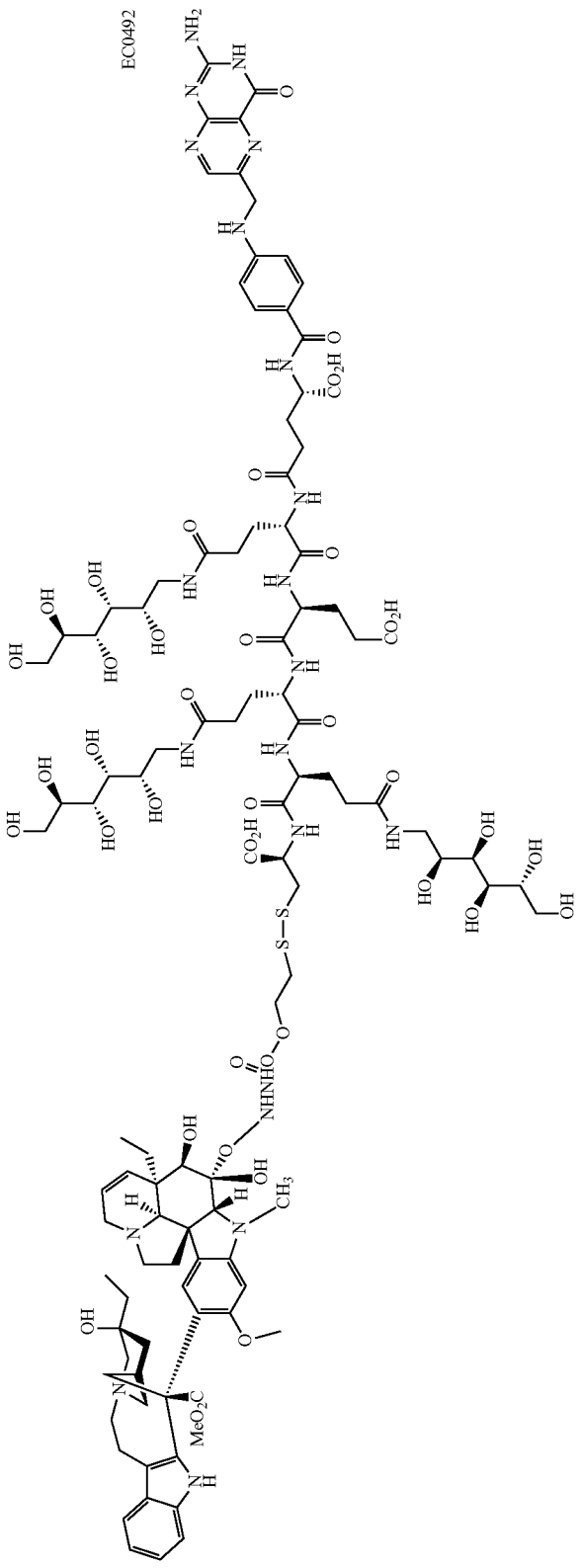

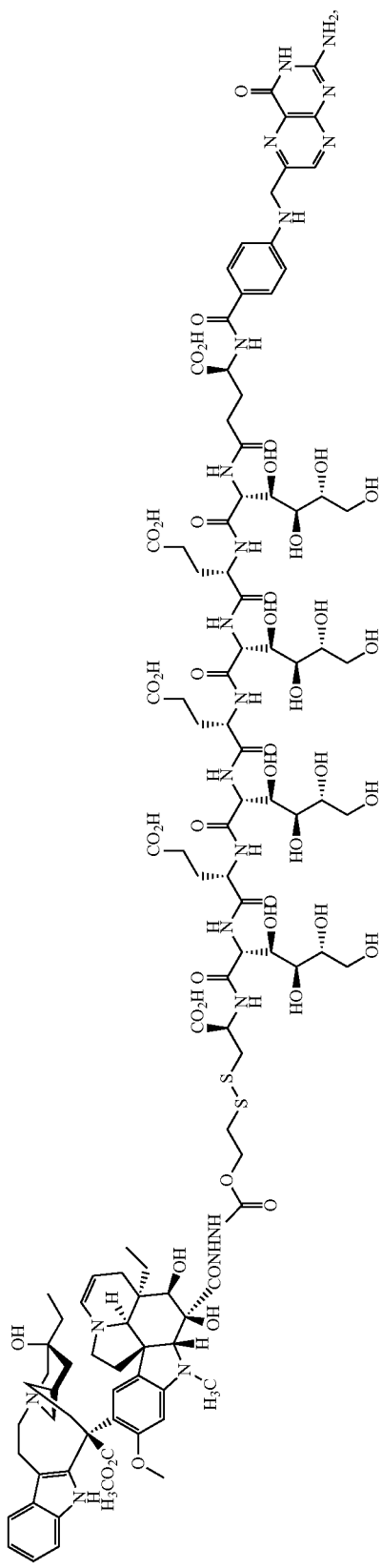
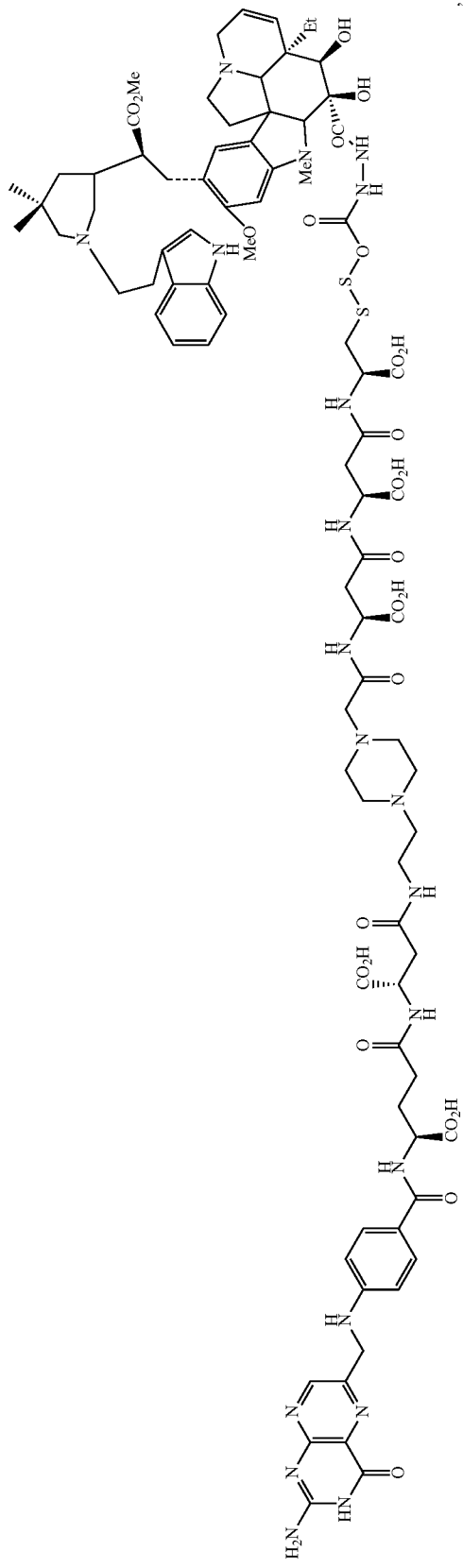

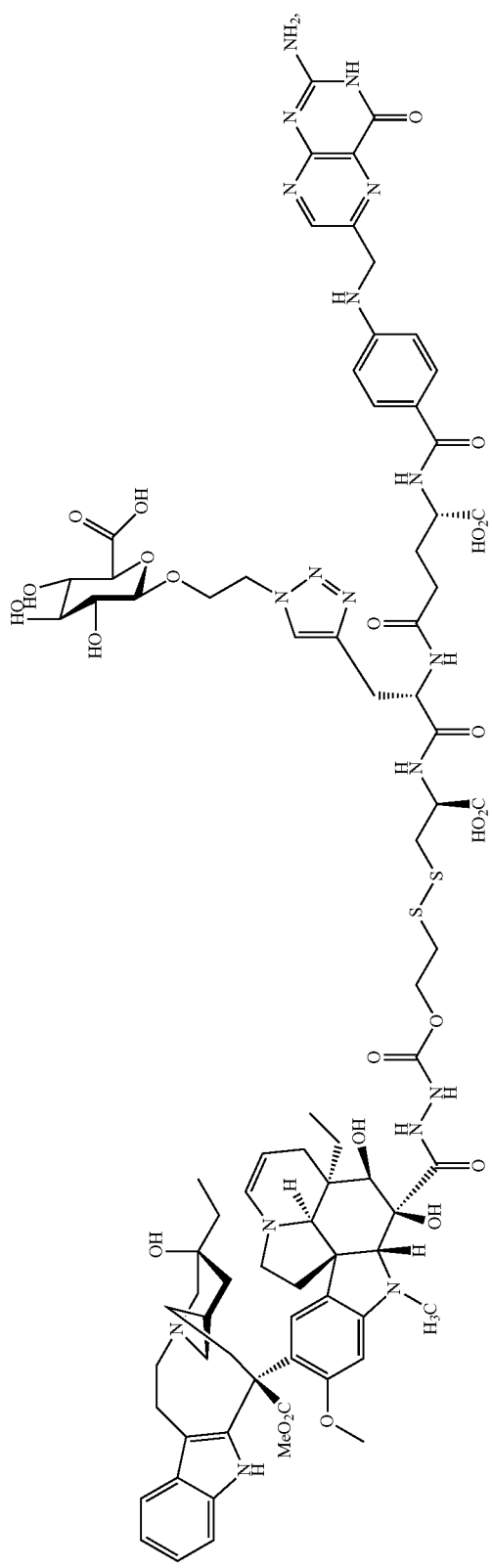
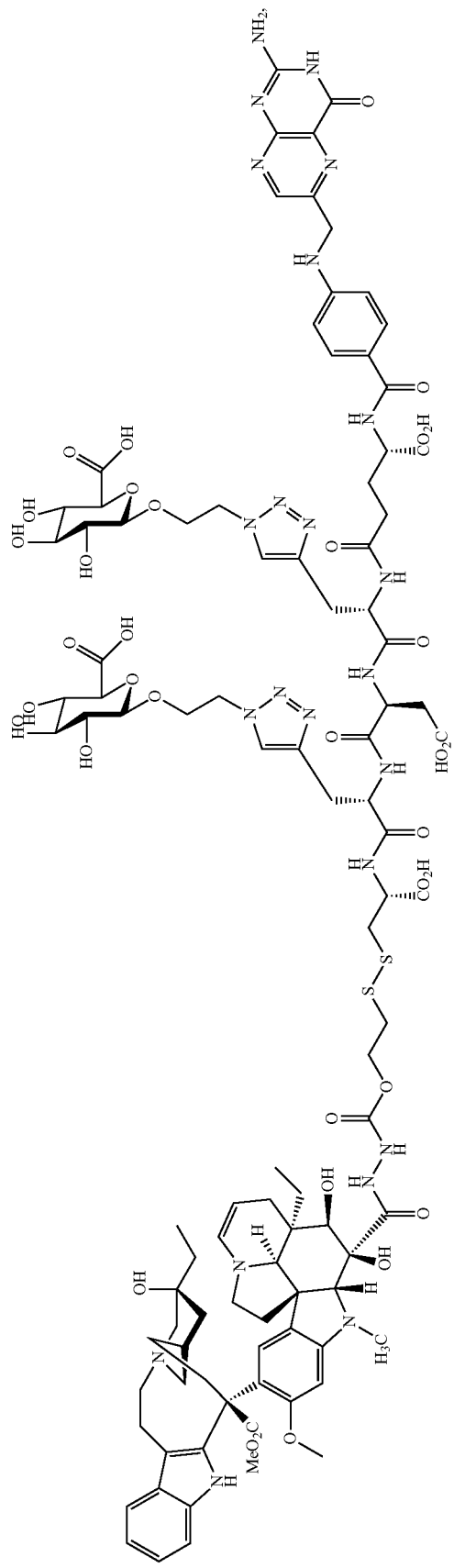

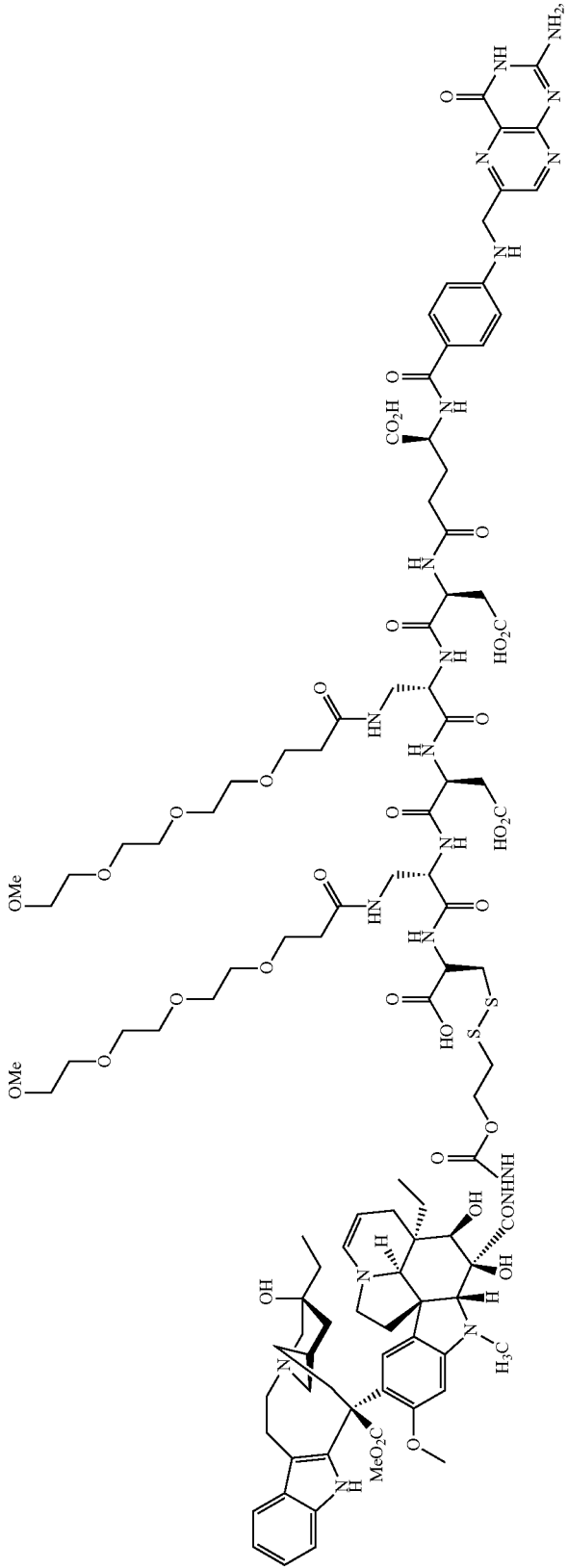
EC0367

-continued
EC0409
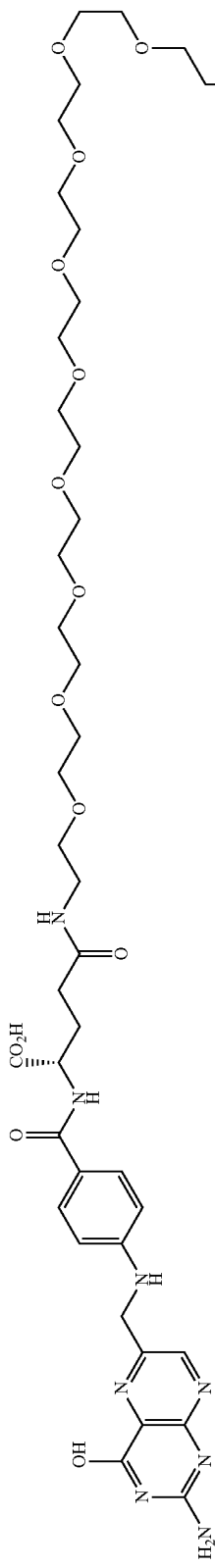
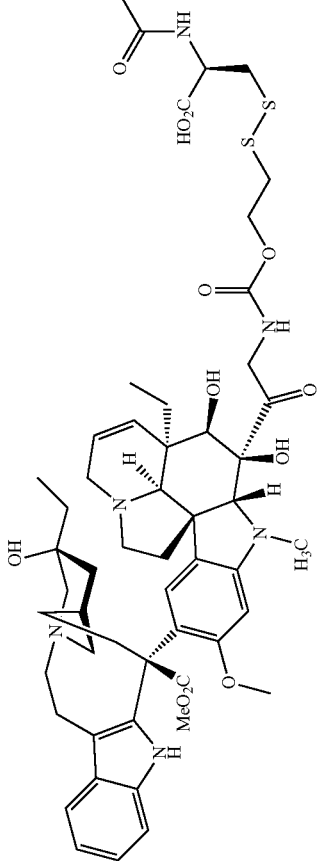

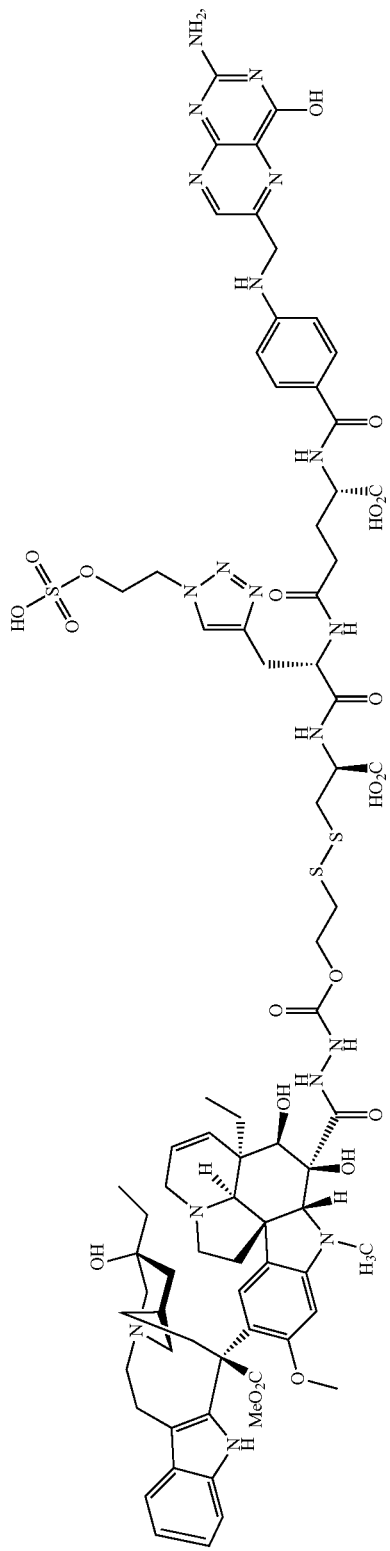
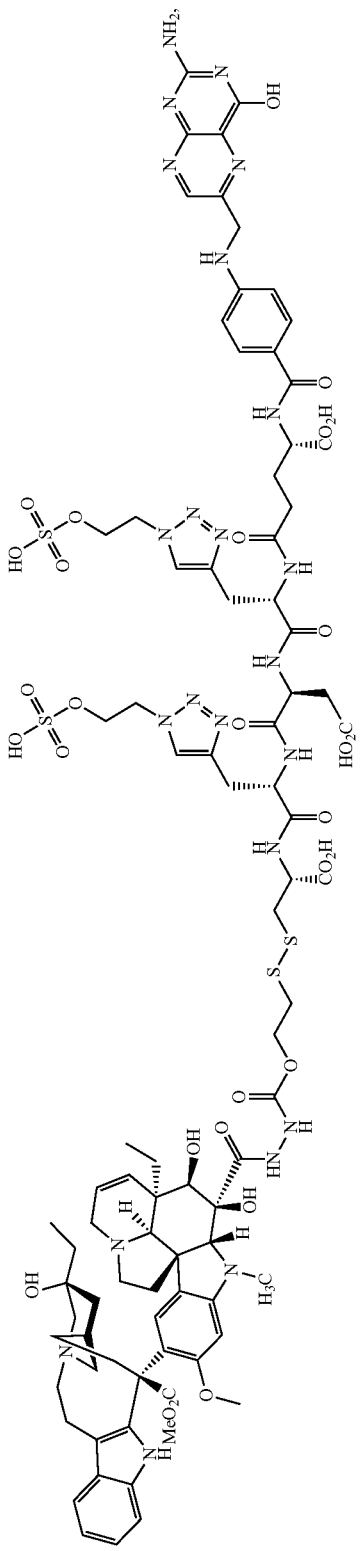

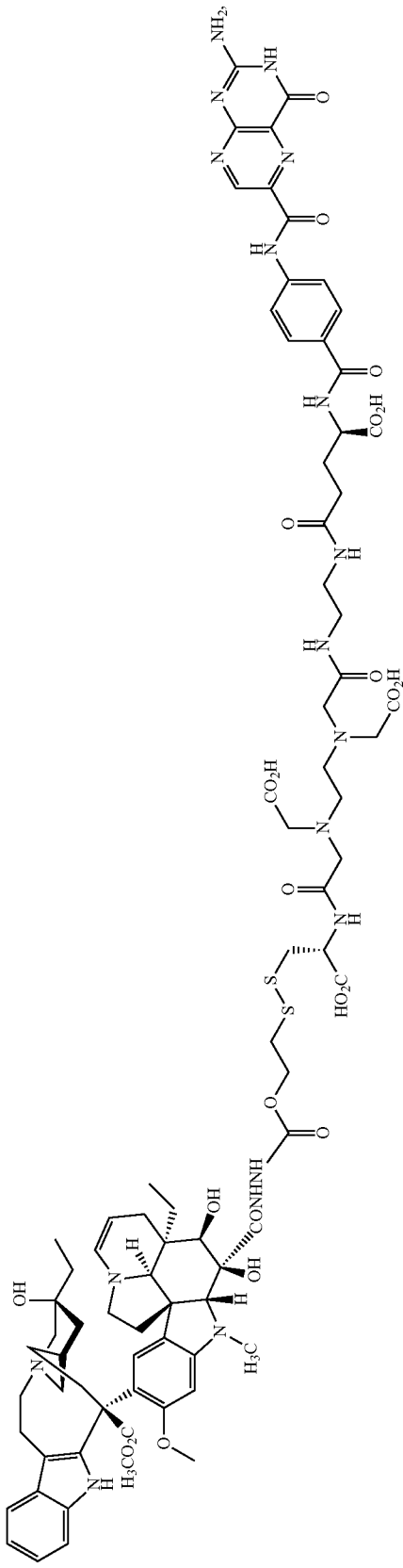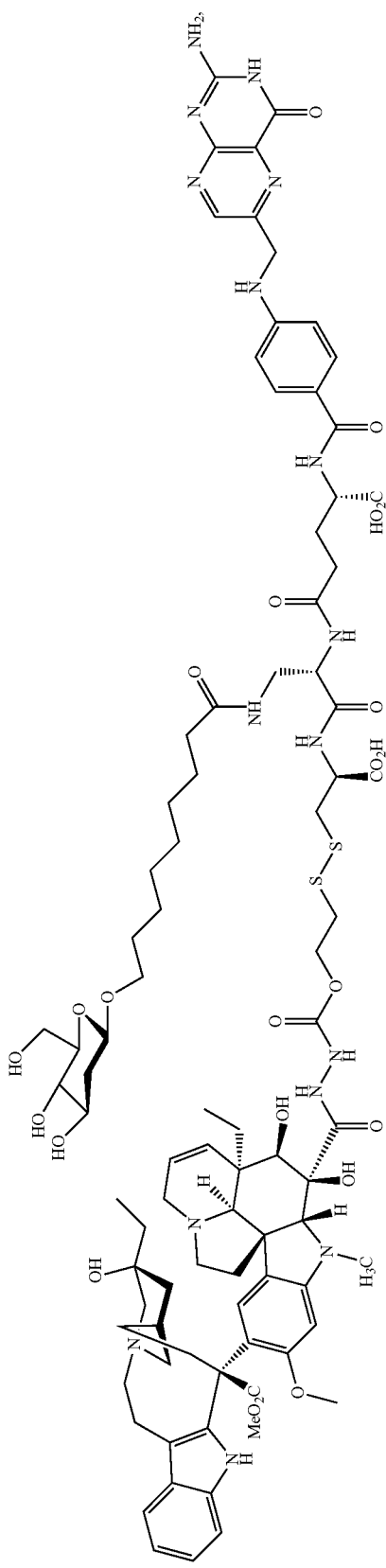

-continued
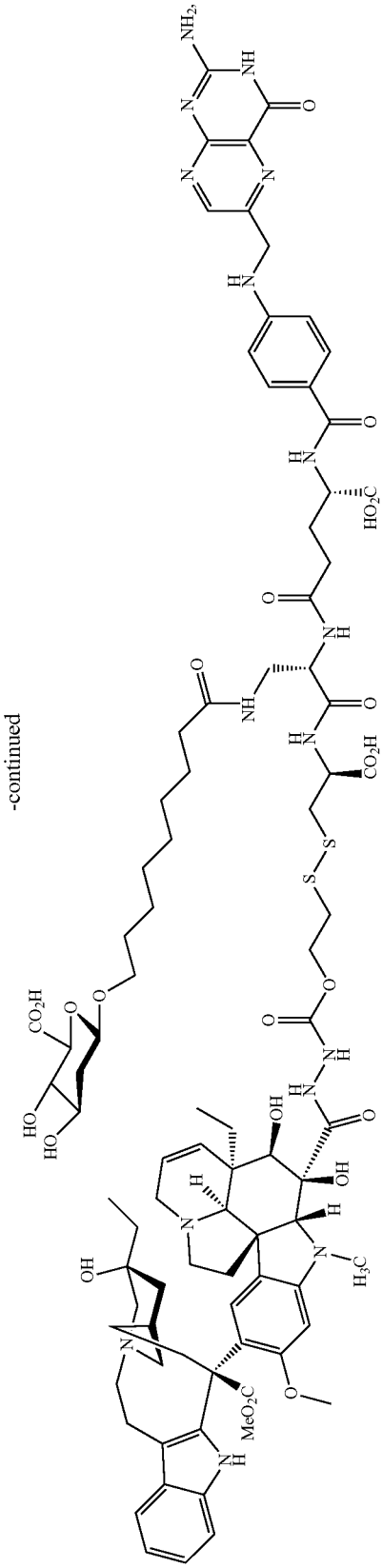
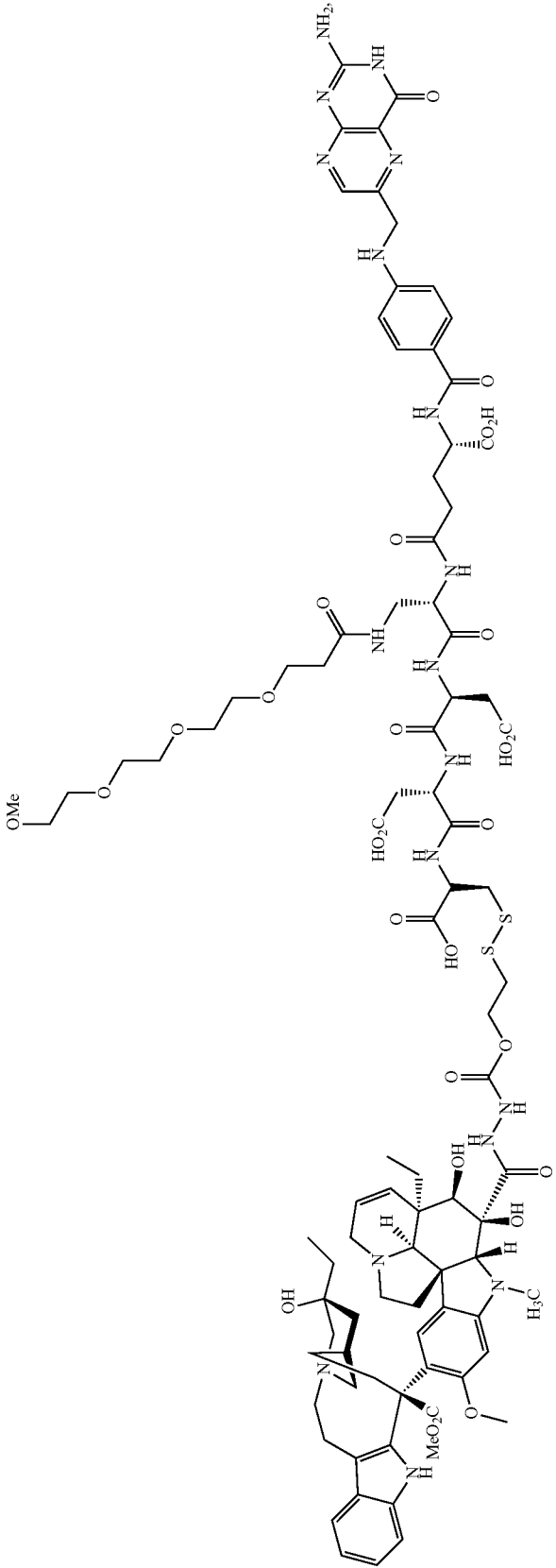

-continued
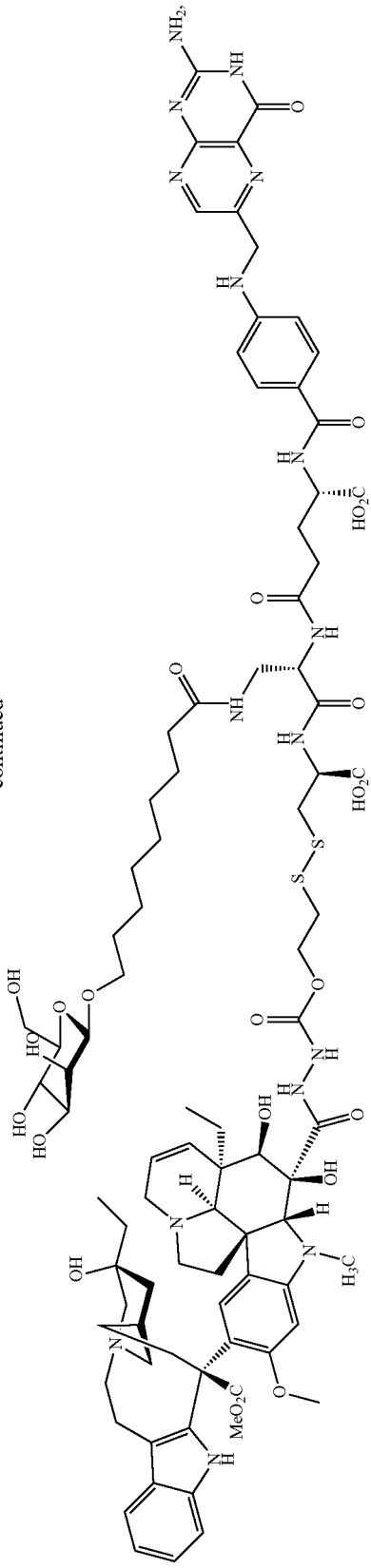
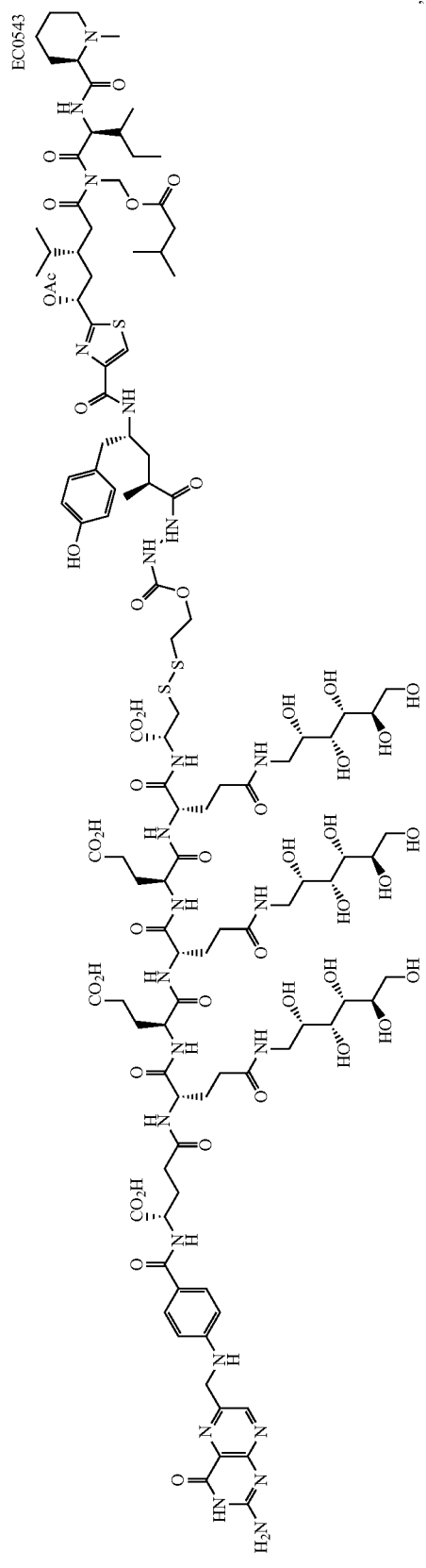
EC0543

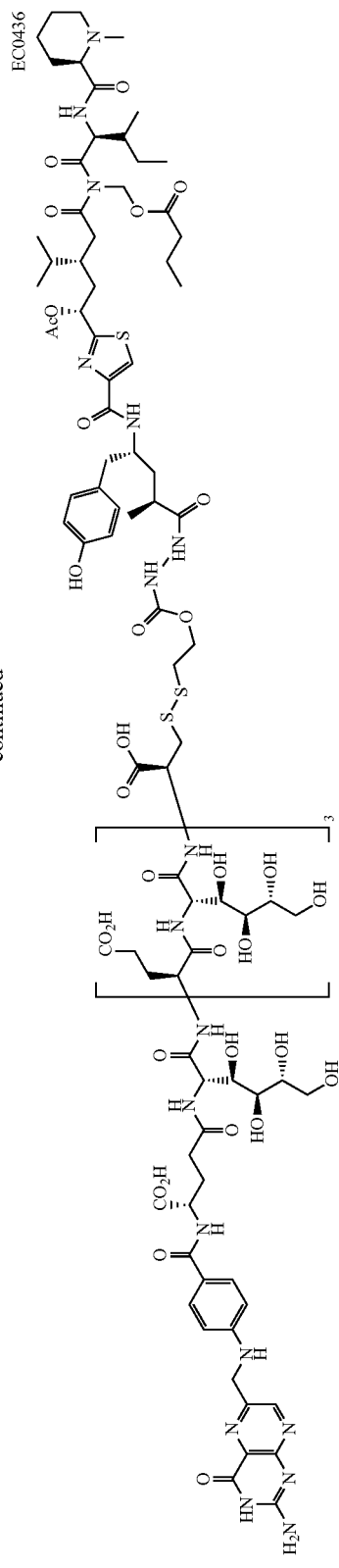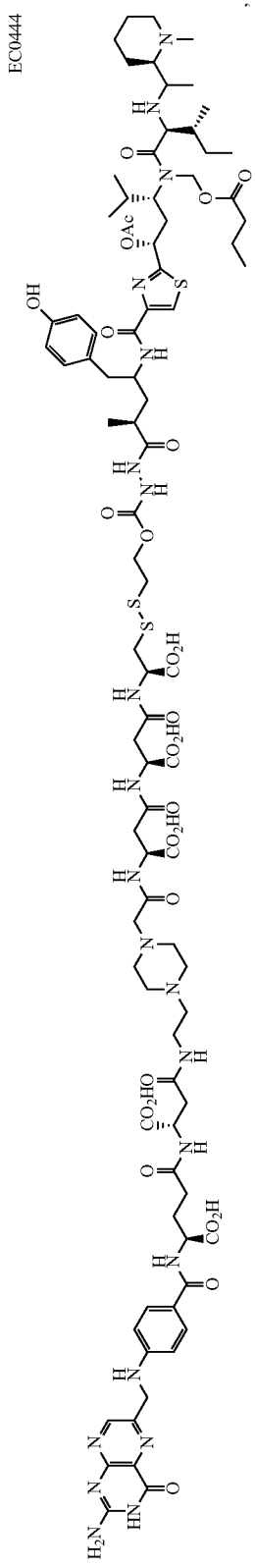

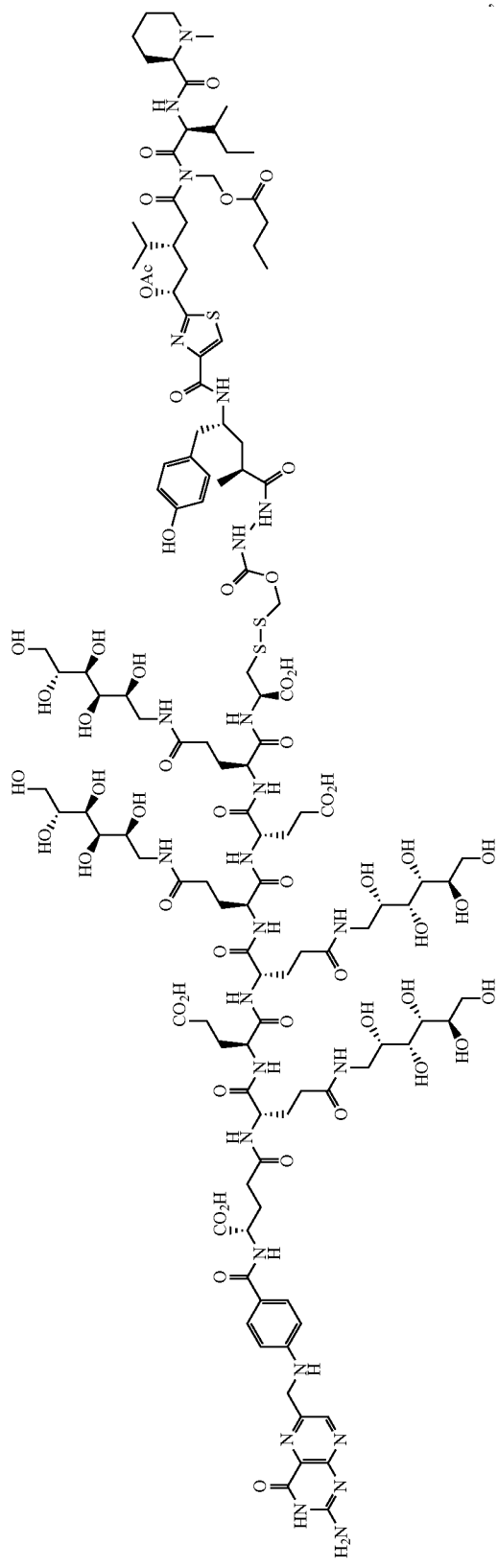
EC0530
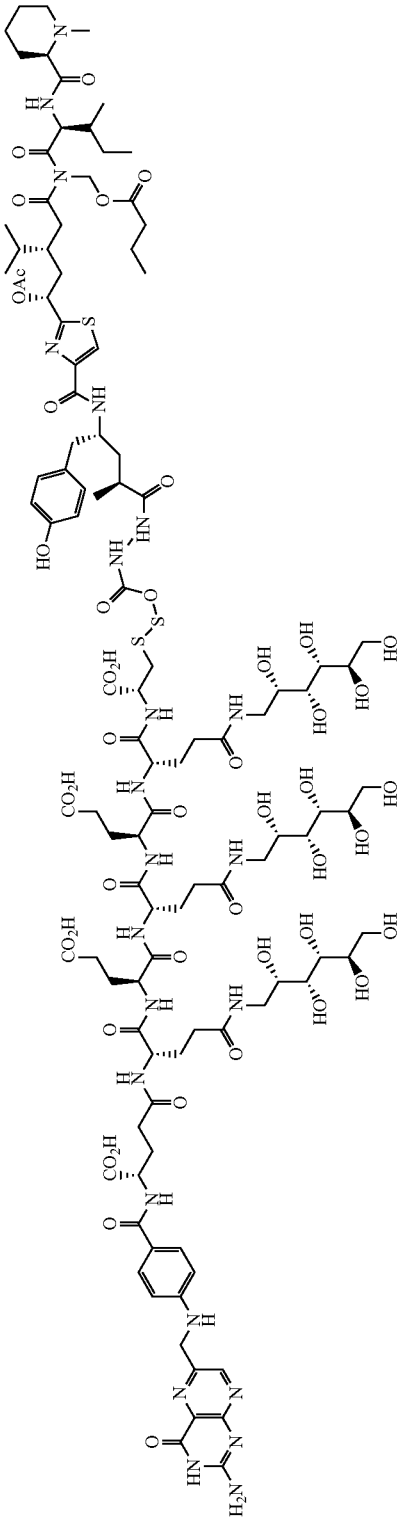
EC0531

-continued
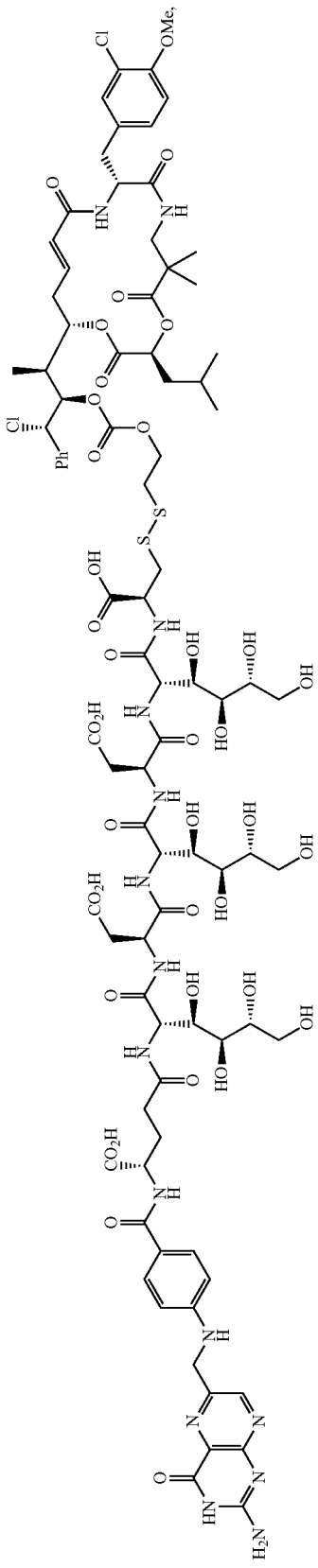
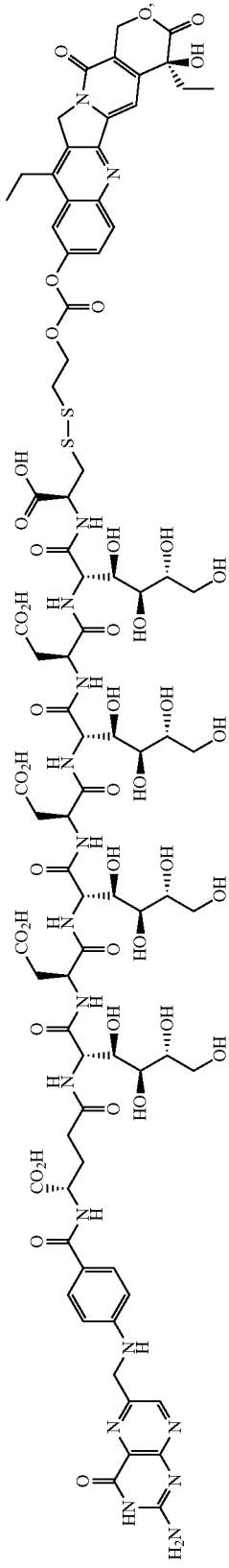

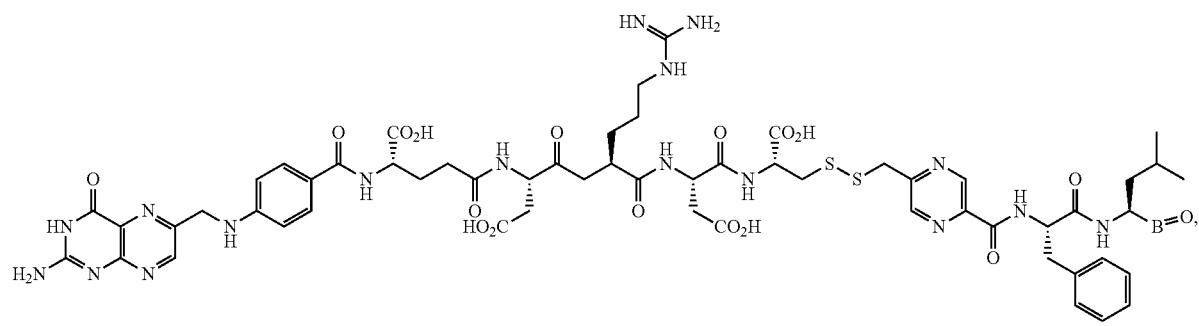
EC0522
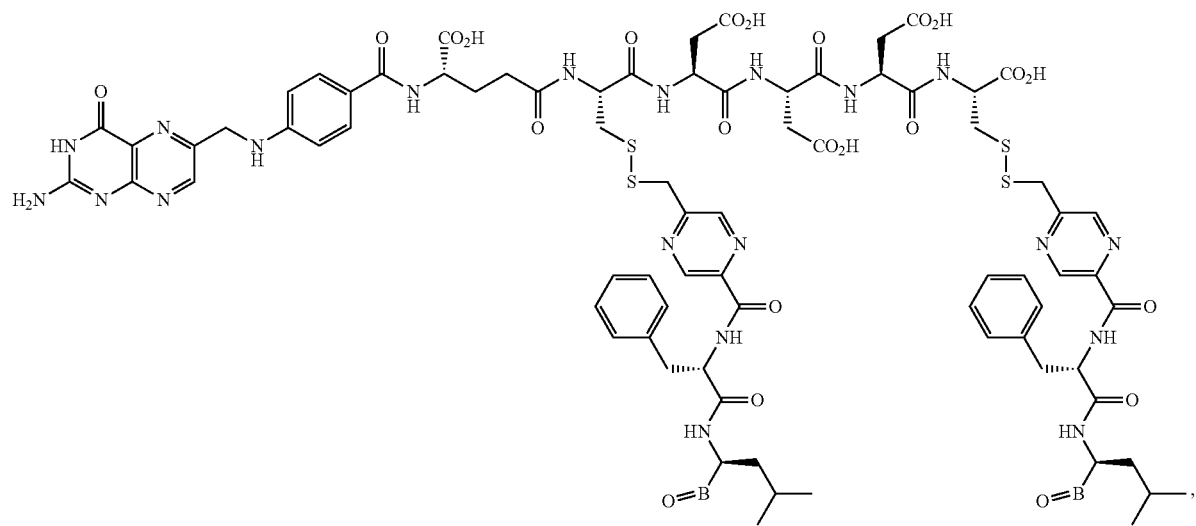
EC0587
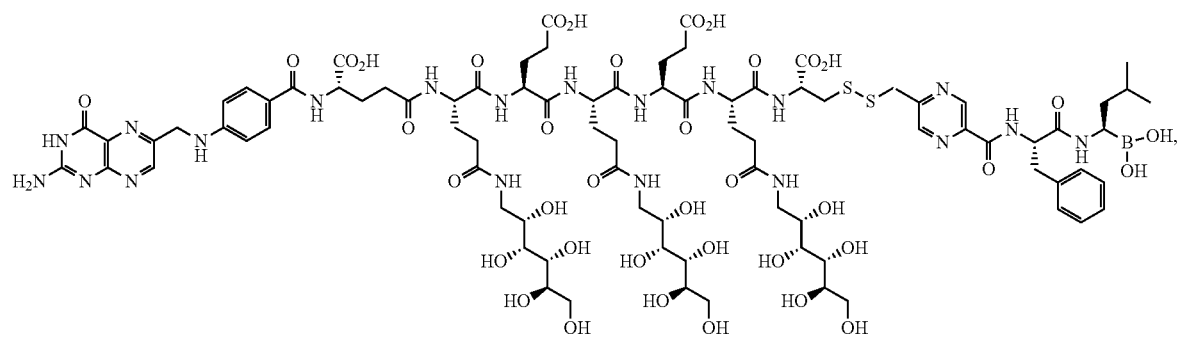
EC0525

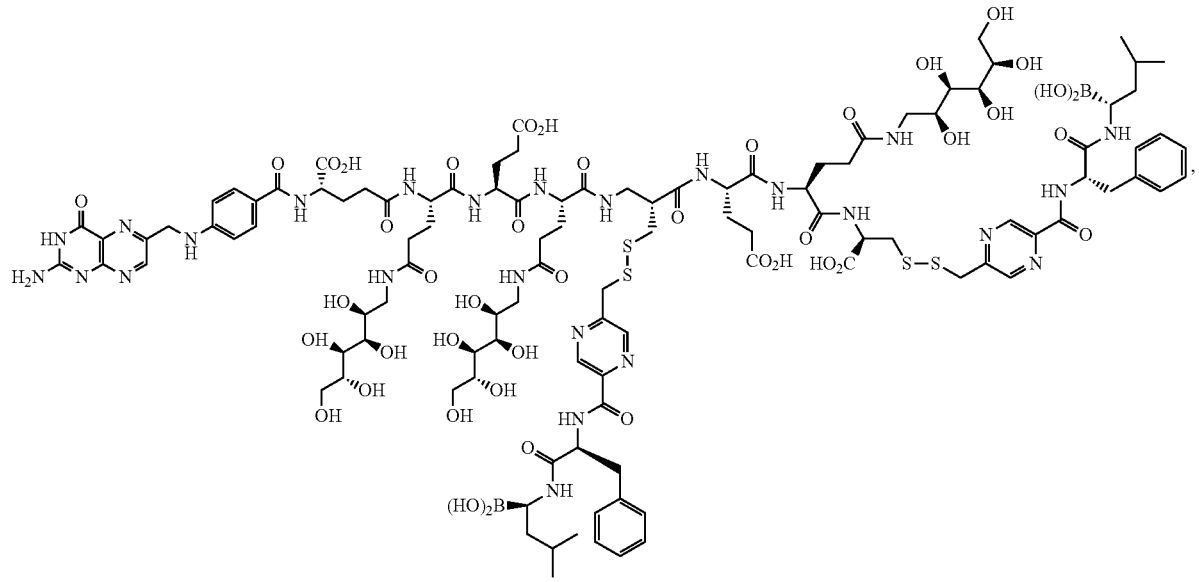
EC0595
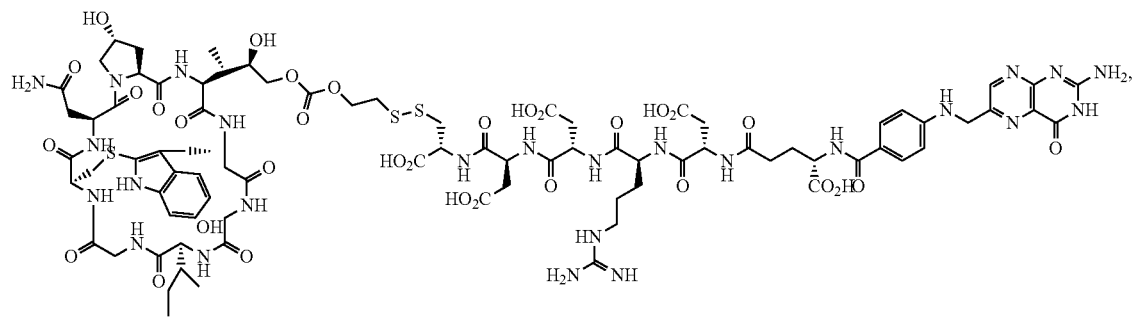
EC0323
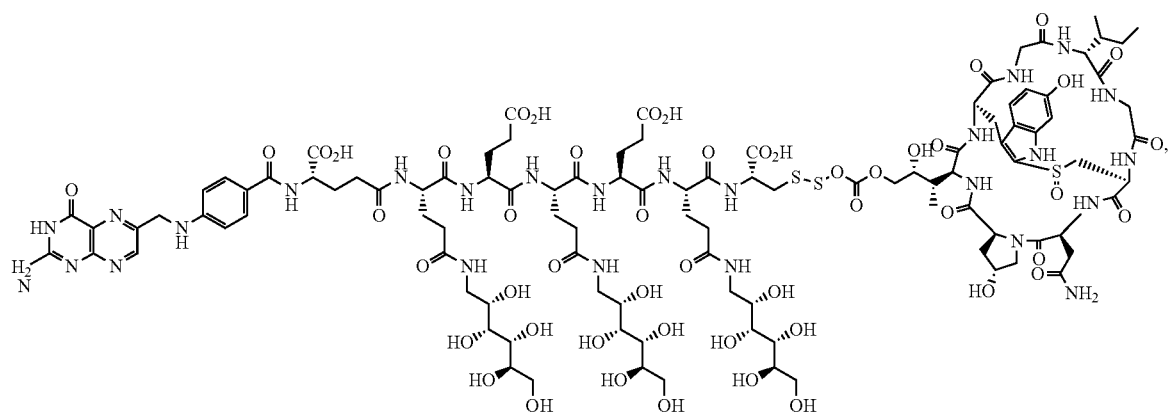
EC0592

-continued
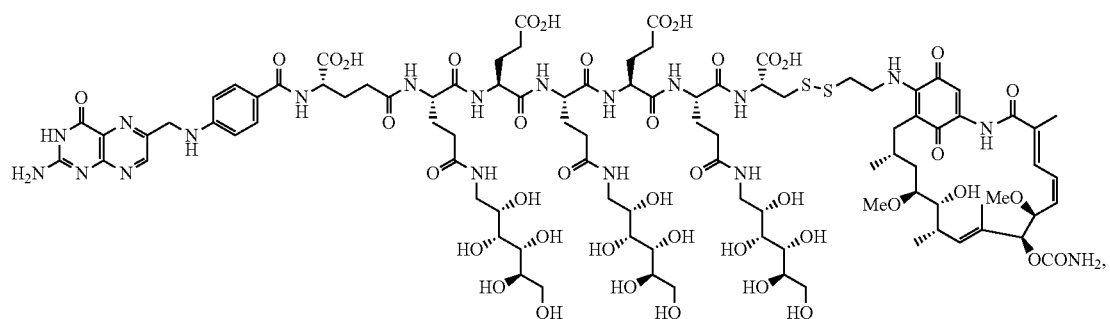
EC0535
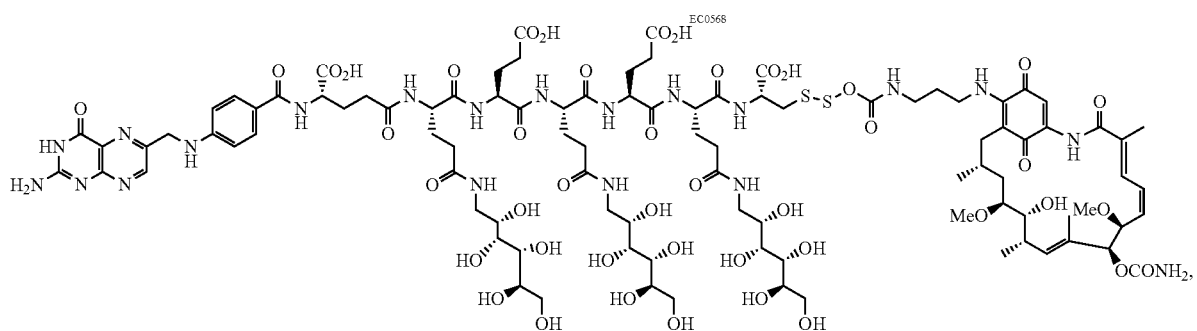
EC0568
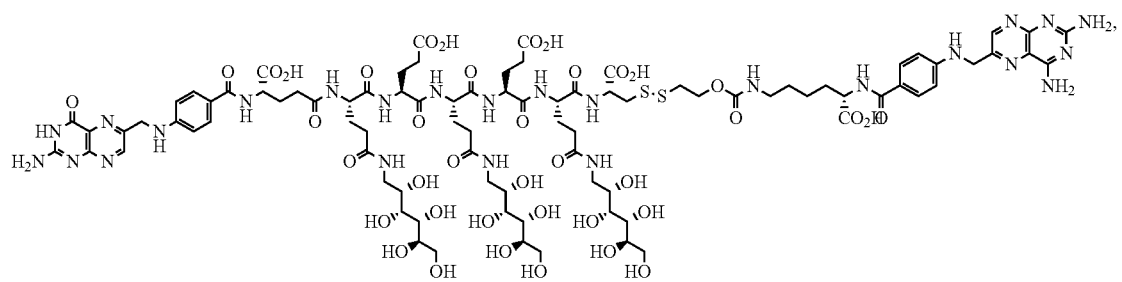
EC0539
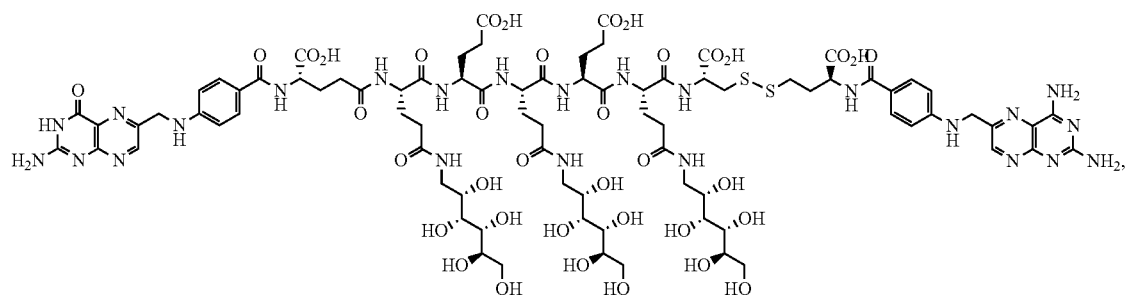
EC0544
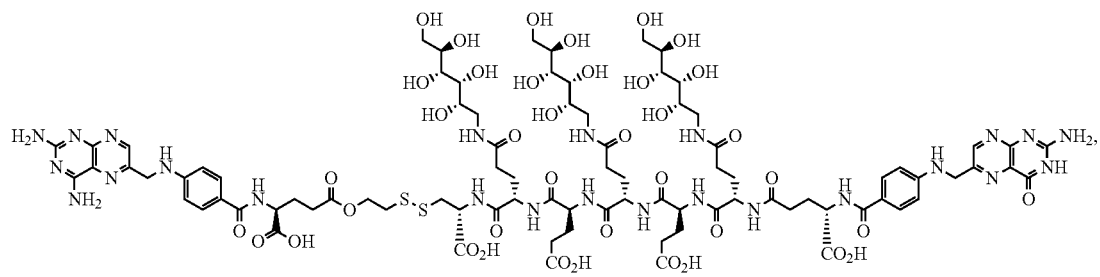
EC0551

-continued
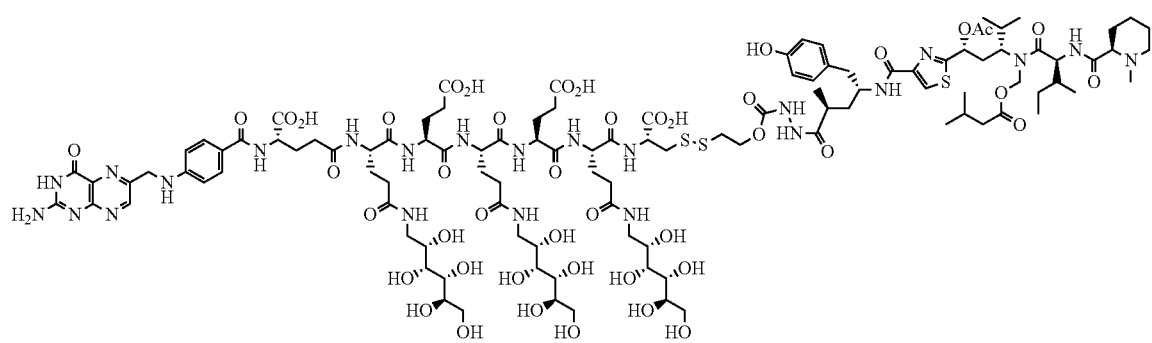
EC0543
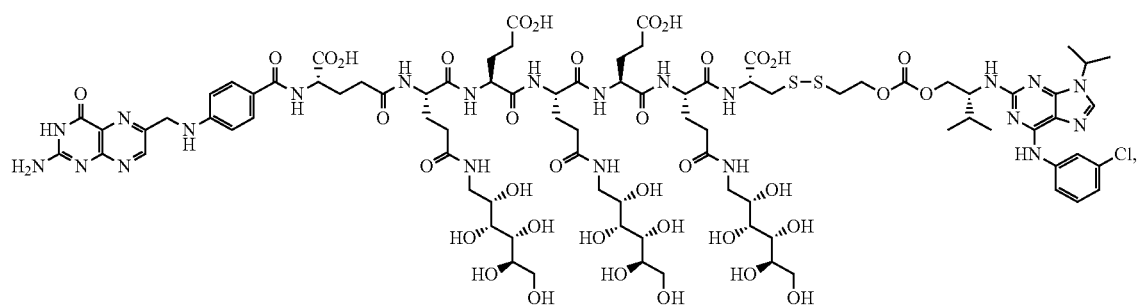
EC0545
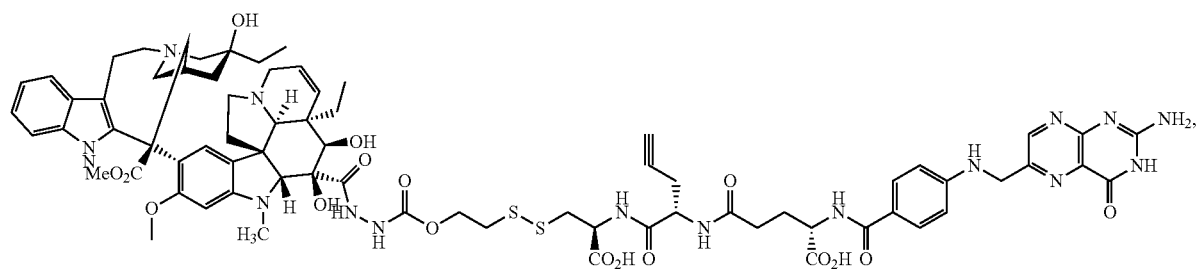
EC0400
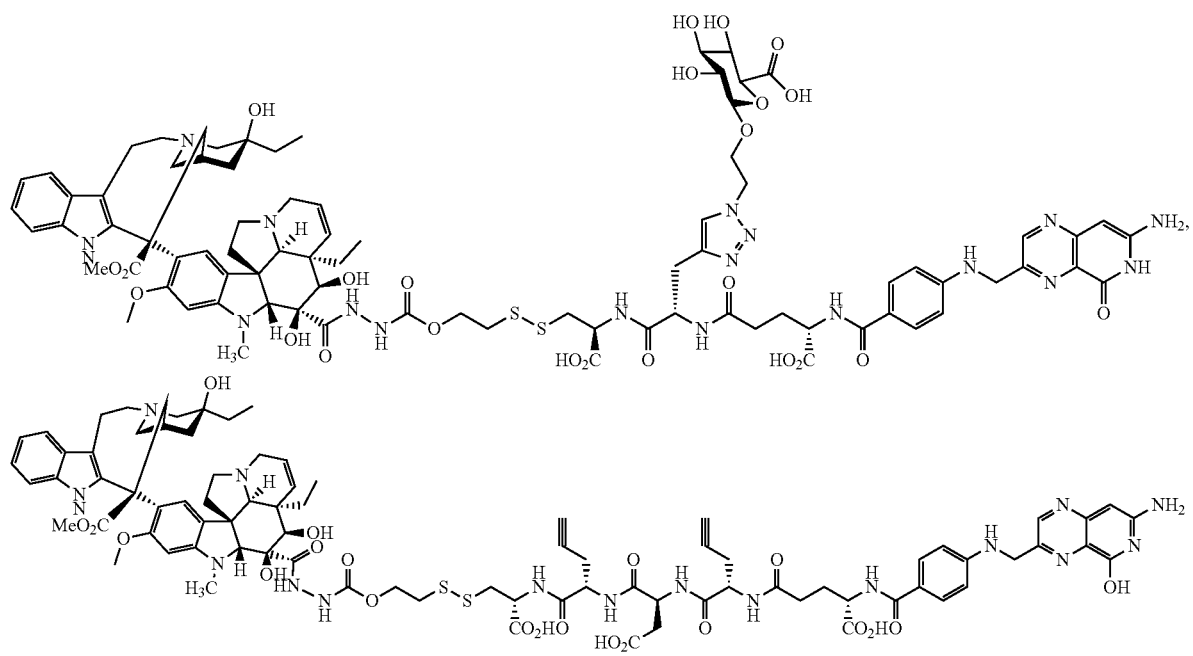

-continued
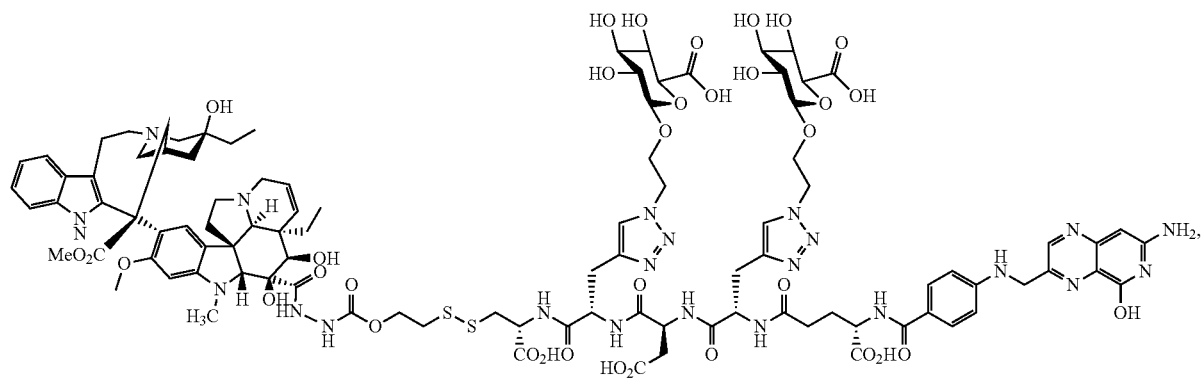
EC0423
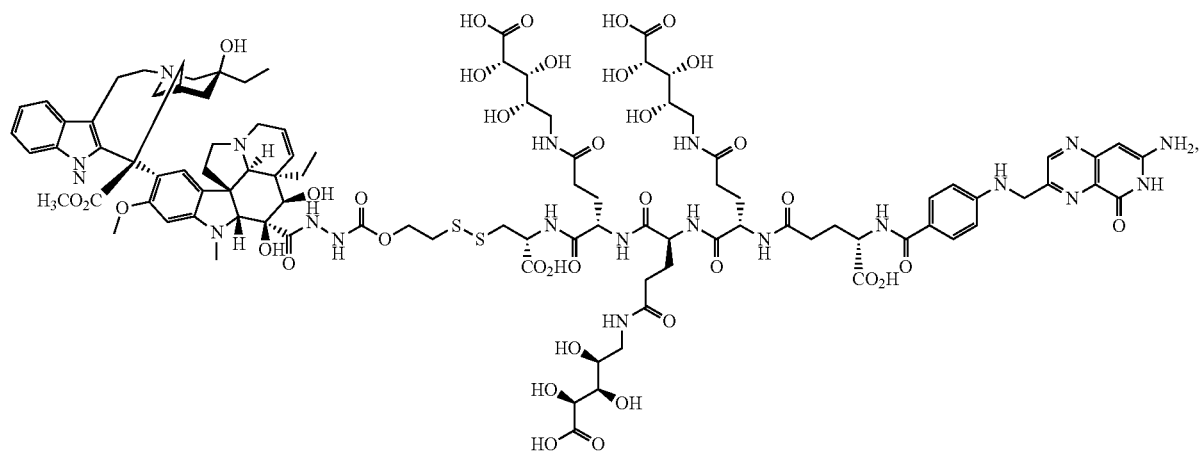
EC0637
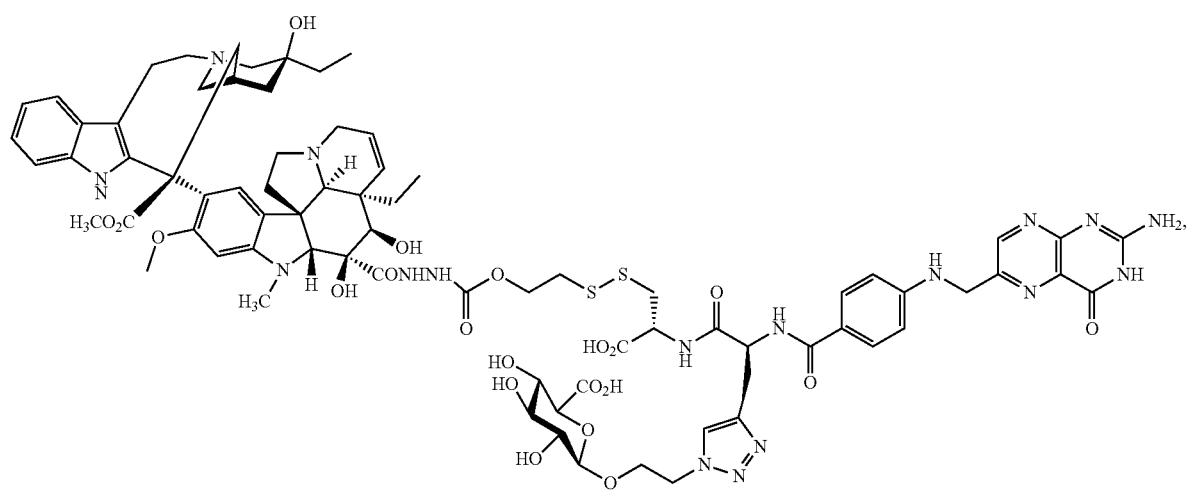

189
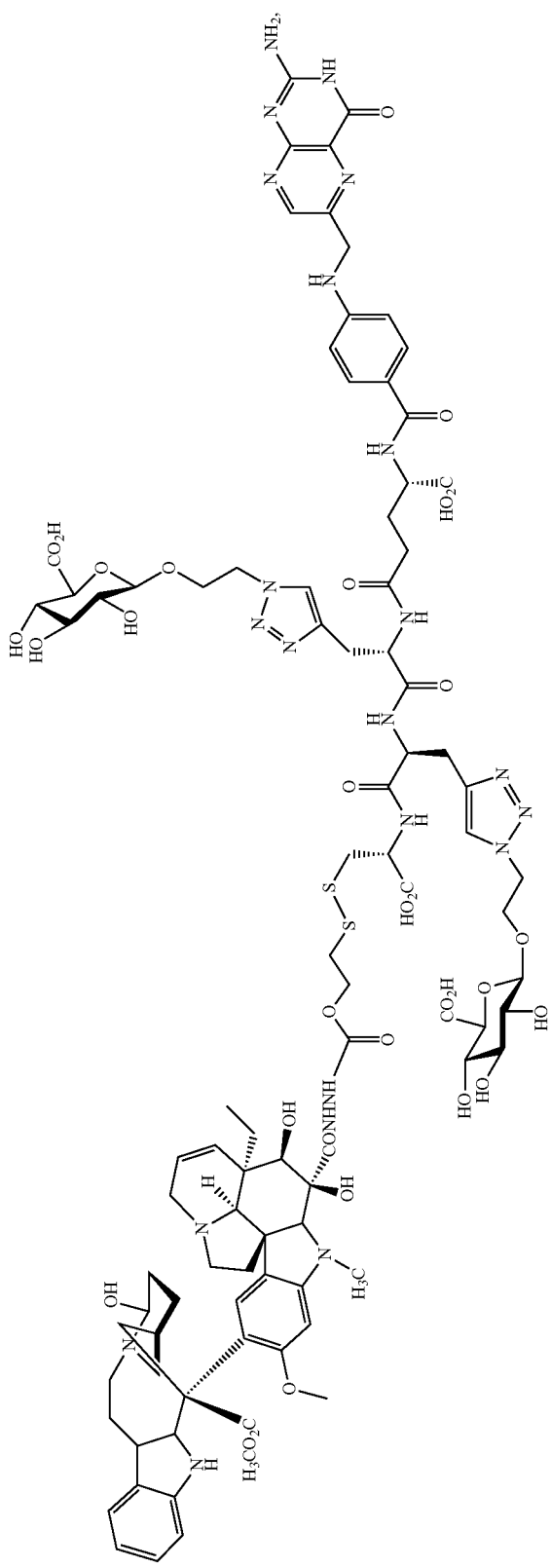
190
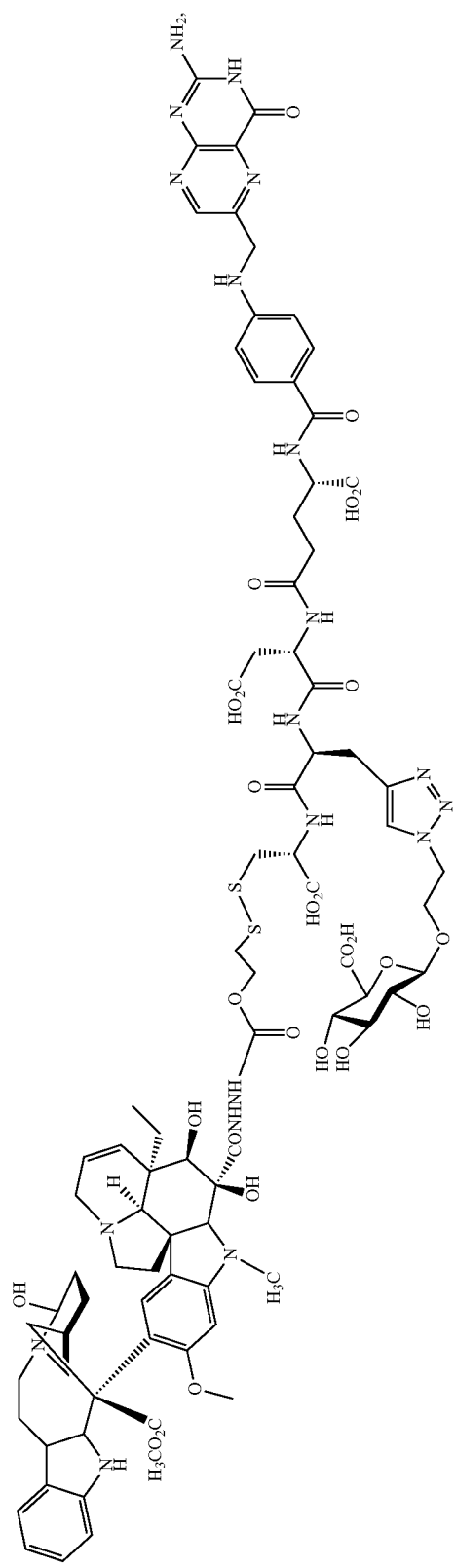

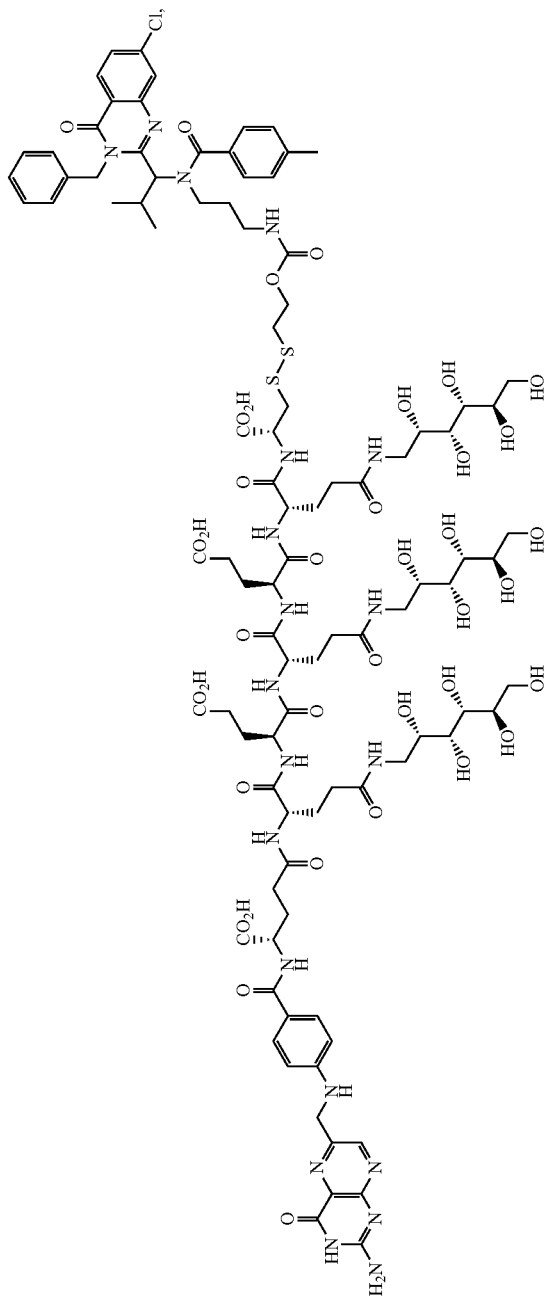

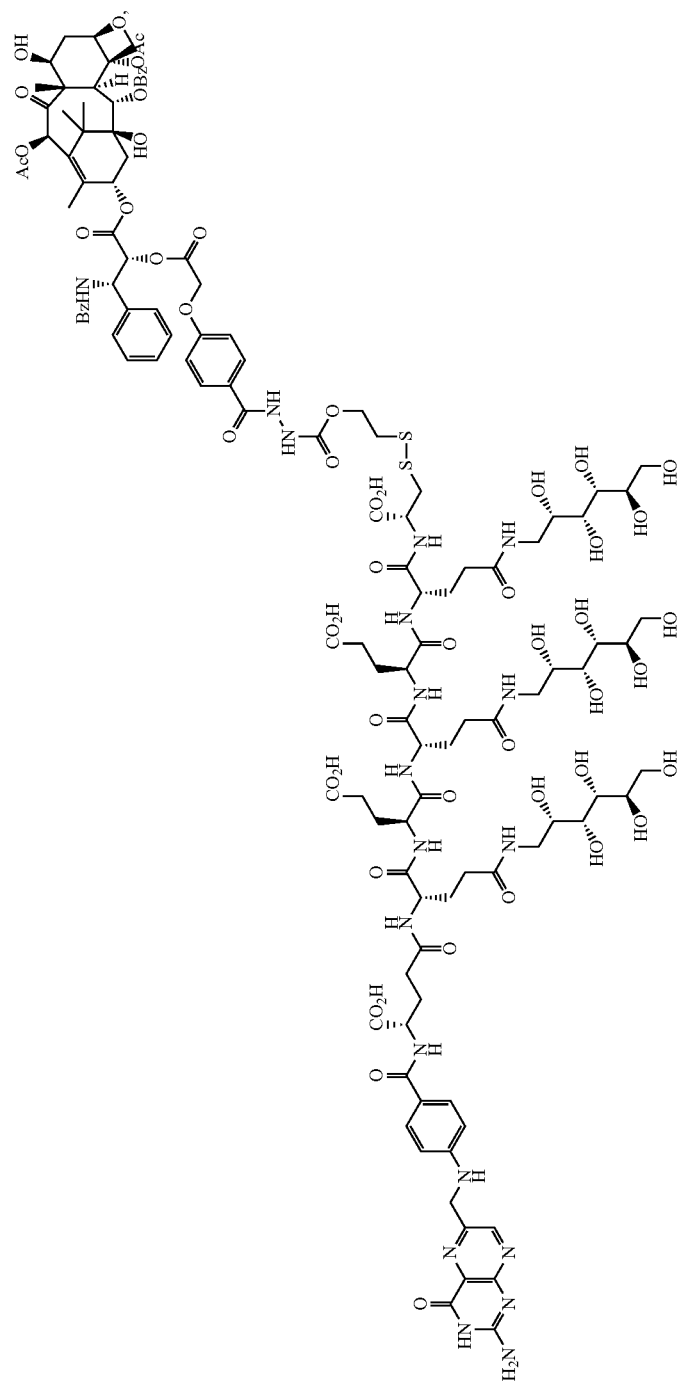

-continued
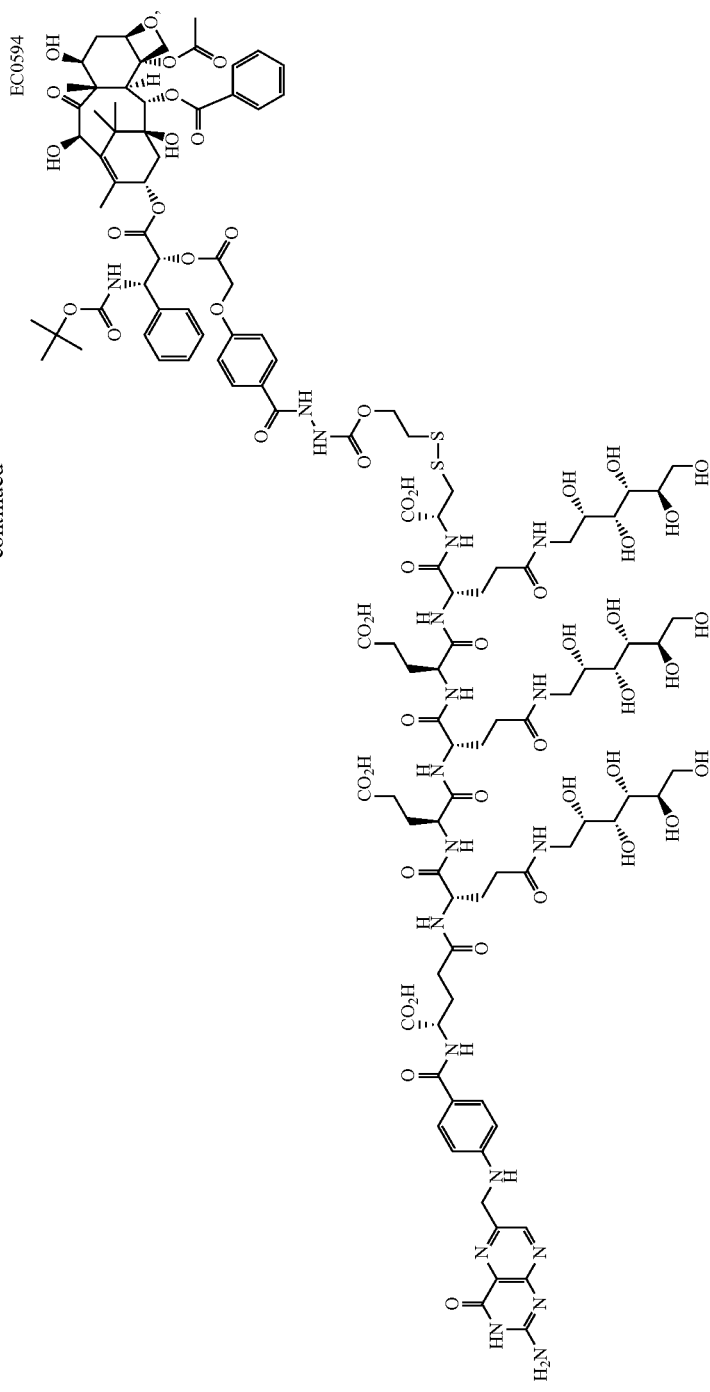
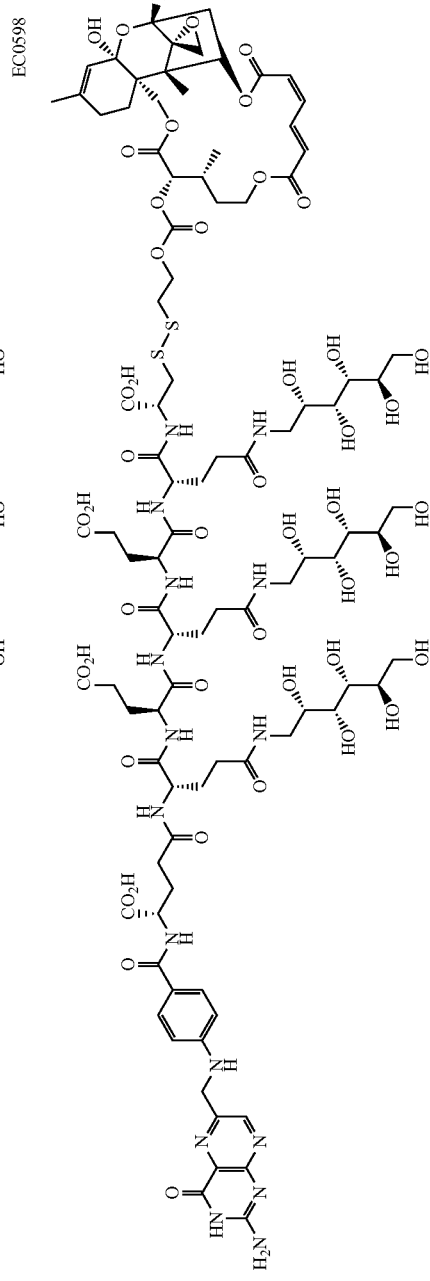

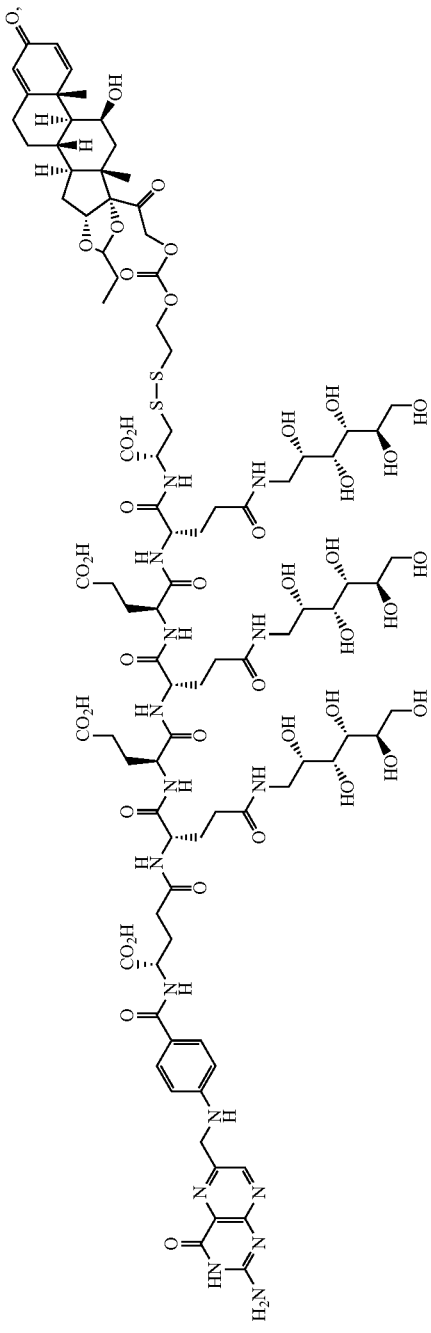
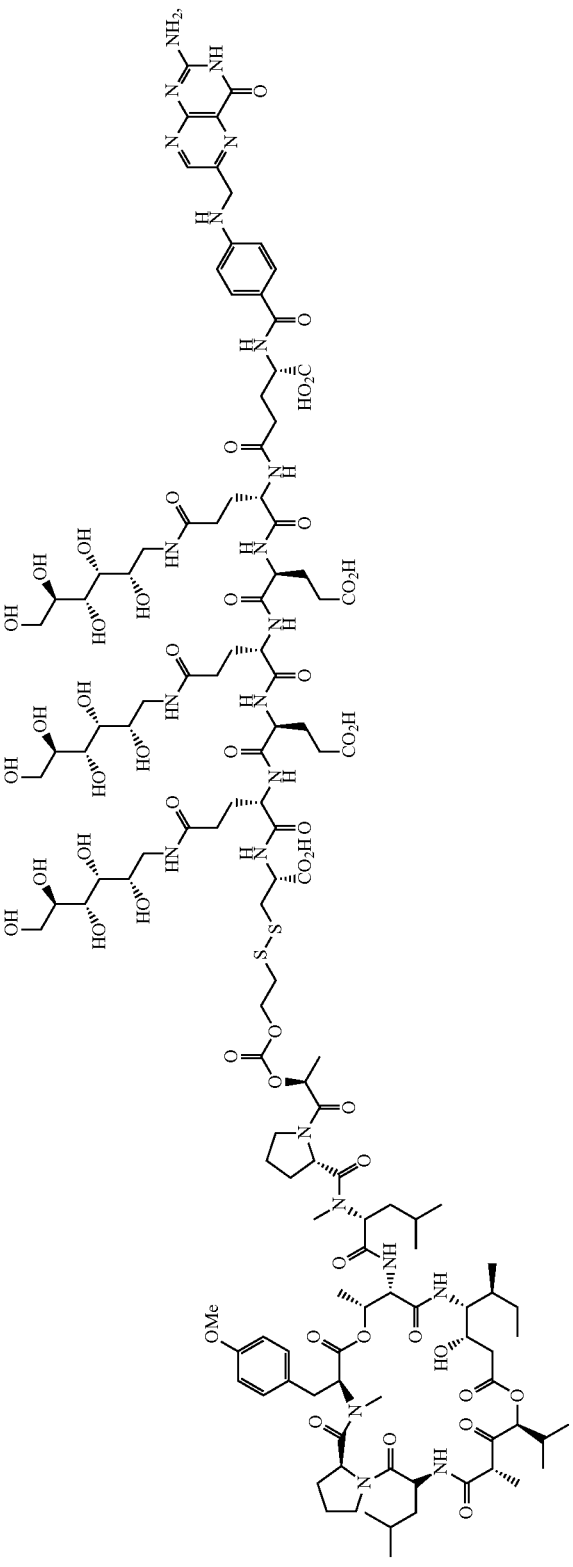

-continued
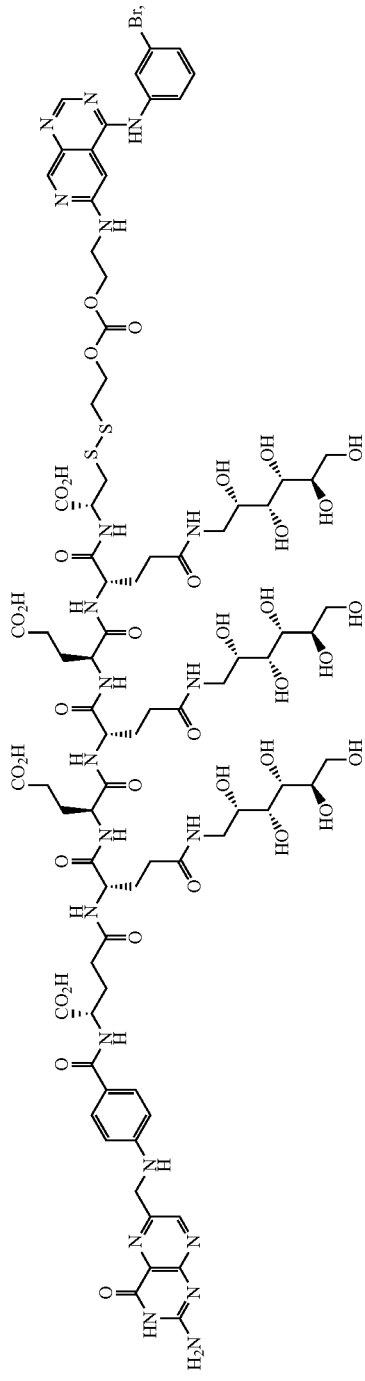
EC0631
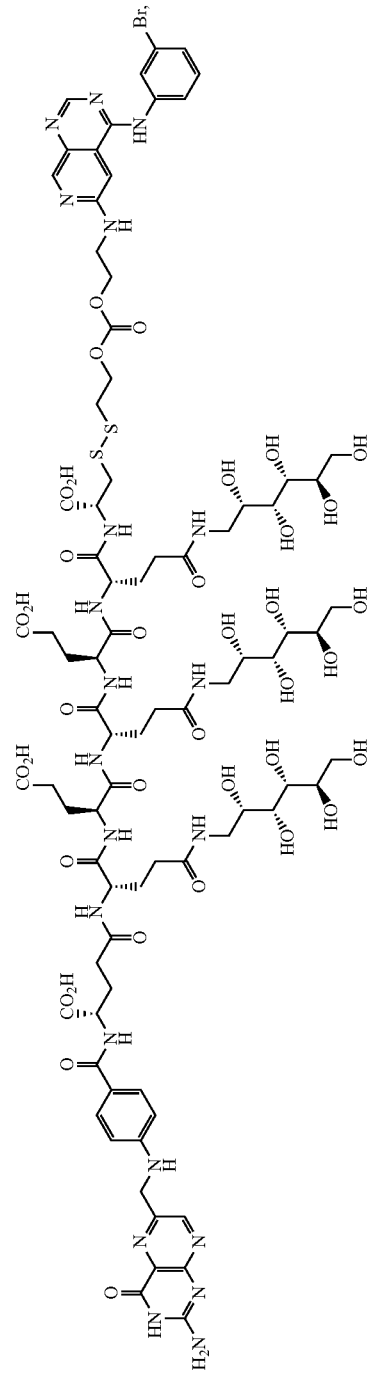
EC0640

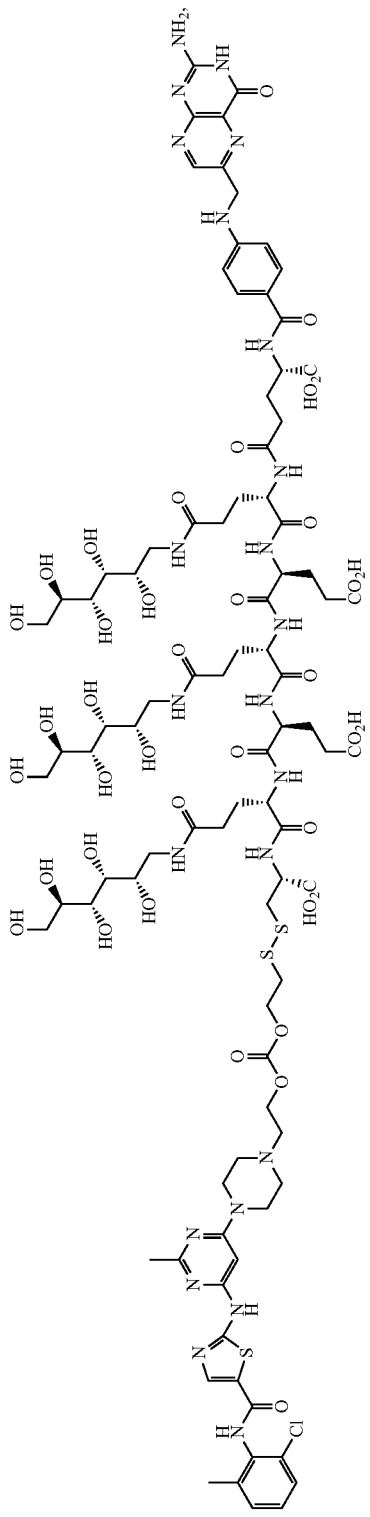

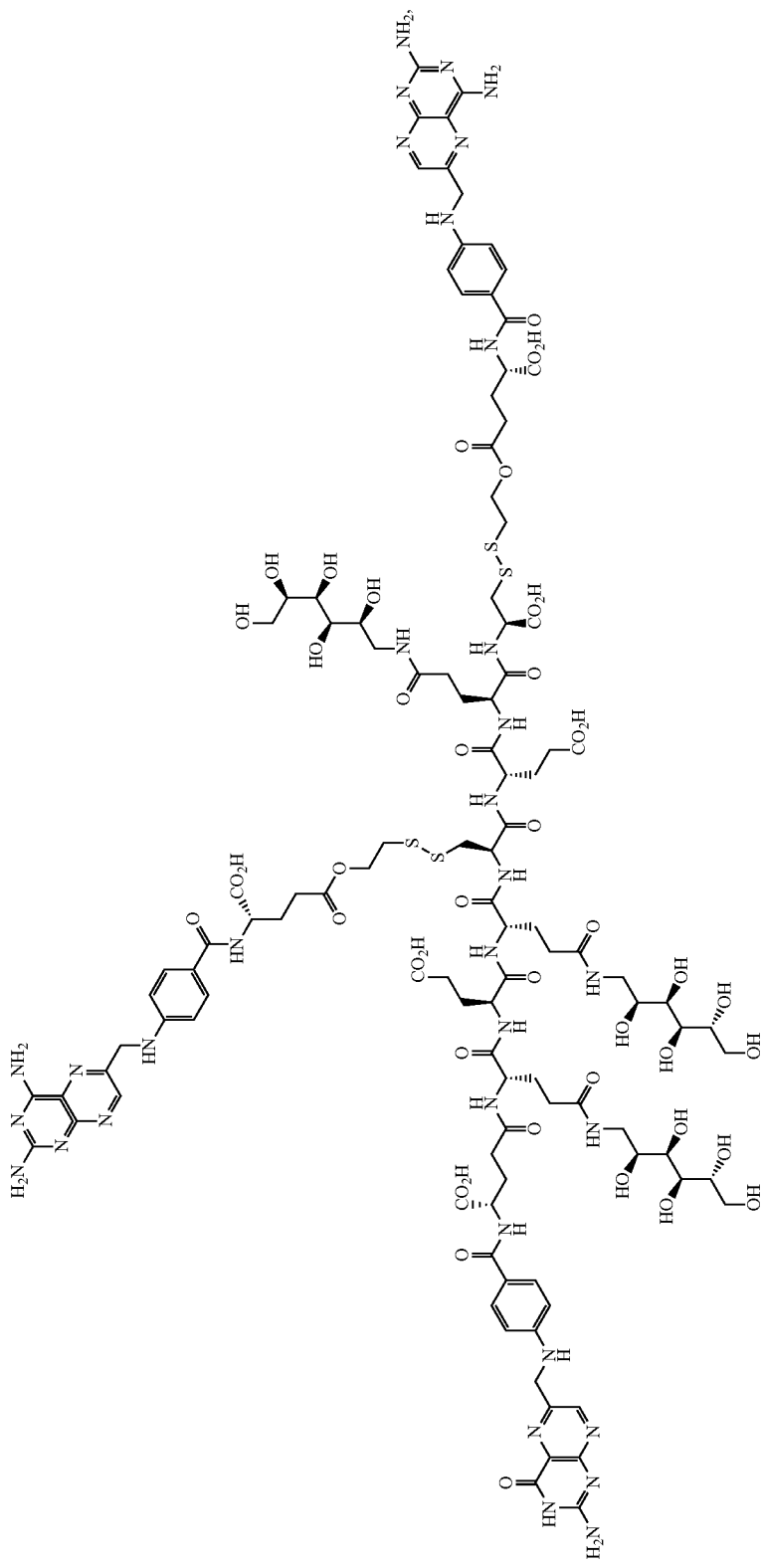

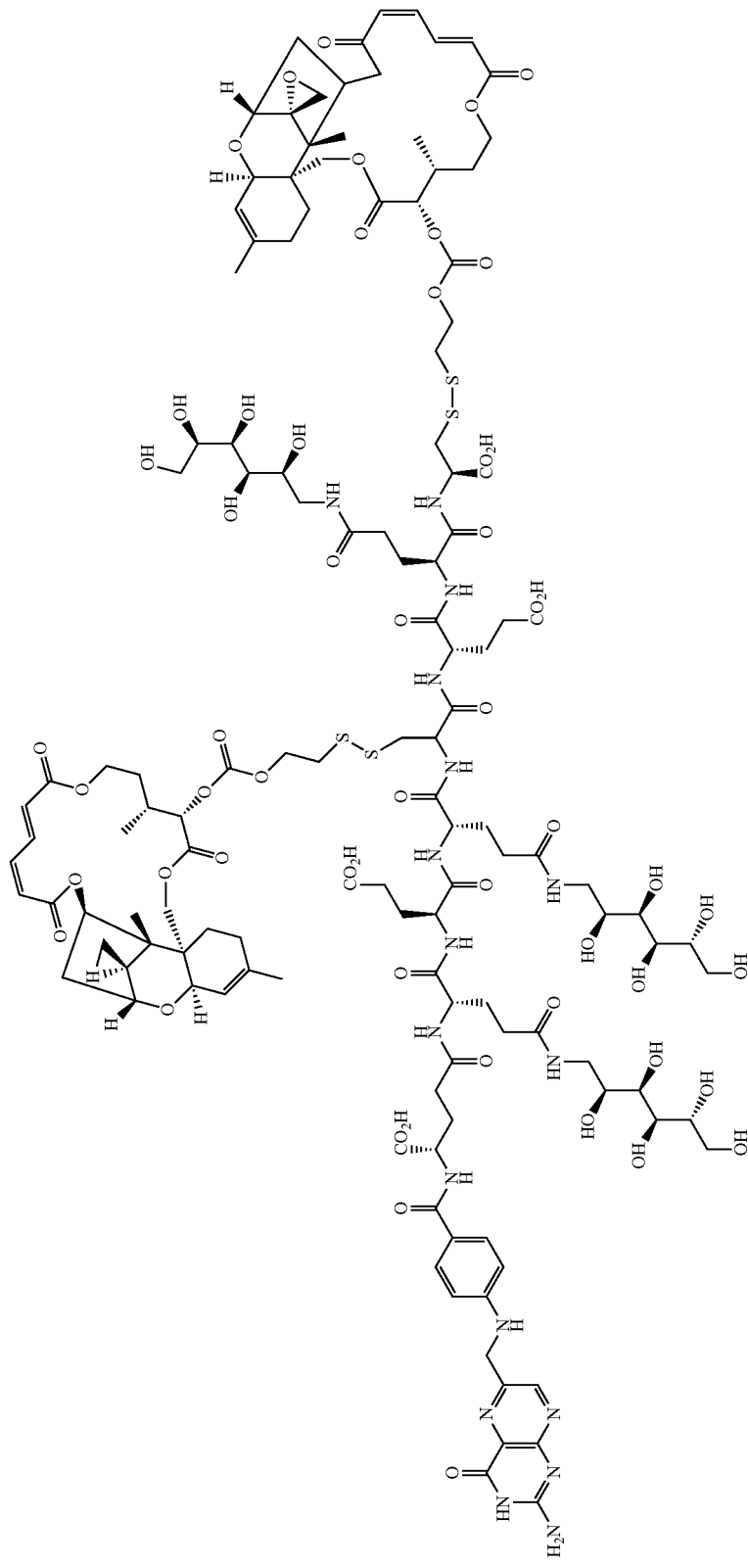

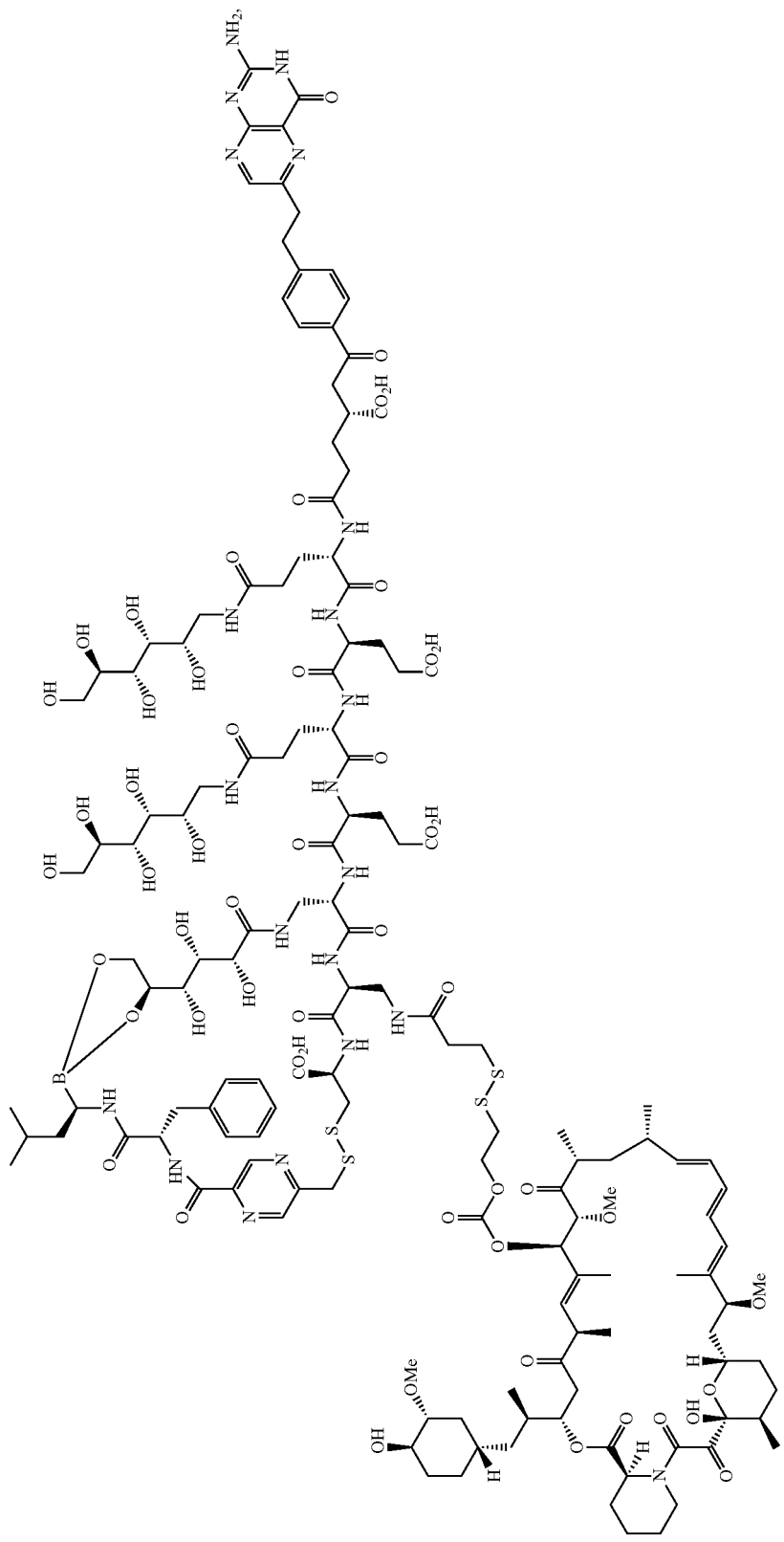

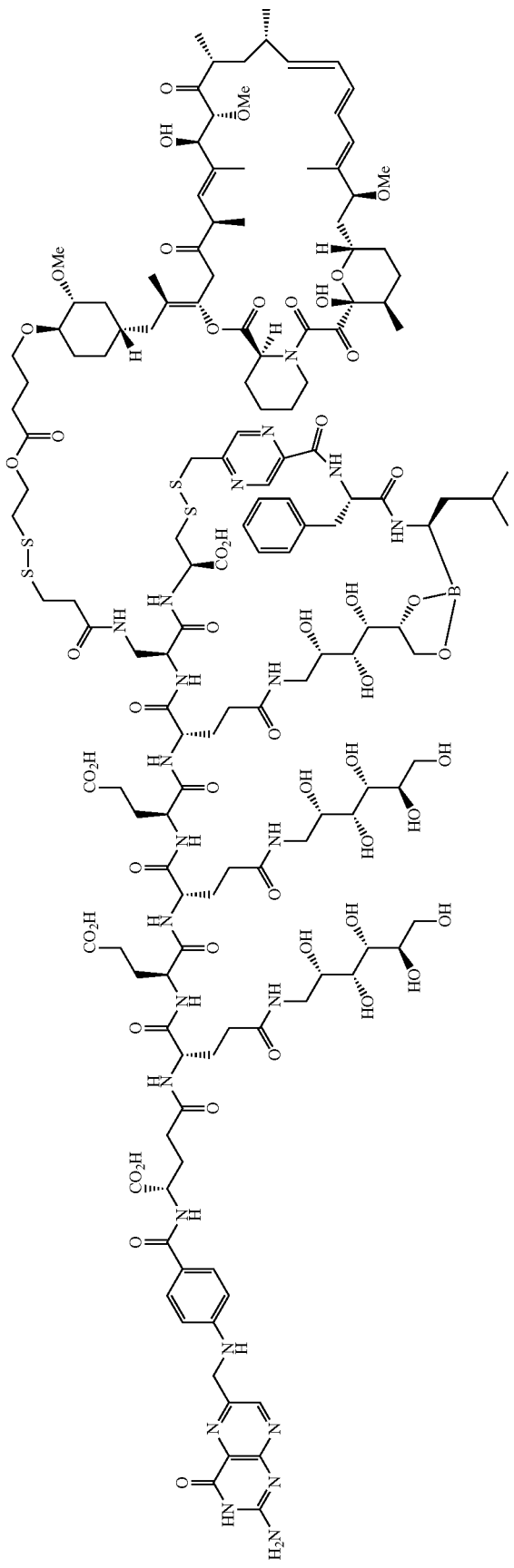

EC0636
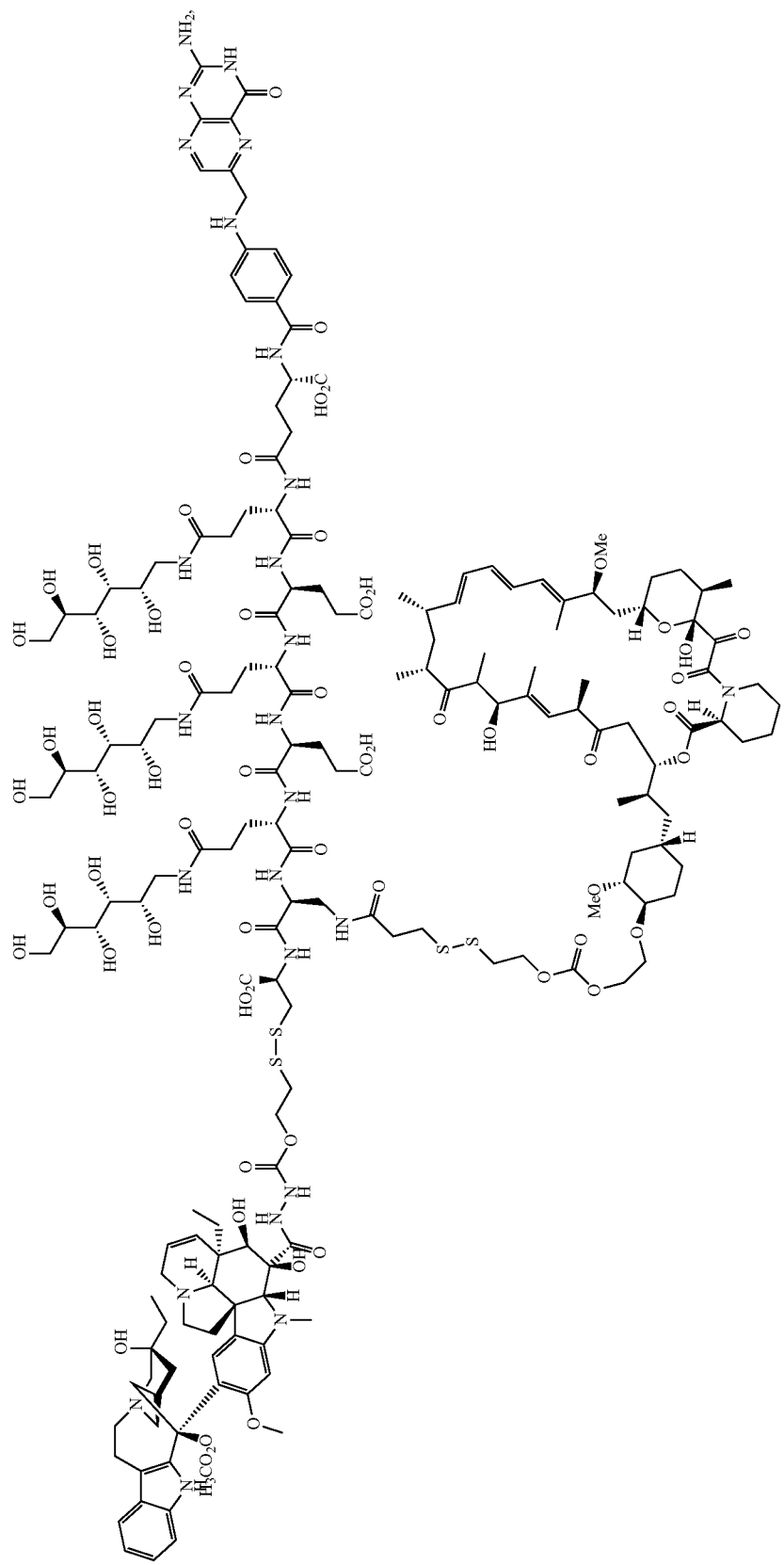

EC0664
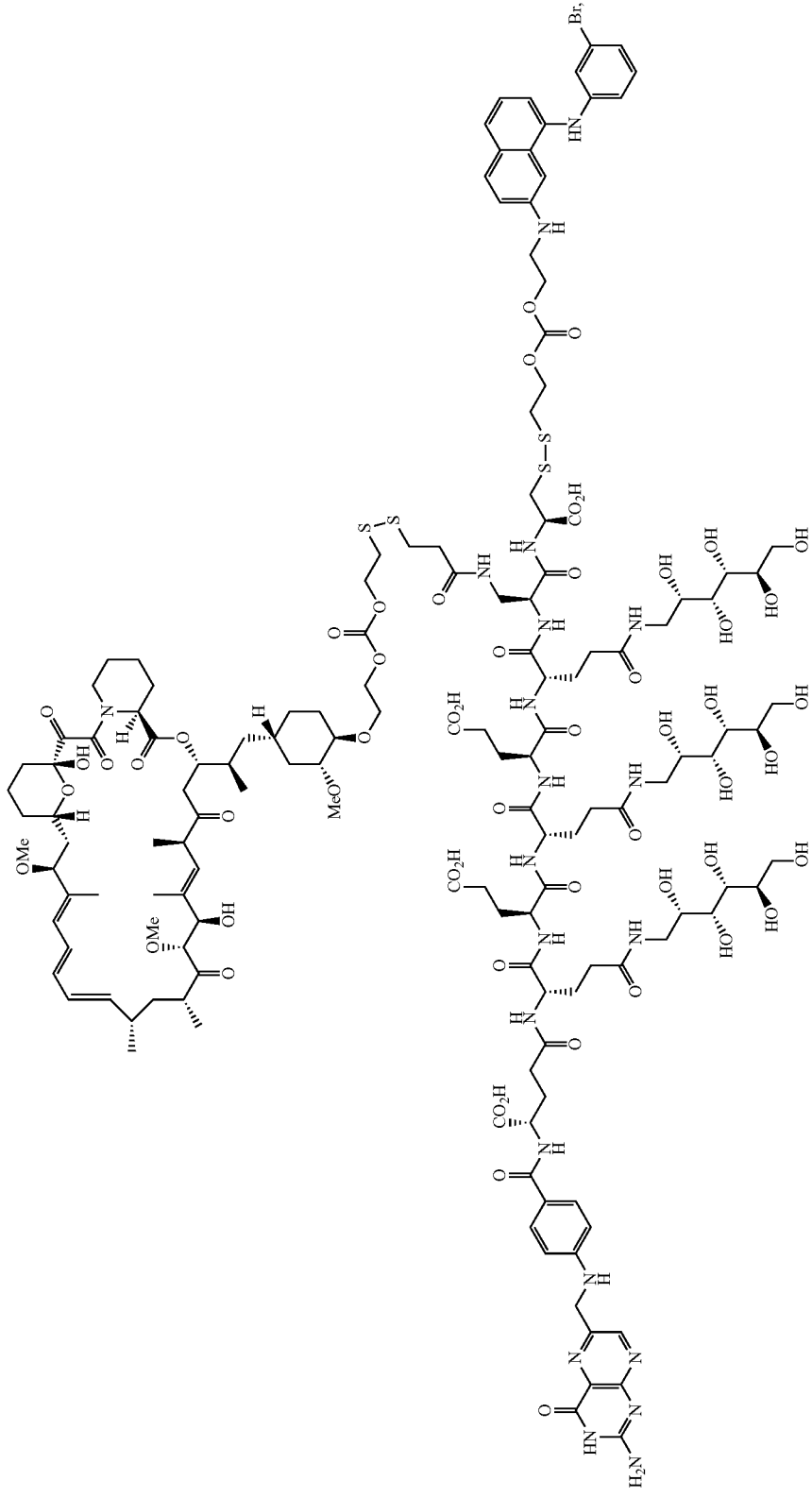

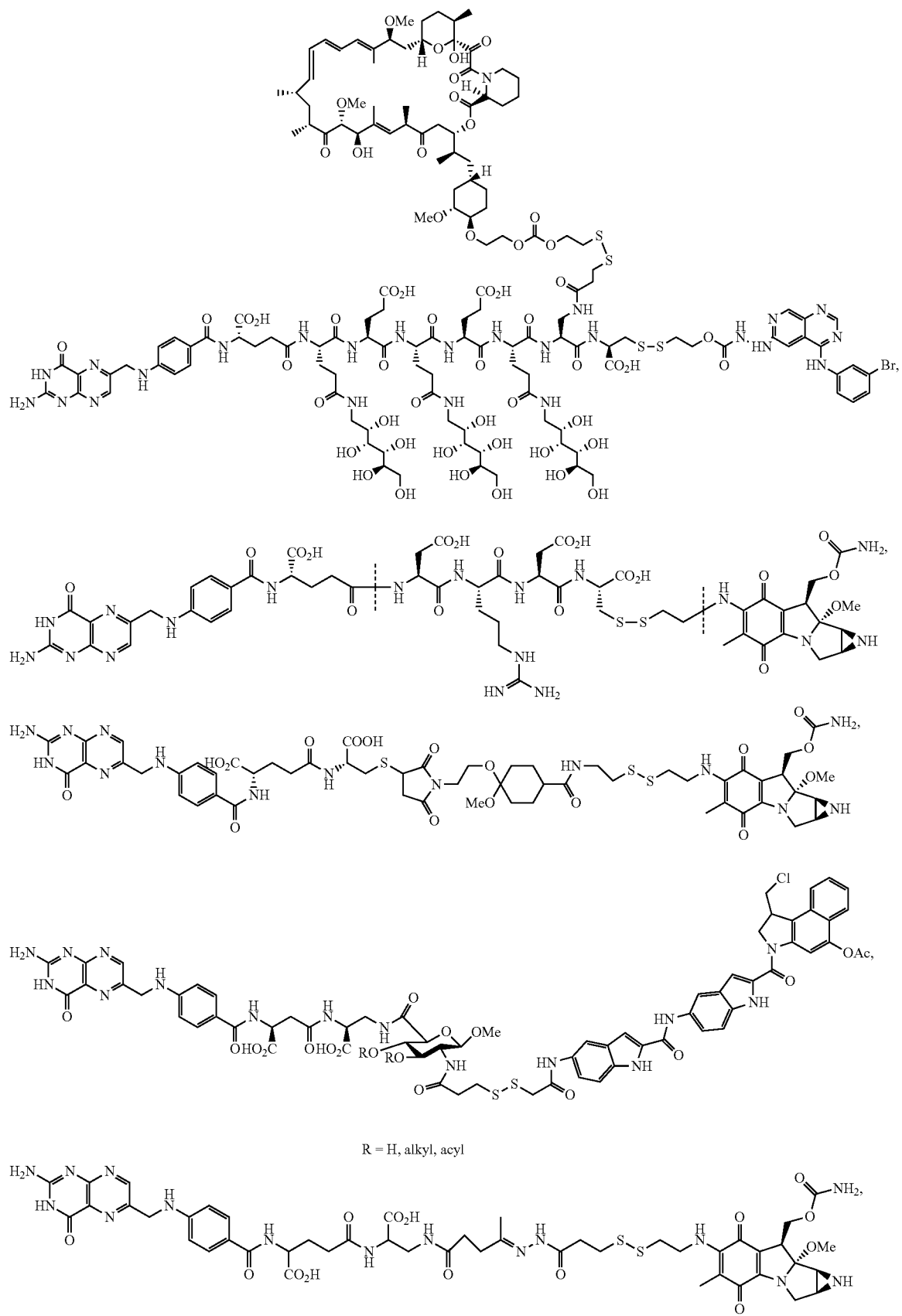

-continued
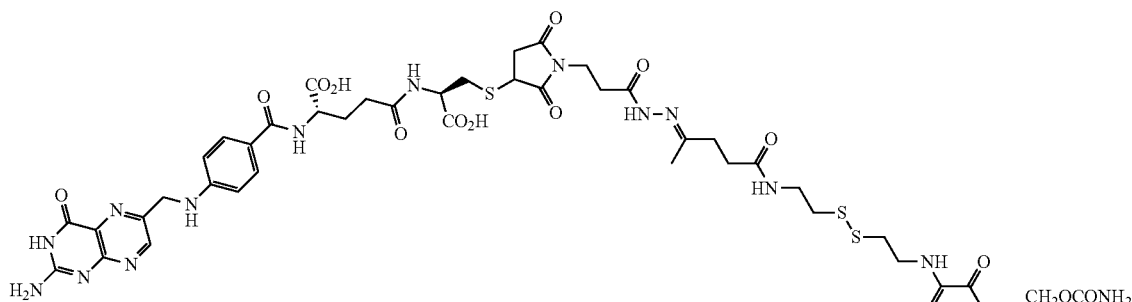
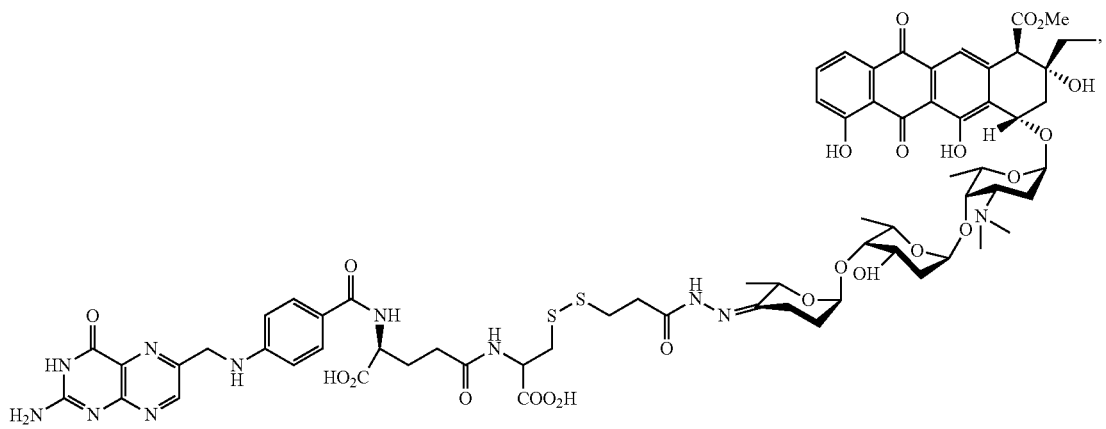
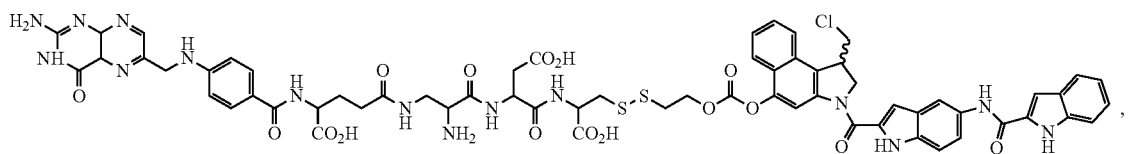
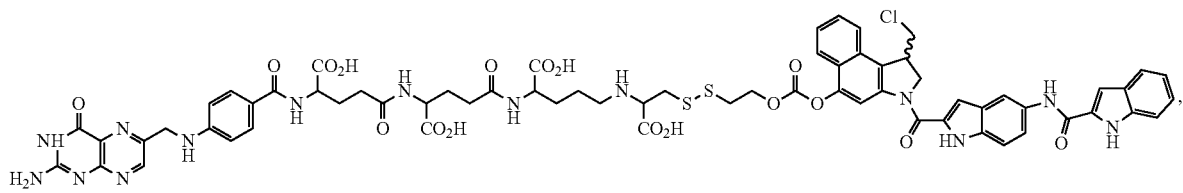
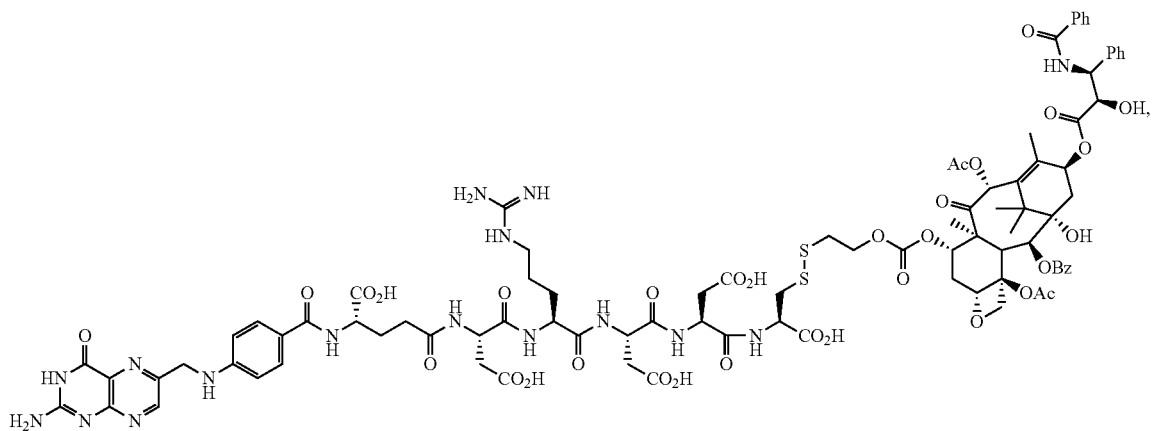

-continued
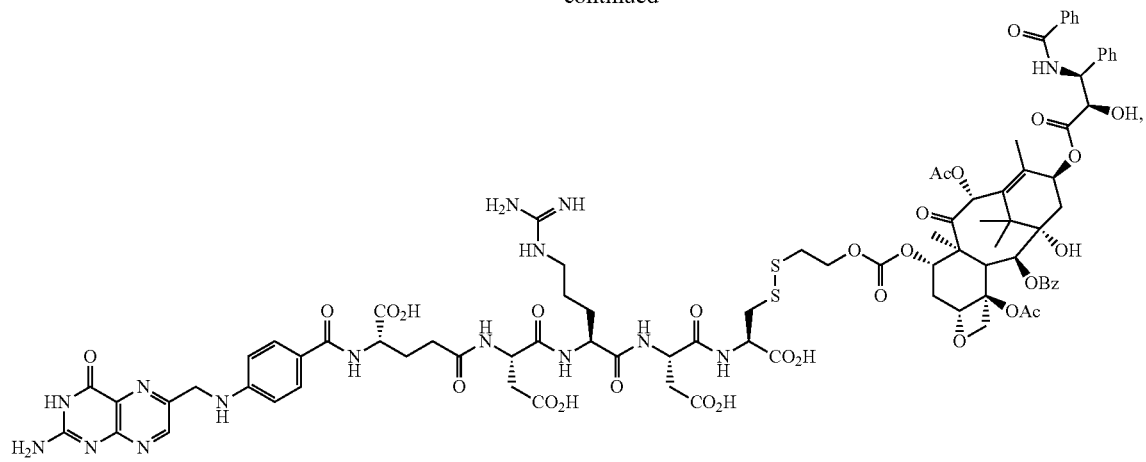
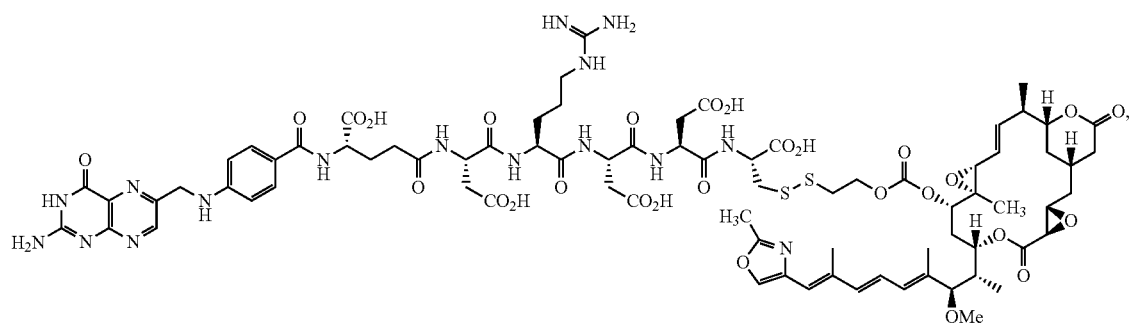
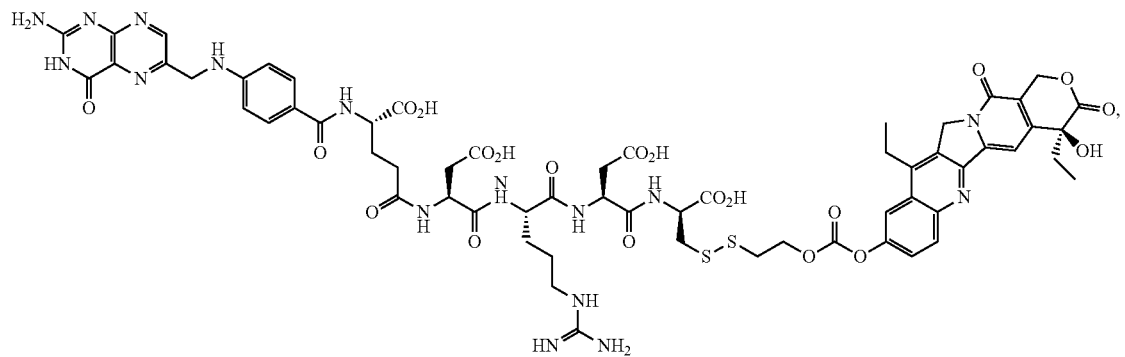
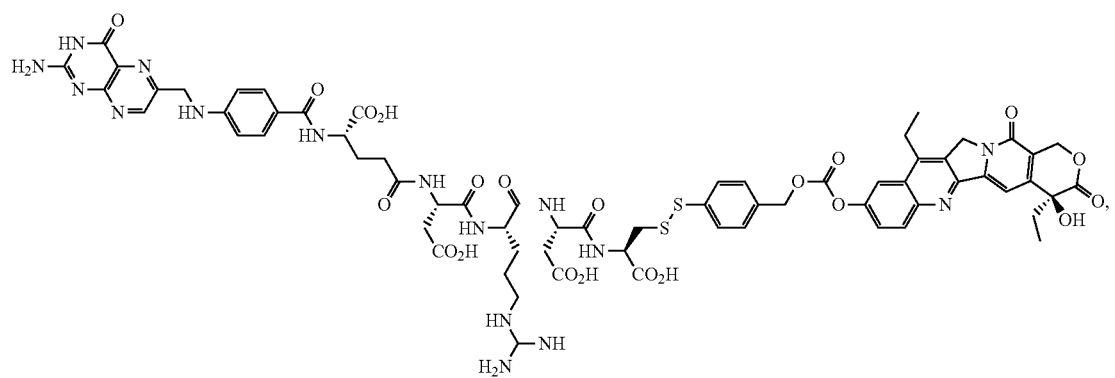

-continued
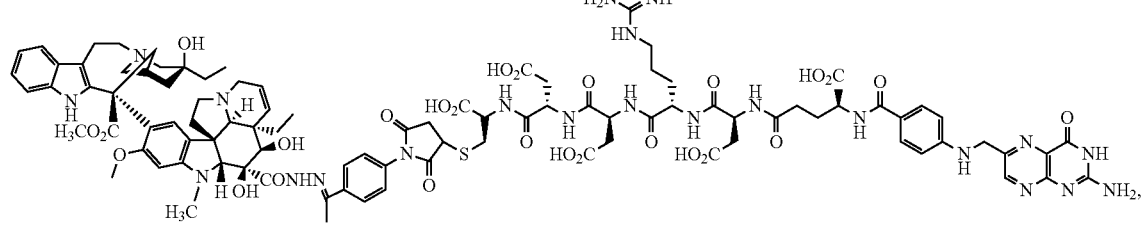
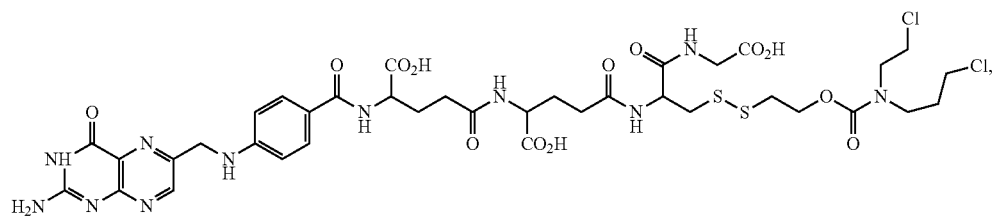
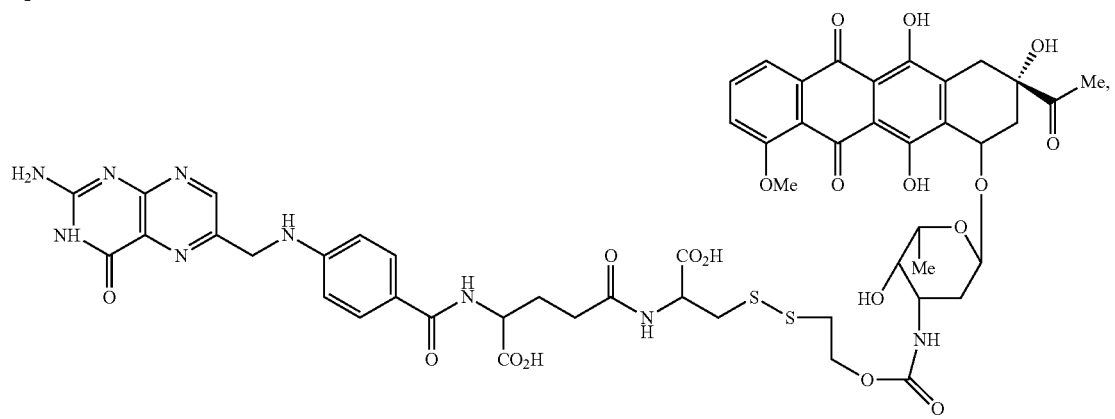
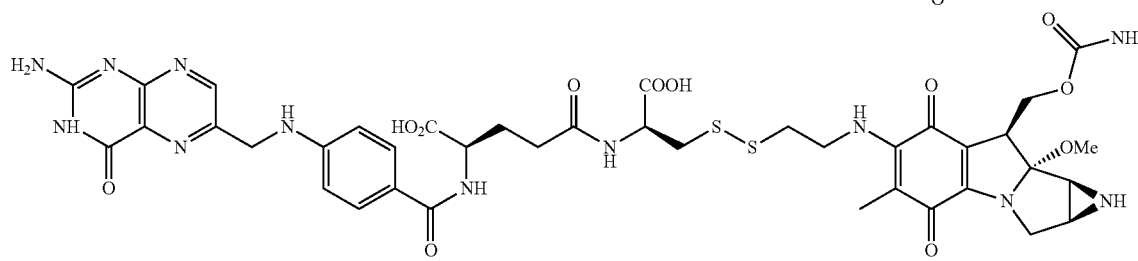
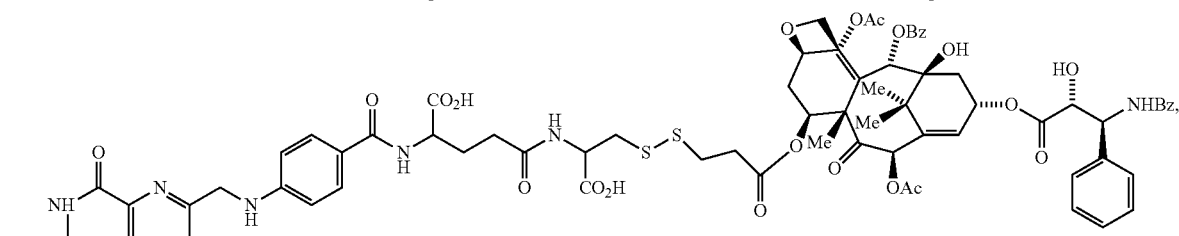
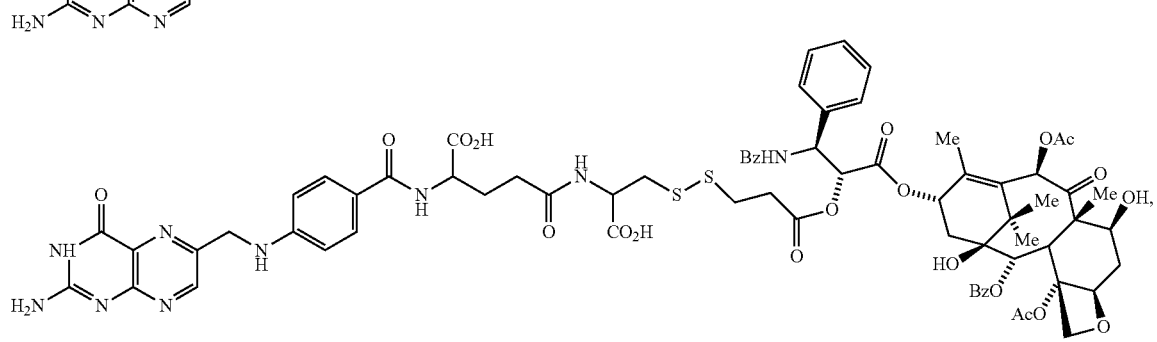

-continued
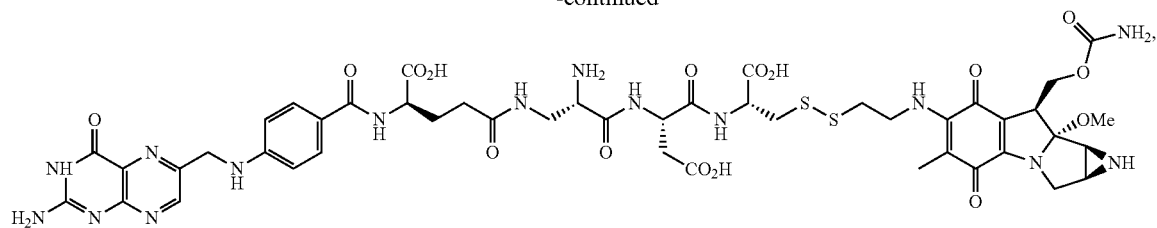
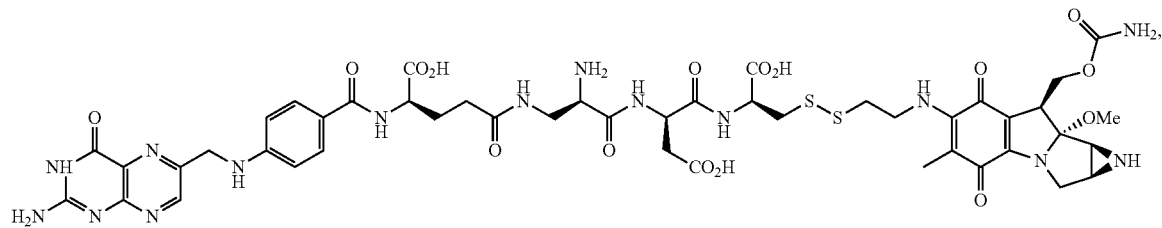
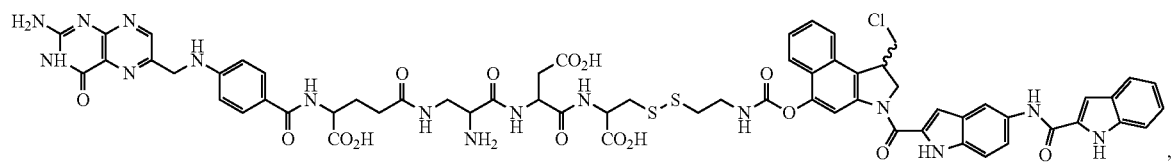
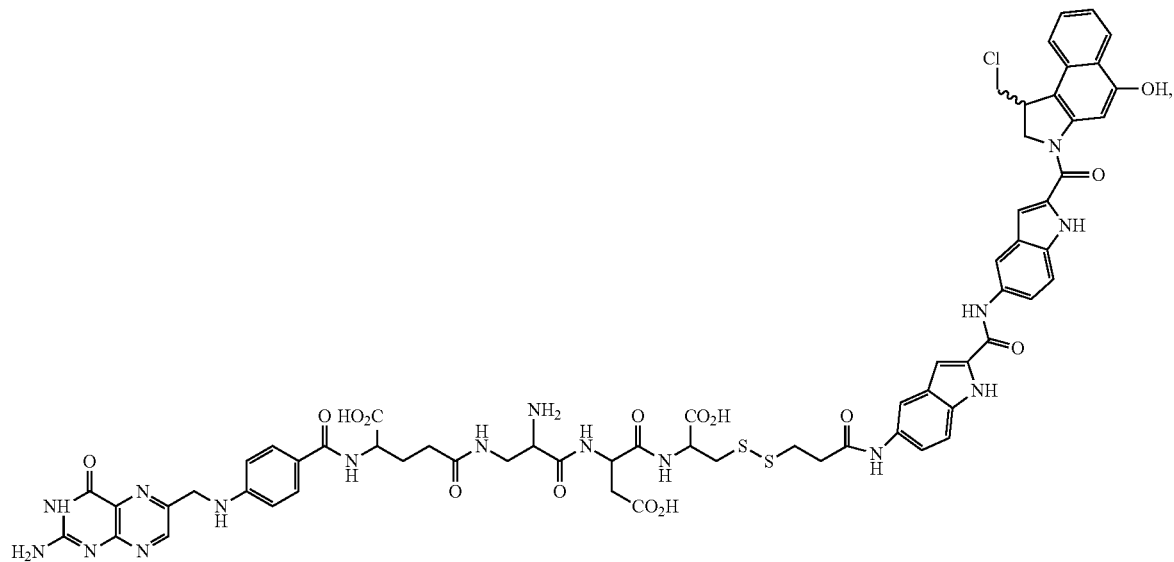 [SMILES: Nc1nc2ncc(CNc3ccc(C(=O)NC(CCC(=O)NCC(N)C(=O)NC(CC(=O)O)C(=O)NC(CSSCCC(=O)Nc4ccc5[nH]c(C(=O)Nc6ccc7[nH]c(C(=O)N8CC(CCl)c9c8cc(O)c8ccccc98)cc7c6)cc5c4)C(=O)O)C(=O)O)cc3)nc2c(=O)[nH]1]
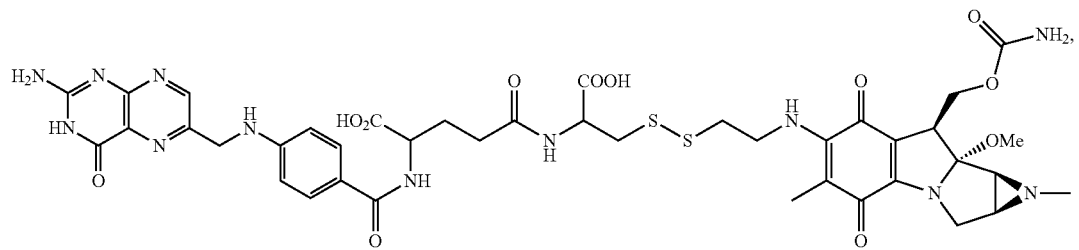

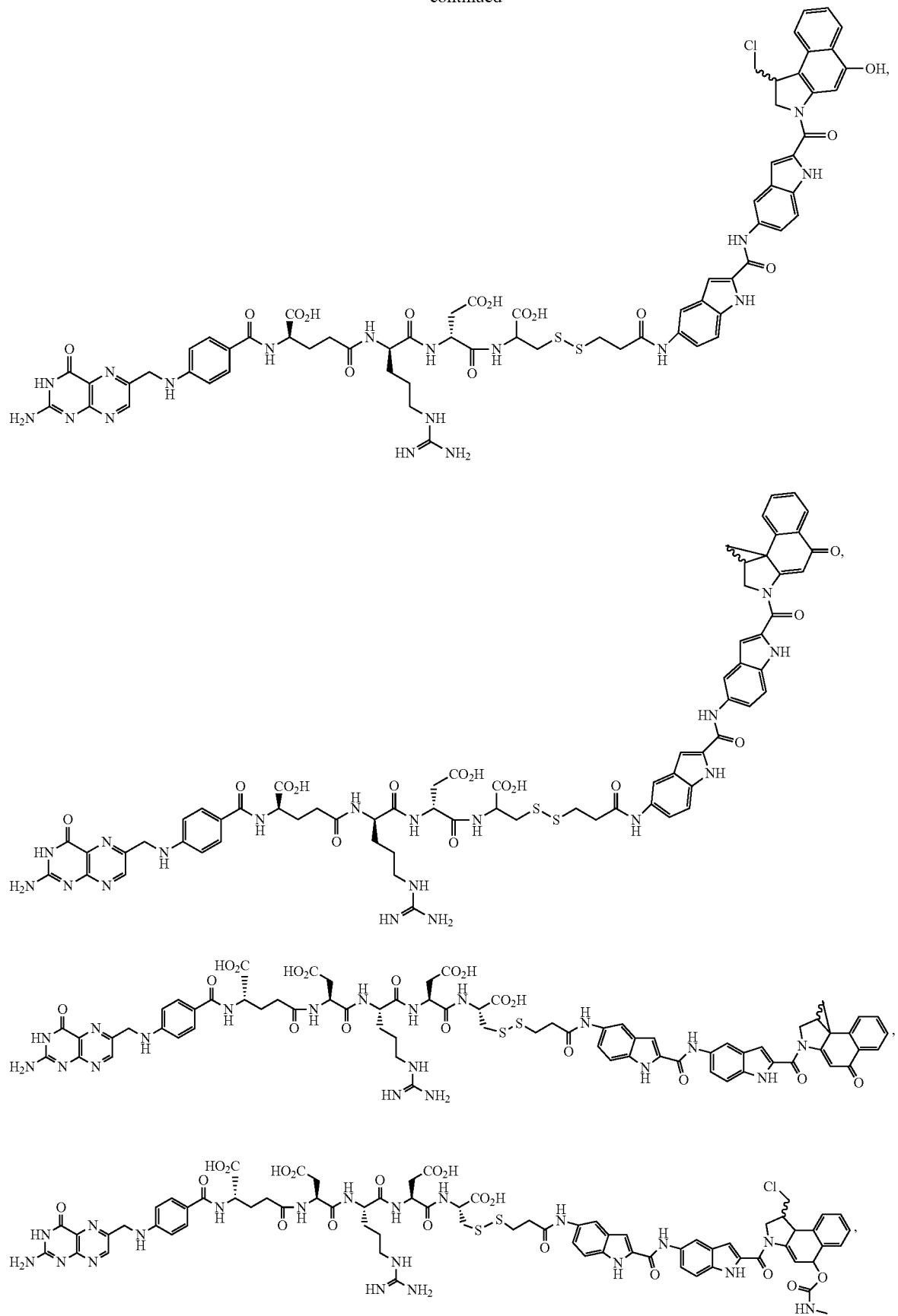

227
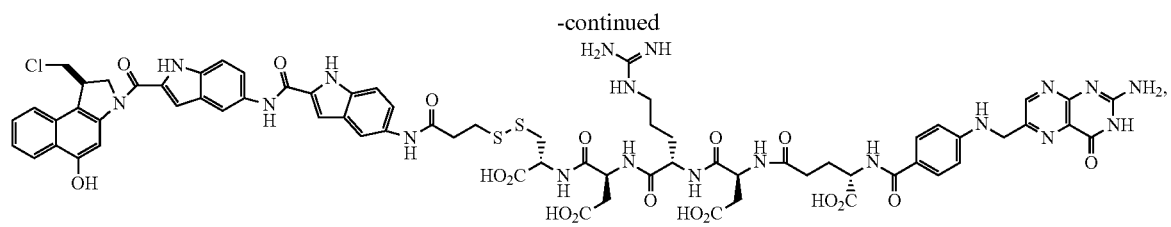
228
-continued
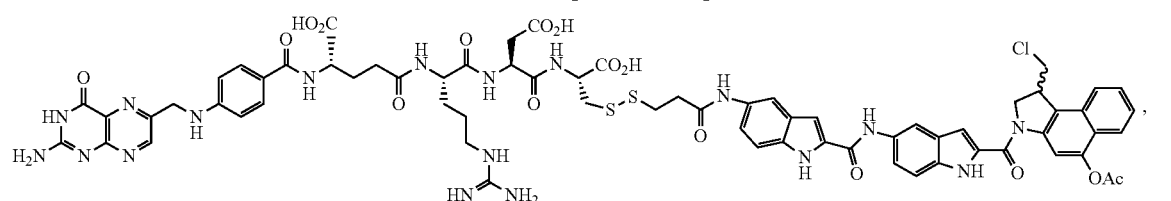
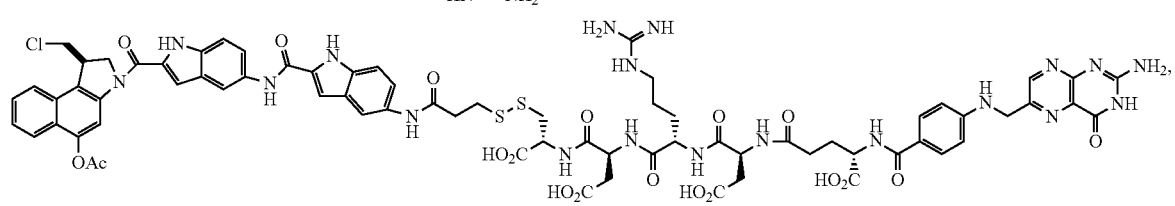

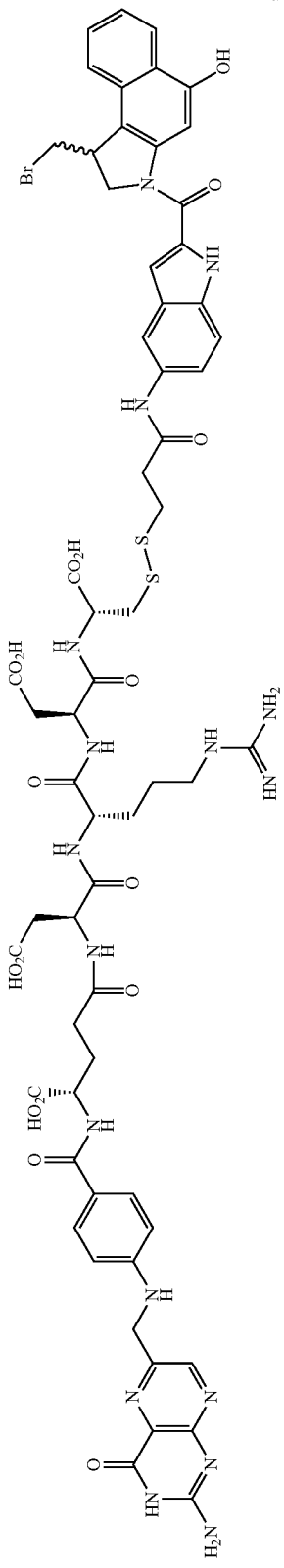
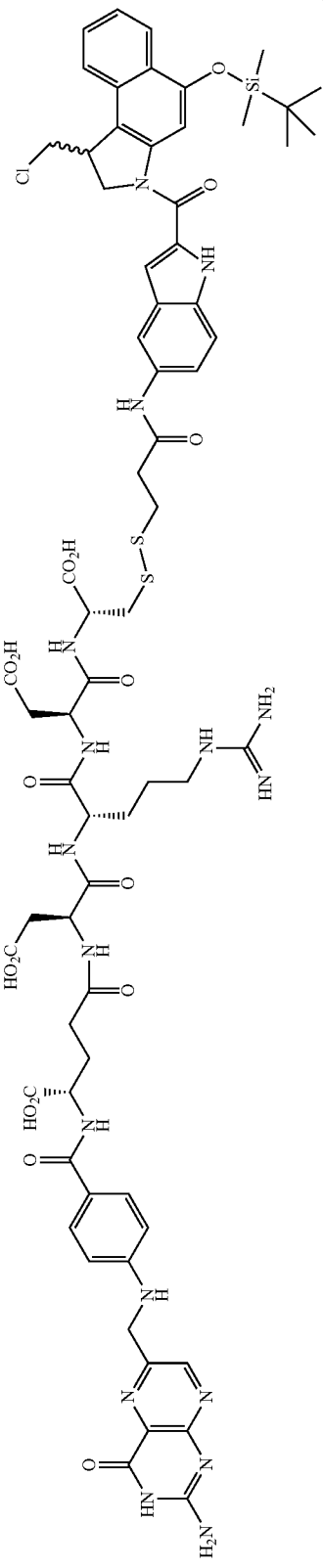

-continued
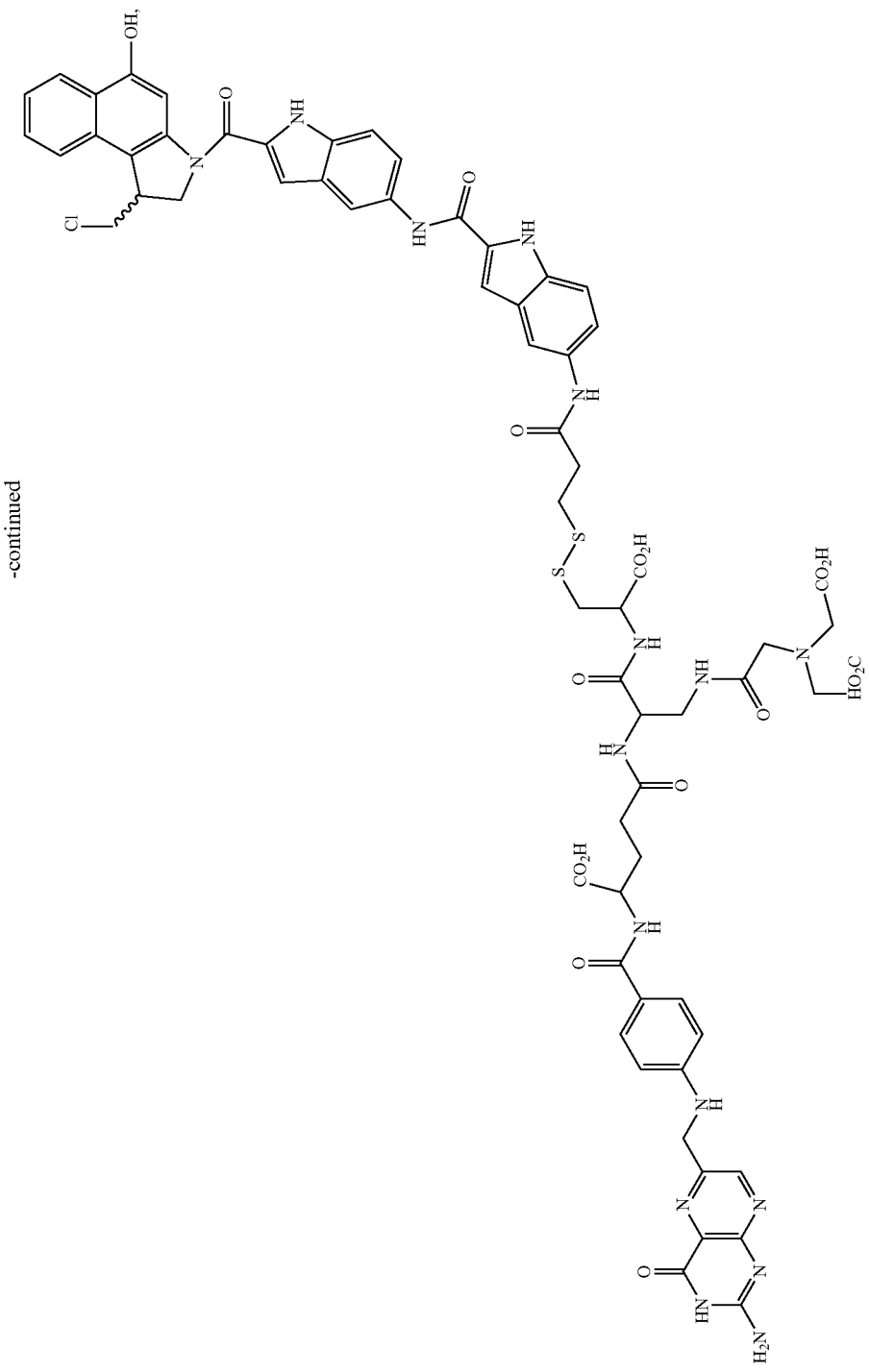

-continued
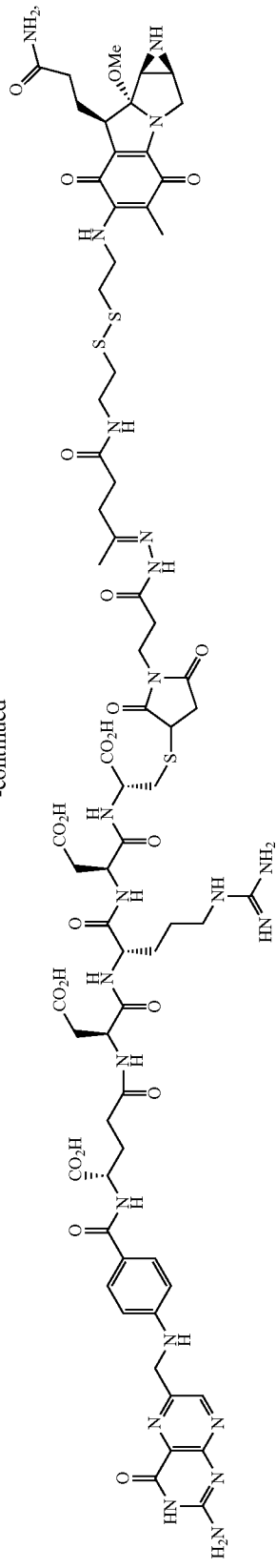
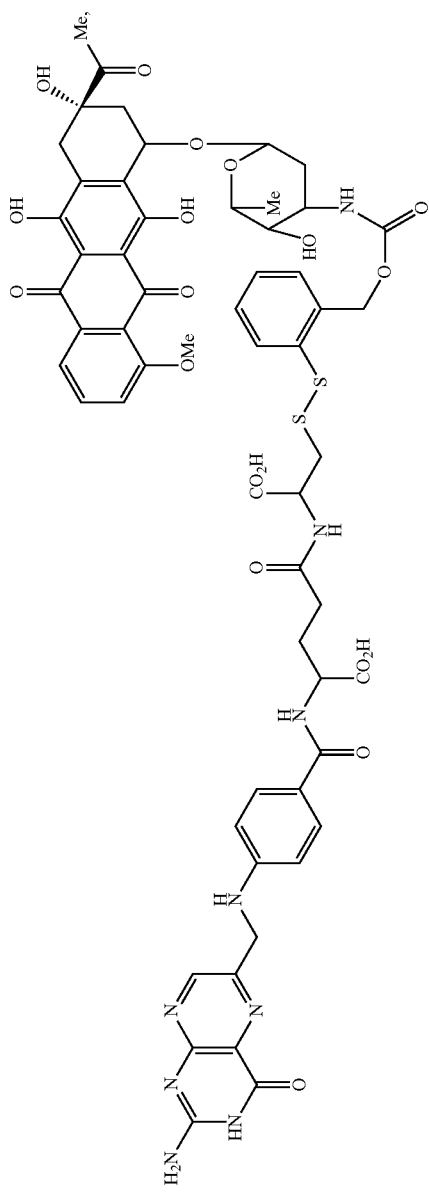

-continued
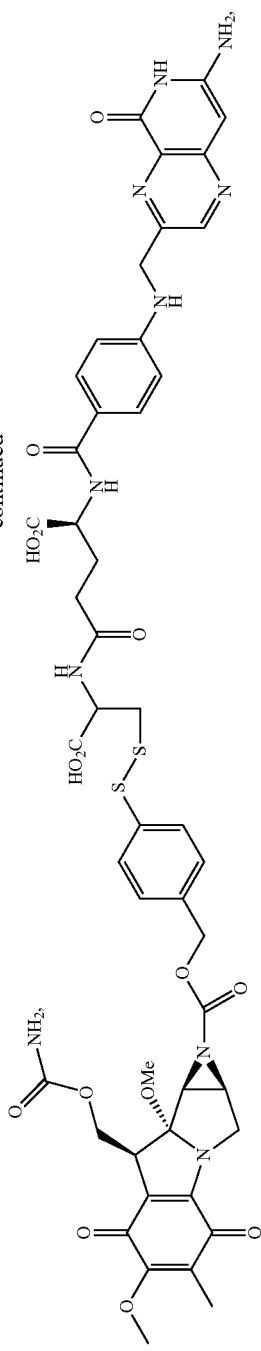
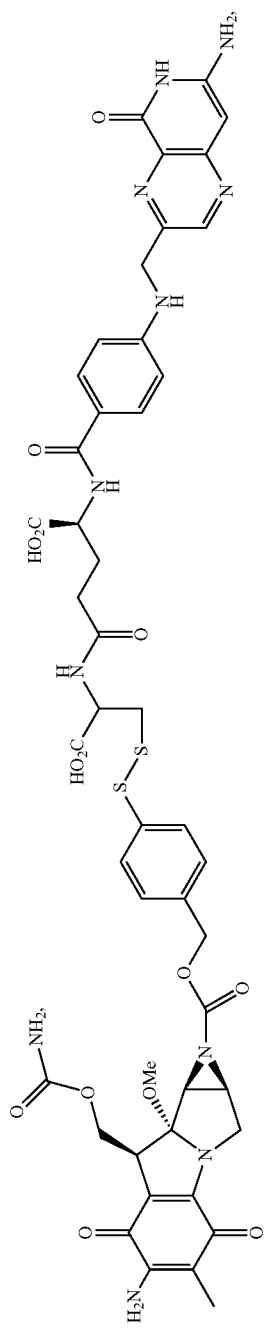

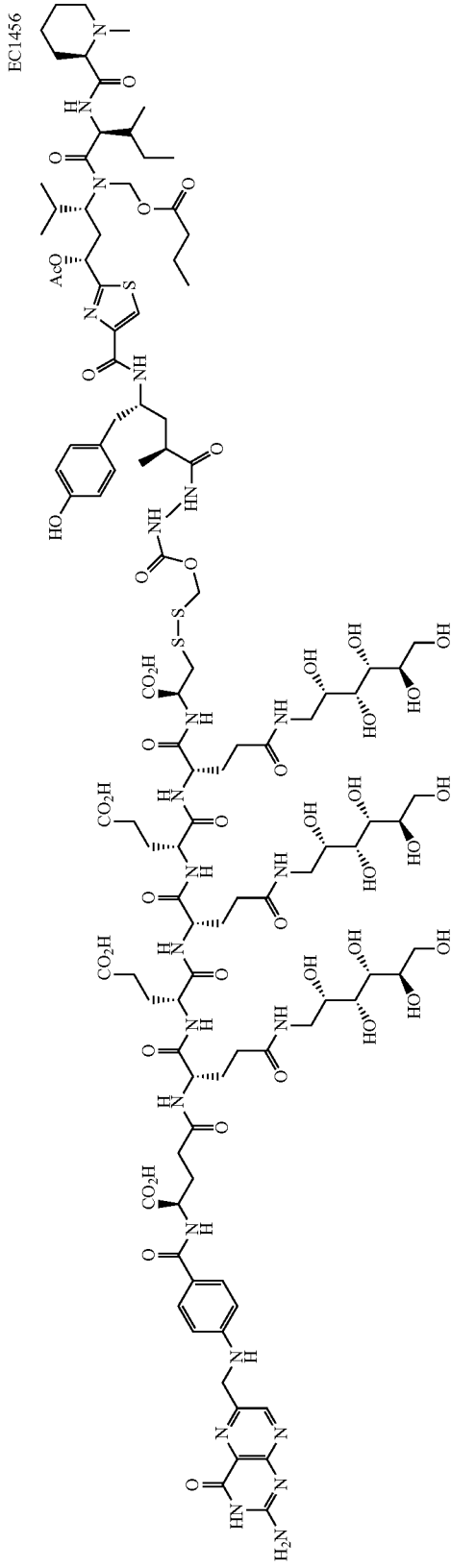
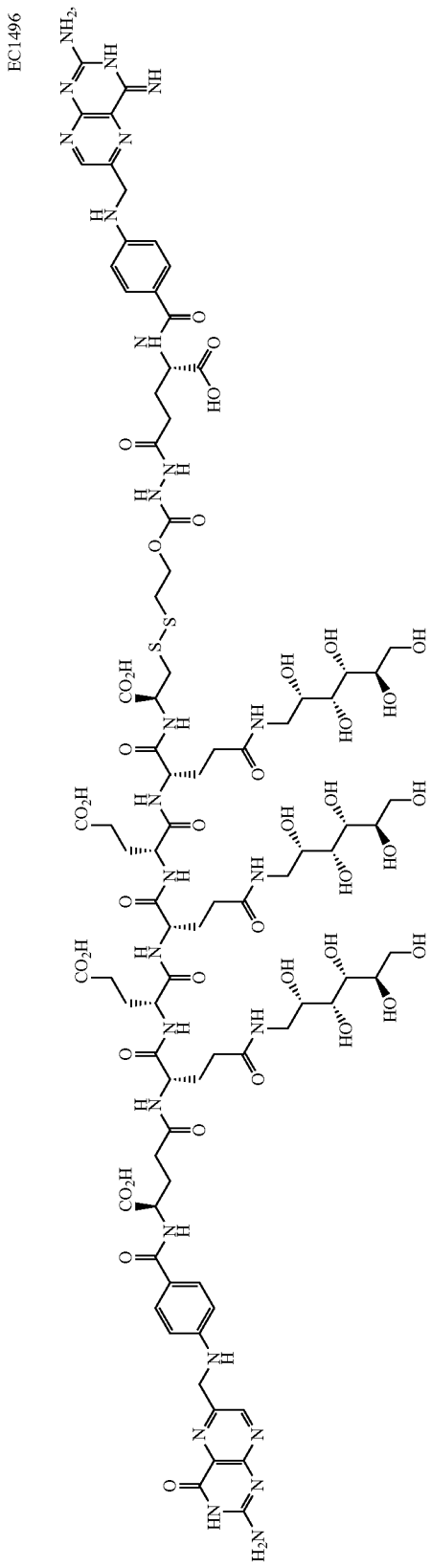

-continued
EC0746
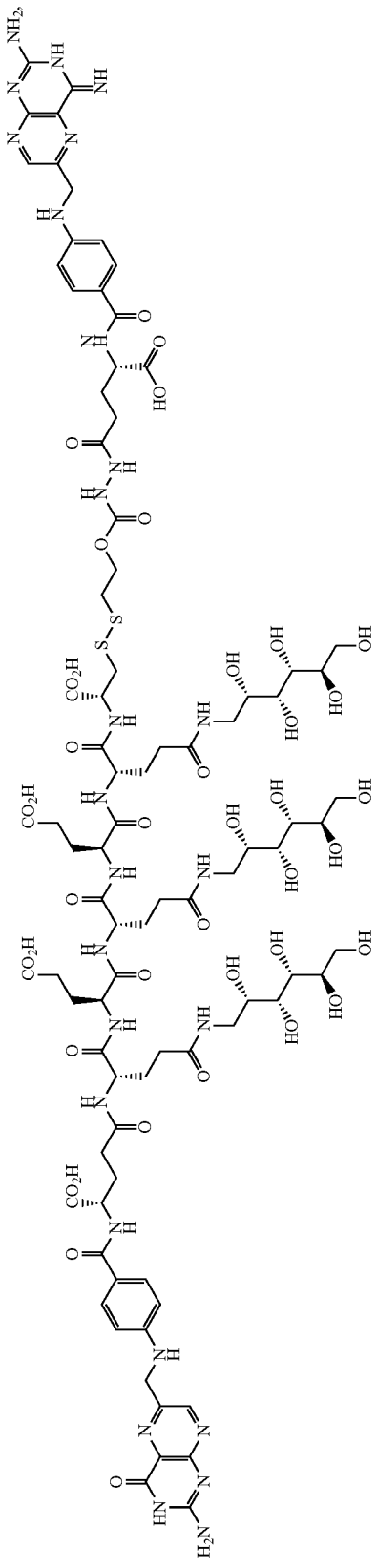
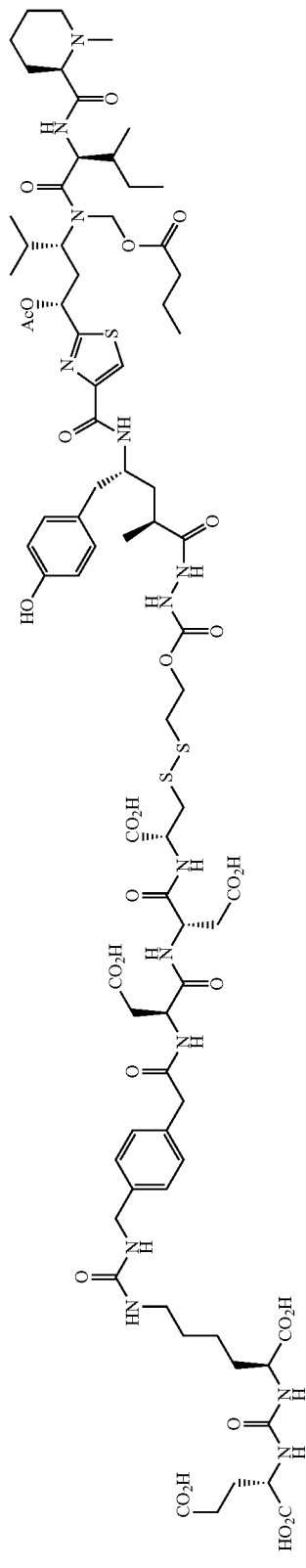

-continued
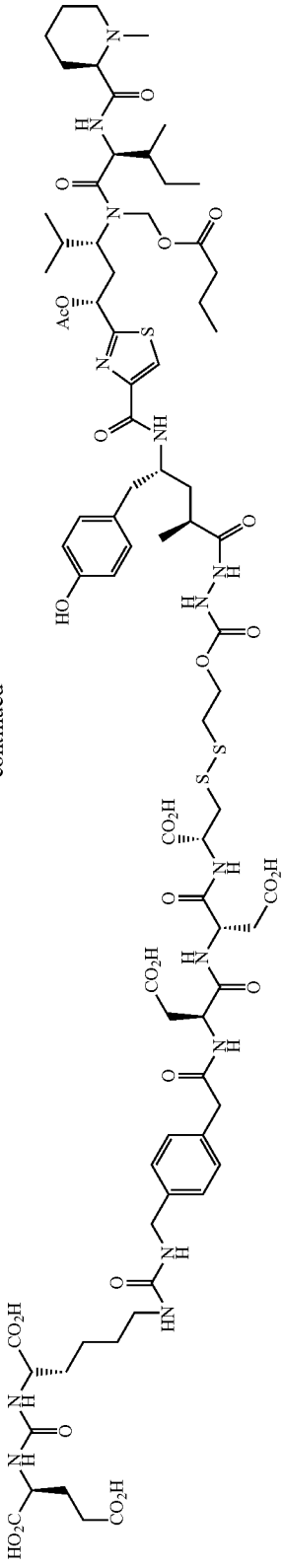
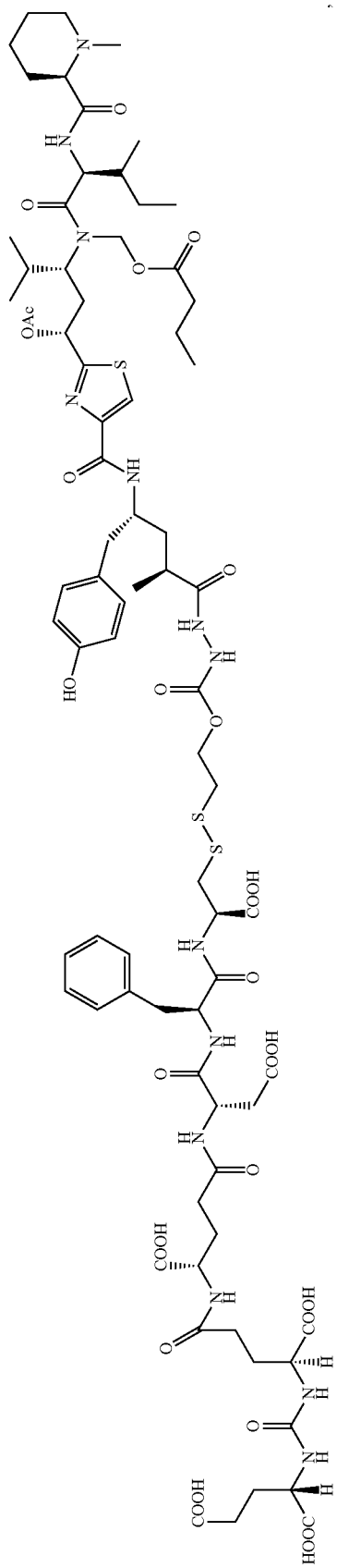

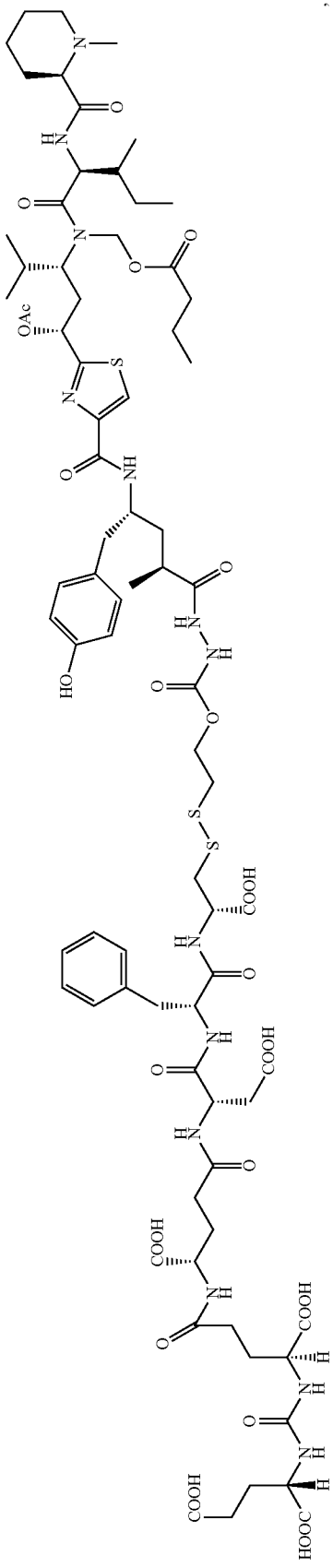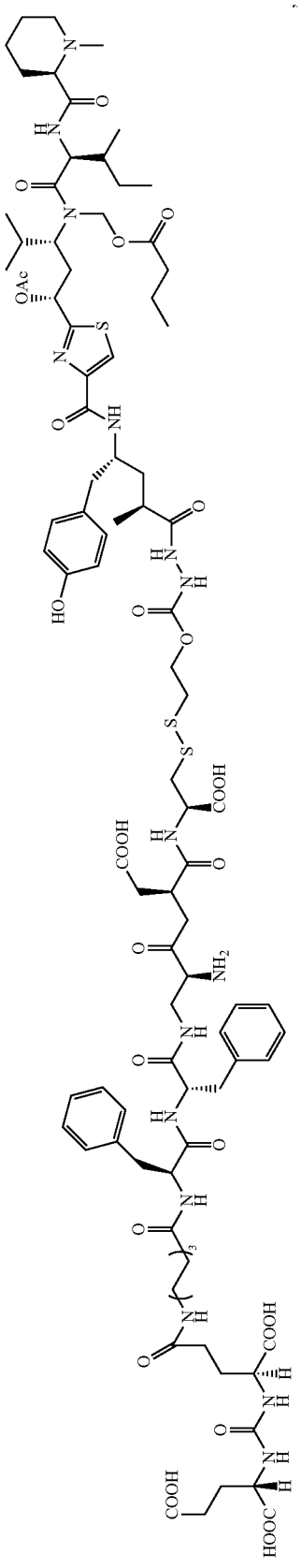

-continued
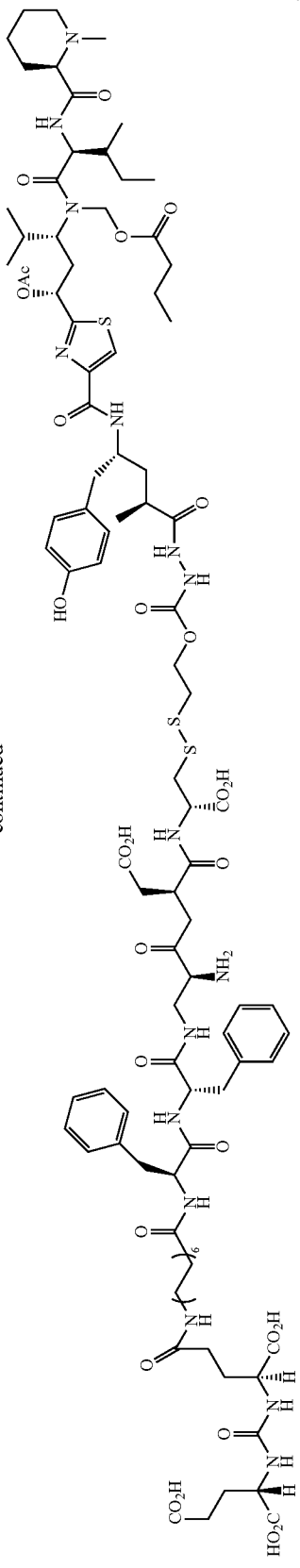 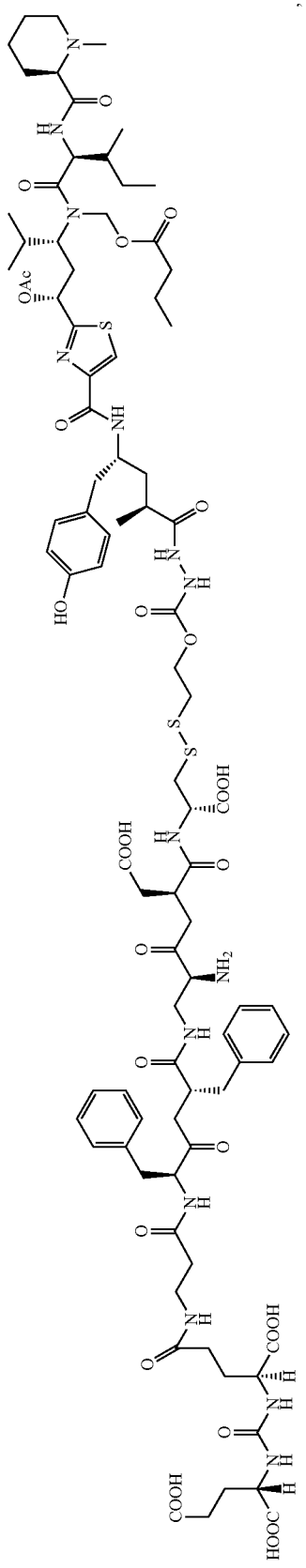

-continued
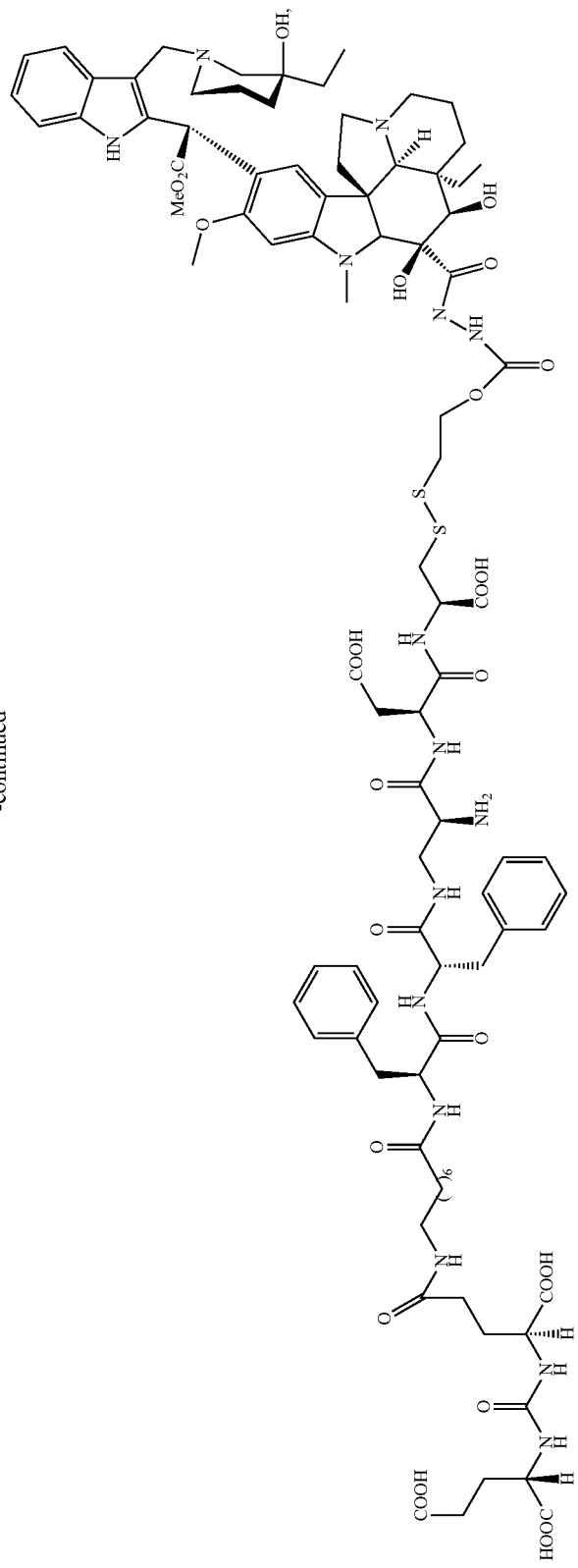

-continued
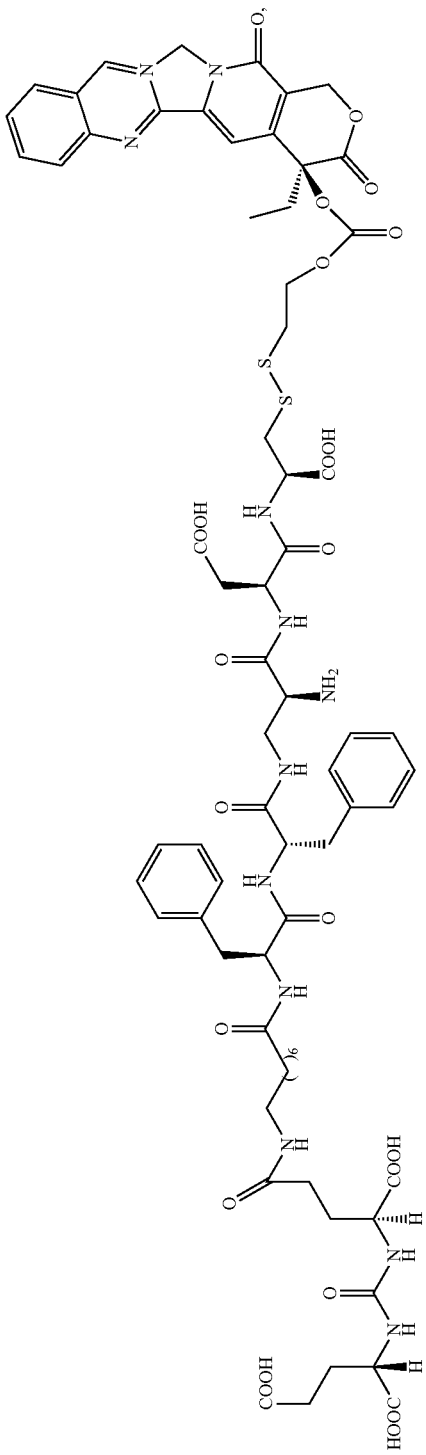
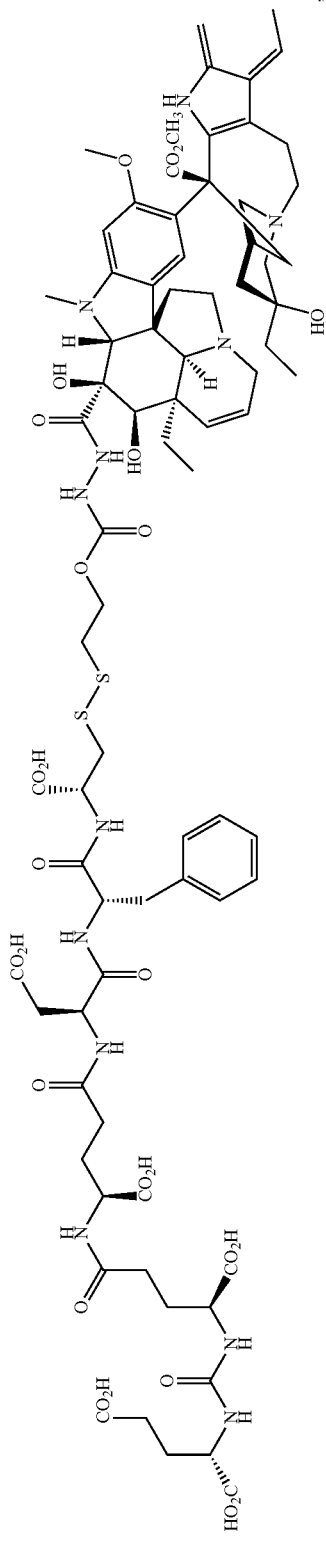

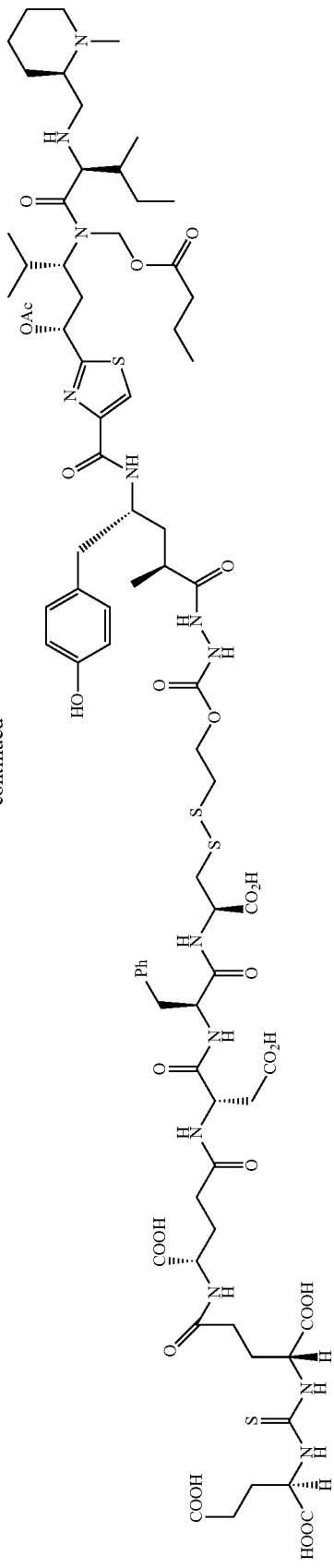
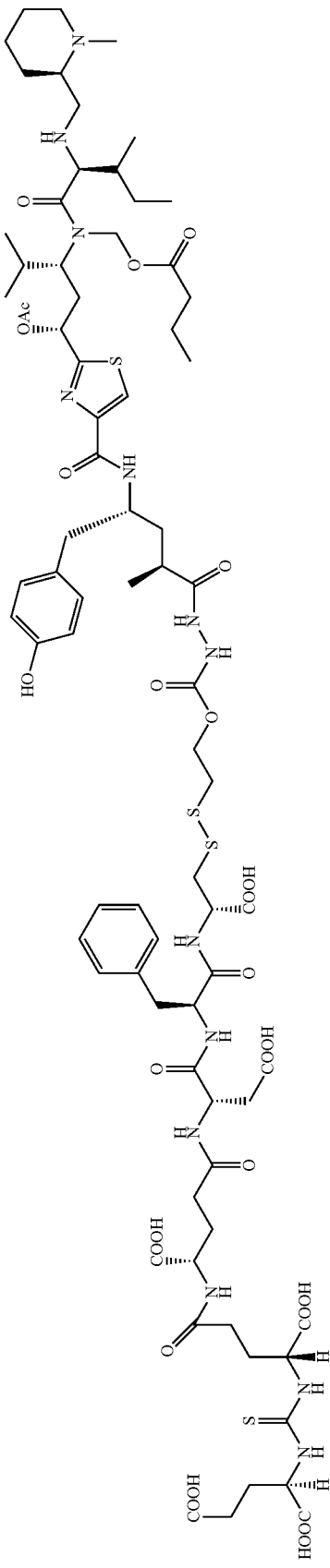

-continued
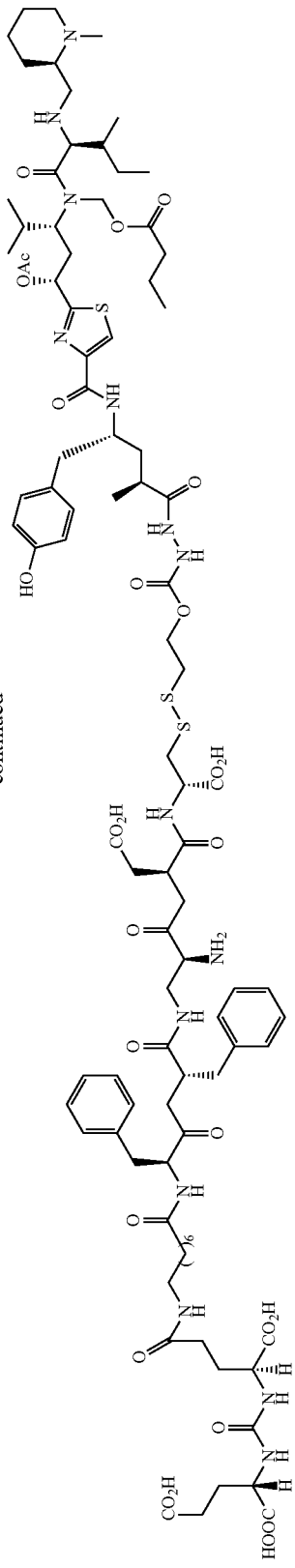
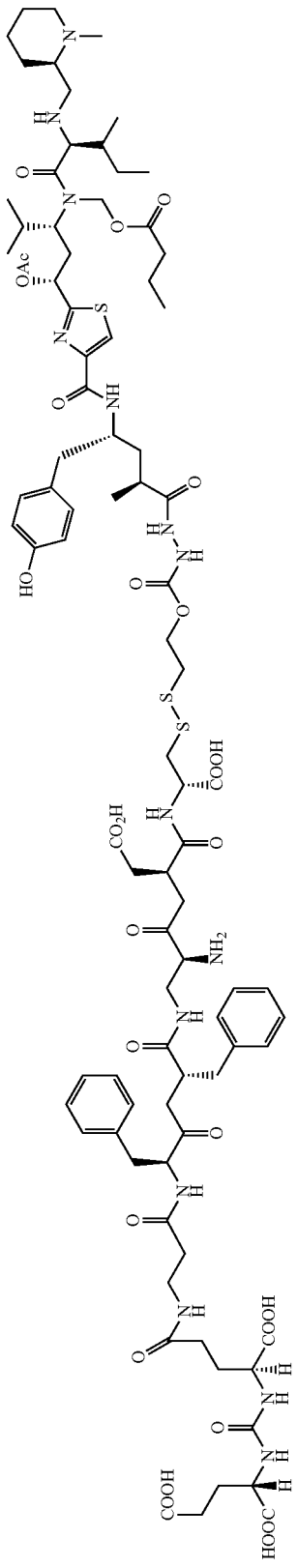

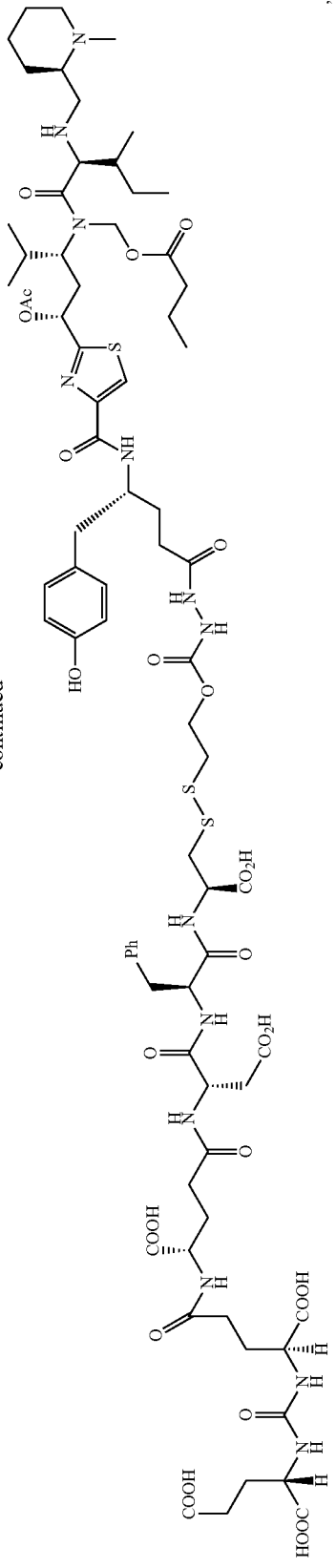
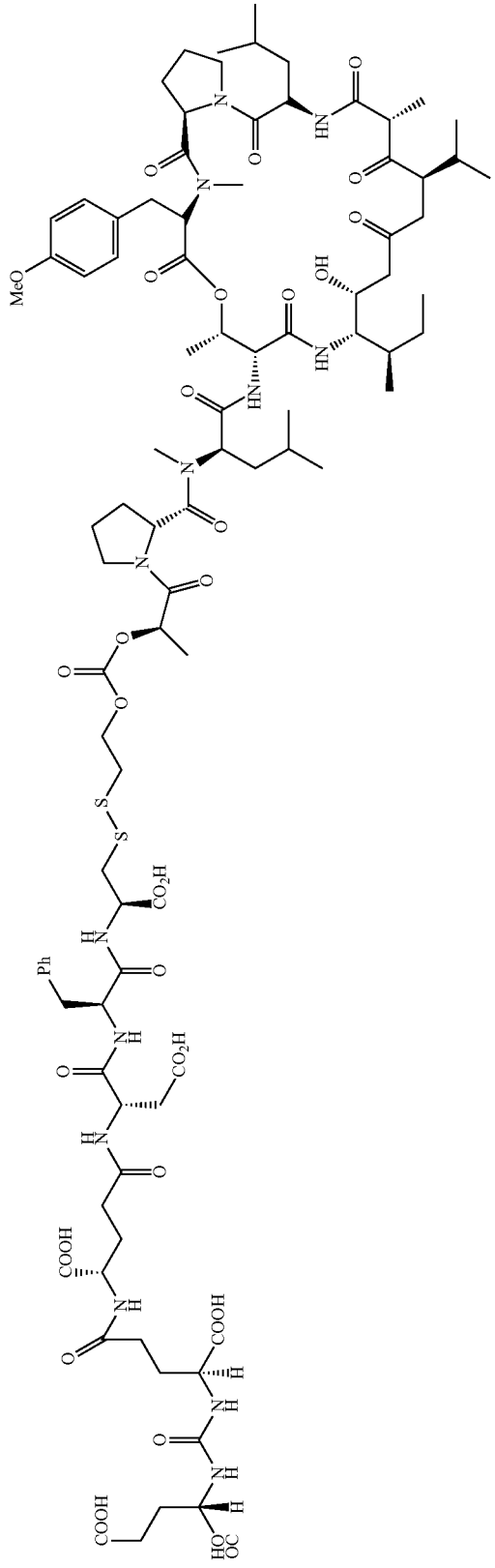

-continued
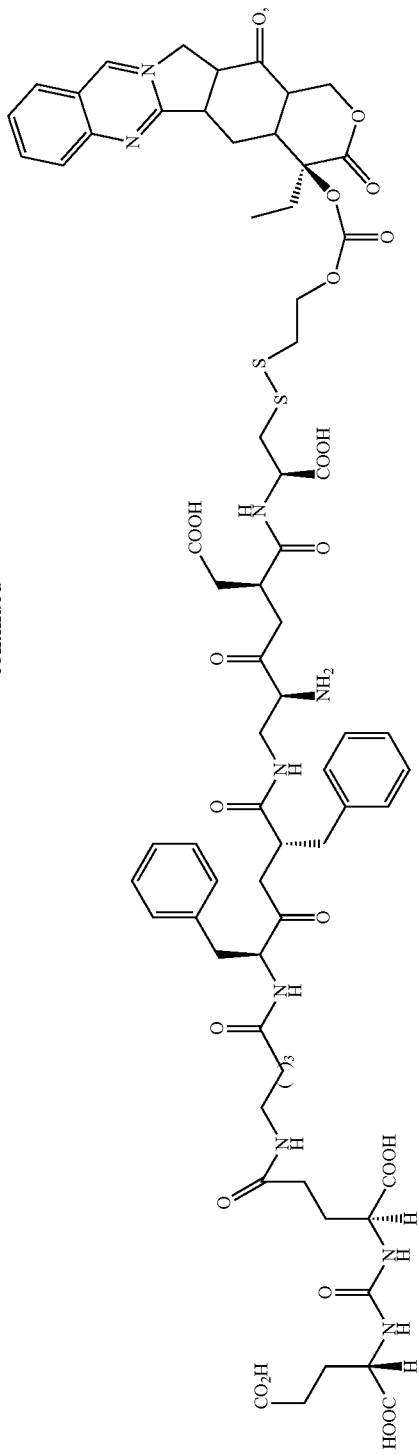

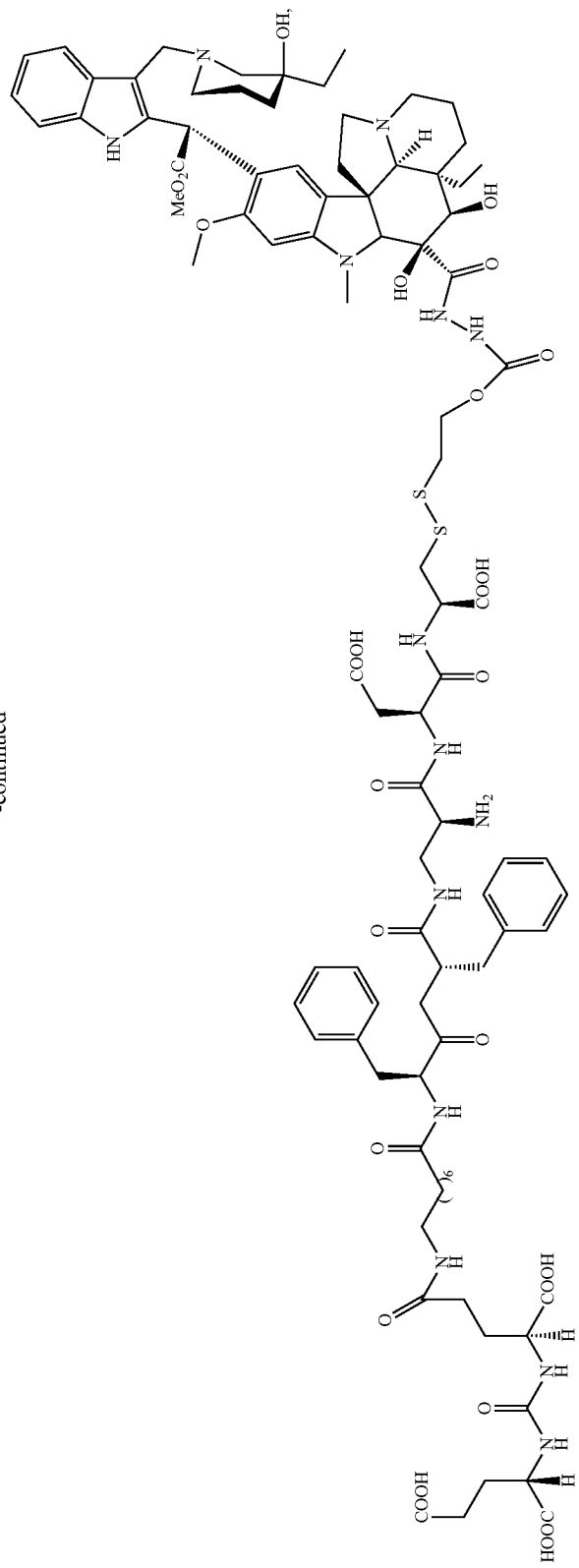

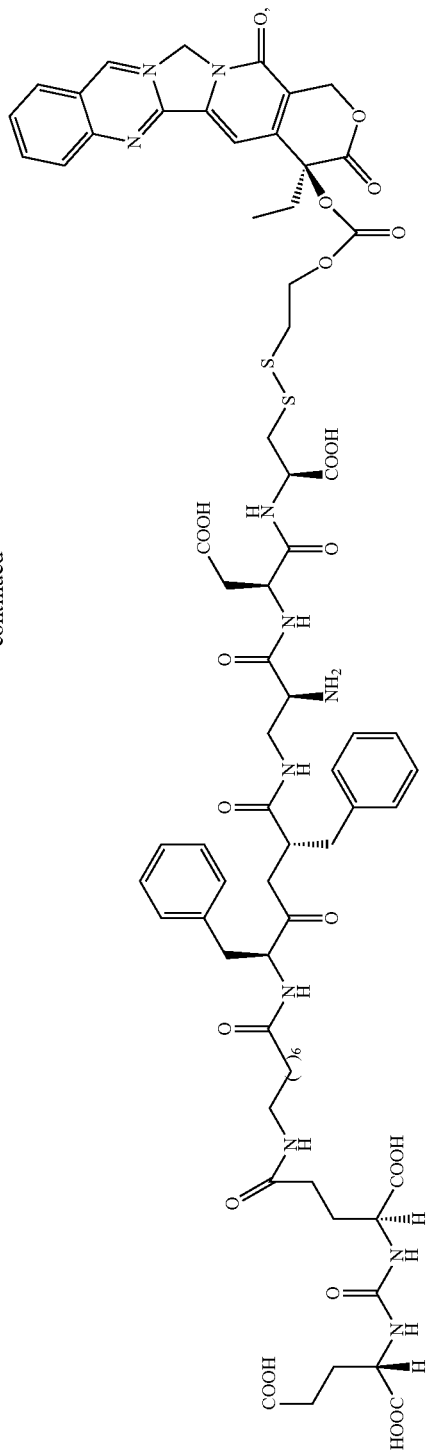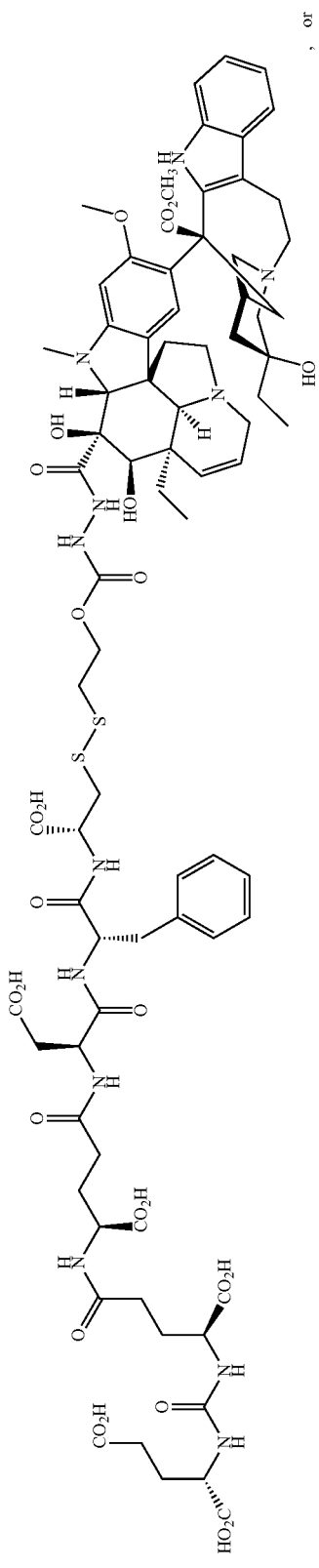

-continued
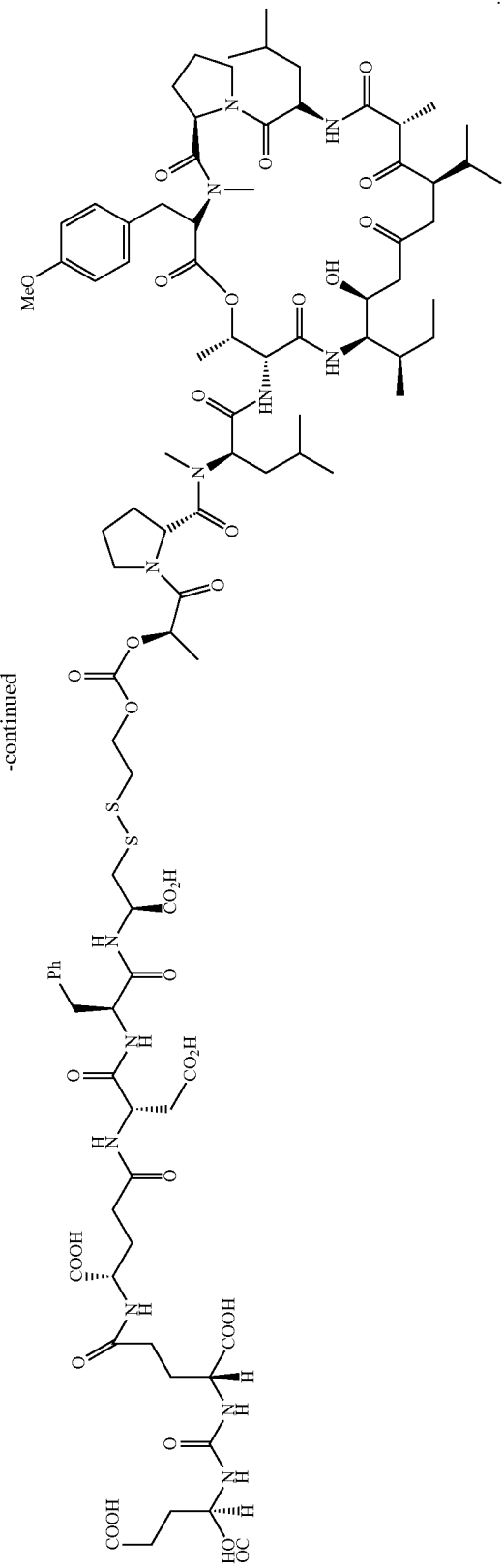

In various embodiments of the methods, uses, and kits described herein, the thiol inhibitor is selected from the group consisting of 5,5'-Dithiobis(2-nitrobenzoic acid) (DTNB); maleimides (e.g. N-maleoyl-β-alanine (N-(2-carboxyethyl) maleimide (NCEM)); p-chloromercuribenzene sulfonate (pCMBS); 4-(N—(S-glutathionylacetyl)amino) phenylarsonous acid (GSAO); 2,2'-dithio-bis-ethanesulfonate (dimesna); oxidized glutathione (GSSG); vinyl sulfone compounds (e.g. methoxy-PEG5000-vinylsulfone); epigallocatechin gallate (EGCG); and 4-acetamido-4'-maleimidylstilbene-2,2'-disulfonic acid (AMS). In one embodiment, the thiol inhibitor is DTNB. In another embodiment, the thiol inhibitor is a maleimide. In yet another embodiment, the thiol inhibitor is NCEM. In one embodiment, the thiol inhibitor is pCMBS. In another embodiment, the thiol inhibitor is GSAO. In yet another embodiment, the thiol inhibitor is dimesna. In one embodiment, the thiol inhibitor is GSSG. In another embodiment, the thiol inhibitor is a vinyl sulfone compound. In yet another embodiment, the thiol inhibitor is methoxy-PEG5000-vinylsulfone. In still another embodiment, the thiol inhibitor is EGCG. In another embodiment, the thiol inhibitor is AMS. Any combinations of these thiol inhibitors are contemplated in accordance with the invention.

In one aspect, the ligand conjugate and the thiol inhibitor are in parenteral dosage forms and may be administered directly into the blood stream, into muscle, or into an internal organ. Suitable routes for such parenteral administration include intravenous, intraarterial, intraperitoneal, intrathecal, intradermal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates or additional chemotherapeutic agents described herein. The preparation of parenteral formulations under sterile conditions, for example, by lyophilization under sterile conditions, may readily be accomplished using standard pharmaceutical techniques well-known to those skilled in the art.

In various embodiments of the methods, uses, and kits described herein, the ligand conjugate is in a composition and the thiol inhibitor is in a composition and the compositions may further comprise pharmaceutically acceptable carriers. The carriers can be excipients. In some embodiments, the pharmaceutically acceptable carriers are liquid carriers. In various embodiments, the liquid carriers are independently selected from the group consisting of saline, glucose, alcohols, glycols, esters, amides, and a combination thereof.

The choice of carrier will to a large extent depend on factors such as the particular mode of administration, the effect of the carrier on solubility and stability, and the nature of the dosage form. Pharmaceutical compositions suitable for the delivery of ligand conjugates or thiol inhibitors described herein and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In one illustrative aspect, the pharmaceutically acceptable carrier may be any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments of the methods, uses, and kits described herein, the ligand conjugate and the thiol inhibitor are administered in therapeutically effective amounts. The unitary daily dosage of the ligand conjugate and the thiol inhibitor can vary significantly depending on the patient condition, the disease state being treated, the purity of the compounds and their route of administration and tissue distribution, and the possibility of co-usage of other therapeutic treatments, such as radiation therapy. The effective amount to be administered to a patient is based on body surface area, mass, and physician assessment of patient condition. Effective doses can range, for example, from about 1 ng/kg to about 1 mg/kg, from about 1 µg/kg to about 500 µg/kg, and from about 1 µg/kg to about 100 µg/kg. These doses are based on an average patient weight of about 70 kg, and the kg are kg of patient body weight (mass).

The ligand conjugate and the thiol inhibitor can each be administered in a dose of from about 1.0 ng/kg to about 1000 µg/kg, from about 10 ng/kg to about 1000 µg/kg, from about 50 ng/kg to about 1000 µg/kg, from about 100 ng/kg to about 1000 µg/kg, from about 500 ng/kg to about 1000 µg/kg, from about 1 ng/kg to about 500 µg/kg, from about 1 ng/kg to about 100 µg/kg, from about 1 µg/kg to about 50 µg/kg, from about 1 µg/kg to about 10 µg/kg, from about 5 µg/kg to about 500 µg/kg, from about 10 µg/kg to about 100 µg/kg, from about 20 µg/kg to about 200 µg/kg, from about 10 µg/kg to about 500 µg/kg, or from about 50 µg/kg to about 500 µg/kg. The total dose may be administered in single or divided doses and may, at the physician's discretion, fall outside of the typical range given herein. These dosages are based on an average patient weight of about 70 kg and the "kg" are kilograms of patient body weight. The physician will readily be able to determine doses for subjects whose weight falls outside this range, such as infants and the elderly.

In another embodiment, the ligand conjugate and the thiol inhibitor can each be administered in a dose of from about 1 µg/m$^2$ to about 500 mg/m$^2$, from about 1 µg/m$^2$ to about 300 mg/m$^2$, or from about 100 µg/m$^2$ to about 200 mg/m$^2$. In other embodiments, the ligand conjugate and the thiol inhibitor can each be administered in a dose of from about 1 mg/m$^2$ to about 500 mg/m$^2$, from about 1 mg/m$^2$ to about 300 mg/m$^2$, from about 1 mg/m$^2$ to about 200 mg/m$^2$, from about 1 mg/m$^2$ to about 100 mg/m$^2$, from about 1 mg/m$^2$ to about 50 mg/m$^2$, or from about 1 mg/m$^2$ to about 600 mg/m$^2$. The total dose may be administered in single or divided doses and may, at the physician's discretion, fall outside of the typical range given herein. These dosages are based on m$^2$ of body surface area.

The ligand conjugate and the thiol inhibitor described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The ligand conjugate and the thiol inhibitor described herein may be capable of existing as geometric isomers. Accordingly, it is to be understood that the present invention includes pure geometric isomers or mixtures of geometric isomers.

It is appreciated that the ligand conjugate and the thiol inhibitor described herein may exist in unsolvated forms as well as solvated forms, including hydrated forms. In general, the solvated forms are equivalent to unsolvated forms and are encompassed within the scope of the present invention. The ligand conjugate and the thiol inhibitor described herein may exist in multiple crystalline or amorphous forms. In general, all physical forms are equivalent for the uses contemplated by the present invention and are intended to be within the scope of the present invention.

In another embodiment, compositions and/or dosage forms for administration of ligand conjugate and the thiol inhibitor are prepared from compounds with a purity of at least about 90%, or about 95%, or about 96%, or about 97%, or about 98%, or about 99%, or about 99.5%. In another embodiment, compositions and or dosage forms for administration of ligand conjugate and the thiol inhibitor are prepared from compounds with a purity of at least 90%, or 95%, or 96%, or 97%, or 98%, or 99%, or 99.5%.

As used herein, purity determinations may be based on weight percentage, mole percentage, and the like. In addition, purity determinations may be based on the absence or substantial absence of certain predetermined components, such as, but not limited to, folic acid, disulfide containing components not containing a drug, oxidation products, disulfide components not containing a folate, and the like. It is also to be understood that purity determinations are applicable to solutions of the compounds and compositions purified by the methods described herein. In those instances, purity measurements, including weight percentage and mole percentage measurements, are related to the components of the solution exclusive of the solvent.

The purity of the ligand conjugate and the thiol inhibitor may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

In some embodiments of the methods, uses, and kits described herein, the ligand conjugate and the thiol inhibitor are in sterile containers or packages. In other embodiments of the methods, uses, and kits described herein, the ligand conjugate and the thiol inhibitor are in sterile, pyrogen-free aqueous solutions. In some embodiments of the uses described herein, the ligand conjugate is in the form of a reconstitutable lyophilizate.

The methods, uses, and kits described herein can be for both human clinical medicine and veterinary applications. Thus, the patient can be human or, in the case of veterinary applications, can be a laboratory, agricultural, domestic, or wild animal. The methods, uses, and kits described herein can be applied to humans (i.e. a human patient), laboratory animals such rodents (e.g. mice, rats, hamsters, etc.), rabbits, monkeys, chimpanzees, domestic animals such as dogs, cats, and rabbits, agricultural animals such as cows, horses, pigs, sheep, goats, and wild animals in captivity such as hears, pandas, lions, tigers, leopards, elephants, zebras, giraffes, gorillas, dolphins, and whales.

In another embodiment described herein, an in vitro assay for identifying a ligand conjugate suitable for co-administration to a patient with a thiol inhibitor is provided. The assay comprises the steps of:
a) adding the ligand conjugate to the culture medium of a first sample of cultured cells, wherein the ligand conjugate comprises a disulfide linkage;
b) adding the thiol inhibitor to the culture medium of the first sample of cultured cells to provide a test sample;
c) adding the ligand conjugate to the culture medium of a second sample of cultured cells to provide a control sample;
d) measuring the non-ligand-specific activity of the ligand conjugate or the nonspecific uptake of the drug in the test sample;
e) measuring the non-ligand-specific activity of the ligand conjugate or the nonspecific uptake of the drug in the control sample; and
f) determining that the ligand conjugate is suitable for co-administration to the patient with the thiol inhibitor if the non-ligand-specific activity of the ligand conjugate and/or the nonspecific uptake of the drug are decreased in the test sample relative to the control sample.

As used herein, the term "in vitro assay" refers to any assay that may be performed using cultured cells. The term "suitable for co-administration" refers to a ligand conjugate that would advantageously benefit from co-administration with a thiol inhibitor. Such benefit can be observed via a reduction in non-ligand-specific activity of the ligand conjugate, a reduction in nonspecific uptake of the drug portion of the ligand conjugate into the cells, or any other suitable assay.

As used herein, the term "adding" refers to placing a solution comprising the ligand conjugate or the thiol inhibitor, or both, into the culture medium in which the cells are incubated. Methods of "adding," such as pipeting, are known to a practitioner skilled in the art.

As used herein, the term "culture medium" means the extracellular medium containing the nutrients and other constituents supporting the growth of cells. Such media can be prepared in the laboratory by methods known to a skilled artisan and are also commercially available. In some embodiments, the culture medium contains thiols. In other embodiments, the culture medium does not contain thiols (i.e. is thiol-free). In some embodiments, the culture medium is Roswell Park Memorial Institute (RPMI) medium (Cellgro, Manassas, Va.).

Cultured cells according to the present invention may include any cell type known in the art that can be cultured in vitro. In some embodiments, the cultured cells express folate receptors on the cell surface. In other embodiments, the cultured cells do not express folate receptors on the cell surface. In some embodiments, the cultured cells are KB cells. In other embodiments, the cultured cells are A549 cells. In yet other embodiments, the cultured cells can be, for example, H23 cells, AN3CA cells, HepG2 cells, RAW264.7 cells, MDA-MB-468 cells, or MDA-MB-231 cells.

As used herein, the term "measuring" refers to determining the amount quantitatively, of the non-ligand-specific activity, non-specific uptake, or other activity of interest. Measuring can be done directly or indirectly. Indirect methods of measuring include measuring of cellular responses such as $^3$H-thymidine incorporation as a measure of cytotoxicity, or, for example, enzymatic reaction products. Direct measuring includes such assays as measuring uptake of radiolabeled molecules into cells.

As used herein, the term "non-ligand-specific activity" refers to activity that is not the result of ligand binding to the cells of interest. When the ligand is folate and the ligand receptor is a folate receptor (FR), the "non-FR-specific activity" refers to activity that is not the result of binding to folate receptors on the cell surface. In some embodiments, non-ligand-specific activity is determined by measuring $^3$H-thymidine incorporation as a measure of cytotoxicity. As used herein, the term "cytotoxicity" refers to cell killing or inhibition of cell growth or division as a result of toxicity.

As used herein, the term "nonspecific uptake" refers to uptake of the drug moiety of the ligand conjugate into a cell where the uptake is not the result of ligand binding to the cells of interest. For example, when the ligand is folate and the ligand receptor is a folate receptor (FR), the "nonspecific uptake" of the drug refers to uptake that is not the result of binding of folate to the folate receptors on the cells. In some embodiments, nonspecific uptake is measured using competition assays. Competition assays are known to a skilled artisan. In some embodiments, the competition assay may include use of a radiolabeled ligand conjugate, and in some embodiments, the radiolabel is $^3$H-thymidine. In some embodiments, a non-radiolabeled ligand is also added to the assay in excess and the uptake of the radiolabeled conjugate (i.e. the drug portion of the conjugate) that is not competed by the excess non-radiolabeled ligand is non-specific uptake.

The previously described embodiments of the ligand conjugate and the thiol inhibitor are applicable to the in vitro assay described herein. In various embodiments of the in vitro assay described herein, the assay further comprises step g) administering the ligand conjugate and the thiol inhibitor to the patient. The term "administering" refers to any suitable means of delivering the ligand conjugate, the thiol inhibitor, or both, to the patient. In some embodiments, the administration is a parenteral administration. Suitable routes for such parenteral administration include intravenous, intraarterial, intraperitoneal, intrathecal, intradermal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In various embodiments of the in vitro assay described herein, the non-ligand-specific activity of the ligand conjugate is decreased by the thiol inhibitor. In other embodiments of the in vitro assay described herein, the non-ligand-specific activity is cytotoxicity. In various embodiments of the in vitro assay described herein, the nonspecific uptake of the drug is decreased by the thiol inhibitor. In yet other embodiments of the in vitro assay described herein, the nonspecific uptake of the ligand conjugate is measured using competition assays in the presence and absence of an excess of non-radiolabeled ligand.

In one embodiment described herein, a method of treatment of a disease is provided. The method comprises administering a ligand conjugate to a patient, wherein the ligand conjugate comprises a disulfide linkage; and administering a system $x_c^-$ inhibitor to the patient. In some embodiments, the disease is cancer or inflammation.

In another embodiment, use of a ligand conjugate in combination with a system inhibitor for the treatment of a disease wherein the disease is cancer or inflammation, and wherein the ligand conjugate comprises a disulfide linkage is described.

In yet another embodiment, use of a ligand conjugate for the manufacture of a medicament for the treatment of a disease wherein the disease is cancer or inflammation, and wherein the treatment comprises treating a patient with the ligand conjugate in combination with a system $x_c^-$ inhibitor, wherein the ligand conjugate comprises a disulfide linkage is described.

In another embodiment, a kit is provided. The kit comprises a ligand conjugate and one or more system $x_c^-$ inhibitor, wherein the ligand conjugate comprises a disulfide linkage.

In various embodiments of the methods and uses described herein, the disease is inflammation. In other embodiments, the disease is cancer. In some embodiments, the cancer comprises a primary tumor. In yet other embodiments, the cancer comprises metastatic tumor cells. The methods and uses described herein can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancers can also be oral, thyroid, endocrine, skin, gastric, esophageal, laryngeal, pancreatic, colon, bladder, bone, ovarian, cervical, uterine, breast, testicular, prostate, rectal, kidney, liver, or lung cancers.

The previously described embodiments of the ligand conjugate are applicable to the methods, uses, and kits utilizing the system $x_c^-$ inhibitor described herein.

In various embodiments of the methods, uses, and kits described herein, the system $x_c^-$ inhibitor is selected from the group consisting of sulfasalazine, glutamate; L-quisqualate; (S)-4-carboxyphenylglycine (4-S—CPG); L-α-aminoadipic acid; and L-homocysteic acid. In one embodiment, the system $x_c^-$ inhibitor is sulfasalazine. In another embodiment, the system $x_c^-$ inhibitor is glutamate. In yet another embodiment, the system $x_c^-$ inhibitor is L-quisqualate. In one embodiment, the system $x_c^-$ inhibitor is 4-S—CPG. In another embodiment, the system $x_c^-$ inhibitor is L-α-aminoadipic acid. In yet another embodiment, the system $x_c^-$ inhibitor is L-homocysteic acid. Any combinations of these system $x_c^-$ inhibitors are contemplated in accordance with the invention.

In one aspect, the ligand conjugate and the system $x_c^-$ inhibitor are in parenteral dosage forms and may be administered directly into the blood stream, into muscle, or into an internal organ. Suitable routes for such parenteral administration include intravenous, intraarterial, intraperitoneal, intrathecal, intradermal, epidural, intracerebroventricular, intraurethral, infrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates or additional chemotherapeutic agents described herein. The preparation of parenteral formulations under sterile conditions, for example, by lyophilization under sterile conditions, may readily be accomplished using standard pharmaceutical techniques well-known to those skilled in the art.

In various embodiments of the methods, uses, and kits described herein, the ligand conjugate is in a composition and the system $x_c^-$ inhibitor is in a composition and the compositions may further comprise pharmaceutically acceptable carriers. The carriers can be excipients. In some embodiments, the pharmaceutically acceptable carriers are liquid carriers. In various embodiments, the liquid carriers are independently selected from the group consisting of saline, glucose, alcohols, glycols, esters, amides, and a combination thereof.

The choice of carrier will to a large extent depend on factors such as the particular mode of administration, the effect of the carrier on solubility and stability, and the nature of the dosage form. Pharmaceutical compositions suitable for the delivery of ligand conjugates or system $x_c^-$ inhibitors described herein and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In one illustrative aspect, the pharmaceutically acceptable carrier may be any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments of the methods, uses, and kits described herein, the ligand conjugate and the system $x_c^-$ inhibitor are administered in therapeutically effective amounts. The unitary daily dosage of the ligand conjugate and the system $x_c^-$ inhibitor can vary significantly depending on the patient condition, the disease state being treated, the purity of the compounds and their route of administration and tissue distribution, and the possibility of co-usage of other therapeutic treatments, such as radiation therapy. The effective amount to be administered to a patient is based on body surface area, mass, and physician assessment of patient condition. Effective doses can range, for example, from about 1 ng/kg to about 1 mg/kg, from about 1 µg/kg to about 500 µg/kg, and from about 1 µg/kg to about 100 µg/kg. These doses are based on an average patient weight of about 70 kg, and the kg are kg of patient body weight (mass).

The ligand conjugate and the system $x_c^-$ inhibitor can each be administered in a dose of from about 1.0 ng/kg to about 1000 µg/kg, from about 10 ng/kg to about 1000 µg/kg, from about 50 ng/kg to about 1000 µg/kg, from about 100 ng/kg to about 1000 µg/kg, from about 500 ng/kg to about 1000 µg/kg, from about 1 ng/kg to about 500 µg/kg, from about 1 ng/kg to about 100 µg/kg, from about 1 µg/kg to about 50 µg/kg, from about 1 µg/kg to about 10 µg/kg, from about 5 µg/kg to about 500 µg/kg, from about 10 µg/kg to about 100 µg/kg, from about 20 µg/kg to about 200 µg/kg, from about 10 µg/kg to about 500 µg/kg, or from about 50 µg/kg to about 500 µg/kg. The total dose may be administered in single or divided doses and may, at the physician's discretion, fall outside of the typical range given herein. These dosages are based on an average patient weight of about 70 kg and the "kg" are kilograms of patient body weight. The physician will readily be able to determine doses for subjects whose weight falls outside this range, such as infants and the elderly.

In another embodiment, the ligand conjugate and the system $x_c^-$ inhibitor can each be administered in a dose of from about 1 µg/m² to about 500 mg/m², from about 1 µg/m² to about 300 mg/m², or from about 100 µg/m² to about 200 mg/m². In other embodiments, the ligand conjugate and the system $x_c^-$ inhibitor can each be administered in a dose of from about 1 mg/m² to about 500 mg/m⁻, from about 1 mg/m² to about 300 mg/m², from about 1 mg/m² to about 200 mg/m², from about 1 mg/m² to about 100 mg/m², from about 1 mg/m² to about 50 mg/m², or from about 1 mg/m² to about 600 mg/m². The total dose may be administered in single or divided doses and may, at the physician's discretion, fall outside of the typical range given herein. These dosages are based on m² of body surface area.

The ligand conjugate and the system $x_c^-$ inhibitor described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The ligand conjugate and the system $x_c^-$ inhibitor described herein may be capable of existing as geometric isomers. Accordingly, it is to be understood that the present invention includes pure geometric isomers or mixtures of geometric isomers.

It is appreciated that the ligand conjugate and the system $x_c^-$ inhibitor described herein may exist in unsolvated forms as well as solvated forms, including hydrated forms. In general, the solvated forms are equivalent to unsolvated forms and are encompassed within the scope of the present invention. The ligand conjugate and the system $x_c^-$ inhibitor described herein may exist in multiple crystalline or amorphous forms. In general, all physical forms are equivalent for the uses contemplated by the present invention and are intended to be within the scope of the present invention.

In another embodiment, compositions and/or dosage forms for administration of ligand conjugate and the system $x_c^-$ inhibitor are prepared from compounds with a purity of at least about 90%, or about 95%, or about 96%, or about 97%, or about 98%, or about 99%, or about 99.5%. In another embodiment, compositions and or dosage forms for administration of ligand conjugate and the system $x_c^-$ inhibitor are prepared from compounds with a purity of at least 90%, or 95%, or 96%, or 97%, or 98%, or 99%, or 99.5%.

As used herein, purity determinations may be based on weight percentage, mole percentage, and the like. In addition, purity determinations may be based on the absence or substantial absence of certain predetermined components, such as, but not limited to, folic acid, disulfide containing components not containing a drug, oxidation products, disulfide components not containing a folate, and the like. It is also to be understood that purity determinations are applicable to solutions of the compounds and compositions purified by the methods described herein. In those instances, purity measurements, including weight percentage and mole percentage measurements, are related to the components of the solution exclusive of the solvent.

The purity of the ligand conjugate and the system $x_c^-$ inhibitor may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

In some embodiments of the methods, uses, and kits described herein, the ligand conjugate and the system $x_c^-$ inhibitor are in sterile containers or packages. In other embodiments of the methods, uses, and kits described herein, the ligand conjugate and the system $x_c^-$ inhibitor are in sterile, pyrogen-free aqueous solutions. In some embodiments of the uses described herein, the ligand conjugate is in the form of a reconstitutable lyophilizate. The methods, uses, and kits described herein can be for both human clinical medicine and veterinary applications. Thus, the patient can be human or, in the case of veterinary applications, can be a laboratory, agricultural, domestic, or wild animal. The methods, uses, and kits described herein can be applied to humans (i.e. a human patient), laboratory animals such rodents (e.g. mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In another embodiment described herein, an in vitro assay for identifying a ligand conjugate suitable for co-administration to a patient with a system $x_c^-$ inhibitor is provided. The assay comprises the steps of:

a) adding the ligand conjugate to the culture medium of a first sample of cultured cells, wherein the ligand conjugate comprises a disulfide linkage;

b) adding the system $x_c^-$ inhibitor to the culture medium of the first sample of cultured cells to provide a test sample;

c) adding the ligand conjugate to the culture medium of a second sample of cultured cells to provide a control sample;

d) measuring the non-ligand-specific activity of the ligand conjugate or the nonspecific uptake of the drug in the test sample;

e) measuring the non-ligand-specific activity of the ligand conjugate or the nonspecific uptake of the drug in the control sample; and f) determining that the ligand conjugate is suitable for co-administration to the patient with the system $x_c^-$ inhibitor if the non-ligand-specific activity of the ligand conjugate and/or the nonspecific uptake of the drug are decreased in the test sample relative to the control sample.

As used herein, the term "in vitro assay" refers to any assay that may be performed using cultured cells. The term "suitable for co-administration" refers to a ligand conjugate that would advantageously benefit from co-administration with a system $x_c^-$ inhibitor. Such benefit can be observed via a reduction in non-ligand-specific activity of the ligand conjugate, a reduction in nonspecific uptake of the drug portion of the ligand conjugate into the cells, or any other suitable assay.

As used herein, the term "adding" refers to placing a solution comprising the ligand conjugate or the system $x_c^-$ inhibitor, or both, into the culture medium in which the cells are incubated. Methods of "adding," such as pipeting, are known to a practitioner skilled in the art.

As used herein, the term "culture medium" means the extracellular medium containing the nutrients and other constituents supporting the growth of cells. Such media can be prepared in the laboratory by methods known to a skilled artisan and are also commercially available. In some embodiments, the culture medium contains thiols. In other embodiments, the culture medium does not contain thiols (i.e. is thiol-free). In some embodiments, the culture medium is Roswell Park Memorial Institute (RPMI) medium (Cellgro, Manassas, Va.).

Cultured cells according to the present invention may include any cell type known in the art that can be cultured in vitro. In some embodiments, the cultured cells express folate receptors on the cell surface. In other embodiments, the cultured cells do not express folate receptors on the cell surface. In some embodiments, the cultured cells are KB cells. In other embodiments, the cultured cells are A549 cells. In yet other embodiments, the cultured cells can be, for example, H23 cells, AN3CA cells, HepG2 cells, RAW264.7 cells, MDA-MB-468 cells, or MDA-MB-231 cells.

As used herein, the term "measuring" refers to determining the amount quantitatively, of the non-ligand-specific activity, non-specific uptake, or other activity of interest. Measuring can be done directly or indirectly. Indirect methods of measuring include measuring of cellular responses such as $^3$H-thymidine incorporation as a measure of cytotoxicity, or, for example, enzymatic reaction products. Direct measuring includes such assays as measuring uptake of radiolabeled molecules into cells.

As used herein, the term "non-ligand-specific activity" refers to activity that is not the result of ligand binding to the cells of interest. When the ligand is folate and the ligand receptor is a folate receptor (FR), the "non-FR-specific activity" refers to activity that is not the result of binding to folate receptors on the cell surface. In some embodiments, non-ligand-specific activity is determined by measuring $^3$H-thymidine incorporation as a measure of cytotoxicity. As used herein, the term "cytotoxicity" refers to cell killing or inhibition of cell growth or division as a result of toxicity.

As used herein, the term "nonspecific uptake" refers to uptake of the drug moiety of the ligand conjugate into a cell where the uptake is not the result of ligand binding to the cells of interest. For example, when the ligand is folate and the ligand receptor is a folate receptor (FR), the "nonspecific uptake" of the drug refers to uptake that is not the result of binding of folate to the folate receptors on the cells. In some embodiments, nonspecific uptake is measured using competition assays. Competition assays are known to a skilled artisan. In some embodiments, the competition assay may include use of a radiolabeled ligand conjugate, and in some embodiments, the radiolabel is $^3$H-thymidine. In some embodiments, a non-radiolabeled ligand is also added to the assay in excess and the uptake of the radiolabeled conjugate (i.e. the drug portion of the conjugate) that is not competed by the excess non-radiolabeled ligand is non-specific uptake.

The previously described embodiments of the ligand conjugate and the system $x_c^-$ inhibitor are applicable to the in vitro assay described herein. In various embodiments of the in vitro assay described herein, the assay further comprises step g) administering the ligand conjugate and the system $x_c^-$ inhibitor to the patient. The term "administering" refers to any suitable means of delivering the ligand conjugate, the system $x_c^-$ inhibitor, or both, to the patient. In some embodiments, the administration is a parenteral administration. Suitable routes for such parenteral administration include intravenous, intraarterial, intraperitoneal, intrathecal, intradermal, epidural, intracerebroventricular, intraurethral, infrasternal, intracranial, intratumoral, intramuscular and subcutaneous delivery. Suitable means for parenteral administration include needle (including microneedle) injectors, needle-free injectors and infusion techniques.

The previously described embodiments of the in vitro assay utilizing the system $x_c^-$ inhibitor are applicable to the in vitro assay utilizing the system $x_c^-$ inhibitor described herein. In various embodiments of the in vitro assay described herein, the assay further comprises step g) administering the ligand conjugate and the system $x_c^-$ inhibitor to the patient.

In some embodiments of the in vitro assay described herein, the cultured cells are KB cells. In other embodiments of the in vitro assay described herein, the cultured cells arA549 cells.

In various embodiments of the in vitro assay described herein, the non-ligand-specific activity of the ligand conjugate is decreased by the system $x_c^-$ inhibitor. In other embodiments of the in vitro assay described herein, the non-ligand-specific activity is cytotoxicity. In various embodiments of the in vitro assay described herein, the nonspecific uptake of the drug is decreased by the system $x_c^-$ inhibitor. In yet other embodiments of the in vitro assay described herein, the nonspecific uptake of the ligand conjugate is measured using competition assays in the presence and absence of an excess of non-radiolabeled ligand.

In another embodiment, the methods, uses, compositions, pharmaceutical compositions, combinations, or kits described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

Example 1

The presence of extracellular thiols can undesirably affect the activity and uptake of ligand conjugates. For example, an increase in extracellular thiols in cell culture media can demonstrate such undesired effects in vitro, and an increase in extracellular thiols in interstitial fluids can have undesirable effects in vivo.

The in vitro extracellular thiol activity can be evaluated in conditioned culture media of the KB cell line and the A549 cell line. Each type of cells was plated in 24-well tissue cultured-treated plates at $1\times10^5$ cells per well in folate-deficient RPMI/10% heat-inactivated fetal bovine serum (FDRPMI/HIFBS; KB cells) or in RPMI medium with folate/10% HIFBS (RPMI+FA/HIFBS; A549 cells) and the cells were allowed to attach to the plates overnight. The cells were rinsed one time with PBS, pH 7.4, and the time course for thiol activity was initiated by adding 500 μL of RPMI medium without phenol red (PR) or serum to each well. The cells were then incubated at 37° C. in a 5% $CO_2$/95% humidified air incubator for increasing periods of time. At each time point, 55 μL of a 4 mM solution of DTNB (Sigma) was added to the appropriate wells (n=3) to achieve a final DTNB concentration of 400 μM. Plates were rocked gently to mix and incubated for 5 minutes at room temperature to allow the DTNB to react with extracellular thiols. The solutions were then removed from the cells, and absorbance was determined at a wavelength of 412 nm. Background absorbance (determined from an aliquot of DTNB solution incubated in an empty well of the tissue culture plate) was subtracted from each value. Thiol concentrations were calculated based on an extinction coefficient of 14,150 $M^{-1}$ $cm^{-1}$. Protein concentrations of cell lysates were determined by the BCA Assay method (Pierce, Rockford, Ill.).

Figure 1:
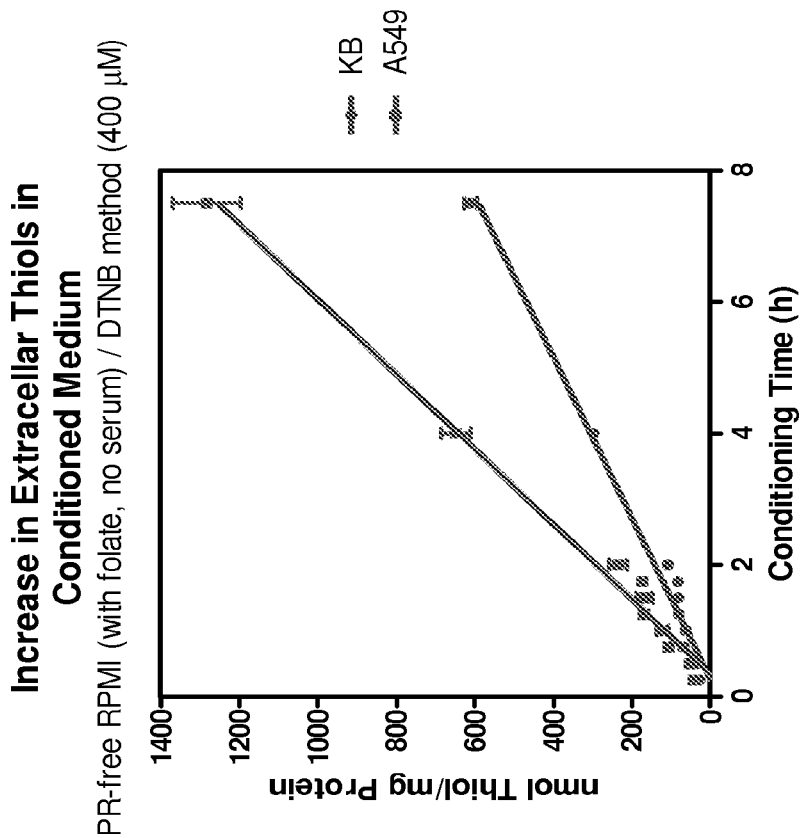
FIG. 1 shows the amount of extracellular thiol activity (nmol of thiol/mg of protein) per conditioning time in conditioned culture media over an 8 hour period. Data obtained for KB cells (closed circles) and A549 cells (closed squares) are shown.

As shown in FIG. 1, a linear increase in in vitro extracellular thiol activity (nmol of thiol/mg of protein) is observed in conditioned culture media for the KB cell line and the A549 cell line over an 8 hour period.

Example 2

Furthermore, the degree of extracellular thiol activity varies among different cell lines. Cells from various cell lines (i.e. H23, AN3CA, HepG2, RAW264.7, MDA-MB-468, MDA-MB-231, KB, and A549 cell lines) were each plated in 24-well tissue cultured-treated plates at $2\times10^5$ cells per well in FDRPMI/HIFBS (FR+cells) or in RPMI+FA/HIFBS (FR−cells) and were allowed to attach to the plates overnight. The cells were rinsed one time with PBS, pH 7.4, and then a 200 μM solution of DTNB in PR-free RPMI or in PR-free RPMI without cystine and glutathione (SH-free) was added to each well (n=3). The cells were incubated for 2 h at 37° C. the solutions were removed from the cells, and absorbance was determined at a wavelength of 412 nm. Background absorbance determined from an aliquot of DTNB solution incubated in an empty well of the tissue culture plate was subtracted from each value. Thiol concentrations were calculated based on an extinction coefficient of 14,150 $M^{-1}$ $cm^{-1}$. Protein concentrations of cell lysates were determined by the BCA Assay method (Pierce, Rockford, Ill.).

Figure 2:
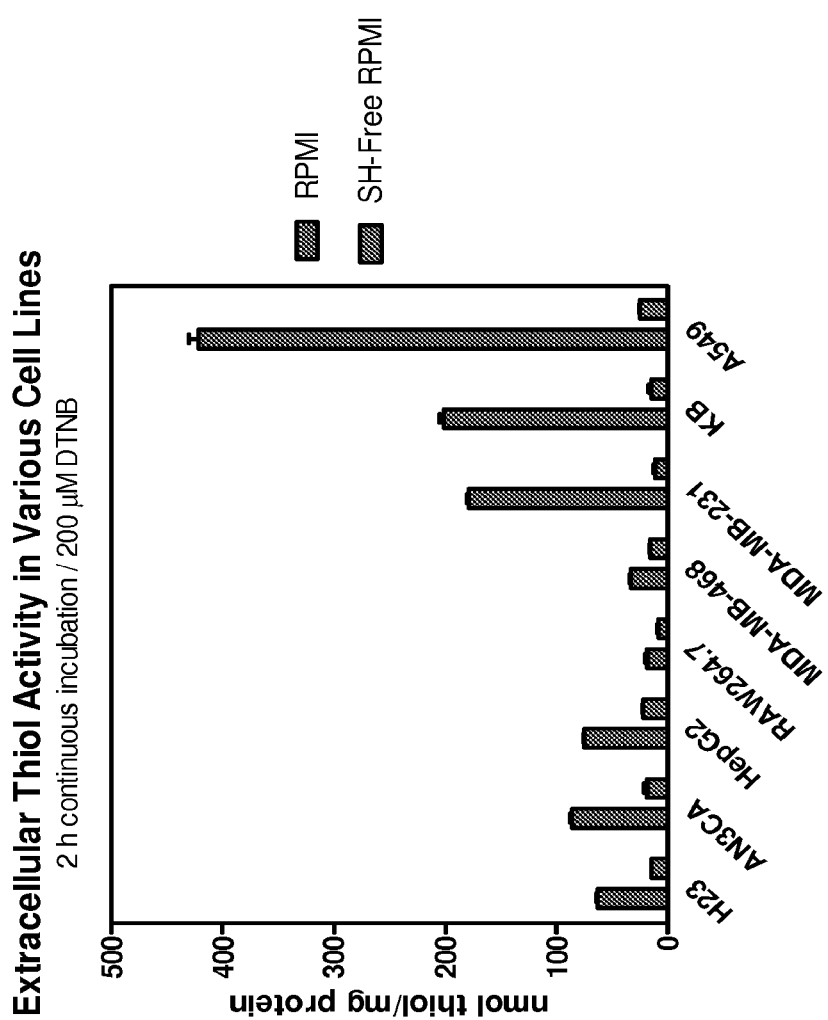
FIG. 2 shows the amount of extracellular thiol activity (nmol of thiol/mg of protein) for various cell lines, as evaluated using RPMI cell culture media and thiol-free (SH-free) RPMI cell culture media. Data obtained for each cell line shown on the X-axis incubated in RPMI medium are shown (left-hand bar in each set of two bars), and data obtained for each cell line using thiol-free RPMI cell culture media are also shown (right-hand bar in each set of two bars).

As shown in FIG. 2, degree of extracellular thiol activity (nmol of thiol/mg of protein) varies among different cell lines, as evaluated using RPMI cell culture media and thiol-free RPMI cell culture media. A549 cells exhibit the highest amount of extracellular thiol activity. In contrast, RAQ264.7 cells exhibit the lowest amount of extracellular thiol activity. Furthermore, as shown in FIG. 2, removal of thiols from the culture medium virtually eliminates the extracellular release of thiols.

Example 3

In addition, the amount of thiol activity correlates with the non-ligand-specific activity of ligand conjugates. In this example, the non-FR-specific activity of an exemplary folate conjugate (EC0531) was investigated in MDA-MD-468, H23, AN3CA, MDA-MB-231, KB, and A549 cells.

Extracellular thiol activity was determined using the DTNB method described above. Non-FR-specific activity of EC0531 was determined using a $^3$H-thymidine incorporation assay. Cells were seeded in 24-well tissue culture-treated plates at $1\times10^5$ cells per well and allowed to attach overnight at 37° C. Serial dilutions of EC0531 were prepared in FDRPMI/HIFBS, and each well received 0.5 mL of EC0531 solution. To assess non-FR-targeted activity in FR+cells, 100 μM FA was included as a competitor along with the drug in the treatment solutions. Cells were incubated for 2 hours in the presence of drug, washed 3 times with media, and then chased in 0.5 mL of FDRPMI/HIFBS (FR+cells) or RPMI+FA/HIFBS (FR−cells) to 72 h at 37° C. Spent medium was then aspirated from the wells, and cells were incubated with 1 μCi/mL $^3$H-thymidine for 4 hours at 37° C. washed two times with PBS, pH 7.4, then treated with 0.4 mL 5% trichloroacetic acid per well. After 15 minutes, the trichloroacetic acid was aspirated from the wells, and cells were solubilized in 0.5 mL 0.25 N sodium hydroxide. Each sample (450 μL) was transferred to a scintillation vial containing 3 mL of Ecolite+scintillation cocktail and then counted in a liquid scintillation counter (LSC). Final results were expressed as percentage of $^3$H-thymidine incorporation relative to an untreated control (non-competed groups) or FA control (competed groups). Sensitivity to the base drug, tubulysin B hydrazide, was determined using the $^3$H-thymidine incorporation assay and the same incubation conditions as described for EC0531.

Figure 3:
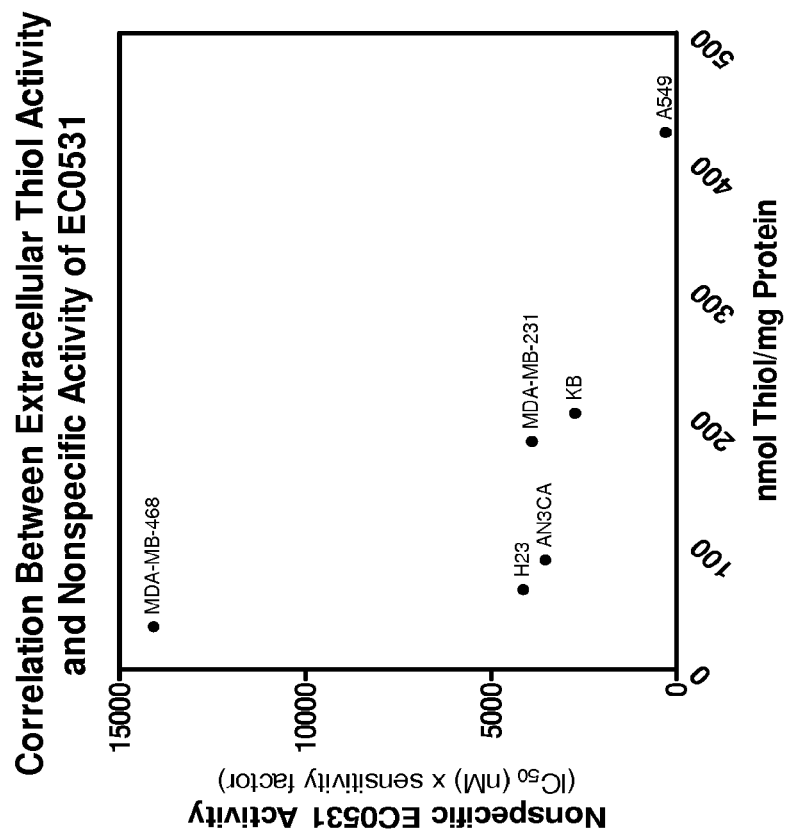
FIG. 3 shows the correlation between the amount of extracellular thiol activity (nmol of thiol/mg of protein) and the non-specific activity of the folate conjugate EC0531 ($IC_{50}$ (nM), adjusted for tubulysin B hydrazide sensitivity) in various cell lines.

As shown in FIG. 3, the extracellular thiol activity ($IC_{50}$ (nM), adjusted for tubulysin B hydrazide sensitivity) of various cell lines correlates with the non-FR-specific activity of the folate conjugate EC0531 FIG. 3 demonstrates the correlation between extracellular thiol activity and non-FR-specific activity of EC0531 (data adjusted for tubulysin B hydrazide sensitivity).

Example 4

Figure 4:
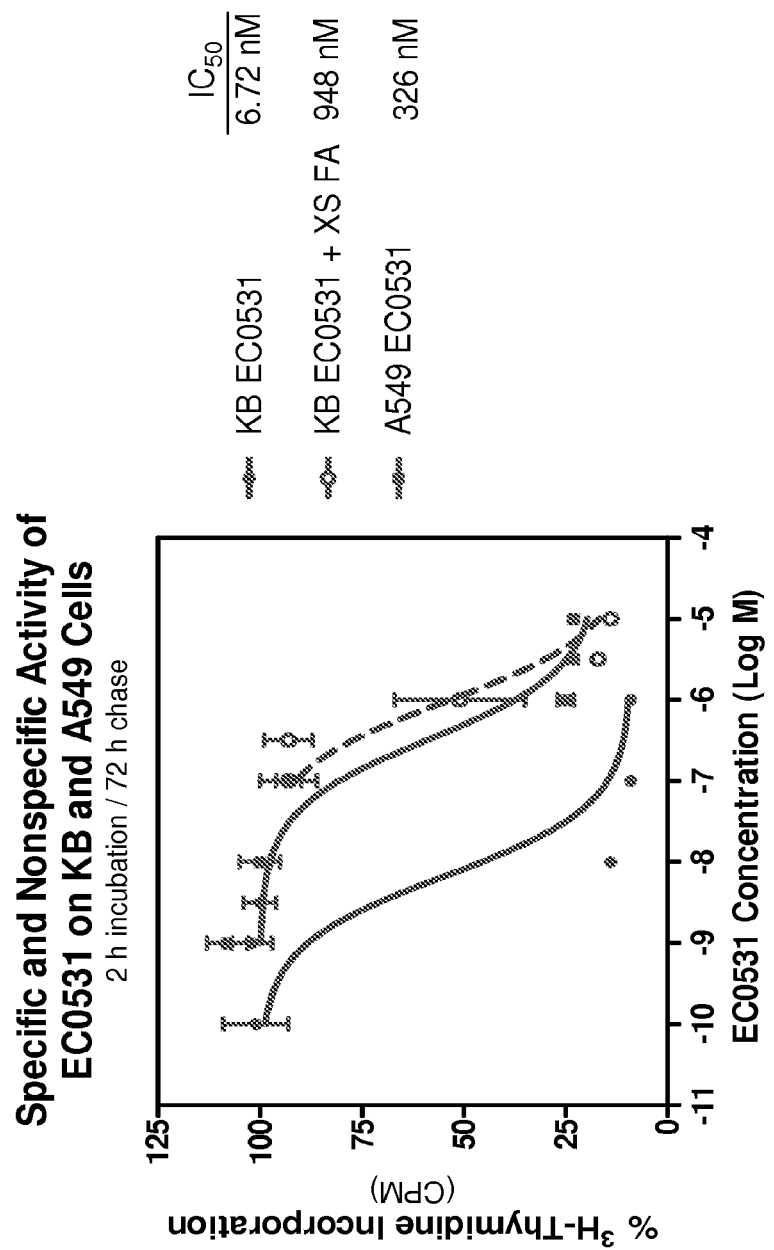
FIG. 4 shows the specific and non-specific activity of EC0531 (% $^3$H-Thymidine incorporation measured in counts per minute (CPM)) at varying concentrations of EC0531 (Log M) applied to KB cells or A549 cells. The specific activity of EC0531 administered to KB cells is shown (closed circles). The non-specific activity of EC0531 in the presence of excess folic acid administered to KB cells is also shown (open circles), along with the specific activity of EC0531 administered to A549 cells (closed squares).

The presence of extracellular thiols can affect the non-ligand-specific activity of ligand conjugates. In this example, the non-FR-specific activity of an exemplary folate conjugate (EC0531) was investigated. The non-FR-specific activity of EC0531 was evaluated in both KB cells (cells known to be FR positive) and in A549 cells (cells known to be FR negative). FR-specific and non-FR-specific activity of EC0531 was determined by the $^3$H-thymidine incorporation assay using the methods described in Example 3 above. As shown in FIG. 4, the non-FR-specific activity of EC0531 is observed at concentrations of about 0.3-1 μM in both KB cells and A549 cells.

Figure 5:
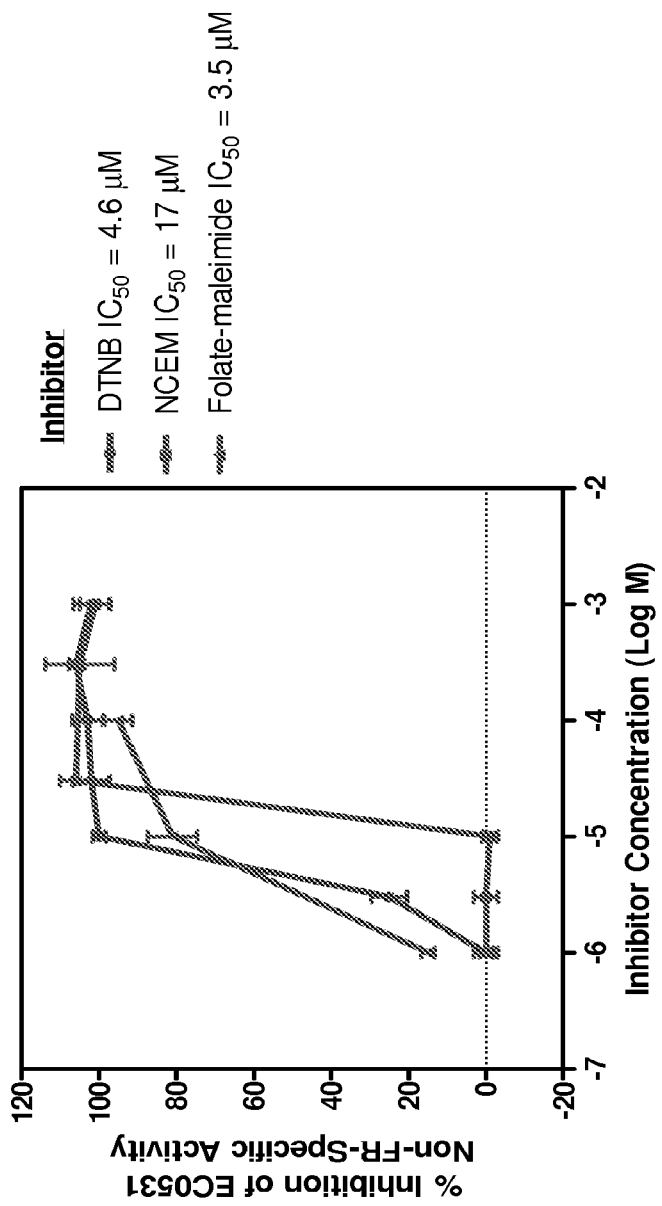
FIG. 5 shows the percent inhibition of non-FR-specific activity of EC0531 (% $^3$H-Thymidine incorporation measured in counts per minute (CPM)) following co-administration of thiol inhibitors and the folate conjugate EC0531 to the culture medium of KB cells. Data obtained using the thiol inhibitors DTNB (closed circles), NCEM (closed squares), and folate-maleimide (closed triangles) are shown.

The effects of three different cell-impermeable thiol inhibitors on the non-FR-specific activity of EC0531 were evaluated in this example: 1) 5,5'-dithiobis(2-nitrobenzoic acid) (DTNB); 2) N-(2-carboxyethyl)maleimide (NCEM), and 3) folate-maleimide. Each thiol inhibitor was separately co-administered with EC0531 (1 μM) and folic acid (100 μM), and the agents were incubated for 2 hours, followed by a 72 hour chase. The inhibition of non-FR-specific activity (i.e. cytotoxicity) was evaluated for each thiol inhibitor. As shown in FIG. 5, DTNB, NCEM, and folate-maleimide all exhibit a dose-responsive inhibition of non-FR-specific activity in KB cells. DTNB exhibited an $IC_{50}$ of 4.6 μM, NCEM exhibited an $IC_{50}$ of 17 μM, and folate-maleimide exhibited an $IC_{50}$ of 3.5 μM.

Figure 6:
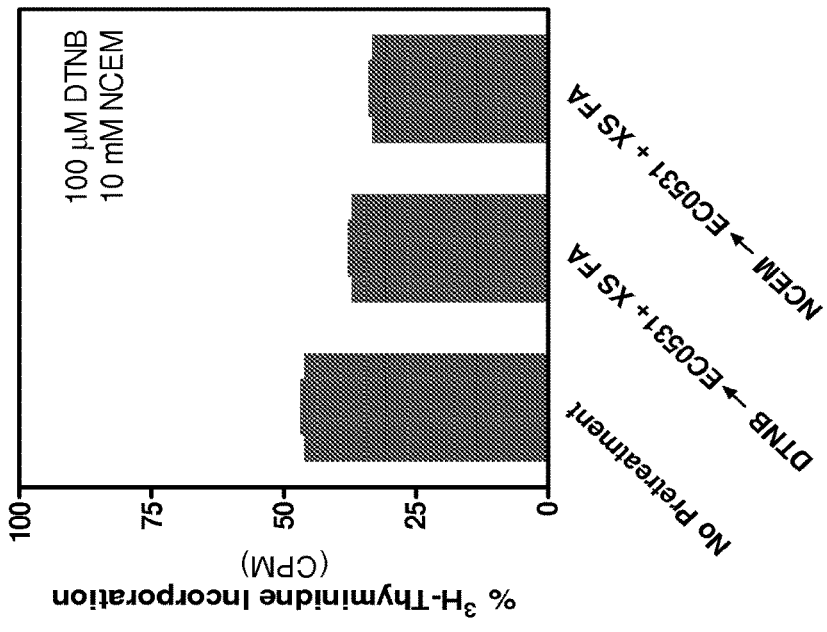
FIG. 6 shows the lack of inhibition of non-FR-specific activity of EC0531 (% $^3$H-Thymidine incorporation measured in counts per minute (CPM)) by pre-treating KB cells with thiol inhibitors prior to administration of both EC0531 and excess folic acid. The first bar shows data obtained with no pretreatment of KB cells with thiol inhibitors prior to administration of EC0531 and folic acid. The second bar shows data obtained with pretreatment of KB cells with DTNB prior to administration of EC0531 and excess folic acid. The third bar shows data obtained with pretreatment of KB cells with NCEM prior to administration of EC0531 and excess folic acid.

However, pre-treatment of cells with thiol inhibitors prior to the administration of EC0531 did not inhibit the non-FR-specific activity. Cells were seeded in 24-well tissue culture-treated plates at 1×10$^5$ cells per well and allowed to attach overnight at 37° C. To assess the effect of various inhibitors on non-targeted activity of EC0531 in the FR+KB cell line, cells were treated concurrently with DTNB (100 μM) or NCEM (10 mM) and 1 μM EC0531 plus 100 μM FA to block all FR-specific drug uptake. Cells were incubated for 2 hours in the presence of drug, competitor, and inhibitor, washed 3 times with media, and then chased in 0.5 mL of FDRPMI/HIFBS to 72 hours at 37° C. Cells were then treated as described above to determine $^3$H-thymidine incorporation. Final results were expressed as percentage of $^3$H-thymidine incorporation relative to an untreated control (non-competed groups) or FA control (competed groups). As shown in FIG. 6, pre-treatment of KB cells with DTNB or NCEM prior to administration of EC0531 and folic acid is not effective to inhibit the non-FR-specific activity in the cells.

Various thiol inhibitors were tested to evaluate their effectiveness in inhibiting the non-FR-specific activity following co-administration with EC0531. The results are shown in Table 1.

TABLE 1

| Action | Inhibitor | Concentration (μM) | Inhibition of EC0531 Nonspecific Activity |
|---|---|---|---|
| Membrane-impermeable sulfhydryl blockers | DTNB | 10 μM | Full inhibition |
| | NCEM | 100 μM | Full inhibition |
| | Folate-maleimide | 100 μM | Full inhibition |
| | pCMBS | 100 μM | >50% inhibition |
| | EC1277 (GSAO) | 3 mm | Full inhibition |

TABLE 1-continued

| Action | Inhibitor | Concentration (μM) | Inhibition of EC0531 Nonspecific Activity |
|---|---|---|---|
| SH-reactive agents | GSSG | 10 mm | Full inhibition |
| | Dimesna | 1 mm | Full inhibition |
| | Methoxy-PEG5000-vinylsulfone | 3 mm | >50% inhibition |
| | EGCg | 100 μM | >50% inhibition |
| Nonspecific anion transport inhibitors | DIDS | 1 mm | Full inhibition |
| | BSP | 1 mm | <50% inhibition |

Example 5

The presence of extracellular thiols can also affect the nonspecific uptake of ligand conjugates. In this example, the nonspecific uptake of an exemplary folate conjugate (EC0531; specifically $^3$H-EC0531) was investigated. The nonspecific uptake of EC0531 was evaluated in both KB cells and in A549 cells.

For $^3$H-EC0531 uptake studies, cells were seeded at 2×10$^5$ cells per well of a 24-well tissue culture plate and allowed to attach to plates overnight. Increasing concentrations of $^3$H-EC0531 and $^3$H-FA were prepared in FFRPMI/HIFBS. To determine non-FR-targeted uptake, 100 μM FA was included in the uptake solutions. Cells were incubated with 0.5 mL of uptake solution for 2 h at 37° C. washed 3 times with ice-cold PBS, and were solubilized in 0.5 mL 1% SDS in PBS, pH 7.4. Cell lysates (450 μL) were added to 3 mL Ecolite+scintillation cocktail and counted in a liquid scintillation counter. Protein concentrations of the remaining lysates were determined using the BCA Protein Assay (Pierce, Rockford, Ill.). Molecules per cell were calculated based on DPM values and previously determined cellular protein conversion factors (2.82×10$^{-7}$ and 2.23×10$^{-7}$ mg protein per cell for KB and A549, respectively).

Figure 7:
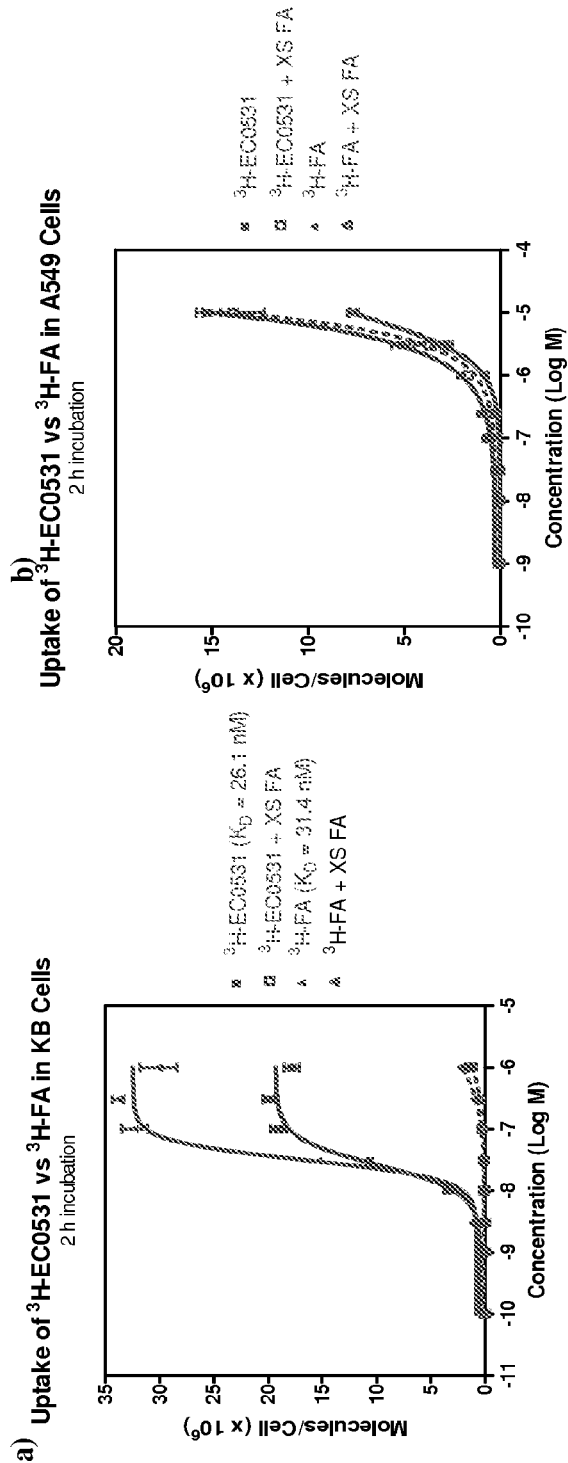
FIG. 7 shows the amount of uptake of $^3$H-EC0531 (molecules per cell×$10^6$) at various concentrations of administered conjugates in both KB cells and A549 cells.

As shown in FIG. 7, the nonspecific uptake of $^3$H-EC0531 (molecules per cell×10$^6$) is observed at concentrations of about 1 μM in both KB cells and A549 cells.

The effects of two different concentrations of DTNB (10 μM and 100 μM) on the reduction of nonspecific uptake of $^3$H-EC0531 into cells were also evaluated in this example. Inhibition of non-FR-targeted $^3$H-EC0531 uptake was assessed by incubating $^3$H-EC0531 in the presence of inhibitors. Cells were seeded at 4×10$^5$ cells per well of a 12-well tissue culture plate, and were treated the next day with 1 μM EC0531 plus the indicated concentrations of inhibitors in 1 mL FFRPMI/HIFBS for 2 hours at 37° C. FA at a concentration of 100 μM was used as a competitor to determine non-FR-specific uptake in KB cells. Wells were then washed 3 times with 1 mL of ice-cold PBS, pH 7.4 and were processed for LSC analysis as described above.

Figure 8:
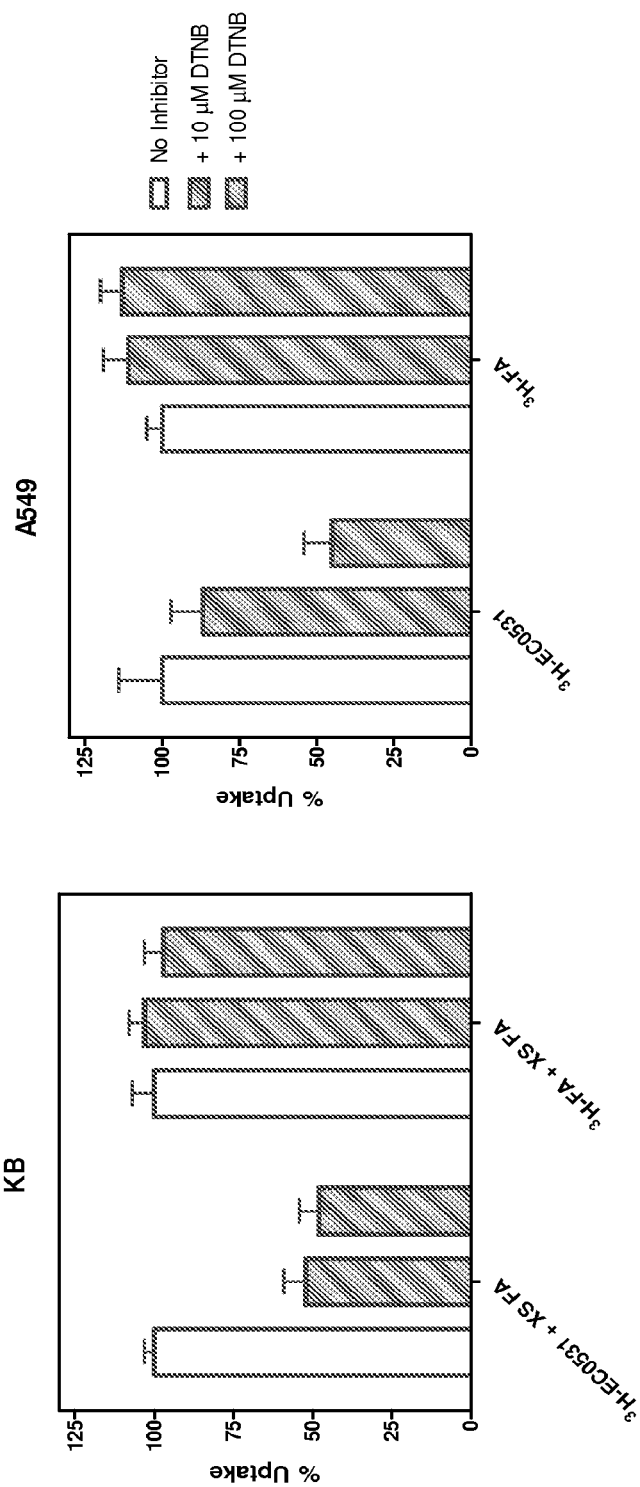
FIG. 8 shows the percent uptake of $^3$H-EC0531 following co-administration of thiol inhibitors and the folate conjugate EC0531 in both KB cells and A549 cells. Left-hand set of bars in each graph—The open bars show data obtained with no thiol inhibitor administered. The middle bar in each set of three data points shows data obtained with co-administration of 10 μM DTNB and $^3$H-EC0531. The last bar in each set of three data points shows data obtained with co-administration of 100 μM DTNB and $^3$H-EC0531. Right-hand set of bars in each graph—The open bars show data obtained with no thiol inhibitor administered. The middle bar in each set of three data points shows data obtained with co-administration of 10

As shown in FIG. 8, DTNB exhibited the ability to reduce the nonspecific uptake of $^3$H-EC0531 in KB cells and in A549 cells. In comparison, the nonspecific uptake of $^3$H-folic acid was mostly unaffected.

The effects of three thiol inhibitors (DTNB, NCEM, and DIDS) on the reduction of nonspecific uptake of $^3$H-EC0531 into cells were also evaluated in this example. In addition to the thiol inhibitors, the effects of a reduced folate carrier inhibitor (e.g. methotrexate) on the reduction of nonspecific uptake of $^3$H-EC0531 were evaluated for comparison. Methods were as described above in this example.

As shown in FIG. 9, DTNB, NCEM, and DIDS reduced the nonspecific uptake of $^3$H-EC0531 in KB cells and in A549 cells. In comparison, reduced folate carrier inhibitors (e.g. methotrexate) were ineffective to reduce the nonspecific uptake of $^3$H-EC0531 in KB cells and in A549 cells.

Example 6

The presence of thiols in cell culture media can affect the non-ligand-specific activity of ligand conjugates. In this example, the exemplary folate conjugate investigated was EC0531. The non-FR-specific activity of EC0531 due to the presence of thiols in cell culture media was evaluated in both KB cells and in A549 cells.
KB Cells KB cells were treated in four different types of culture media: 1) FDRPMI with no serum added; 2) FDRPMI with 10% FBS added; 3) thiol-free FDRPMI with no serum added; and 4) thiol-free FDRPMI with 10% FBS added. The KB cells in each type of culture media were administered two different treatments. First, EC0531 was administered to KB cells in the various culture media, and the $IC_{50}$ values were evaluated. Second, EC0531 plus folic acid was administered to KB cells in the various culture media, and the $IC_{50}$ values were evaluated.

A modified RPMI medium (SH-free RPMI), in which glutathione (GSH) and cystine were omitted, was prepared to evaluate the activity of EC0531 in the absence of low molecular weight thiols. Additionally, the effect of high molecular weight thiols (from serum proteins) on EC0531 activity was assessed in medium containing no HIFBS. A dilution series of EC0531 was prepared in RPMI medium with and without 10% HIFBS or SH-free RPMI medium with and without 10% HIFBS. To assess non-FR targeted activity in the FR+KB cells, 100 µM FA was included in the solutions with EC0531. Cells (1×10$^5$/well) were incubated for 2 hours in the presence of drug, washed 3 times with media, and then chased in 0.5 mL of FDRPMI/HIFBS to 72 hours at 37° C. $^3$H-thymidine incorporation was determined as described. The non-FR-specific activity of EC0531 was subsequently evaluated in each type of culture media.
A549 Cells A549 cells were treated in four different types of culture media: 1) FDRPMI with no serum added; 2) FDRPMI with 10% FBS added; 3) thiol-free FDRPMI with no serum added; and 4) thiol-free FDRPMI with 10% FBS added. The non-FR-specific activity of EC0531 was subsequently evaluated in each type of culture media. The A549 cells in each type of culture media were administered one treatment. EC0531 was administered to A549 cells in the various culture media, and the $10_{50}$ values were evaluated. The administration of EC0531 plus folic acid was not evaluated, as A549 cells do not have folate receptors.

A modified RPMI medium (SH-free RPMI), in which glutathione (GSH) and cystine were omitted, was prepared to evaluate the activity of EC0531 in the absence of low molecular weight thiols. Additionally, the effect of high molecular weight thiols (from serum proteins) on EC0531 activity was assessed in medium containing no HIFBS. A dilution series of EC0531 was prepared in RPMI medium with and without 10% HIFBS or SH-free RPMI medium with and without 10% HIFBS. To assess non-FR targeted activity in the FR+KB cells, 100 µM FA was included in the solutions with EC0531. Cells (1×10$^5$/well) were incubated for 2 hours in the presence of drug, washed 3 times with media, and then chased in 0.5 mL of FDRPMI/HIFBS RPMI+FA/HIFBS to 72 hours at 37° C. $^3$H-thymidine incorporation was determined as described. The non-FR-specific activity of EC0531 was subsequently evaluated in each type of culture media.

As shown in Table 2, the presence of thiols in culture media increases the non-FR-specific activity of folate conjugates in KB cells and in A549 cells. Elimination of cystine and glutathione from the incubation medium significantly attenuated the nonspecific activity of EC0531.

TABLE 2

| Cell Line | Treatment | EC0531 $IC_{50}$ (nM) | EC0531 + Folic Acid $IC_{50}$ (nM) |
|---|---|---|---|
| KB | FDRPMI/no serum | 7.0 | 540 |
|  | FDRPMI/10% FBS | 6.7 | 948 |
|  | SH-free FDRPMI/no serum | 7.8 | 830 |
|  | SH-free FDRPMI/10% FBS | 9.2 | 2323 |
|  | Conditioned FDRPMI/10% FBS | 8.3 | 57 |
| A549 | FDRPMI/no serum | 164 |  |
|  | FDRPMI/10% FBS | 295 |  |
|  | SH-free FDRPMI/no serum | 575 |  |
|  | SH-free FDRPMI/10% FBS | 1133 |  |

Example 7

Because the presence of thiols in cell culture media can affect the non-ligand-specific activity of ligand conjugates, this example evaluated if the replacement of cell culture media would affect the nonspecific activity. In this example, the exemplary folate conjugate EC0531 was investigated in KB cells.

KB cells were suspended in FDRPMI/HIFBS, seeded at 1×10$^5$ cells/well in 24-well tissue culture plates, and were allowed to attach overnight. The following day, cells were incubated in 500 µL of a solution containing 1 µM EC0531 plus 100 µM FA in FDRPMI/HIFBS to assess non-FR-targeted activity. The treatment solution was removed every 30 minutes and replaced with fresh medium containing 1 µM EC0531 plus 100 µM FA for a cumulative 2 hour incubation. Alternatively, one group of cells was treated with the same concentrations of EC0531 and FA continuously without media changes. Total activity of EC0531 (i.e. in the absence of excess FA) was also assessed using both pulse conditions. After the drug incubations, cells were washed, replenished with fresh media, and processed for $^3$H-thymidine incorporation as described above. Final results were expressed as percentage of $^3$H-thymidine incorporation relative to an untreated control (non-competed groups) or FA control (competed groups). The total treatment time for each group was 2 hours, followed by a 72 hour chase.

Four groups of cells were evaluated in the example and are shown in Table 3.

TABLE 3

| Group | Amount of EC0531 Administered (µM) | Amount of Folic Acid Administered (µM) | Number of Pulses | Time of Each Pulse |
|---|---|---|---|---|
| 1 | 1 | 0 | 1 | 2 hours |
| 2 | 1 | 0 | 4 | 30 minutes |
| 3 | 1 | 100 | 1 | 2 hours |
| 4 | 1 | 100 | 4 | 30 minutes |

As shown in FIG. 10, replacing the cell culture media in KB cell culture every 30 minutes eliminates the non-FRspecific activity of EC0531 following co-administration of EC0531 and folic acid. In particular, replacing the cell culture media in KB cell culture every 30 minutes eliminates the non-FR-specific activity of EC0531. In other words, when the "reducing" medium is replaced with a fresh oxidized medium every 30 minutes, the non-FR-specific activity of EC0531 is diminished.

Example 8

Various thiols can be tested in vitro to determine their effects on extracellular thiol activity in cells. In this example, the extracellular thiol activity of A549 cells was evaluated.

A549 cells were incubated in five different groups: 1) SH-free RPMI medium (negative control); 2) SH-free RPMI medium plus GSSG (1.6 µM); 3) SH-free RPMI medium plus cysteine (189 µM); 4) SH-free RPMI medium plus GSSG (1.6 µM) plus cysteine (189 µM); and normal RPMI medium including SH (positive control). The cells underwent 2 hours of continuous incubation.

A549 cells were plated in 24-well tissue cultured-treated plates at 2×10$^5$ cells per well in RPMI+FA/HIFBS and were allowed to attach to the plates overnight. A 200 µM solution of DTNB in the indicated PR-free media was prepared. The cells were rinsed one time with PBS, pH 7.4, and then 500 µL of the appropriate DTNB solution were added to each well (n=3). The cells were incubated for 2 hours at 37° C. The solutions were then removed from the cells, and absorbance was determined at a wavelength of 412 nm. Background absorbance determined from an aliquot of DTNB solution incubated in an empty well of the tissue culture plate was subtracted from each value. Thiol concentrations were calculated based on an extinction coefficient of 14,150 M$^{-1}$ cm$^{-1}$. Protein concentrations of cell lysates were determined by the BCA Assay method (Pierce, Rockford, Ill.).

FIG. 11 shows the individual effect of GSSG (1.6 µM) and cysteine (189 µM) on the extracellular thiol activity in A549 cells, as measured by thiol (i.e. SH) concentration (µM). Thiol-free RPMI cell culture media was used as a negative control, and RPMI cell culture media containing thiols was used as a positive control. Cysteine appears to be responsible for stimulation of the extracellular thiol activity in A549 cells, but GSSG appears to have no effect.

In addition, cysteine is the predominant thiol released by cells, at levels reaching 11 to 42 µM (for KB and A549 cells, respectively) following only a 2 hour conditioning period at 37° C. Cells were plated in 24-well tissue cultured-treated plates at 2×10$^5$ cells per well in FDRPMI/HIFBS (KB cells) or RPMI+FA/HIFBS (A549 cells) and were allowed to attach to the plates overnight. The conditioning time course was initiated by adding 500 µL of fresh FDRPMI/HIFBS to each well. Plates were incubated at 37° C. for the indicated time periods. At each time point, 450 µL medium was removed (n=3) from the appropriate wells and added to a tube containing 50 µL of 100 mM NCEM to quench all thiol reactions. Quantitation of cysteine, glutathione, homocysteine, and cysteinylglycine was done by LC/MS/MS analysis. Analytes were extracted from the FDRPMI/HIFBS using a 96-well protein precipitation plate and acidified acetonitrile. L-cysteine-$^{13}$C$_3$, $^{15}$N was added as an internal standard during the extraction. Following centrifugation, the supernatants were collected, evaporated to dryness, and reconstituted in 0.2% formic acid. The extracted samples were injected into a UPLC/MS/MS system using an HSS T3 C18 reverse phase column implementing a mobile phase gradient. Detection was conducted by monitoring the NCEM conjugates of the thiol compounds, and quantitation was achieved using standard calibrators of the NCEM conjugates. The effects were observed independently of cell type or FR expression status.

Example 9

System $x_c^-$ is a cystine/glutamate antiporter, and has been shown to be involved in regulating the extracellular redox state of the cysteine/cystine couple in vitro. In this example, the effect of system $x_c^-$ inhibitors on extracellular thiol activity in A549 cells was evaluated.

A549 cells were administered system $x_c^-$ inhibitors in four different groups: 1) no inhibitor (negative control); 2) glutamate (5 mM); 3) quisqualic acid (0.3 mM); and 4) quisqualic acid (1 mM). A549 cells were plated in 24-well tissue cultured-treated plates at 2×10$^5$ cells per well in RPMI+FA/HIFBS and were allowed to attach to the plates overnight. Solutions of DTNB with and without the indicated concentrations of system $x_c^-$ inhibitors in PR-free RPMI were prepared. The cells were rinsed one time with PBS, pH 7.4, followed by the addition of 500 µL of DTNB solution+/−system $x_c^-$ inhibitor to each appropriate well (n=3). The cells were then incubated for 2 hours at 37° C. the solutions were removed from the cells, and absorbances were determined at a wavelength of 412 nm. Background absorbance determined from an aliquot of DTNB solution incubated in an empty well of the tissue culture plate was subtracted from each value. Thiol concentrations were calculated based on an extinction coefficient of 14,150 M$^{-1}$ cm$^{-1}$. Protein concentrations of cell lysates were determined by the BCA Assay method (Pierce, Rockford, Ill.).

As shown in FIG. 12, system $x_c^-$ inhibitors glutamate (5 mM) and quisqualic acid (0.3 mM and 1 mM) significantly reduce the release of extracellular thiols in A549 cells as measured by thiol (i.e. SH) concentration (µM). Furthermore, quisqualic acid demonstrated a dose-dependent reduction of the release of extracellular thiols.

Example 10

The presence of extracellular thiols can affect the non-ligand-specific activity of ligand conjugates. In this example, the non-FR-specific activity of an exemplary folate conjugate (EC0531) was investigated. The non-FR-specific activity of EC0531 was evaluated in KB cells.

The effects of the system $x_c^-$ inhibitor sulfasalazine on the non-FR-specific activity of EC0531 were evaluated in this example. Sulfasalazine was co-administered with EC0531 (1 µM) and folic acid (100 µM). The inhibition of non-FR-specific activity (i.e. cytotoxicity) was evaluated. KB cells were seeded in 24-well tissue culture-treated plates at 1×10$^5$ cells per well in FDRPMI/HIFBS and allowed to attach to the plates overnight at 37° C. A dilution series of sulfasalazine was prepared in FDRPMI/HIFBS medium containing a final concentration of 1 µM EC0531 and 100 µM FA. Cells were incubated for 2 hours in the presence of drug, FA competitor, and inhibitor, washed 3 times with media, then chased in 0.5 mL of FDRPMI/HIFBS to 72 hours at 37° C. Cells were then treated as described above to determine $^3$H-thymidine incorporation. Final results were expressed as percentage of $^3$H-thymidine incorporation relative to an untreated control (non-competed groups) or FA control (competed groups).

As shown in FIG. 13, the system $x_c^-$ inhibitor sulfasalazine exhibits a dose-responsive inhibition of non-FR-specific activity in KB cells. Sulfasalazine exhibited an IC$_{50}$ of 170 µM.

Example 11

Furthermore, among various system $x_c^-$ inhibitors, sulfasalazine appears to be a more potent inhibitor than glutamate. In this example, the non-FR-specific activity of an exemplary folate conjugate (EC0531) was investigated. The non-FR-specific activity of EC0531 was evaluated in A549 cells.

The effects of the system $x_c^-$ inhibitors sulfasalazine and glutamate on the non-FR-specific activity of EC0531 were evaluated in this example.

A549 cells were seeded in 24-well tissue culture-treated plates at $1 \times 10^5$ cells per well in RPMI+FA/HIFBS and allowed to attach overnight at 37° C. The next day, cells were treated concurrently with increasing concentrations of EC0531 and a constant concentration of inhibitor (1 mM sulfasalazine or 5 mM glutamate in FDRPMI/HIFBS). Another group received no inhibitor (i.e. EC0531 only) and was also included. Cells were incubated for 2 hours in the presence of drug and inhibitor, washed 3 times with media, and then chased in 0.5 mL of FDRPMI/HIFBS to 72 hours at 37° C. Cells were then treated as described above to determine $^3$H-thymidine incorporation. The inhibition of non-FR-specific activity (i.e. cytotoxicity) was evaluated for each system $x_c^-$ inhibitor. Final results were expressed as percentage of $^3$H-thymidine incorporation relative to an untreated control.

As shown in FIG. 14, both sulfasalazine (1 mM) and glutamate (5 mM) inhibit the non-FR-specific activity of EC0531 in A549 cells, as measured by percentage of $^3$H-Thymidine incorporated in cells (counts per minute). Sulfasalazine exhibited a greater inhibition of non-FR-specific activity of EC0531 in A549 cells compared to glutamate.

Example 12

The presence of extracellular thiols can affect the non-specific uptake of ligand conjugates. In this example, the nonspecific uptake of an exemplary folate conjugate (EC0531; specifically $^3$H-EC0531) was investigated. The nonspecific uptake of EC0531 was evaluated in both KB cells and in A549 cells.

The effects of the system $x_c^-$ inhibitor sulfasalazine on the reduction of nonspecific uptake of $^3$H-EC0531 into cells were evaluated in this example. In addition to sulfasalazine, the effects of a reduced folate carrier inhibitor (e.g. methotrexate) on the reduction of nonspecific uptake of $^3$H-EC0531 were evaluated for comparison.

Inhibition of non-FR-targeted $^3$H-EC0531 uptake was assessed by incubating $^3$H-EC0531 in the presence of inhibitors. Cells were seeded at $4 \times 10^5$ cells per well of a 12-well tissue culture plate, and were treated the next day with 1 µM EC0531 plus the indicated concentrations of inhibitors in 1 mL FFRPMI/HIFBS for 2 h at 37° C. Wells were then washed 3 times with 1 mL of ice-cold PBS, pH 7.4 and were processed for LSC analysis as described above.

As shown in FIG. 15, sulfasalazine reduced the nonspecific uptake of $^3$H-EC0531 in KB cells and in A549 cells. In comparison, reduced folate carrier inhibitors (e.g. methotrexate) were ineffective to reduce the nonspecific uptake of $^3$H-EC0531 in KB cells and in A549 cells.

Example 13

In the system $x_c^-$ pathway, xCT is known to be the functional subunit of system $x_c^-$. siRNA-mediated knockdown of xCT shows effects on extracellular thiol activity. In this example, the non-FR-specific activity of an exemplary folate conjugate (EC0531) was investigated. The non-FR-specific activity of EC0531 was evaluated in KB cells and in A549 cells.

Knockdown of xCT by siRNA transfection of A549 and KB cells was achieved by incubating cells for 48 hours in the presence of xCT siRNA (Ambion). Transfection complexes were formed by preparing a solution of 25 nM xCT siRNA and 100 µL RNAiMAX reagent (Invitrogen) per mL Opti-MEM medium (Gibco). Additionally, a nonspecific (NS) siRNA (Ambion) was also prepared accordingly and used as a control for all assays. Transfection complexes were allowed to form for 15 min at room temperature, and then 100 µL of transfection complex (2.5 pmol siRNA and 1 µL RNAiMAX) were added per well to 24-well tissue culture-treated plates. Controls that received Opti-MEM medium only (i.e. no siRNA) were also prepared. Next, A549 cells and KB cells were suspended in RPMI+FA/HIFBS (A549) or FDRPMI/HIFBS (KB) and were added to the wells ($5 \times 10^4$ cells/well). Plates were placed in an incubator at 37° C. and transfection was allowed to proceed for 48 hours. After the transfection period, wells were washed two times with FDRPMI/HIFBS, and EC0531 activity (i.e. cytotoxicity) and extracellular thiol activity (DTNB assay) were assessed as described above.

As shown in FIG. 16, siRNA-mediated knockdown of xCT causes a reduction of extracellular thiol activity in both KB cells and in A549 cells, as measured by percentage of UTC (nmol of thiol/mg of protein).

Furthermore, as shown in Table 4, the siRNA-mediated knockdown of xCT reduced non-FR-specific activity of EC0531 in both KB cells and in A549 cells.

TABLE 4

| Cell Line | Treatment | EC0531 IC$_{50}$ (nM) | EC0531 + Folic Acid IC$_{50}$ (nM) |
|---|---|---|---|
| KB | No siRNA | 54.8 | 258 |
| | NS siRNA | 49.6 | 434 |
| | xCT siRNA | 252 | 1775 |
| A549 | No siRNA | 121 | |
| | NS siRNA | 128 | |
| | xCT siRNA | 3797 | |

The invention claimed is:

1. A method of treatment of a disease, the method comprising
   a. administering to a patient a ligand conjugate, or a pharmaceutically acceptable salt thereof, of the formula B-L-D, wherein B is a cell surface receptor targeting ligand, D is a drug, and L is a releasable polyvalent linker comprising a disulfide linkage and at least one polyhydroxyl containing spacer linker; and
   b. administering a thiol inhibitor to the patient.

2. The method of claim 1, wherein the thiol inhibitor is selected from the group consisting of 5,5'-dithiobis(2-nitrobenzoic acid) (DTNB), (N-(2-carboxyethyl) maleimide (NCEM), p-chloromercuribenzene sulfonate (pCMBS), 4-(N—(S-glutathionylacetyl)amino) phenylarsonous acid (GSAO), 2,2'-dithio-bis-ethanesulfonate (dimesna), oxidized glutathione (GSSG), methoxy-PEG5000-vinylsulfone, epigallocatechin gallate (EGCG) and 4-acetamido-4-maleimidylstilbene-2,2-disulfonic acid (AMS).

3. The method of claim 2, wherein the disease is a cancer.

4. The method of claim 3, wherein the cancer is selected from the group consisting of a carcinoma, a sarcoma, a lymphoma, Hodgkin's disease, a melanoma, a mesothelioma, Burkitt's lymphoma, a nasopharyngeal carcinoma, a leukemia and a myeloma.

5. The method of claim 3, wherein the cancer is selected from the group consisting of oral, thyroid, endocrine, skin, gastric, esophageal, laryngeal, pancreatic, colon, bladder, bone, ovarian, cervical, uterine, breast, testicular, prostate, rectal, kidney, liver and lung cancer.

6. The method claim 3, wherein B is a folate.

7. The method claim 6, wherein B is of the formula

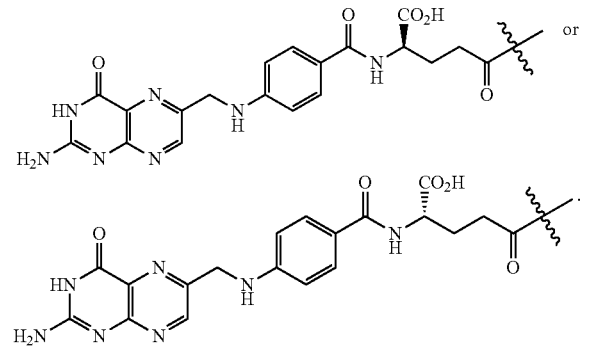

8. The method of claim 7, wherein D is selected form the group consisting of a vinca alkaloid, cryptophycin, bortezomib, thiobortezomib, a tubulysin, aminopterin, a rapamycin, everolimus, sirolimus, paclitaxel, docetaxel, doxorubicin, daunorubicin, α-amanatin, verucarin, didemnin B, geldanomycin, purvalanol A, ispinesib, budesonide, dasatinib, an epothilone, and a maytansine.

9. A method of treatment of a disease, the method comprising
a. administering to a patient a ligand conjugate, or a pharmaceutically acceptable salt thereof, of the formula B-L-D, wherein B is a cell surface receptor targeting ligand, D is a drug, and L is a releasable polyvalent linker comprising a disulfide linkage and at least one polyhydroxyl containing spacer linker; and
b. administering a thiol inhibitor to the patient, wherein the thiol inhibitor is selected from the group consisting of 5,5'-dithiobis(2-nitrobenzoic acid) (DTNB), (N-(2-carboxyethyl) maleimide (NCEM), p-chloromercuribenzene sulfonate (pCMBS), 4-(N—(S-glutathionylacetyl)amino) phenylarsonous acid (GSAO), 2,2'-dithio-bis-ethanesulfonate (dimesna), oxidized glutathione (GSSG), methoxy-PEG5000-vinylsulfone, and 4-acetamido-4-maleimidylstilbene-2,2-disulfonic acid (AMS).

10. The method of claim 9, wherein the thiol inhibitor is 5,5'-dithiobis(2-nitrobenzoic acid) (DTNB).

* * * * *